(12) United States Patent
Barrat et al.

(10) Patent No.: US 9,063,123 B2
(45) Date of Patent: Jun. 23, 2015

(54) TRANSGENIC MICE EXPRESSING HUMAN TOLL-LIKE RECEPTOR 8

(75) Inventors: Franck Barrat, San Francisco, CA (US); Robert L. Coffman, Portola Valley, CA (US); Cristiana Guiducci, Albany, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 265 days.

(21) Appl. No.: 13/434,805

(22) Filed: Mar. 29, 2012

(65) Prior Publication Data

US 2012/0252051 A1 Oct. 4, 2012

Related U.S. Application Data

(60) Provisional application No. 61/469,055, filed on Mar. 29, 2011.

(51) Int. Cl.
| | | |
|---|---|---|
| *C12N 5/16* | (2006.01) | |
| *G01N 33/50* | (2006.01) | |
| *A01K 67/027* | (2006.01) | |
| *C07K 14/705* | (2006.01) | |

(52) U.S. Cl.
CPC .......... *G01N 33/502* (2013.01); *G01N 33/5023* (2013.01); *A01K 67/0271* (2013.01); *A01K 67/0278* (2013.01); *A01K 2217/052* (2013.01); *A01K 2227/105* (2013.01); *A01K 2267/0387* (2013.01); *C07K 14/705* (2013.01)

(58) Field of Classification Search
USPC ........................................ 800/3–20; 435/325
See application file for complete search history.

(56) References Cited

U.S. PATENT DOCUMENTS

| | | | |
|---|---|---|---|
| 4,861,719 | A | 8/1989 | Miller |
| 4,873,191 | A | 10/1989 | Wagner et al. |
| 5,168,062 | A | 12/1992 | Stinski |
| 5,175,384 | A | 12/1992 | Krimpenfort et al. |
| 5,385,839 | A | 1/1995 | Stinski |
| 5,602,299 | A | 2/1997 | Lazzarini |
| 6,037,521 | A | 3/2000 | Sato et al. |
| 6,066,778 | A | 5/2000 | Ginsburg et al. |
| 2003/0096787 | A1 | 5/2003 | Perricaudet et al. |
| 2009/0253134 | A1 | 10/2009 | Brunner et al. |
| 2009/0288176 | A1 | 11/2009 | Bollinger et al. |
| 2010/0266619 | A1 | 10/2010 | Elson |

FOREIGN PATENT DOCUMENTS

| | | | |
|---|---|---|---|
| EP | 0 178 220 A2 | | 4/1986 |
| EP | 0 178 220 A3 | | 4/1986 |
| EP | 0 453 242 A1 | | 10/1991 |
| JP | 2009-207465 | * | 9/2009 |
| WO | WO-89/07150 A1 | | 8/1989 |
| WO | WO-90/02806 A1 | | 3/1990 |
| WO | WO-90/08832 A1 | | 8/1990 |
| WO | WO-95/02697 A1 | | 1/1995 |
| WO | WO-96/01313 A1 | | 1/1996 |
| WO | WO-02/22809 A2 | | 3/2002 |
| WO | WO-02/22809 A3 | | 3/2002 |
| WO | WO-2010/062322 A2 | | 6/2010 |
| WO | WO-2010/062322 A3 | | 6/2010 |
| WO | WO-2012/135549 A2 | | 10/2012 |
| WO | WO-2012/135549 A3 | | 10/2012 |

OTHER PUBLICATIONS

Liu et al., Mol Immunol. 47:1083-90, 2010.*
Heil et al., Science 303:1526, 2004.*
Medzhitov et al., Immunol. Rev. 173:-89-97, 2000.*
Gorden et al. J Immunol. 174:1259-68, 2005.*
Barrat et al., J Exp Med. 2202:1131-9, 2005.*
Jurk et al. Nat Immunol 3:499, 2002.*
Hemmi et al. Nat. Immunol 3:196- 200, 2002.*
Lund et al. PNAS 101:5598-603, 2004.*
Olsen, GABA in the Nervous System, 2000, p. 81-95.*
Srivastava (PNAS, Nov. 23, 1999, vol. 96, No. 24, p. 13783-13788).*
Bowery (Pharm. Rev., 2002, vol. 54, p. 247-264).*
MacDonald (J. Biol. Chem., Nov. 22, 2002, vol. 277, p. 44938-44945).*
Mombereau (Neuropsychopharmacology, 2004, vol. 29, p. 1050-1062).*
Cowan (Xenotransplantation, 2003, vol. 10, p. 223-231).*
Wall (1996, Theriogenology, vol. 45, p. 57-68).*
Ebert (1988, Mol. Endocrinology, vol. 2, pp. 277-283).*
Mullins (1990, Nature, vol. 344, p. 541-544).*
Hammer (1990, Cell, vol. 63, p. 1099-1112).*
Mullins, 1989, EMBO, vol. 8, p. 4065-4072.*
Taurog, 1988, J. Immunol., vol. 141, p. 4020-4023).*
Chuang (Eur. Cytokine Netw., vol. 11, p. 372-378).*
MGI description of diabetes types, 2014.*
MGI description of rheumatoid arthritis, 2014.*
Akira (2001). "Toll-Like Receptors and Innate Immunity," *Advances in Immunology* 78:1-56.
Altschul et al. (1990). "Basic Local Alignment Search Tool," *J. Mol. Biol.* 215:403-410.
Bernstein et al. (1985). "Gene Transfer with Retrovirus Vectors," *Genetic Engineering: Principles and Methods* 7:235-261.
Bihl et al. (2003). "Overexpression of Toll-like Receptor 4 Amplifies the Host Response to Lipopolysaccharide and Provides a Survival Advantage in Transgenic Mice," *J Immunol* 170:6141-6150.
Bradley et al. (1984). "Formation of Germ-Line Chimaeras from Embryo-Derived Teratocarcinoma Cell Lines," *Nature* 309:255-256.
Campbell et al. (2000). "Collagen-induced Arthritis in C57BL/6 (H-2$^b$) Mice: New Insights Into an Important Disease Model of Rheumatoid Arthritis," *Eur. J. Immunol.* 30:1568-1575.

(Continued)

*Primary Examiner* — Michael Wilson
(74) *Attorney, Agent, or Firm* — Morrison & Foerster LLP

(57) ABSTRACT

Provided herein are human Toll-like receptor 8 (TLR8)-expressing transgenic s and methods of use thereof.

11 Claims, 24 Drawing Sheets

(56) References Cited

OTHER PUBLICATIONS

Diebold et al. (2004). "Innate Antiviral Responses by Means of TLR7-Mediated Recognition of Single-Stranded RNA," *Science* 303(5663):1529-1531.
Evans et al. (1981). "Establishment in Culture of Pluripotential Cells from Mouse Embryos," *Nature* 292:154-156.
GenBank Accession No. NP_619542.1, last updated on May 6, 2014, located at http://www.ncbi.nlm.nih.gov/protein/NP_619542, last visited on Jun. 11, 2014, six pages.
Gordon (1980). "Genetic Transformation of Mouse Embryos by Microinjection of Purified DNA," *Proc. Natl. Acad. Sci. USA* 77(12):7380-7384.
Gossler et al. (1986). "Transgenesis by Means of Blastocyst-Derived Embryonic Stem Cell Lines," *Proc. Natl. Acad. Sci. USA* 83:9065-9069.
Haskell et al. (1995). "Efficient Production of Transgenic Cattle by Retroviral Infection of Early Embryos," *Molecular Reproduction and Development* 40:386-390.
Henikoff et al. (1992). "Amino Acid Substitution Matrices from Protein Blocks," *Proc. Natl. Acad. Sci. USA* 89:10915-10919.
Hickman-Davis et al. (2006). "Transgenic Mice," *Pediatric Respiratory Reviews* 7:49-53.
Higgins et al. (1988). "CLUSTAL: A Package for Performing Multiple Sequence Alignment on a Microcomputer," *Gene* 73:237-244.
Jaenisch (1988). "Transgenic Animals," *Science* 240:1468-1474.
Karlin et al. (1993). "Applications and Statistics for Multiple High-Scoring Segments in Molecular Sequences," *Proc. Natl. Acad. Sci. USA* 90:5873-5877.
Lan et al. (2007). "Stabilized Immune Modulatory RNA Compounds As Agonists of Toll-Like Receptors 7 and 8," *Proc Natl Aced Sci USA* 104:13750-13755.
Lavitrano et al. (1989). "Sperm Cells as Vectors for Introducing Foreign DNA Into Eggs: Genetic Transformation of Mice," *Cell* 57:717-723.
Lo (1983). "Transformation by Iontophoretic Microinjection of DNA: Multiple Integrations Without Tandem Insertions," *Mol Cell Biol* 3:1803-1814.
McCormick (1985). "Human Gene Therapy: The First Round," *Nature Biotechnology* 3(8):689-693.
Pearson et al. (1988). "Improved Tools for Biological Sequence Comparison," *Proc. Natl. Acad. Sci. USA* 85:2444-2448.
Robertson et al. (1986). "Germ-line Transmission of Genes Introduced Into Cultured Pluripotential Cells by Retroviral Vector," *Nature* 323:445-448.
Smits et al. (2008). "The Use of TLR7 and TLR8 Ligands for the Enhancement of Cancer Immunotherapy," *The Oncologist* 13:859-875.
Sparwasser et al. (2007). "BAC to Immunology—Bacterial Artificial Chromosome-Mediated Transgenesis for Targeting of Immune Cells," *Immunology* 121:308-313.
Thompson et al. (1989). "Germ Line Transmission and Expression of a Corrected HPRT Gene Produced by Gene Targeting in Embryonic Stem Cells," *Cell* 56:313-321.
Van Der Putten et al. (1985). "Efficient Insertion of Genes Into the Mouse Germ Line Via Retroviral Vectors," *Proc. Natl. Acad. Sci. USA* 82:6148-6152.
International Preliminary Report on Patentability mailed on Jan. 14, 2014, for PCT Patent Application No. PCT/US2012/031307, filed on Mar. 29, 2012, five pages.
International Search Report mailed on Jun. 20, 2012, for PCT Patent Application No. PCT/US12/31307, filed on Mar. 29, 2012, three pages.
Written Opinion mailed on Jun. 20, 2012, for PCT Patent Application No. PCT/US12/31307, filed on Mar. 29, 2012, four pages.
Cervantes et al. (2012). "TLR8: The Forgotten Relative Revindicated," *Cell Mol Immunol* 9:434-438.
Davila et al. (2008). "Genetic Association and Expression Studies Indicate a Role of *Toll-Like Receptor* 8 in Pulmonary Tuberculosis." *PLoS Genetics* 4(10):e1000218.
Demaria et al. (2010). "TLR8 Deficiency Leads to Autoimmunity in Mice," *J Clin Invest* 120:3651-3662.
Gorden et al. (2006). "Oligodeoxynucleotides Differentially Modulate Activation of TLR7 and TLR8 by Imidazoquinolines," *J Immunol* 177:8164-8170.
Gringhuis et al. (2010). "HIV-1 Exploits Innate Signaling by TLR8 and DC-SIGN for Productive Infection of Dendritic Cells," *Nature Immunol* 11:419-426.
Guiducci et al. (2013). "RNA Recognition by Human TLR8 Can Lead to Autoimmune Inflammation," *J Exp Med* 210 2903-2919.
Kugelberg. (2014). "Making Mice More Human the TLR8 Way," *Nature Reviews Immunology*, 14:6.
Lee et al. (2003). "Molecular Basis for the Immunostimulatory Activity of Guanine Nucleoside Analogs: Activation of Toll-Like Receptor 7," *Proc Natl Acad Sci USA* 100:6646-6651.
Ma et al. (2006). "Toll-Like Receptor 8 Functions as a Negative Regulator of Neurite Outgrowth and Inducer of Neuronal Apoptosis," *J Cell Biol* 175:209-215.
Peng et al. (2005). "Toll-Like Receptor 8-Mediated Reversal of CD4+ T Cell Function," *Science* 309:1380-1384.
Sacre et al. (2008). "Inhibitors of TLR8 Reduce TNF Production from Human Rheumatoid Synovial Membrance Cultures," *J Immunol* 181:8002-8009.
Deane et al. (2007). "Control of Toll-Like Receptor 7 Expression is Essential to Restrict Autoimmunity and Dendritic Cell Proliferation," *Immunity* 27:801-810.
Supplementary European Search Report mailed on Nov. 12, 2014, for EP Patent Application No. 12765327.7, filed on Mar. 29, 2012, seven pages.

\* cited by examiner

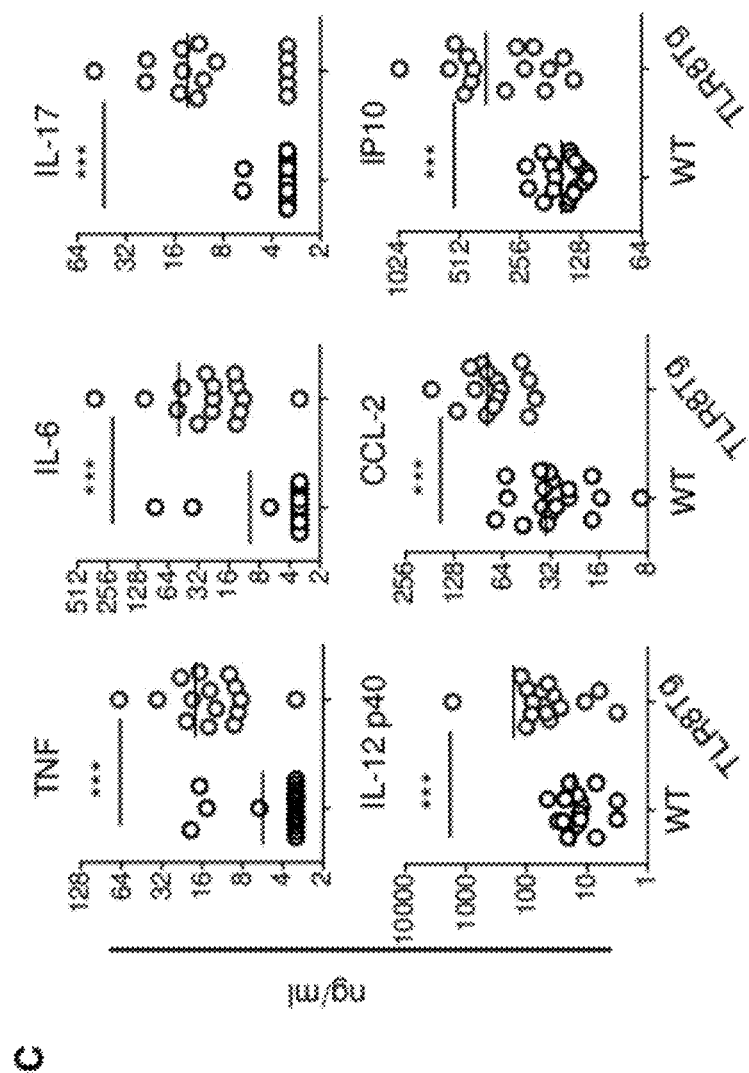

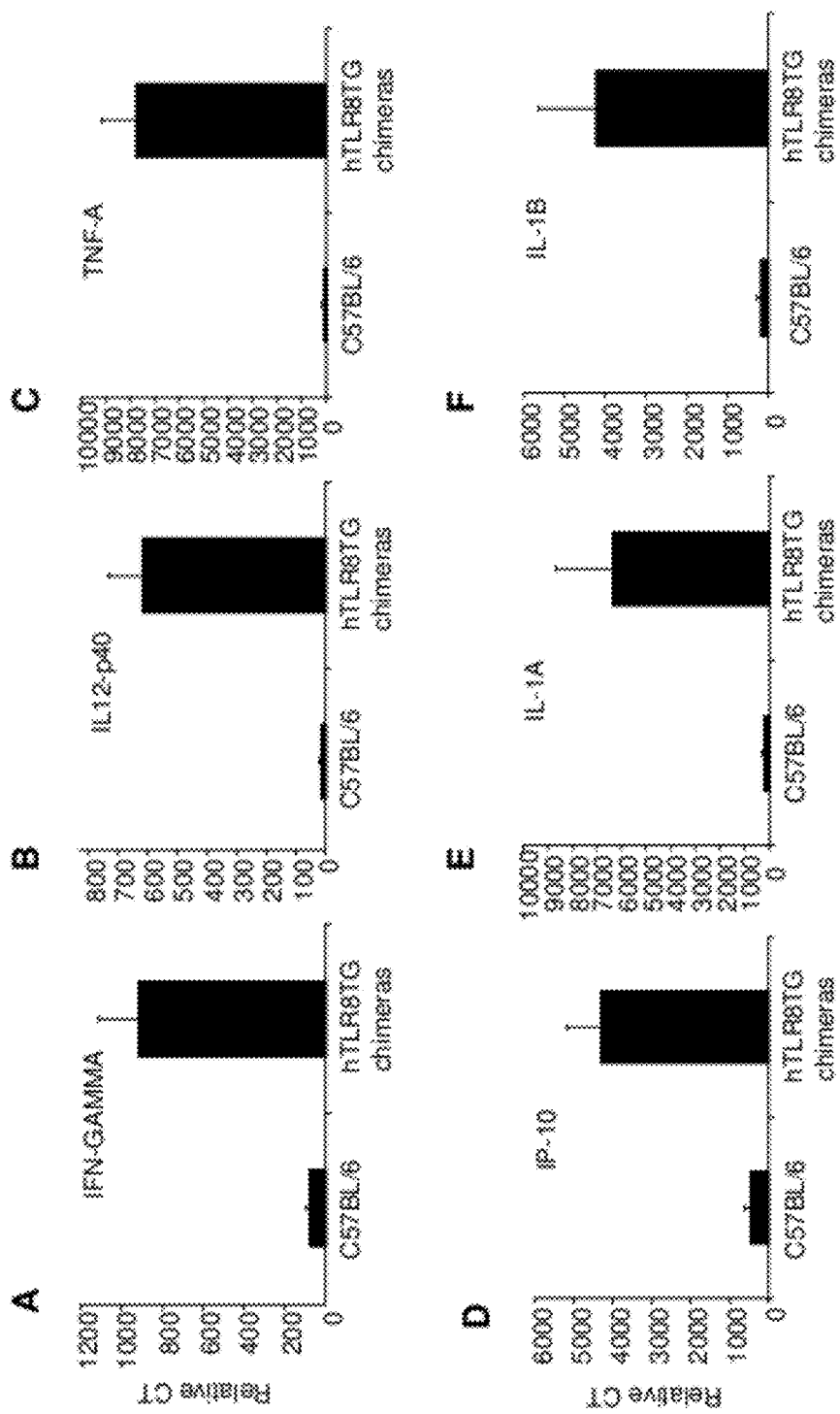

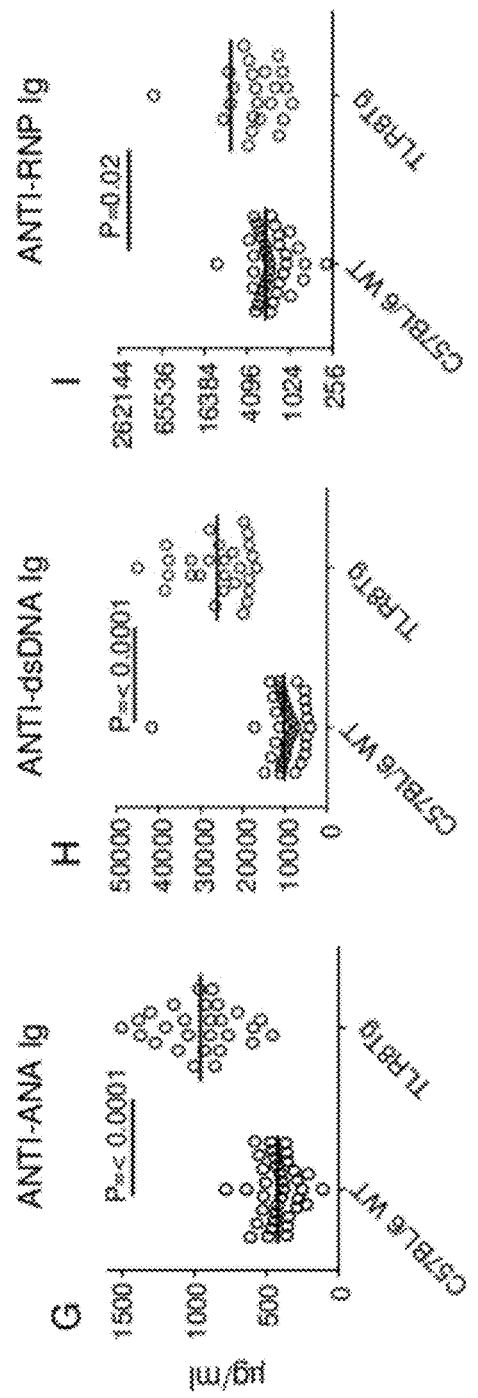

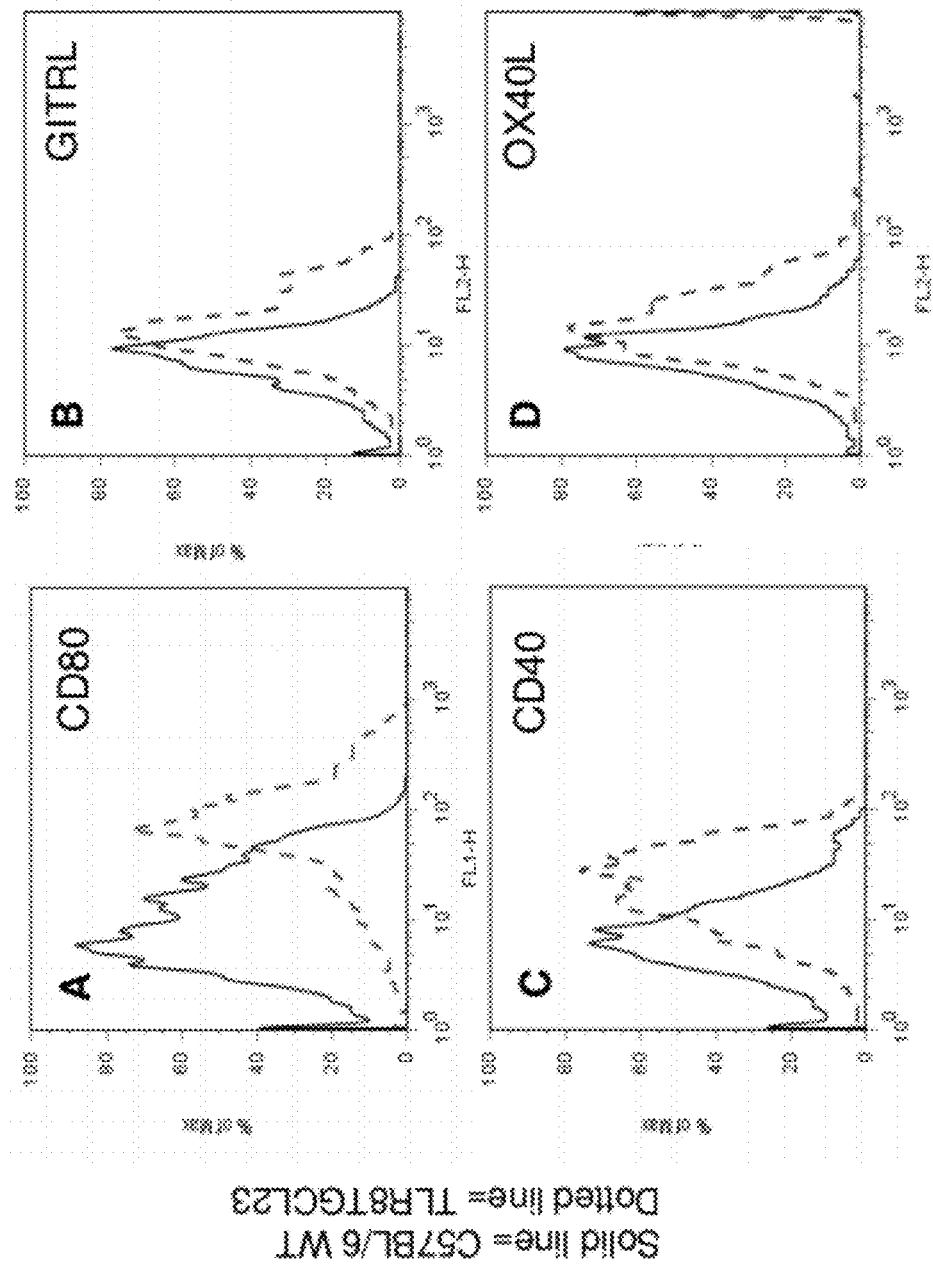

SEQUENCE LISTING

```
<160> NUMBER OF SEQ ID NOS: 5

<210> SEQ ID NO 1
<211> LENGTH: 145837
<212> TYPE: DNA
<213> ORGANISM: Artificial Sequence
<220> FEATURE:
<223> OTHER INFORMATION: Sequence of construct BAC_RP11-1137P1_TLR7-KO

<400> SEQUENCE: 1
gaattcagct gtgaatacgt ctggtcctgt gcttgttttg gttggtaggc tattaattac      60
tgcctccatt tcagaacttg ttattgatct attcagggat ttgactttt cctgatttag     120 tcttgggagg gtgtatgtgt ccaggaattt atccatttct tgtagatttt ctagtttatt     180
tgagtagagg tgattttagt attctctgat aatagtttgt atttctgtgg gatcagtggt     240
aataacccct ttatcatttt gtattgtgtc tatttgattc ttctctcttt tctcctttat     300
tagtctggct agtggtctat ctattttgtt aatgttttca aaaaaccagc tcctggattc     360
actgattttt tgaagggttt ttcatgcctc tatcttcttt agttctgctc tgattttagt     420
tatttcttgt cttctgctag cttttgaatg tttgctctcg cttctctagt tctttttatt     480
gtgatgttag ggggtcgatt ttagatctgt ccctgctttc ttttgtgggc atttagtgct     540
ataactttcc ctctaaacac tgcgtttgct gtgtcccaga gattctggta tgttgtgtct     600
ttgttctcat tggtttcaaa taacttattt atttctgcct taattttgtt atttatccag     660
tagtcattca ggagcaggtt gttcagtttc catgtagttg tgcagttttg agtgagtttt     720
taatcctgaa ttttaatatg attgcactgt ggtctgatag actgttatgg tttccattgt     780
tttgcatttg ctgaggagtg ttttacttcc aattatgtgg tcaattttag aataactgtg     840
atgtggtgct gagaagaatg tatattctgt tatttgaggt ggagagttct gtagatgtct     900
attagttgtg cttggtccag agctgagttc aagtcctgaa tatccttgtt aattttctgt     960
ctcattgatc tgtctaatat tgacagtggg gtgttaaaat ctcccactat tattgtgtgg    1020
gagtctaagt ctccttctag gtctctaaga acttgcttta tgaatctagg tgctcctgta    1080
ttgggtgcac atatatttag gataattagc tcttcttgtt acattgatcc ctttaccatt    1140
atatagtacc cctctcttgtc ttttttttaat ctttcttggc ttaaaatctg ttttatcaca    1200
gactaggatt gcaacccctg ctgggttttt tttcttttt tttttttctt tttttttag    1260 atggcgtttt gctcttgttg cccaggctag agtgcagtgg catgatcttg gctcaccaca    1320 accccacct cccaggagca agcaattctc ctgcctcagc ctcccgagta gctgggatta    1380
caggcatgtg ccaccacgcc ttgctaattt tgtattttta gtggagatgt ggtttctcca    1440
tgttggtcag gctagtcttg aactcccgac ctcaggtgat cccgctgcct cagcctccca    1500
aagtactggg attacaggtg tgagccacct cgcctgacca acacctgttt ttttttttt    1560 ttgctttcca tttgcttggt aaatattcct ccatcccttc attttgagcc tatgtgtgtc    1620
tttgtacatg agatgcatct cctgaataca gcacactgat gggtcttgac tctttatcca    1680
atttgccagt ctgtgtcttt taattggggc atttagccca tttacattta aggtgaatac    1740
tgttatgtgt gaatttgatc ctgtcattat gatgcttgct ggttattttg cccattagtt    1800
```

```
gatgcagttt cttcatagtg tcgacggtct ttacaatttg gtacgttttg cagtggctgg   1860
taccagtttt tccttttgat atttagttct tccttcagga gctcttgtaa ggcaggcctg   1920
gtggtgacaa aatgtctctc agctttgttt ttctgtaaag gattttattt ctccttcgct   1980
tatgaagctt agtttggctg gatatgaaat tctgggttga aaattccttt tttaagaatg   2040
ttgaatattg gcctctcttc tggcttgtag ggtttctgcg gagagatctg ctgttagtct   2100
gatgagcttc cctttgtggg taacccgacc ttttctttg gctgcctttg acatttttc    2160 cttcatttca accttggtga atctgatgat tatgtgtctt ggggttgctc ttctcgagga   2220
gtatctttgt ggtattctct gtatttcctg aatttcaatg ttggcccgtc ttgctaggtt   2280
ggggaagttc tcctggataa tatcctgaag agtgttttcc aacttggttc cattctcccc   2340
atcacttcca gatacaccaa tgaaacatag gtttggtctt ttcacatagt cccatatttc   2400
ttggaggctt tatttgttcc tttcattctt tttctctaa tcttgtcttc acgttttatt    2460
tcattaagtt gatcttcaat atctgatatc ctttcttcca cttgatcaat tcggctatta   2520
atatttgtgt atgcttcaca aagttctcgt gctgtgtttc tcagtccat cagatcattt    2580 atgttcttct ctaaactggt tattctagtt agcaattcct ctaaccttt ttcaaggttc    2640 ttagcttcct tgcattgagt tagaacatgc tcctttagct ctgaggagtt tgttattacc   2700
caccttttga agcctacttc tgtcaattgg tcaaactcat tctccattca gttttgtttc   2760
cttgctggcg agaagttgtg atcctttgga ggagaagagg cattctggtt tttgaatttt   2820 tcagccttt tgcactggtt tttcctcatc tttgtggatt tatctaccttt tggtctttga   2880 tgttggtgac ctgcagatgg ggttttgtg tgggcatcct ttttgttgat gttgatgtta    2940
ttgctttctg tttgttaatt tttcttctaa cagtcaggcc tctctgcttc aggtctgctg   3000
gagtttgccg aagtccactc cagaccctgt ttgcctgggt atcccagcg aaggctgtag    3060 aatagcaaag attactgcct gttcctgcct ctggaagctt catcccagag gggcactcac   3120
tggatgccac ctgagctct cctgtatgag atgtctgtca accctgctg ggaggtgtct    3180 cctagtcagg aggcacgagg gtcagggacc cacttgagtt ggcagtctgt cccttagcag   3240
agctcgagca ctgtgctggg agatccactg ctctcttcag agctggcagg caggaacatt   3300
aaaatatgct gaagctgtgc ccacagccgc cccttccccc aggtgctctg tcccagggag   3360
ataggagttt tatctataag tccctgactg gggctgctgc cttcttca gatgtgccct     3420 gcccagagag gaggaatcca gagaggcatt ctggctacag tggctttgcc aagctgcagt   3480
gggctatgcc tagttcgaac ctcctggcag cttttgtttac actgtgaggg gaaaaccacc   3540
tactcaagcc tcagtaatgg catacacttc ttcccccacc aagcttgagc atcccaggtc   3600
aacttcagac tgctgcgctg gcagcaagaa tttcaagcca gtggatctta gcttgctggg   3660
ctctgtaggg gtgggatccg ctgagctaga ccacttggct ccctgactgc agccccttt    3720 tcagggagt gaacagttct gtctcgctgg tgttccaggc gccactgggg tatgaaaaaa   3780
aaaaactcct gcagttagct cagtgtctgc ccaaatggcc aaccagtttt gtgcttgaaa   3840
cccagggccc tggtcacata ggcacccaaa ggaatctcct ggtctgtggg ttgcaaagac   3900
tgtgggaaaa gtatagtatc tgggctgaa tgcactgttc ttcatggcac agtccctcat    3960
ggcttccctt ggctagggga gggagttccc cgaccccttg cacttcccag gtgagatgac   4020
accccaccct gcttctgctc accctccgtg ggctgcacct actatctaac cagtcccaaa   4080
gagatgagct gggtacctct gttggaaatg cagaaatccc ccaccttctg cattgatctt   4140
gctgggagct gcagaccgga gctgttccta tttggccatc ttcccagcca cctggtaatt   4200
```

```
taactcttat gggccaaaat ggcaaaagtc atctgtggtc aaatcacaga gcccattacg    4260
tctgtcaaag gtcatggaat tgataagatt ttggagttag atggaacatt catgactgaa    4320
tgattcccat cttattttac agatgaggaa actaaggctc aaagagacta agtaactggc    4380
ttagtaaggt tacacagttc cctagaggaa agctggggg tagaaaatgg ggcttttcgg     4440
ccaggcgtgg tggctcccga ctataatccc agcactttgg gaggttgagg tgggtggatc    4500
acttgaggtc aggagtttga gaccagcctg gccaacatgg taaaacccg tctctactaa     4560 aaatacaaaa attagccggg catggtggca cacacatgta attccagcta ctccagaggc    4620
tgaggcagga gaatcatttg aaccagggag gcagagattg cagtgtgctg agattgagcc    4680
agtgcactct agcctgggtg acagagagag actctgtctc aaaataaaca aacaaatgaa    4740
caacaacaac aacaacaaaa agaaaatggg ggcttttctg ttctttaagc agagatgttt    4800
gcattaaccc aggcaacttc aatgattcta atcactagtg cataacagtg aaggagctta    4860
ttaaacctca gggcagtgag gaaaagcaaa aaatacggta cggtaacttc catcagaacc    4920
tgaaatactt gcatccactg atttggttgt cctttgcctt cctccaaaaa caaggtcttc    4980
atttcactca ctgtgtttgc gtggtccttt ttcaggtcgt tatgctaaca tgagaaccaa    5040
aataacaaca ctgggtaatg gagattttt aaataatggt gatctgtaag gcagtggttc      5100
tcaaagtgag gccctggact agcagcatct gcatcaccaa aaacctcagg agaaagttga    5160
aaaccaccct gatagttaag tccatgctag ttgctaatgt aatggtccct gtctgttgcg    5220
taaggaagga tcatttcctt ctctgataaa aatggctctg gctctggtaa gttatactca    5280
aatttaatta tatttcatgg taaatcttgt cagctgaaaa gttatgccaa cttggtggac    5340
aatggcagag aatacaagtt tctgacttac ctcaaggttt gaatgtacct agagcagaag    5400
tttctgatat ttgtactcac ttaaccaaca actataattg ccgggcactg ttgtggttgc    5460
ttgggatatt tcagttgtta ctaatgcttt ggttttatgg aaagacaaag acaatgctgg    5520
tcttctagca gcacaaagta taaggtaatg ttcctatatt attcatagtc cattggcaaa    5580
aatgcagtta ttatcaaaaa acattaaaat taaaagtatt taagtcatt gtaataaggg      5640 attcaacaaa cactcaatat ctaagtaatt tccaatgatt tcagtaatat gagtattggc    5700
tttaaaaagt aatgttttag agccaagtgc agtggctcac gcctgtaatt ccagcacttt    5760
gggagtcaga ggcaggagga tcgcttgagt cttagagttc aagacctgcc taggcaacat    5820
ggcgagaccc tgtctctaca aaaaatttaa aaattagctg gcatggtgg tgcatgcctg      5880 tggtcccagc tactcaggag gctgagatga gaggattgct tgagcctgga atatcaaggc    5940
tgcagtgagc catgatcaca ccactgcaat ccagcctggg tgacagagtg agactttgtc    6000
tcaaaaaaaa caaacaaaa aacaaatag agaataaaag gtttagaaac agatacaact      6060
ggctctagga aaacaactca actgttgaga gcaataagtc atatgtactg acagcctatc    6120
aaattgagat gttaataaga aatcggccaa cttttttttt tttttttttt ttttaacaga    6180
aggtaaggag aatgcaggtt aaccagtgga atttcaggtc agttcagtca agagagtttt    6240
gactatgcct gttggtctca aacttggtta tcaattggaa tcacatgagc agccttgaaa    6300
attccaaata cccagactac acccaagagt agttaaatca gaagctttgg tgtcaacata    6360
gtaatcagga actttgtaat gatcccattc cggtgtgcag ccgaaattga gaagctccag    6420
tttaaggtca tgggccatga agctttcaag ttctgccacc tcctctcaac attaatgtgt    6480
atcagctttg ggaaactaca tgtagaaggt atgaagaatg gcagaaagta tataagggga    6540
```

-continued

```
caaatcacca ccattaattc cacaaatcag tacaggtcag tagctacagt ttggagaatt      6600
taaaacattt tcctctttag taagaattcc tacaaagaaa tgcccattta aaatcctgat      6660
ctatttcaat tgcttgccag aaatgttgta ccaatttgca ctctcaccca aagtccctaa      6720
atcctgacaa acactgtgaa ttgatcatct ttttcctgtt ttccaatctg ataatttaac      6780
agtactgggg tattgtttta tttgcatttc tgtaagaact ttatttttatt gactacaaat     6840 attttacttt ccaggatcta taaagcaata tagcaatata aataatatta tataagcata     6900
ctcaaacctt gttaacctat caccgattat tgcaatacta tttttagatt ttttcttcaa     6960
ttgcaaaaat actttattac tgattaaaaa tagtatatat gcactgataa aattttgata     7020
aatgcaaaga caagtaatga aaatcatcag caataacaat ggctaaaagt ggagtataca     7080
tacaaacaaa tacttgtttt gaactttttt ttggtttact cttagcatag tatcttttttc    7140 catgtcatgt agtattctaa tgtgtgactt ttggaggctg catagtattc taaagtaata     7200
tgttttgaat ccaatattct tcaaaaaaat atggaacaac agatcttggc ttaaatatga    7260 attttttttac atttctgttg tatatactac aagtggtgga ttgctacttt ggtggttccc   7320
gatgaaccat aactcctggt attcacactt ctgtggtgta tccttccata ttaacctcgg    7380
gctcggccaa taaataggac attagcaaga atgatgtaag caaatgcttg ataagtgctg    7440
gcacactgga gcttatgtct cttgaaatgc tcactctcag gatcaaacca ccatgaaaag    7500
aaacccaagc tagccacatg gggaagaaaa gaggaaaaga tcactccctc tcaaccttcc    7560
ccactgggga actagacatg tgaacaaagc catctgatta caacctcaca ggagacccca    7620
actgaaacca accaaagaac agcccagcag agccccagcc aaccaaagaa tcatgaacaa    7680
ataaagtggt tactgtttta agcagatatg ttttgggttg gtttgttaca cagcaagaga    7740
taagcaaaat gtgacagcat ctaatatgaa tacctgcttt agatatgaaa agaaaccct    7800 tagatatgaa aagaaaccc ttaggatcat aaactcaaga agaatttttt gtttttatct    7860
agtcagattg ctgaggtcct ggctgtttag atgacttaca gaaagaactt gggtagtaga    7920
gtcaagatat gaatagtaac ccagttttat tactagagat ttgacttcgt tgagcatcag    7980 cttttcttgtg ggcgagttag gttttaacaa tagctgcctt gcaggtgttt tatttttaag   8040
cattatgaat gatggtgcct ccagttccat aacaagatga aggcatatgc agatgtgagt    8100
taacattttc attggctggc catgtatgtt gaatcccaaa caagtggtct tcactacacc    8160
tcaccactca caaatctact tatgagtctc agatggtgag ctagatggtc agtaataccc    8220
acctcaggaa aactgcttct gagtttacaa gacagcaggc ggaacagctc aaagaccaat    8280
gcatgcataa atagtctttc cttttttttca ccaggtcaac tactcgatta tttgcactgg    8340
gggccttttt tcaaagcatc tgaccttttg gactcgtctg gtgaaatcta gtatgtactt    8400
aggaccagcc ttcaacacaa aggaaggttt ttgttacatt cgtttgcata tcctgtcaag    8460
gatatcttca gaacactttc atttcacagt aaaatgaaac ttacggaaga actaagcagt    8520
gaagtgcttc atactttcat ttaaaagggg aatgagaaac aaaagacaag gttaattatg    8580
acaccggggc tttacaatgc taaaaatatc ctatatacaa agggatatgt aggctgtgtt    8640 cttttttccat gtcattacaa agaacaggct caaggtatct gcaaatttct aataaaaata   8700
ttattacttg aaaaatgtcc atggttgtat ctaactgaag ggattaaaac ttttagactt    8760
gttatacaaa taccatgata cttgtcatca aagtcctcct tttcatcaag cagaccctga    8820
cttacagcat ctgagagtgg aaaaaactag catgaaccgt aaggcagtgg gattcatacc    8880
tacctctcac tcacacgttc atccaaacca agcaagttgc ataaagcaac ctgagacttt    8940
```

```
atacttccac atgctggcaa cacagcatta actagactcg ggcaacttgt ttaagggggtt   9000 tatttaggtt cctatcagta aagaggtgtt tttccagctt tgggagaata tgtatgatgc   9060 caagttttt ttttttaag tttaaatact tttataagtt taatgttggc attggatgtt   9120
tacatattaa ctggtacaat ttacatcggt tttatactta cctattttg caaagatgtc   9180 atgtacacaa agatacatat tcaataactg agaaacaagt gaaacttctg atctatactt   9240
tcaggtttgt ttcataaaga tatttctgat aaggattatc agcatacaag tttcacctct   9300
tccagaagga cactgtcatt ttatctaaga gtttactctg ggttttattg cagaacacaa   9360
attccctcaa ttgcttttt cttgcaggtg tctttttcca gaatttttc ttataaccag   9420 cctttctcct cacccaaagg ccagaatgaa gtcgaaaaaa cctatagata acagctttca   9480
cagttgttct cttgccttt tgtgtactga cgtatattac agttctgact ggcagcttca   9540
ggacacttgg aagcaagggg gccactctgt tggggatcac tgcagtatgc ccacatgtca   9600
ggtttctgac agatgtgatc agcctgggag tggaggaaac aaatggtgtc tgaatatgac   9660
taaaacgtcc agtagacaat gcagaaataa gagaggcatt cctggcacag tttcggtggg   9720
ctggagatgc aaaaatattc aggagccata gattcctgaa gctgctctca tcgcaccagc   9780
aaaggcagag gcagccatct tgccagcctg ctatgatgcc aagtttcttt cttttttttt   9840 tttttttt tgagatgaag tctcgctctt gtcccccagg ctggagtgca atggtgtgat   9900
ctcggctcat ggcaacatcc acctcccggg ttcaagcaat tctcctgcct cagcctcccg   9960
agtagctgtg attacaggtg cctgccaaca cacccagcta atttttcgtat ttttagtaga  10020 gacggggttt caccatgttg tacaggctgg tctcgaactc ctgaccttag gtgatccgcc  10080
cgccttggcc tcccaaagtg ctgggattac aggcgtgagc caccacgccc agccaatgcc  10140
aagtttctat tgaaccactt tgatgtctat gtctgagtca aatggcagag ccgggactca  10200
aatctaggtc ttctgtccac gaccatatct ttgttcaatc accactctgg atgctgatca  10260
agtctgacct tcctttttcat ttcagagcat tcaccccagg aatccttcaa tgtttaaatc  10320
tctagattaa aatatggtac tgctgggcat ggtggctcac tcctataatc taaaaaaatt  10380
gggaggctaa ggtgggagga ttgcttgaga ccaggagatc aaggcagtg tggaaaacat  10440 agtgagaccc tgtttctaaa aataaataag taaaatagaa taaaatatgg cactaaacta  10500
gggtggccag ataaaataca ggacacccaa ttaaatttga atttcagata ataaataatt  10560
ttttagtaga agcatgtccc gatttgctaa atttggcaac cctacactaa accttaccta  10620
cccaccaagg gctgttccca gtcctcctca tttccaccta aaaagaaagg agaaataacaa  10680 caagacctag aaaacaaagt gtgagttgcc ccagccagtg agaggccagt tctcaaaaga  10740
taaagagaag aactgtatcc tctccatcca gtgatctctc ttgagctaat ttacagatgg  10800
gggactagac caataacgta ggatcttctg tgccatcact cagactgggg tagttcactg  10860
gagccacagc taactcttca gaagaagatc tttcggaggc ccaaggctat ttatcgcact  10920
agtgcttgca ataccaaaga tcagaaacca cccaaacgtc cgttagagaa atggttaagt  10980
aaattgtgaa acttctagaa aatgggatgt tttccagcta tgagaaaaaa aaaatgcaga  11040
tgctcctgag ataaaggtat agaaggaact gcaaatgaaa aaaacaagag agtaagagag  11100
tatatgctaa cgaagtatga caaaggcagg gccagaagaa tatgtttta tttgctagta  11160 tgcctaaaga aactctggaa agataagcaa ggaactaata agaatggttt cttgtgggga  11220
tgggtgtggg attgggtgga tggtctacaa gaagagcaga aaagttttta ctatgtatct  11280
```

```
acctatgtat ttatgtatgt atgtatatat gtatgtatat gcatggatgt atgtatagat    11340
acatttatct gtacagaaaa gagttaacat ggtagccagt tgccatggct caagcctata    11400
attccagcac tttgagaggc caagggtgga tcgcctgagg tcaggagttc gagaccagcc    11460
tggacaacat gatgaaaccc catctctact aaaaatacaa aaattaacc aggcatggtg     11520 gggggcgcct gtaatcccag ctactcggga ggctgaggta ggagaatcac ttgaacccag    11580
gaggcggagg ttgcaatgag ccgagattgc gccattgcac tccagcctgg caacaacag    11640 tgaaactcga tctcaaaaac aaaaaaccaa gaaacatggc aggcctgaga ctgctctcct    11700
tagaaaggcc tgcttgtaag gttggccttt ggctcatgtc tgggaacttg gatttcaggg    11760
tggttcccac cattcccaga actaagaaga gtggctcact gctcttacac tgtttgtaca    11820
aataatatgg ttttgctgc acacctgctt tcctattggg aggctggaat tttggtatgt     11880
gctgggcaga gtgtgcctac atgaccagcc ccgagtaaac accctgggca ctgaatctct    11940
aacgagcctc cctggtagac agcagttggc atgtgttttc tcaatttgtt gcagaaggaa    12000
tcaagtacat ccatgtgact aaagtcgag gggatgcttg gaaggttggg cctggtttct     12060
tctgggcatc acctcatgca ccattgtcct ttgctgcttt tggttcgtat cttttcactg    12120
caataaatca tagctgtgac catactttat tgagttctgc gactcctagt ggatcacgaa    12180
gcctggggtg gcggagtctt ggggacctcc gacacagtac acagtctctg tctctctctc    12240
tctctctctg tcccacacac cccatatctt tctattcagc tctatgtaag aattctgtac    12300
cacacaaata tgtattaaaa tgaaataaaa aataaaaaag gcctttgctt tatatttgcc    12360
taaccaaaag ctccattcaa tctgcttttc tttccttctt tgtttccttc cttctttct     12420 tctttctttt ctcctgtcct tcattctttc ctttccttcc tttctgccgg cctgccttgt    12480
ctccctccct ccccaccctt tcttttcctc tctctttctt tccttcactc tctccctttc    12540
ttcctttgtt tctctgtctc tagttttcca tttactacgt agaagttctt accatatgac    12600
tatgtatttt ccagcaaaat tgaagaaaaa gttaaaaagc tattgcccta tatttgccaa    12660
ctaaaagccc cattcaaaat gtctcaaggg gagagagaga agaaaagcaa aagaaacaaa    12720
gaatacaact aacttcactg cctcactctc tattaaggag acagaaaatt ctcatagctt    12780
ttaaacaaca gtgtcaggtt tggtgtgttt ttctgttgtt cagctttaac acagcactgt    12840
ttcaaaacct taaggctttg tcctagaaga aaatgttcct gtttgaacat ataaaacaat    12900
ccagcatata actagaaata caggtctgcc aatcatggta acactttgt gacaaaactt     12960 aaagttatct ttggcggtga tatacatttt taagaagtta ttacatatgc aaagattgta    13020
gagaaattac agagacacaa tcaaactcac tatgtaaaca ctgagtagtt cttgaatcag    13080
aaagaaaata aagctataaa agatattttg gggacaaatt gaaaaaatgt gaatacagaa    13140
tctatatgag atattacaaa ttattagttt ttaaatgtta ctttaagttc tgggatacat    13200
gtgcagaatg tgcaggtttg ttacatgggt atacatgtgc catcgtggtt taccgcacct    13260
atcaacccga catctaggtt ttaagcccca catgtattag gtatttgtcc taatgttgtc    13320
tctccccttg ctccccaccc cctgataggc ccgagtgtgt gatgttcccc tccctgtgtc    13380
catgtgttct tattgttcaa ctcgcactta tgagtgagaa catgcggtgt ttggttttct    13440
gttcctgtgt tagtttgctg agaatgatgg tttccggctt catccatgtc cctacaaagg    13500
acatgaactc attctttttt aaggctgcat agtattccat ggtgtatatg tgccacattt    13560
tctttatcca gtctattatt gatgggcttt tggattggtt ccaagtcttt gcatttgtga    13620
atagtgctgc aataaacata cgtgtgcatg tgtctttata gtagaatgat ttataatcct    13680
```

```
ttgggtatat accagtaatg ggatggctgg gtcaaatggt atttctggtt ctagatcctt   13740
gaggaattgc cacgctgtct tcctcaatgg ttgaactagc ttacacgccc gccaatagtg   13800
taaaagtatt cctatttctc cacatccttt ccagcatcta ttgtttcctg acttttaat    13860 gattgccatt ctaaatggcg tgagatggta tctcattgtg gttttgattt gcaattctct   13920
aatgaccagt gatgatgagc ttttttttca tgtttctttg ttgcataaat gtcttctttt   13980
gagaagtgtc tgttcatatc tttcactcac tttctgatgg ggttgtttgt tttttctta    14040 taagtttctt tgagttcttt gtagattctg atattagcc gtttgtcaga tgagtagatt    14100
gcaaaaattt tctcccattc tgtaggttgc ctgttcactc tgatgatagt ttcttttgtt   14160
gtgcagaagc tctttagttt aattagatcc catttgtcaa ttttggcttt tgttgccatt   14220
gcttttggtg tttttagtcat gaagtctttg cccacgccta tgtccagaat ggtattgcct  14280
aagttttctt ctagggtttt tatggtttta ggttttatat ttaagtcttt aatccatctt   14340
tagttaattt ttgaataagg tgtaaggaaa gggtccagtt tccatttttct gcatacagct  14400 agccagtttt cccagcacca tttattaaat agggaatcct ttccccattg cttgtttttg   14460
tcaggtttgt caaagatcag atggttgtag atgtgtcgtg ttatctctga gggctctgtt   14520
ctgttccatt ggtctatatc tctgttttgg taccagtatc atgctgtttt ggttactgca   14580
gccttgtagt atcgtttgaa gtcaggtagt gtgtaatgcc tccagctttg ctcttttttgc 14640 ttaggattgt cttggctata tgggctcatt ttttattcca tatgaaattt aaagtagctt   14700
tttctaattc tgagaagaaa gtcaatggta tcttgatggg gatggcattg aatctataaa   14760
ttacttttgg cagtatgtcc attttcacga cattggttgt tcctatccat gagcatggaa   14820
tgttcttcca tttgtttgtg tcctctctta tttccttgag cagttgtttg tagttctcct   14880
tgaagaggtc cttcacgtcc cttgtaagtt ggattcctag gtattttgtt ctctttgtag   14940
caattgtgaa cgggagttca ctagatttgg ctctctgttt gtctgttatt ggtgtatagg   15000
aatgcttgtg atttttgcac attgattttg tattctgaga atttgctgaa gttggttatc   15060
agcttaagga gttttttgggc tgagatgatg gggttttcta agtatacaat catgtcatct   15120
gcaaacagag acaatttgac ttcctctctt cctatttgaa tatgctttat ttctttctct   15180
tgcctgatta ccctggccgg aacttccaat actatgttga accttgtctt gtgccggttt   15240 ccaagggaa tgcttccagc ttttttcccat tccgtatgat attggctatg ggtctgccat    15300
aaatagctct tattattttg agatatgttc catcaatacc tagtttattg agagtttta    15360 gcatgaaggg atgttgaatt ttattgaagg ccttttctgc atctattgag ataatcatgt   15420 ggttttgtc attggttttg tttatgtgat ggattacgtt tattgatttg catttgttga    15480
acaagccttg catcccaagg atgaagctga cttgattatg gtggataagc ttttttgatgt  15540 gctgctggat tcagtttgcc agtatttac tgaggatttt tgcattgatg ttcatcaggg    15600
atattggcct gaaattttct ttttttgttg tgtcactgcc aggttttggt atcaggacaa   15660
tggtggcctc ataaaatgag ttagggagga gtctctcttt ttctattgtt tggaatagtt   15720
tcagaaggaa tggtaccagc tcctctttgt acctctggta gaattcggct gtgaatacat   15780
ctggtcctgt gcttttttg gttggtaggc tattaattac tgcctcaact tcagaacttg    15840
ttattgatct attcagggat ttgacttctt cctggtttag tcttgggaga gtttgtgtgt   15900
ccattaattt ttccatttct tctagatttt ccagtttatt tctgtagagg tattgattgt   15960
agtctctgat ggtagtttgt atttctgtgg gatcagtggt gatatcccctt ttatcatttt  16020
```

```
ttattgtgtc tatttgattc ttctctcttt tcttctttat tagtctagct agtggtctat    16080
ctatttgtt  aatcttttca aaaatccagc tcctggattc attgatttt  tgaagggatt    16140
tttgtgtctc tatctccttc agttctgctc tgatcttatt tcttgtcttc tgctagcttt    16200
tgaatttgtt tgctcttgct tctctagcta attgtgatgt tagggtgtcg atatcagatc    16260
tttttaactt tctgatatgg gaatttagtg ctataaattt ccctcttaat actgctttag    16320
ctgtgtccca gggattctgg tacattgtat ctttgttctc cttggtttca aagaacttat    16380
ttatttctgc tttaatttca ttatttaccc agtagtcatt caggagcagg ttgttcagtt    16440
tccatgtagt tgtgcggtgt tcagtgagtt tcttaatcct gagttctaat ttgattgcac    16500
tgtggtctga gagactgttt gttgtgattt ccattatttt gcatttgctg aggagtgttt    16560
tacgtccaat tatgtggtca tttttagaat aactgcgatg tgctcctgag aagaatgtat    16620
attctgttga tttggggtgg agagttctgt agatgtctat taggttcgct tggtcgagag    16680
ctgaattcaa gtcctggata ttcttgttaa ttttctgtct cgttgatctg tctaatattg    16740
acagtggggt gttaaagtct ctcactatta ttgtgtggga gtctaagtct ctttgtaggt    16800
ctctaagaac ttgttttatg aatctgtgtg ctcctgtatt gggtgcatat atatttagga    16860
cagttagctc ttccttgtttt attgatccct ttaccattat gtaataccct tcttcgtcta    16920
ttttcatctt tgttggttta aagtctgttt tatcagagac taggattgca accccccccc    16980
cttttttttc tttccatttg cttggtaaat attcctccat cactttcttt tgagcctatg    17040
tgtgttttg cacgtgagat gggtctcctg aatacagcat accaataatg ggtcttgact    17100
ctatccaatt tgcctgtcca tgtcttttaa ttggggcatt tagcctattt acatttaagg    17160
ttaatattat gtgtgaatct gatcctgtca ttatgatgat agctggttat tttgcacatt    17220
aattgattca gttctcttcat agtgtcattg gtcttcatat tttggtgtgt ttttgcagtg    17280
gctggtactg gttttctttt acctatttag tgcttccttt gggagctcct gtaaggcagg    17340
tctggtggtg acaaaacacc tcagcatttg cttttctgga aaggatttta ttctttttt     17400
gcttatgaag cttcatttgg ctggatatga aattctgggt tggaaattct tttctttatg    17460
aatgttgaat attagccccc actctcttct ggcttgtagg gtttctgcag agagatccac    17520
tgttagtctg atgggcttcc ctttgtaggt aacctgacct ttctctctgg ctgcccttaa    17580
tatttttttct ttcttttcaa ccttggagaa tctgatgatc atgtgtcttg gggttgctct    17640
tctcgaggag tatcttagtg atgttctctg ttttccttta atttgaatgt tggcctgtct    17700
tgctaggttg gggaagttct gctggataat atcctgaagt gtgtttttcca acttgtttcc    17760
attatccctg tcacttttag ctacaccaat caatcgtagg tttggtcttt tcacatagtc    17820
ccatatttct tggaggcttt gatccttcct tttcattctt tttctctaat cttgtcttca    17880
cgccctatat ttgtaagttg atcttcaatc tctgatatcc tttcttctgc ttgattgatt    17940
cacctattga tacttgcgta tgcttcacga cattctcgtg ctgtgttttt cagctccatc    18000
gggtcattta tgttcttctc taaactggtt attctagtta gcagttcctg taacctttta    18060
tcaaggttct tatcttcctt gcattgggta gaacatgttc ctttagctca gaggagttta    18120
ttattaccca ccttctgaag cctacttctg tcaatttgtc aatctcattc tccgtccagt    18180
tttgtgtcct tgctggagag gagttgtgat catttggaag agaaaaggca ctctgctttt    18240
tggaattttc agcatttttg cacttgtttt ttctcatctt catggattta tctgcctttg    18300
atctttgatg ctgatcacct ttggatgggg ttttgtgtg gaggtccttt atgttgatgt    18360
tgatgttatt gctttctgtt agttttctca ataggtccct cttctgcagg tctgctgcag    18420
```

```
tttgctggag gtctactcca gaccctgttt gcctgggtat caccagtgga ggcctgctcc    18480
ttctcctgga agctttgtcc cagaggggca ctggcccgat gccagctgga gctctcctgt    18540
atgaggtgtc tgttgacctc tgttgggagg tctctcccag tcaggaggca caggagtcag    18600
ggacccactt gaggaggcag tctgtccctt agcagagttc aagtgctgtg ctgggggaa     18660 tcctccacgt caggatcagc tgctcttttc agagctggca ggcaggaaag tttaagtctg    18720
ctgaactaca cccacagctg ccttttcccc caggtgccct gtcccaggga gatggaagtt    18780
ttatctgtaa ttccctgact ggggctgctg ccttctttc agagatgccc tgcccagtga     18840
ggaggaatct agagaagcag tcaggccaca gccgctttgc catgctgtgg tgaattctgc    18900
ccagtctgaa cctcccagcc tccttagcac tgtcagggga aaactgccta ctaaagcctt    18960
agtaatggtg gatgcccctc cccccaccaa gctcgattgt cccaggtcca tttcagactg    19020
ctgtgccggc agtgagaatt tcaagccagt ggctctttgc ctgctgggct ctgtaggagt    19080
gggacccact gagcccgacc acttggctcc ctggcttcag cccctccag gagagtgaaa     19140 ggttctgtct tgctggggtt ccaggtgcca ctggggtaca aaaataact cctgcagcta     19200 gctctgtgtc tgcccaaaca gccacccagt tttgtgcttg aaacccaggg ccctggtggt    19260
gtaggcacac aagggaatct cctgatccgc gactgcaaaa cgatgggaa aaacgcagta     19320 gctgggctgg gtagcacagt ccctcatggc ttcccttggc tggggaggg agatcccttg     19380 gctccttgta ctttccaggt gaggtgatga cccaccttgc ttctgctcac cctctgtggg    19440
ctgcacccac tgcctaacca gtcccagtga gatgaacttg gtacctcagt tggaaatgca    19500
gaaatcacct gccttctccg ttggtctccc tgggagctgg agaccggagc tgttcctatt    19560
cagccacctt gccagattgg ccaatattac aaattatgaa ttctcttagg tgtcatcctt    19620
atttcaggag atacaggatt aagtgtttag ggttaaaatg tcgtgttgtc tgcaacattt    19680
taatgattag ggaaataaat acattatata cacatacaaa aaagtaaaac caatgtggct    19740
cactatcaac aattgttgaa ttcagacagc tatatgggct gcattgtgca attgtttcaa    19800
tttttcaata tatctgaaaa tttttttaagt aaaaagttgg gaagaaaaaa gattttcttt   19860
taaaaactag tatattaata taaatgaatt caagtagaat gatataatca gttattagaa    19920
aatcaattac cactcagcta ttgaatccac catactgagt taagaagaac ttagtatctt    19980
ttgaataaga aaacataggc tttattgatg cttgactact agacaagttg caactcctag    20040
taaattcaac cagctagtga ctgtaattag atgactgatc acgtcaatca attaatctgc    20100
ctaatgatcg acctctgaaa attggcctaa ttaattgttc ttattttcat gatcactttc    20160
attttcatca tcataaagag tgatctctta agtacctaga atggatcctg aggacaacac    20220
attcttaact caagggtct gcaatatcag tgtgggaact aggagatatg aatgaaacat      20280
aaataaccag gctgagtgtg gtggcttgtg tctataatcc cagcactttg ggaggctgag    20340
gtgggtggat cacctgggt caggagtttg agaacagcct agccaacata gtgaaacccc      20400
atctctagta aaaatacaaa aataagctag gtgtggtggt gtgcacctgt agtcccagat    20460
actcaggagg ctgaggcacg agaattgctt gaatctggga ggtggaggtt gcagcaagcc    20520
aagatgacac cactacactc cagtctgggg acagagcgag actctggccc caaacaaaca    20580
aacaaacaaa caaccataaa taaccacgca agaaagcata atatatatgc taaattcata    20640
atttcataat ctcttgggat cttagcatat aaaacctggg tgtgtcttta ttgatcatac    20700
agcctcatcc ctcactttaa agataaatgg tttatttta tgtagtcaaa tttttcagtg     20760
```

-continued

```
ttttctttaa gactctggga ttgttgctgt tggttccttt tccttgtttg tttggtgtta   20820
tcgtcatact tagcactact tttctacttc aagattagaa aaaatattga cctatagttt   20880
ctttcatata tatatatata tatatatata attatacttt aagttctagg gtacatgtgc   20940
acaacatgca ggtttgttac atatgtatag atgtgccatg ttggtgtgct gcaactccaa   21000
aagagtcatg cccatttgaa ttaattttgg aaatgtctgt ttttcttttt gtacttggtt   21060
catagcaact gccctagggc accaaccatc cagggaaact ttgatgcatc ttacactttg   21120
gtcctgatga gagggaggca taaatgagaa aagctcttat tctgcagtta atacagagca   21180
agcggctgag tttgaagcag ccatggagaa cattctagaa cagggttgtc tagtcgtttg   21240
gctcccttgg gtcacattgg aagaagaatt gtcttgggc cacacataaa atacactaac    21300
aatcgctgat gagcttaaaa aaaaatctca taatatttaa agaatgttta caaatttgtg   21360
ttgggccgca ttcaaagctg tcctgggctg catgtggccc atgggtggtg ggttggacaa   21420
gtttcctcta gaatcaacaa aattctgcaa ttccgtgtgc taacagaaga gccttaccag   21480
ttgtggtgac aggctagaca gccaggtaga gaattcaata ggagcggaaa taactgtcca   21540
cgaacagcgt agggcctgac aatctgaaag aagcaatatt ctacctagtt cgaagatctt   21600
aagcttacac agaaagggcg cttacactga tacagaaaca aaactatgca gaatccaatc   21660
aaatgattaa cttaggtggg gttttgcagtc ttttttgtaga agaagaaagg attggccggg   21720
cgcggtggct cacgcctgta atcccagcac tttgggaggc cgaggcgggc ggatcacgag   21780
gtcaggagat cgagaccaac cccgctaaaa cggtgaaacc ccgtctctac taaaaataca   21840
aaaaattagc cgggcgtagt ggcgggcgcc tgtagtccca gctacttggg aggctgaggc   21900
aggagaatgg cgtgaacccg ggaggcggag cttgcagtga gccgagatcc cgccactgca   21960
ctccagcctg ggcgacagag caagactccg tctcaaaaaa aaaaaaaaaa aaaaaaaaa    22020 aaaagaagaa gaaaggattg ggtattgtat ataattcacc tccaaagacc tgggcagcat   22080
gattgcaccc ctgtaaagct atgggtttac cagtagcagc taggtacata ggtttagagt   22140
aacccattca ggttcctcag aaggacctga tgagctcttg gctgaaatca ctgattgttc   22200
aaaacctgca ggatactgag aaggcaaacc ccaaatttca tgggataaaa tgacagtttg   22260
tacgagaaaa atcaccttag atgtctacct ttccaagtct cagcacccag ttaaaatctc   22320
taattaaaag tcatctcagt aactgaggtt gcctttcact tcccgaatgc ccaaacattt   22380
ttcaactctg ggaacctta aaaatgagaa cagaaataac caagacactt aaaaacattg    22440
tatcgatgtt tcctggttaa ggcatctgca caaacttggg gttgtatatg cttgaatagt   22500
taagagaaat atagcctatt aagacaatag cttgtgactc ccagataaag tatataattg   22560
agtgattgat cttttcaagt tgaaatctaa ataatttatg tggacactta gaaatttaat   22620
aaaacaaaac tagttttgtt tcaccatact tcttttcct ctctcaaaaa aaatttttt    22680 tatactttaa cttctagggt acatgtgcac aacgtgcagg tttgttacat atgtatacat   22740
gtgccatgtt ggtgtgctgt acccattaac tcgtcattta acattaggta tatctcctaa   22800
tgctatccct cccccctccc tccacccccac aacaggcccc ggtgtgtgat gttccccttc   22860
ctgtgtccaa gtgttctcat tgttcaattc ccacctatga gtgagaacat gtgatgtttg   22920
gttttttggc cctgcgatag tttgctgaga atgatggttt ccagcttcat ccatgtcccc   22980
ataaaggaca tcaactcatc cttttttatg gctgcatagt attccatggt gtatatgtgc   23040
cacattttct taatccagtc tatcattgat ggacatttgg gttggttcca agtctttgct   23100
attgtgaata gtgctgcaat aaacatacgt gtgcatatgt ctttatagca gcatgattta   23160
```

```
taatcctttg ggaatatacc cagtaatggg attgctgggt caaatggtat ttctagttct    23220
agatccttga ggactcgcca cactgtcttc cacaatggtt gaactagttt acagtcccac    23280
caacagtgta aaagtgtgcc tatttctcca catcctctcc agcacctgtt gtttcctgac    23340
tttttaatga ttgccattct aactggtgtg agatggtatc tcattgtggt tttgatttgc    23400
atttctctga tggccagtga tgatgagcat tttttcatg tgtctgttgg ctgcataaat    23460
gtcttctttt gagaagtgtc tgttcatatc ctttgcccac tttctgatgg ggttgtttgt    23520
ttttttcttg taagtttctt tgagttcttt gtagattctg gatattagcc atttgtcaga    23580
tgagtagatt gcaaaaatgt tctcccattc tttaggttgc ctgttcactc tgatggtagt    23640
ttcttttgct gtgcagaagc tctttagttt aattagatcc catttgtcaa ttttggcttt    23700
tgttgccatt gcttttggtg ttttagacat gaagtccttg cccatgccta tgtcctgaat    23760
ggtattgcct aggttttctt ctagggtttt tatggtttta ggtcttacgt ttaagtcttt    23820
aatccatctt gaattaattt ttgtataagg tgtaaggaag ggatccagtt tcagcttcct    23880
acatatgtct agccagcttt cccagcacca tttattaaat agggaatgct ttccccattt    23940 cttgttttg tcaggtttgt caaagatcag atggttgtag atgtgtggta ttatttctga    24000
gggctctgtt ctgttccatt ggtttatatc tctgtgttga taccagtacc atgctgtttt    24060
ggttagtgta gccttgtagt atagtttgaa gtcaggtagc gtgatgcctc cagctttgtt    24120
cttttggctt aggattgact tggtgatgcg ggctctttt tggttccata tgaactttaa    24180
agtagctttt ttccaattct gtgaagaaag tcattggtag cttgatgggg atggcactga    24240
atctataaat taccttgggc actatggcca ttttcacgat attgattctt cctgtccatg    24300
agcatggaat gttcttccat ttgtttgtgt cctctttat ttcgttgagc agtggtttgt    24360
agttctcctt gaagaggtcc ttcacatccc ttgtaagttg gattcctagg tattttattc    24420
tctttgaagc aattgtcaat gggagttcac tcatgatttg gctctttgtc tgttattggt    24480
gtgtaacaat gcttgggatt tttgcacatt gattttgtat cctgagactt tgctgaagtt    24540
gcttatcagc ttaaggagat tttcggctga gacaatgggg ttttctagat ataaaatcat    24600
gtcatctgca aacagggaca atttgacttc ctcttttcct aattgaatac cctttatttc    24660
tttctgctgc ctgattgccc tggccagaac ttccaacact atgttgaata ggagtggtga    24720
gagagggcat ccctgtcttg tgccggtttt caaagggaat gcttccagtt tttgcccatt    24780
cagtatgata ctggctgtgg gtttgtcata gtagctctta ttattttgag atacgtccca    24840
tcaataccta atttattgag agtttttagc atgaagggct gttgaatttt gtcaaaggcc    24900
ttttctgcat ctattgagat aatcatgtgg tttttgtctt tggttctgtt tatatgttgg    24960
attacgttta ctgatttgcg tacgttgaac cagtcttgca tcccagggat ggagcccact    25020
tgatcatggt ggataagctt tttgatgtgc tgctggattc ggtttgccag tattttattg    25080
aggatttttg catcgacgtt catcagggat attggtctac aattctcttt ttttcttgtg    25140
tctctgccag gctttggtat caggatgatg ctggcctcat aaaatgagtt agggaggatt    25200
ccctcttttt ctattgattg gaatagtttc agaaggaatg gtgccagctc ctccttgtac    25260
ctctggtaga attcggctgt gaatccgtct cgtcctgggc tttttttggt tggtaagcta    25320
ttattgcctc aatttcagag cctgttattg gtctattcag agattcaact tcttcctggt    25380
ttagtcttgg gagggtgtat gtgtcgagga atttatccat ttcttctaga ttttctagtt    25440
tatttgcgta gaggtgttga tagtattctc tgatggtagt ttgtatttct gtgggatcgg    25500
```

```
tggtgatatc ccctttatca tttcttattg cgtctatttg attcttctct cttttcttct   25560
ttattagtct tgctagtggt ctatcaattt tgttgatctt tccaaaaaac cagctcctag   25620
attcactgat ttttttgaagg gttttttgcg tctctatctc cttcagttct gctctgatct   25680
tagttatttc ttgccttctg ctagcttttg aatgtgtttg ctcttgcttc tctagttcat   25740
ttaattgtga tgttagggtg tcaattttag atctttcctg ctttcgcttg tgggcattta   25800
gtgctataaa tttccctcta cacactgctt taaatgtgtc ccggagattc tggtacgttg   25860
tgtctttgtt ctcgttggtt tcaaagaaca tctttatttc tgccttcatt tcgttatgta   25920
cccagtagtc attcaggagc aggttgttca gtttccatgt agttgagcag ttttgagtga   25980
gtttcttaat cctgagttct agtttgattg cactgtggtc tgagagacag tttgttataa   26040
tttctgttct tttacatttg ccgaggagtg ctttacttcc aactatgtgg tcaatttggg   26100
aataggtgct gtgtggtgct gagaagaatg tatattctgt tgatttgggg tggagagttc   26160
tgtagatgtc tatcaggtcc gcttggtgca gagctgagtt caattcctgg atatccttgt   26220
taactttctg tcctgttgat ctgtctaatg ttgacagtgg ggtgttaaag tctcccatta   26280
ttattgtgtg ggagtctaag tctgtttgta ggtctctaag gacttgcttt atgaatctgt   26340
gtgctcctgt attgggtgca tatatattta ggatagttag ctcttcttgt tgaattgatc   26400
cctttatcat tatgtaatgg ccttcttttgt ctcttttgat cttttgttggt ttaaagtctg   26460 ttttatccga gactaggatt gcaacccctg ccttttttttg ctttccattt tcttggtaga   26520
tcttcctcca ctcttttatt ttgagcctat gcatgtctct gcatgtgaga tgggtttcct   26580
gaatacaaca cactgatggg tcttgactct ttatccaatt tgccagtctg tgtctttttaa   26640 ttggggcatt tagcccattt acatttaagg ttaatattgt tatgtgtgaa tttgatcctg   26700
tcattaggat gttagctggt tatttttgctc gttagttgat gcagtttctt cctggcgtca   26760
atggtcttta caatttggta tgttttttgca gtggcttgta ccggctgttc ctttccatgt   26820
ttagtgcttc cttcaggagc tcttgtaggg caggcctggg ggtgacaaaa tctctcagca   26880
tttgcttgtc tgtaaaggat tttatttctt cttcacttat gaatgttagt ttggctggat   26940
atgaaattct gggttgaaaa ttcttttctt taagaatgtt gaatattggc ccccactctc   27000
ttctggctta tagagtttct gccgagtgat cagctgtcag tctgatgggc ttcccttgtg   27060
ggtaacccaa ccttttctctc tggctgccct taacattttt tccttcattt caactttggt   27120
gaatctgaca attatgtgtc ttggagttgc tcttctcgag gagtatcttt gtggcgttct   27180
ctgtatttcc tgaatatgaa tgttggcctg ccttgctagg ttggggaagt tgtcctggat   27240
aatatccaga agagtgtttt ccaacttggt tccattctcc ccgtcacttt caggtacacc   27300
aatcagatgc agatttggtc ttttcacata gtcccatatt tcttggaggc tttgtttctt   27360 tcttttttatt cttttttctc taaacttctc ttctcgcttc atttcattca tttgatcgtc   27420
aatcactgat actctttctt ccagttgatc gaatcagcta ctgaagcttg tgcattcatc   27480
acatagttct cgtgccatgg ttttcagctc catcgggtcc tttaaggact tctctgcatt   27540
ggttattcta gttagccatt cgtctaattt ttttttcaagg ttttttaactt ctttgtgatg   27600 agtttgaact tcctcctttta gctcggagaa gtttgatcgt ctgaagcctt cttctctcaa   27660
ctcgtcaaag tcattctcca tccagctttg ttccgttgct ggtgagggggc tgcattcctt   27720 tggaggagga gaagcactct gattttttaga attttcagtt tttctgttct gtttttttccc   27780 catctttgtg gttttatcta cctttggtct ttgatgatgg tgacatatag atgggggtttt   27840 ggtgtggatg tcctttctgt ttgttagttt tccttttttaac actccggacc ctcagctgca   27900
```

```
ggtctgttgc agtttgctgg aggtacactc cagatcctgt ttgcctgggt atcagcagcg      27960
gaggctgcag aacagcgaat attgctgaac agcaaatgtt gctgtctgat tgttcctctg      28020
gaggtttctt ctcagagggg tacccggcca tgtgaggtgg cagtctgccc ctactggggg      28080
atacctccca gataggctac tcgggggtca gggacccact tgaggaggca atctgtccat      28140
tctcagatct ccagctgtgt gctgggagaa ccactactct cttcaaagct gtcagacagg      28200
gacatttaag tctgcagagg tttctgctgc cttttgttca gctatgccct gcccccagag      28260
gtggagtcta cagaggcagg cagccctcct tgagctgtgg tgggctgcac ccagttcaag      28320
cttcctggcc actttgttta cctactcaag cctcagcaat gacaggcgcc cattcccag      28380 cctcgctgct gccttgcagt tcaatctcag attgctgttc tagcaataag tgaggctcca      28440
tgggcgtggg accctccgag ccaggcgcgg gatataatct cctggtgtgc catttgctaa      28500
gaccattgga aaagcacagt attagggtgg gagtgacccg attttccagg tgctgtgtgt      28560
cacagctttg cttggctatg aaagggaatt ccctgacccc ttgtgcttcc caggtgaggc      28620
aatgcctcgc cctgctttgg ctcatgctcg gtgtgctgca cccactgtcc tgcgcccact      28680
gtctgacaag ccccagtgag atgaacccag tacctcagtt ggaaatgcag aaatcaccca      28740
tcttctgcat tgctcacgct gggagctgta gactggagct gttcctattc agccatcttg      28800
gaaccaccct acagtttctt tcaatacttt tcatgttcaa tgtcttacac ttaaattttt      28860
caactacatg aaatttattt tgatataaga aatgaggttg gccaggcgc agtggctcac      28920 acctgttatc ccaaaacttt gggaggctga agtgggcgaa tcatgagatc aggagttcaa      28980
aaccagcctg gccaatatag tgaaacccca cctctacaga aaatacaaaa aattagccga      29040
gcgtggtggc gggtgcctgt aatcccagct actcggagg ctgaggcagg agaatcgctt       29100
gaacctggga ggtggaggtt gcagtgagca gagattgcgc cactgcactc cagcctgggt      29160
gacagagtga gactacatct caaaaaataa ataaaaagac aaatgaggtt ggacaatagc      29220
ttgatttttt aaaaactcca agccagttgc ccaataatcc attttgccat tgatgtgact      29280
tgaaactaaa cacccatatg tgcttttact taattctgct cacttctcag tttcactgat      29340
gcactggtac tatgccattg gaggcaatac agcattctaa tgcatttaca gatatggaag      29400
agaaatcctc ccctttatt ttcattcaga aattgcctgg ctattctcac atgtggtctt       29460
accccagtca gacccaacac ctcactttta taacaaatat ttggtaatgc accctttgtt      29520
atatgaaagg agatatttgt ggataatgta accccagtct tcatgataaa caaaaaggcc      29580
cagctgattt ccaaaatgca ccccagttta gaatcagtct ggcaagtatc acatgaaatc      29640
ctattggtat ttgattggga tcacacagca tttgcaaatc aatttaagca acatttctat      29700
ttttacaata ttgtggcctc tagccccaat aacaattatt tctcttcatt tacttatatc      29760
tttgtgtctg ggcagggtcc tgccaggaaa cagacggcat gttaaagtga gaaactgatg      29820
agttcagcaa agtgactatt tatatatttg gacaggattt aaggaagtaa gaaaggatga      29880
tgcaacactt cagaggggag tctttccgac ctcaggctga aggagaagga acgattactg      29940
gaattcaggg aggagagcat caccaaacaa gagcttcatt agaggactgc agccaacgca      30000
gggccaggcg gagggagcca gagggaggca ggctctgctc tccctcttcc tgcccttcag      30060
tttccaacca cggcctccta ttggccaaac ccaaccagaa gccagcgagc aagggggctac      30120 tgatgaagca catatagctc agcctccaga gacacagaac aggataaaag gctgagacag      30180
tgggtctggt ggggcaaaga gaaagcttgc acctgccagg taaagcatta tagtccccat      30240
```

```
cctcccccca ccaccttagt tcttgtgcat ttcccatcag ttttcttcca aagcatttca   30300
gatctcactg atttgaatgg gacctcttct tctattacca atttggatca gtaattattt   30360
atgtatgaga aaactattga ttttacata tcgttgcata gcagagtggt ttaataagga    30420
gacatttggt ttttactgcc tgtgtgggta tcacttgcta tgtgacttga ggcaaatcca   30480
atatttcttc tgttataaat tccagtattt gtaaaaaatg gtaataaga tctctatttt    30540 atatagtttt agtatttaat gagataatac atataaagtc attaaaacag tgtctggctc   30600
ataaaaaacc ctcaataaat gtcacttatt actgtatctg gttttgagc tgctctattg    30660 caccattgag ttttcagccc agtatatgtt aaccctgatc attatctgca gaagtccccg   30720
tgccacactc tacatcatcc aaattctctc caggtggact aagtagatta agaactttta   30780
aacataacta ccatattttg gctctatcta caaaatgtcc aataatcagt taagaaagga   30840
acaattctct tggggcccac actttgagaa gcaaatgcag ctgaactttt ttagaggaaa   30900
gtgagtgaac caactggtag ctttgccact gcttaaaaac cagcatcctt tccagctggg   30960
tctaagacag aataaggtaa atttagatat gtctctaata tatctataga acagtggttc   31020
tcaacccggg gtgttttgc ccttagggg ataatttgca atgtctggag acatctgtga     31080
ttgtcataac tggaagggg cagtgctatt ggcatctagt gggtatagag caagggtgct    31140
accaaatatc ctatggtgca acagagaatt atctggtcaa aaatgtaaat agtgctgagg   31200
gtgagaaacc ctgctataaa aacgaaagaa atttggtcta cagagttgtt tggatttaga   31260
caagacgttg ccccaatagt ggtgatagaa ataagaggaa cccgtgctt ttgcaaagcc    31320 catatctggg gtggcttaaa taatcatgct cctccccatc ccccgacctg atctttgtag   31380
ttggaaactc cagggctggc tgcctgtagt ctttgtgact acacttcctg cctcccatca   31440
cttcatctca gaagactcca gatataggat cactccatgc catcaagaaa ggtattttaa   31500
acattggaac acatatagat aatttaagta ggtagatgta tgtgctgtta taaggaagtg   31560
gggaggagag aagagggaac cgaaatcata tgcacaaaaa ttttttttag aatataaata   31620
aaaaatgtgg tagtctaaaa tgtcaattct tcaaagataa agttaggctt tcagtaacgt   31680
tagaaatggt tttctggaat atgtctccag tctacctaac tttgaggaag taaatactgt   31740
aaatagatgt ttcaaacgca ttttaaagca atgatcctag catgtcttta agctacagta   31800
ttgtgctgtc tttgaaatgt aaactttgat gtcttctctt tctcttagtt gatgctattg   31860
ggcccatctc aagctgatct tggcacctct catgctctgc tctcttcaac cagacctcta   31920
cattccattt tggaagaaga ctaaaaatgg taagaacagc tcagaaacc ttaaaaagtg    31980 ttatctgtaa tctttgtgga aacaactgaa accagctggc aagagcaata ttgaagaatc   32040
tgtacttagg ttatttgctg ggggaaagtg cttcctgata tttcacaatt ggcattaatg   32100 aaggggggcat gtcacaattt cagattaatc aacgcttgct ctgttcaact tcctacaaga  32160
attaaatatg tgctgtgggg aggaggagca gatgtttgaa ttggggacat agcttctatg   32220
tatctcattt cttcagccta caattttggc tttaaagcca taacaaatca ctgaattact   32280
gaagttactt tgtgcttttt ccagcatatg gtgttgtctt aatgactgtg tggatgaaag   32340
tgtgtgggca ggctcatagc aataaaatac gggaaatccc cggcttgag tgctgtcaaa    32400 gaaaactaaa tttggacagt agataaagat actatcagga ctattgcaat cggcagaaag   32460
agacctcagt atagaaaggg gctcaattcc aaatacagcc aaagaccagt aaagatttct   32520
ggccaaggag tagagtgggg gtcagtggat ggaaaattac taagaggaaa catcaagggt   32580
aaaaggattc tggctaaacc gacctgacag gattcttgct gaagacaggc cagggtgatc   32640
```

```
agacctcacc tgtggatggt gggagatgag gaatttgatc agatattgag ggtgatcaca    32700
taccaagagg agtggattat caataaaatg acttagcagg attcctgctt gaactgggca    32760
atgcaaagat ggacatgaag ccaaaggccg aagcctaggg gtgtagtaga gcctgattaa    32820
gttgaattaa ggagagtctt tgtcagcgct ggctctccca gtcactagtt gggggggcct    32880
tgtgcctgtc atcaaagtcc tctgaaactc aatttctctg actatgaaat aggcattaga    32940
atccctcccc tgttgccttc cagggccact gtgaggctca aataatagac tattttcaa     33000 gtcctttgca agtggtatga tgcaagtgtg agttattagg tatgccaaaa cttagtcgga    33060
aaaagacgtc aagggccttt ttctgaaatt attttgtcac ttaaatcaga cacattctag    33120
atccgaatgt tagctcctag gctcattttg tgtcaaagtt ctaatgaagc attaaccatg    33180
gggctattgt tacaaaggaa acaactgctt acggtttcat ttcctagaaa cccagatgtc    33240
tattttaatg caaacctatg cccacatctg tctttgcccc ttgatgggtg gcataatggg    33300
aatgatagta atacagagag ctcacatttc ttgaccactc aactatcatg ctgagggcta    33360
gatagacatg attctatttt ggcctcaaag tagccctata aggtagagat aacgaaactg    33420 gggcttgag aggttaagga gcttgggtgg ctctgaaagc tgtgctgaag actcttctgt     33480
tcttcctaga ccaagcccag cacacacgca ataaagatga ggttggatat gatggcttcc    33540
tactcaagta caaaggggaa atagtatatc ttttctaaga aaagacgtga aaataatttt    33600
caatataaga aattcaaaag gcaaaaaagc acagggaaaa tattcaactg tattgagtca    33660
tatggcagat cctttgatct agagattaca cttttagaaa ctcttcttaa agaagtgacc    33720
atgagactgg ataaaaaaat gtggcacata taccatgg aatactatgc agccataaaa      33780
aggaatgaga tcatgtcctt tgcagggaca ttgatgaagc tggaagccat tatcctcagc    33840
aaactaacac aggaacaaaa aaccaaacac cgcatgttct cacttataag tgggagctga    33900
acagtgagaa cacatggaca cagggagggg aacaacactc actgaggcct gtaggaggag    33960
ggtggggcag gagagagcat tagggtaaaa agctaatgca tgctgggctt aatacctagg    34020
tgatgggttg atctgtgcag caaaccacca tggcacgttt aactatgtaa caaacctgca    34080
catcctgcac atgtacccca gaacttaaaa aaacaagcaa taaataatt ttaaaaaaac      34140 aaaagaagtg atcgtggaca tggaaaacta tttaccaaga tggtcagtgc agccaggcaa    34200
aaaaaaaaaa aaaaaaaaaa tcatgtccca tgttgggaag gggtgaatta attgtagtag    34260
actcattaaa tggaatatta tgtaatcatc aaatcatgtt ttttaaaata atactgaatg    34320
acctaagaaa gcactcatgg tataatgtta aatgaaaaaa gcaagctaga aatggataag    34380
taccgtgtat tcctcatgtt tttactgcac ctgctaggca aatactagat gctcactaaa    34440
tgttggataa tctgtgatga tggtttacat aaacacatgt gttgcatatt ctaatttcat    34500
tcaacatccc tactttataa ccattttaca gttggcaaat cagaggctca tgaggtcaag    34560
tgatttatga aagtcagaga gctcttacat gacagaacaa ggactaaaaa ccaaattttt    34620
gtactgacaa agccttggct gttactagaa tgcttctcac catgtgaaat agatgcaggg    34680
atgggaaatt actattagaa gggaccatct cccaaaatgt caatagtggt tcagcaaatt    34740
taaaagtaaa aatattattc tgctcttaac ctataggaaa tttctttatg gctaaaaaaa    34800
ggttattaag taatcaattt attaaattaa tacaatctga ttatttaaaa atttggaacg    34860
ctgtactaaa attaaaaatc atcattacag attaaccagc cagtacctct gcaccccaag    34920 aataaaataat gtatatcccc gaaactcacc gaagtttagg gctggggttg gcaaactatg    34980
```

```
gcccatgggc tatatcccac ctgctgtaca gctcatgagc taaggggttt ttttttaatt    35040
gttgttttta aaagactgaa aaatatcaga gcaaaattac tattttgtga catataaaag    35100
ttacattcaa gtttcagtgt ttacaaatgg ttttattgtt tgagtatttg tttacttatt    35160
gttgataagt gcttttgcac tacgatggca aactattcaa ggagttgggt agtgtgacag    35220
agaacctgat ggcctgcaaa gattaaacca tttactaact ggccctttac agaaaaagta    35280
cgtcaggccg gggcttatag aaaacaaagg gataaggtat aaggtcaaat aggtttgaga    35340
gccctatggt ctttggtgac tgttgtgatg cataatagct gttgagttcc taatttatgt    35400
aagacaactt tatatccttt tattctttta gtttgaaaac taagtctgtt gggctaaaat    35460
gataggaagt aaatgataac tctctccttt ttttaaaaaa aagcaagtgg tttacaacct    35520
tgtacttaaa cgttttggtg acataatgaa actgatattc atggtatttg tactttacag    35580
agattaaact aaaattaaaa atatttcaaa attcacaaat aggggatatt tgttaataaa    35640
tctatttggg aaattcctag cagaggctca gtctataaaa tgaatagcat ttcagcaact    35700
tcccttattc acagtgcttg gttattctct agggagacat acacaacaca tctctagtta    35760
ccaaacaatt cagtgtgata taaacatggc aaaaagtcaa tgaatttgag ggcaaggttt    35820
ccagcaatcg ccccggccat tgcttacttc ttccatgccc tttctaagtt ttcttcagcc    35880
aggcagccat cccctctggt ttctcccaga ccccgctgc aggctccccg ccatcacaga    35940
aagcccctcg ctcacacgtc ttggctcaag caactctttg tcttagaaat gcagatccca    36000
acatttcctt ttaaactcag gcaacttggc ttttttctgc tctgtgatct tgaaagtcgc    36060
ttggaggaac agctgagtgc atggggctgt tgtcctctca gggctaacat gttgtagccc    36120 aggggggtgcc caggggcctt tctgactggt tggttagttg ggtaaaagag tagagtcagg    36180
agagcaggaa atccttctt aactcactat aaaaataaaa gcgttcccca ggcctcaaat    36240
agtctcatct caagataaat ttccttttgc caagattgct gctgaaaata atccattgta    36300
gccagataat agctatgcaa agaatatata atagactggc aggggcatgc ctaccgattc    36360
aatacagaaa ggtgagggtt tcatttgctg gggtgtagtg ggtgggagaa ttccttattg    36420
caatcacact ctacttctcc atccagaaaa ctctccaacc ctcctggagg actctccatt    36480
ttctcctctt tctcctcctt gtgtacctac ctagaccatc tgctcccata tgtcctgtct    36540
gacttcctgt tccagttacc tatcactgcg taagagatca cctcaaaatg caatggcttc    36600
aaacaacaac aatcatatac tgctttctat catgggtcca ggagttgact ggactcatta    36660
ggcagctctc ccacagggtc tctcttgggg tggcagtcag gcggtgactg cgactggaat    36720
cacctgaaga ctcactctcc aggtctgatg cctgggctag gagactcaac agctaggtgc    36780
cgaagcagct gcagctcctc aagtgtctct gtctccatgt ggtctctcta atatggtggt    36840
tgtcgtatag ccaggcttct tacaagggtg atgactcagg actccaaagc aagtgggtga    36900
gagaaaggga gagagggaga aacagggaga gagagagaga aagtgtgtgt gtgccagtac    36960
gcgcgaggtg aaagctgtat tgcctgtgaa ctacccacca tgtctttcgt cctcttgaca    37020
ggaaacctcc tagaaatgtt tgctgtctcc aaatccctct ccttacgttc ttccaagaac    37080
tttgaagtca tattttatgt agctactcct tcaaaacata tctggtgttc ggccagttct    37140
tacgccctcc agcactgcta cctgggactt ctgcttgaat gactgtaata gcctctcaac    37200
tagtctccct gctttcaccc ttgcccctca ctgtctattc tcaacacagc agccagcagc    37260
atccttctca aatgtaagtc agaccaactg attgtcagct caaaaatttg caatgcatct    37320
gcattccacc cagagcagag accgccatcc atggaatggt agagaaagcc caacatgctc    37380
```

```
agggacactc cctctctgac ttcatctcct attgttctcc tacacccct gcttcagcaa    37440 tattggcccc gttgccattt ttgtgaatat tctagcatgt tttcaccttg gggcctttgc    37500
tccaggctaa tccatctgtc tggaatgcat ttcccctgga tgtctgttat ggatgacttt    37560
gtcctttcct tgaggtcttt gtttagatat caacttctta atgatgccta tccaagctgc    37620
cctatttatc gtcacaatcc taccccacat tcctgatcct tttcactctg ccctgttttc    37680
tttttcagta acacttatca cttgacatgc aatatcattt ctgacagtta tatattttg     37740 tgattattta gagaacataa gctatagttg agtggaaatc ttttctattt tgtccactga    37800
tgtcccaaac acctagagaa gtacctggca tgttgcaggc atcaataaat acttgttgaa    37860
tttttccttt ttcacaattt ccttctacgt tgttatgatg agatcttatt tcctctgtaa    37920
tttgatttta aaagttttaa taaaaaacaa tacatattat ttatgataaa aagtcaaaga    37980
gtagagaagg gtataacata aaaatagaag tccccctctt cccagggaag gccccttat     38040 accactgccc agaagaaatt gctattaaag gtttcttgtg tattcttttcc tacttttctc    38100 tgcaaataca aatatatgca tatatattta tcataaatgc attatatgtt atatgttatt    38160
ttaatgctgc tttaaaaatc ccctttattt tttgtaactt agtagtagat catgcatagc    38220
tttttatgtc gatacccaca gctctaccac attcttttta agggacattt gatattttac    38280
tattggtagt ttcccatttt taaccattct ctcaaatcaa tggattgtca tgtaattctt    38340
cctattctta ctatttcaga aagctgaatc aaactagcaa aatagtttta tctaaagaca    38400
tataaggccg ggcgtagtgg ctcttgcctg taatcccagc actttgggag gctgaggcag    38460
gcagaccacc tgaagtcagg agtttgagac cagcctggcc aacatggtga aaccccgtct    38520
ctgctaaaaa tacaaaaatt agctgggagt ggtggcggct gtctgtaatc ccagatactc    38580
aggaggctga ggcaggagaa tcacttgaac cgggtaggca gaggttgcgg tgatccaaga    38640
tcgggccagt gtactccagc ctgggcgaca gagtgagact ctgtctcaaa ataaataaat    38700
aaataaataa taaagacata taatgcttac tttaaagaaa aacaaaacaa aacatgtact    38760
agttattttt ttcctccctc tgtggaattc ttagaaggtt tatggtagtt tgaagctttg    38820 catgaccat tttgaaacag cagcagcctg aggttccagg gggttatgaa gactcccagc     38880
tgaggacaga ccctggcaga taagtttcag ggggctctac accaaccatt agagtcatag    38940
aataagcaca atagaaaagg accattaagg tcagttagcc aaactccaga gtttgttgat    39000
gagaaagtca aggttcagga taattcagtt ggtagccctg tagcagacag agagactgaa    39060
aacaaatctg actttcagtt cacgtggtgc taaccctag aataaataaa cacgaggaga     39120
aatcagacta atcccagtct tcttctaact tgtcacaaga cacaaaccac ttaccttcac    39180
ttcctcattt tttccatcta atagttccca gttatataca tgtccttctc actcctctga    39240
ttgcaaccag acatctctta caagtttaca agttttgaa gataaaaacg ctatttggaa     39300
agcgtaaagt taaaaacagc ttggtaaatg tttttttttt tttctattag taattcgatc    39360
tctacaactg taaatattgt ggtaggaatc taatacagat ctaaaatcag taaaattcaa    39420
tcttgaatat gggcttcagt cctgccatca aaatagtgca tccaggtgga taggttttgc    39480
caccttgaag agttgtttat tcaaactttt gtttgaagag taggaaagca gtgttaccct    39540
taggcctgac ttagcccttg ccccacaatc tattgttttt tctcaccata gatttccctg    39600
acagcagaga gagagttctg tgctcaagag atacacacag cttctgacaa tagagcagca    39660
gagtatttgg ttcctaattg agcaggaatg gtgtttgact catcatcatt tccctacttt    39720
```

```
gtctagcaca gtaccttgca cagagtagat tctcaataat gtttgttgaa tgactgtggg   39780
agcatataat tcataatgga gacaaagctc aatgaggctt taaatttcta aatccacaaa   39840
atgccctcat gtaacattgc tggatgatat ggtttagctg tgtccccacc taaatctcac   39900
cttgaattgt agctcccata atccccacgt gttgtgggag ggacccagtg ggaggtaatt   39960
gaatcatggg ggcgggtttt tcccatgctg ttctcatgat agtggataag tctcacaaga   40020
tctgatggtt tcataaacgg cagttcccct gcacatgctc tcttgcctga cgccatgtaa   40080
gacgtaattt tgctcctcct tcaccttcca ccatgattgt gaggcctcct cagtcatgtg   40140
gaactgtgag tccattaaat ctcttttttct ttataaatta cccaaactcg gatatgtttt   40200
tattagcagc atgagaacag actaatacaa tggacattgg atgcaattca tttaaaaaat   40260
catcttaaaa atatctttct ttttctccc tcaagttggt cccactcaaa acataaacac   40320
accatttttt tttttttttg tcttgagaca gagtcttgct ctgtcaccca ggctggagtg   40380
cagtggtatg atcgtggctt actgcaacct ctgcctcccg agttcaagca attctcctgc   40440
gtcagcctcc tgagtagctg ggattacagg tgcatgccac catgcccggc taattttgta   40500
tttttagtag aaatagggtt tcaccatgtt ggccatgctg gtctcaaact cctcacctca   40560
ggtgatcctc ccgccttgga ctcccaaagt gctgggattt catgtgtgag ccagtgtgcc   40620
cagccaccat ttttaatac ttgtaaattt tccctataaa aacaaaccaa tttctctatg   40680
ccccaaaacc gctaagtagc acaaaataga aacattagag taccaagaat acttgaactg   40740
aaaaggaaat taatcaaaat gcagacacac attataccaa gtgcatttgc tgtagctgtg   40800
taaggcaact tgaatagaat tggtcaacaa tgagtctgaa tcttggtttg aaattgcctg   40860
tctgatctct gcttcctcat cagtaaaatg agaatattta tatggccttt caacttcagt   40920
gtgagggatc aatgatgtaa tataaacaac aagtctgcct tagaacctgg cacaccataa   40980
gtaataaaag gcagccaata ttttaaaaaa tacacaaatc atggtctgat ggctgtccaa   41040
tataaattct ctattttcca ttttaactaa agagacgata tattgagaaa atagaaacac   41100
ctgtgtgtat gaaatcaccc attcccattt ttacaataat tagtttgcta attgagcatc   41160
caaatttacc cagtgtattt gcatgtgtaa ttagctgtga ttcaatacca aagccaggcc   41220
tatcatggta tactatgcta ttttacaagt caaattactg aaagatgcat gtctttaggc   41280
aatcattaca aataaaaaaa aaaaaaccga agcaaaacaa aataacatag attatttgta   41340
tcagatggac aaaacagacc tggcttgatg ccgaacccct aaatctcaaa ataacgatag   41400
ttgaagctaa ggttccagct taagtctgaa gcaggtagtt tccaatggct tgaaaggaga   41460
aatttctaca ctgaaggaaa tttccattgg aataaaggaa tatttcacac ttttaagtca   41520
tcttctctag atggtctttt gggtatactt tctctttaaa taacagattt agaagcactt   41580
tgttcatttg tttagaatta attccattca caagtttaac acagcctaag gtttggtcta   41640
gaccaggggt ctgccagcta tgacctctgg gctaaatctg tcccttcacc tgctttttt   41700 tttttttttt ttccaacctg tgagctaaga atgggtttta ctattctaat aaatagtgag   41760 ttcattttc tccctcacct gcttgatcag agcccaactt tctcattgca gttaatcttc   41820
cttctggcat ggatcttgga atgcaaactt gctgggatct ccgagttcca ggcttcccgt   41880
gcagccggtg tggagagcca agagatgttt tgtttggcat aaagcattcc aagggtcagt   41940
gggcttgggc tcaactattg agcataggac aagggcagcc ccatcctgac tgtgactctt   42000
cccacaagag acaaacgagc tctgtgccttt cactgggggtt tcaggttcaa agggacagag   42060
cgtctgagaa aaaggattat gaaagagtcc gtctgcagct ccacttcccg tgcccttcca   42120
```

```
atgataccat cctcgtttct tctgtggcat gctccccact tcaatccttc cttcagaggc   42180
cccaaaccct ccttggtctct ccttgtcacc ttgtgaaaat ctgatcttca gggaaaaatt   42240
ccttactatt tatactagta taatgtgaat cttctatggg attttaagaa agttcaaagc   42300
cttggtttac tcagcaaata tttagcttgc actcactatg tggcgggcat cctaatgatg   42360
gagtatatgt aaagacaaaa aaagtttccg gacctcaaag tgttctccat ctataggggc   42420
agatgactga gttgacatct cgagaagtag aatagcagag tggctaagag tgccagctct   42480
gtctcaatca cctaggtctc acctcagcat taatttcact ttcctcattg taaatgagca   42540
tatctcttag aattgggata agcattaaat aatatagact tggaatgaat ttgcttagaa   42600
ctaattccat gcacaagttt atcacagcct aaggtttggt ctagaccaga ggtctgccaa   42660
gtatgacctg tgggctcaat ctgtcccact acctattgtt gttgttgctg ttgttttta   42720 atgacctgtg agctaagaat gggttttact attctaatta gttacattct caatggttat   42780
ttaagtacct ccataatatc ctcaattttg cctaaaatat ttaccatctg cccctttaca   42840
gaataagttt gctgacttat tggtctggac caatgctatc taataaaact ttctgcaatg   42900
atgaaaatgg tctctatctg tacccttgaa tacagcagcc actagcctaa tgtggctttt   42960
tgagctcttg aaatatagtt agtgtgacta agagattgaa ttttaattaa tttaaattta   43020
tggagccaca tgtgactatg acattagagc agctctagac agcctgaagt ctaaagactc   43080
tatgctttgt cggtgctccc ctctctcaat tgaatcaact accctgaggc tgcatgagtc   43140
aaggggaagg ccacactctt caatcagatt ttttgccctg gactggcttt cattgtctac   43200
tagaaaatgc ttaatgggaa gtgcttagaa aatgtacatg gcatacact  taattaatct   43260 aagttgctgc tttgtctgta tccattaaat ctgctttatt ttggggtaaa ctacagtaga   43320
agttggcttt ttcaaccctg caaagcctta aaattcagga tgtcttactc aacttaaagt   43380
gtagagttgc agccagagca caactgtatt tccttctagc cctgcttgca gaatggctaa   43440
cttcagtcct atttcatttc tcttgtaaga ctgctaaaaa cagtaagaag ccaccaacat   43500
cattatgaat attgccaaat catttcgcct aagagtaaag tcacagttgg catgtgttct   43560
gccctccaag acaagatagc ataggtgaca gttttatcag atatcttgtg atggcataat   43620
ataggccacc cagctttcca gcctctgata tctgagtctt cccaatagcc tgatgacatc   43680
cgcatcacat attttaggtt cgctcatgga cagtaactta tttccaaatt ctatactggt   43740
taaaattagg tttgcatttg tgcaatagaa aatccaattg acattggctt agcataacaa   43800
ttttttgatt tctcataaac tcttggcagt cagcaggtcc aagccattat ttctgctctg   43860
ctctctgagg tcatataagg aaggatctgg atgctctggg tcatctacgt catctaactg   43920
gttgctgtgc catccctagc tcattttcct catgtgcatt gcccaagatg gctggctaca   43980
acatccacat tacaagaagc caggtggaag cagacaggag aaagaggaga aaggggaact   44040
gccccaccgt ttaaggacat gtcccagaaa ctgtacacct cacttcctcc caaatttcac   44100
tggctatcac ttagtcatat agccacactt agctgcaagt gtgtctggga gatataatta   44160
tttttcacag tggtatatgc ccaactacaa atggaggttc tgtcattatg agatgagaga   44220
aaggcagaaa acatgttgag agatgtgtag caatctctgg actccacggg gataaaaaag   44280
aattgagagt atcaaaattc aggatcaaaa tcaaaattaa agataaaaaa tatcaataac   44340
tatcacctgg aataagaaca acgtacagtt cagctacaca tatacaagtg gcagcatctt   44400
gtctggaagg aactaatggt ctttctacat tgtatttag atatgtattt ttttttctcc   44460
```

```
cttccacagg attttgagct ccttaagggc agagactttg tgtctcctgc tcctagtagg    44520
catccaacac gtatctgtca actgaaagaa tgaatatgag tcagtagata catattagaa    44580
ttctaatatc cactggctgg gtccttggtg tgtcccatat tgttgtttct gtgtccatca    44640
ttcttttgca gggtatcttc tactgggcac agaacctgcc tcagaggggc atatgggtaa    44700
tgaactacca agaaggagt agaacccagt tcttccaacc ctccacccag agtgcttttc     44760
acaacctcat gtgtaataag tgcagtagga gatgagagga gggagtgatt acttctgtct    44820
ggtttgatcc cagaaggttt tttgaagaaa gtgttttga atgagacatt atgaaaacag     44880
agcttcttaa acctttccc ccaaggaatc cctgggcaga tagaagagac agaaatctga     44940
cctctgctta gtctggggt atagactgaa ggaacctact caaggagaa attttttctca     45000 tttttcttta cttcacgatt catatatgca ggcattcatt ctttcattca tgtatctcac    45060
agacataacg aggtcctaat taagtgccag gcattgtttt acatgagacc acaagaggcc    45120
ctaccctctt gcagcttaca ttcttgtaca gaatagacat catacgaata agcaacataa    45180
atcatcaaga taatttctga ccgtggtaag ggctatgacc gaaatcaaac agggtagtca    45240
gttacagagt gcatataacct ctctgtgcct cagttgactc atctgtaaaa tggagataat  45300
aatagaggtc taggctaggc atggtggctc atgcctgtaa tcccagcact ttgggaggcc    45360
gaggtgggtg gttcacttgg ggtcaggcat tccagaccag cctaaccaac atggtgaaac    45420
cccgtctcta ctaaaaatac aaaaattagc caggcctggt ggtgcatacc tgtaatccca    45480
gctacttggg aggctgaagc aggagaatcg cttgaacccg ggaggtggag gttgcagtga    45540
accgagatta tgccattgca ctccagcctg ggcaataaga gcgaaactca gtctcaaata    45600
ataataataa taataataat aataataata gtctataatt ccaaaaccca aaactgaaag    45660
ctttgtccta actcagttga ttgcaaacat aatatgatct gaatgcattt ggaggtagat    45720
cttgacctga actgaagtta tttattcttt taataaata aatgagttat ttattctttt     45780
taataaataa atgagtcatt tattctttt aataaatgag ttattctttt taataaataa    45840
taaactgagt tatttattct ttttaataaa taataaataa ctgagttatt tattcttttt    45900
aataaataat aaatgagtta tttattcttt taataaata ataaataact gagttattta    45960 ttctttttt tttaataatt ccacttagag tggacaatcc tatatgtcac tgcagaaatt    46020
ttgtgtgttt gattatggaa tgctgcccca ggcctcaata gttattacat aatttaggt    46080 acatgtagcg tattaccttc taaaatttga aaaattccga attccaaaac acatgtagca    46140
ccaaaggttt cggataaggg attgaagacc tgtagtatcc attattgtga ggattaaatg    46200
aatgaatata tggaaaacac ttaaaatgat gcctggcatg tggtaagtgc tacgtaagtt    46260
aactactatt actattatta tcactattct tacatgagaa gatatttaga taagttggtc    46320
agggaaagcc tctctgagga tgtgtcactt gaataggcaa ctaaggggtg gtaatgaccg    46380
ggctgtggga agaggaggag aaagatgatt tcaggaatag gaaacagcaa gtgccaagac    46440
tgtggtggtt acaaggctgg cttgaatgca gaacagaaaa cagaccagat ggctgatatg    46500
tggtaaagga ggggaaagat ggctcaaggt cagagaggta ggctgaagtc agaacaccct    46560
tgatataagc aatggtagag actttggatt tcatttaaag tgtaatagga agacattata    46620
gttgatctga ttcaggttta taagaacgc tctgatgctg ttggatgaat gaattataga    46680
ggagaagggg gagcagggag agcaatttgg agtctagcat agtggtccag atgagaccta    46740
atgactaatt ggagttggga ggtggtaata gtcaaagaga aaagtggaca ggtgcgagaa    46800
aaaagtttag aaataagtgg ggggcggggg aggttttctg attaatttgc attctaattt   46860
```

```
ataatatgtc actgtgtaga ggctaaaaat ttcacagtca ttgtctcagg tgtgttaagg   46920
ccagtggcgt gctggacccc acttgaaatt ggccatggag ggaatattta cactatagaa   46980
attgacaaat gctacaaatc aagacaacaa atcaggcaaa gcttcttgtt aaacatttac   47040
catcacacca ctggtgaagg tgacttgatt tttccacaac taaacttcct tcatttcaca   47100
gcctccattt tccctgatca cgaaaacact taaactaggc acatcctcgg aaacgcagta   47160
tgaggactgc tgtgtcaatc acttcatgtt tttaactcaa ttcagcgatc ctcccacttc   47220
ttcccaggct ctcatttagg tacatgggaa tgggatggga agagggacct ggttcatgat   47280
tgtcatttac ccaccttggc cccctctgaa gtacaactcc actctctgct ttacaatatc   47340
actctgggca gcattaccaa ttgcctcctg atagtgggat ctatgaaccc attatgtctt   47400
tggacaaaag catagccagg ggttgggtcc agggcctggg atcctataac cgtacaaatc   47460
ctattatcag ggactataaa atcctattat cagggaccat agccatccct ctatcttgac   47520
tcaactcctc ctccctgagt agtgaacatt tttcctaaat ctctgagaaa gactggtgct   47580
ctagaaagat gtaccatatt tatttaaggg cttcctgtac ccactggcat attgccatat   47640
attctgaggt atctgagtgc tccttttgag aaacatagcc ttaaaggata agtagaaatc   47700
tggtgggtga aaatggtagg gaagaggact tctaacggag ggacttgcaa gtcagggaac   47760
ttgggtttat cgactagtga ggctagtaga ggaattcaat caggtaagcc ggacaagtag   47820
acagggtaca aattatggaa gactttggat gccatgataa aaagcttcag ctcatactgt   47880
aaaaaataaa ataaaataag aaggttgggt gcagtggctc atgactgtaa tttcagcact   47940
ttgggaggct gaggtgggac gatcgcttga gcctgggaaa caatttcaag gagttcacag   48000
caagaaactg actgattaag gtttgggaag cttgatagat agggtagact gggaaagtga   48060
gagaggaggc tttggagtgg accaaggata gagggatctc agctgatatt atgtcagcta   48120
aaacctcaaa gcaaggagga tgttaagaac aatgaaggag gtcagctgga ctctcaatgt   48180
ttttaacgat agggaggaaa agatagggg gtgacaagaa gaagagacaa ttttgtacct   48240
ctaactccaa caaactttag acctgaaaaa tcccttctga gccatcttgc attggagaaa   48300
aaaaattgct tatttacctc caattagagg aattaaggga agtaggattt ttttgttttt   48360
cttttgagac agggtcttgc tctgtcaccc tggctggggt gcagtggtgt gatcacggct   48420
cactgcaacc tcaaactctt gggcttaaga ggtcctccca actcaacctc ccgagtagct   48480
gaactacagt tgtgtgccac catgcccagc taatttttta ttttctgtag agagaggggt   48540
ctcacgctat gttgcccagg ctagtcttga actctggcct caagcgatcc gcctgccttg   48600
tcctcccaaa gcgttggtat tagaggcatg agccaccaca tctggtggaa gtaggcattt   48660
ggtttcttag ataacaacat gattggttga ttcagtcact tgggaagata aaagcattaa   48720
ctgagctaga tccctatggt agagacacag gctggaccac tccatgcgta agtactaaac   48780
taaaaccagt gttctggagt agacattgct agaaatcctg aaacttgaga gccagtccac   48840
ggttaaagca ttctgtaagg cagagccagt ggaaggtaat aaggtgattt ttaaagctct   48900
tctgcacttc ccatattccc ttttagggcc tttctcccta gggtcccagt gtctgtcatg   48960
ctaaacctag atgcacaaca atcatcttta tgggtagttt cccatatgtc ccagtttgcc   49020
tgacagactc ttggtttatg cctatagtct tggtgtaatt attaccagcc ccacttcatt   49080
cttgtaagta tactaatgga tcagtttatac ggttcctctg attatgtatc acctaggcag   49140
tgccctgact ctactactat ctcctctcca aatttatgta atgtaaaccc aatgtgtagg   49200
```

```
gaaaatgctc atcctaaaat ctccttggag gggataattt gcaagattct ttgcaaaaac   49260
aatccaagac aagagccaga ttatggaatg tcagtgccag aatggcagga atgtatgttt   49320
tctaatcaaa tgccacttac tactgggtaa ccttgggcta atcagttaat attgctgagc   49380
gatgtcttca tttgtaaaac gggaatctta gaatattctg agactcaaat actatgaaag   49440
actcatgtaa tgtgtaccag gcaggttta gcaggccgac ataaattgca ctaaagtctt    49500
catgtgttat ttttcatggg tgtatccata ttctaacatt tcttcaccct ccaaatttca   49560
gactttggca gtgaatctat ggctctgcaa ttttagtgtt ccatgtaaca acgaatagga   49620
aaatgctgct tctaccctct cgaaagctat tttgctaaag agctaagatg ctaaaagcta   49680
aatatgtaac taaatagttg caaatctcag taactgacaa atacagtcat gggtcactat   49740
agggctcgag gaagttccta tactttctag agaataggaa cttcggaata ggaacttccg   49800
cgccgcacac aaaaaccaac acacagatca tgaaaataaa gctcttttat tggtaccgaa   49860
ttcgccaggg agctctcaga cgtcgcttgg tcggtcttta ttcgaacccc agagtcccgc   49920
tcagaagaac tcgtcaagaa ggcgatagaa ggcgatgcgc tgcgaatcgg agcggcgat    49980 accgtaaagc acgaggaagc ggtcagccca ttcgccgcca agctcttcag caatatcacg   50040
ggtagccaac gctatgtcct gatagcggtc cgccacaccc agccggccac agtcgatgaa   50100
tccagaaaag cggccatttt ccaccatgat attcggcaag caggcatcgc catgggtcac   50160
gacgagatcc tcgccgtcgg gcatgcgcgc cttgagcctg gcgaacagtt cggctggcgc   50220
gagcccctga tgctcttcgt ccagatcatc ctgatcgaca agaccggctt ccatccgagt   50280
acgtgctcgc tcgatgcgat gtttcgcttg gtggtcgaat gggcaggtag ccggatcaag   50340
cgtatgcagc cgccgcattg catcagccat gatggatact ttctcggcag gagcaaggtg   50400
agatgacagg agatcctgcc ccggcacttc gcccaatagc agccagtccc ttcccgcttc   50460
agtgacaacg tcgagcacag ctgcgcaagg aacgcccgtc gtggccagcc acgatagccg   50520
cgctgcctcg tcctgcagtt cattcagggc accggacagg tcggtcttga caaaaagaac   50580
cgggcgcccc tgcgctgaca gccggaacac ggcggcatca gagcagccga tcgtctgttg   50640
tgcccagtca tagccgaata gcctctccac ccaagcggcc ggagaacctg cgtgcaatcc   50700
atcttgttca atggccgatc ccatggttta gttcctcacc ttgtcgtatt atactatgcc   50760
gatatactat gccgatgatt aattgtcaac acgtgctgct gcaggtcgaa aggcccggag   50820
atgaggaaga ggagaacagc gcggcagacg tgcgcttttg aagcgtgcag aatgccgggc   50880
ctccggagga ccttcgggcg cccgccccgc ccctgagccc gccctgagc ccgccccgg    50940 acccacccct tcccagcctc tgagcccaga aagcgaagga gcaaagctgc tattggccgc   51000
tgccccaaag gcctacccgc ttccattgct cagcggtgct gtccatctgc acgagactag   51060
tgagacgtgc tacttccatt tgtcacgtcc tgcacgacgc gagctgcggg gcgggggga   51120 acttcctgac tagggagga gtggaaggtg gcgcgaaggg gccaccaaag aacggagccg   51180
gttggcgcct accggtggat gtggaatgtg tgcgaggcca gaggccactt gtgtagcgcc   51240
aagtgcccag cggggctgct aaagcgcatg ctccagactg ccttgggaaa agcgcctccc   51300
ctacccggta gaatgaagtt cctatacttt ctagagaata ggaacttcgg aataggaact   51360
tcaagcttat aacttcgtat gcattagccc ttctttgcaa aacacaactg cctagtttac   51420
caaggagagg cctggctgtt taaattgttt tcatatatat cacaccaaaa gcgtgttttg   51480
aaattcttca agaaatgaga ttgcccatat ttcaggggag ccaccaacgt ctgtcacagg   51540
agttggaaag atggggttta tataatgcat caagtcttct ttcttatctc tctgtgtctc   51600
```

```
tatttgcact tgagtctctc acctcagctc ctgtaaaaga gtggcaagta aaaaacatgg   51660
ggctctgatt ctcctgtaat tgtgataatt aaatatacac acaatcatga cattgagaag   51720
aactgcattt ctaccgttaa aaagtactgg tatatacaga aatagggtta aaaaaaactc   51780
aagctctctc tatatgagac caaaatgtac tagagttagt ttagtgaaat aaaaaaccag   51840
tcagctggcc gggcatggtg gctcatgctt gtaatcccag cactttggga ggccgaggca   51900
ggtggatcac gaggtcagga gtttgagacc agtctggcca acatggtgaa accccgtctg   51960
tactaaaaat acaaaaatta gctgggcgtg gtggtgggtg cctgtaatcc cagctacttg   52020
ggaggctgag gcaggagaat cgcttgaacc cgggaggtgg aggtggcagt gagccgagat   52080
cacgccactg caatgcagcc cgggcaacag agctagactg tctcaaaaga acaaaaaaaa   52140
aaaaacacaa aaaaactcag tcagcttctt aaccaattgc ttccgtgtca tccagggccc   52200
cattctgtgc agattgagtg tgggcaccac acaggtggtt gctgcttcag tgcttcctgc   52260 tcttttcct tgggcctgct tctgggttcc atagggaaac agtaagaaag aaagacacat    52320
ccttaccata aatgcatatg gtccacctac aaatagaaaa atatttaaat gatctgcctt   52380
tatacaaagt gatattctct acctttgata atttacctgc ttaaatgttt ttatctgcac   52440
tgcaaagtac tgtatccaaa gtaaaatttc ctcatccaat atctttcaaa ctgttttgtt   52500
aactaatgcc atatatttgt aagtatctgc acacttgata cagcaacgtt agatggtttt   52560
gatggtaaac cctaaaggag gactccaaga gtgtgtattt atttatagtt ttatcagaga   52620
tgacaattat ttgaatgcca attatatgga ttcctttcat tttttgctgg aggatgggag   52680
aagaaaccaa agtttataga ccttcacatt gagaaagctt cagttttgaa cttcagctat   52740
cagattcaaa acaacagaa agaaccaaga cattcttaag atgcctgtac tttcagctgg    52800
gtataaattc atgagttcaa agattgaaac ctgaccaatt tgctttattt catggaagaa   52860
gtgatctaca aagtgtttg tgccatttgg aaaacagcgt gcatgtgttc aagccttaga    52920
ttggcgatgt cgtattttcc tcacgtgtgg caatgccaaa ggctttactt tacctgtgag   52980
tacacactat atgaattatt ccaacgtac atttaatcaa taagggtcac aaattcccaa    53040
atcaatctct ggaataaata gagaggtaat taaattgctg gagccaacta tttcacaact   53100
tctgtaagct ttattgtgtt tcatagtttc cgttcttctt ctgtgagaac aaggataatg   53160
gcattaaaaa atcagctttt ggtcattata aattgtcttc tattaaaaca catatacaca   53220
taaaatcact tgaagacaat ttaaacatct tctgaaatgg atcaagagga agggaaactg   53280
aaaataatgc aactcagaaa ccacagagta ttttgacatg aggttaagca ccgtggtttg   53340
ttgtaggaaa ataacagcac accaacagat ggttttatc tgaattcttt ggtaatcttg    53400
acatgtcatt cttctaactt tctgagggcc tcagtgcag ttttgtagga ctggagctgt    53460
tcacagacgg tccccacaaa gctctgaacg tggggcttct ctgctgactg gcctctggtt   53520
ggctccaccc cggaaggaac tcccagattc tccatgaatt ccgcttccac catcaagcct   53580
tggtccaagc ccctttcaac cttgacttgg ccaggaagtg tcctttctct tcagatagat   53640
actacacctt agcaagactt ggcattttta gaatccaagc caagggaggc acttggcaag   53700
gcaaatgtta tggatgagaa aaaggcaaaa caagtgtctg cagtttgtag aggagagaga   53760
ggatgagtct gattgtagcc ctgaccctga gtcaggatct ctcggcccca tttgcaggtc   53820
tacttccagc tccatctgtc tggacactct tttaggtcca gatcatctct tacatgtggc   53880
caaggaatat agagtatgca aggggatgta gcgacctgag agtgtgagta acttgtgccc   53940
```

```
atctccaagg aagctgtgat ggggatagca aggacacaca ctcttcttat ttataatgcc   54000
tttccccctc ccatgagata tgcttttat ttacttcctc cttctcatcc taagtcgggt   54060
gaacaagagg accaggttgc acatcctact acttatttat ggcccaattt taacatgggg   54120
gtggagttga ggttggaatt gttcctccgc ctctgctgca catgctcagt aagcaagaac   54180
actgttgatg ggaaaggctt agtcacagac agtgggagca catccctcct ggagctttg    54240 ggtcgctgtg ctccagaaac agttagttat agcacaccct gctcctggca tctactggaa   54300
ggtgaagccc ttgaccctaa gaaacattgg gaatgatttg taccctccaa agtccaatag   54360
ctatgtcgga gggaaacgat caaagaacat gattgaggag actcaaacag agatgtgctt   54420
cagacaacac caagacagaa aattaatcca ttttaccaag ttaacaatgt actgaaggcg   54480
aacaagagac caacccacct gccaaccaac gctatgaaga aggagggttg atcagtctgg   54540
ctaacatggt gaaacccat ctctactaaa tatcaaaat tagctgggcg tggtggcaca    54600
ctcctgtaat cccagctact cgggaggctg aggcaggaga atcgcttgaa cctgggaggc   54660
agaggttgca gtgagctagg atcaagccac tgcactccag cctgggtgag agagtgagac   54720
ttggtctcca aaaaaaaaaa aaaaagaagg agggttaaaa agagaataag tcccaaactc   54780
ataagatggt gtggaaaggg ccctggtgac ataggggcca cccatgccag tgagaatgaa   54840
atcacaacag ggcagtttca cactgtttca ggttttatt ttttcttctt cttctttccc    54900
tcctttcttc ttttgcctcc ccctccctct cggtttcctt tttggctcta gacacccaca   54960
gcaagtgtca agcaatgtac aagaatgaaa agaagacagc cgttgttgca ggtggatgct   55020
tctgtttgga aggtgtggtt ttgtgtgcac ttttggttgg aaacctatgt ctctctcaca   55080
cacatgtccc ccacctgctt cagtgagcat gatcttctaa aattggctcc atggaatctt   55140
ccctaggtga cactggctgg actctgacac attcaaattc attctttcta cttatctcaa   55200 cttttcaagca ctaattcagt ctttaagatt cccctaatct caggttgtaa ttcatttcta  55260
acatgtttgt catgacatca gtggttgcat gtcttcatat gtttatcact gcccctctt    55320 gggaatttat attaattaaa cattttggaa aagctcagac ttaaaatgac tgagaaggtt   55380
catgttacag tgtctcacac tgaacactca ctaaaaatag tctggtaaaa tccagaagga   55440
aatgggaagt cctgggggcc tcatggcagt tttcagactt ccctagagca aagatgagcc   55500
agacagcggc tccacaaaac agaaaatggc tctcaatatt cttctggcca gtggcaacta   55560
ctgagggtaa aactagacag agacggctaa ctaggaagcc atattgctct tgtatgacac   55620
atggctgctt tacttctcac tggccaaggc aaaaccatga ggcattgatt ccaggggatt   55680
tcataacagt gaattgcatg agttgacttg agcaaaagaa gtttgtagta acatctccat   55740
gaaccatatc tgaggcccat tatccagggg gaccacactg ctgagaagat tgcttgggct   55800
gttttgggag ccagaactag gttgttgtcc tgctatcacc ctgggatggt ggttacatcc   55860
ctgcaccagg tccagatgga ggcccaccaa acagaactta gtaacaggtg acatgcatta   55920
aataaaacag tttatagctc ccatctctct tctgggccta cttttctcat gattgatttc   55980
tttgcctttg gattgaggca ttgtaactaa aattcccagt taatttacaa cgttccaagg   56040
gttgtttcaa cacatcactc ctgtccatta acacattgtg atggattaat ttgtgagatg   56100
atcaactctc cagaacaggc cacctaagaa aacagaacac aggaagcatg ttctgaatgg   56160
agaagatgca ttttaaagta atcccaactt tggctcctgc tcatgagggc aggcccacaa   56220
agggaatgac aggcaaggag gggagtgagga ggatcttagg aagaagggct caagatgaag  56280
tcactggtat cccgacaatg tcattcagta aggggtggag gggaaggagg aagggaagtc   56340
```

```
acatctatta agcagcaaat gcaaattaaa tgcttcctttt attcccttga atcttcacat    56400
cacctctatg aggctagtat tagcagctcc atcttaaaga tgatgggtta actcagagat    56460
aaaggtgaga tcagagaggc aaagtcaact gctcaatctc tgggacccag gagtccgcat    56520
ccctggaata cttttgaagc aactggcttg cagagcagtt tgggaagcac cacatcttcc    56580
tttgtgacac cagggactgt tattacaggg atcactttag taaggaaagc ccagaccccc    56640
aagctgtgct caatttcctt cctttttgtgt ataaactttg gtgctctcaa cctacttccc    56700
gggagtggag ctgcacttaa actcaaattg cttcccgctg ggcactgttt ttggacaggt    56760
ataatttaac tatataggac tggcatttct gtttagggcc caaaggtgaa gacaatttga    56820
acaagaacac tagggcagaa ttagatagac aggggcaggt ggttaatgga attgaagtct    56880
cgtaagtcct gatagagttg ctgattacat ttgtgggtaa aaggatgtct ttaccgtaac    56940
ttccataaca tcttactgat agacgctgtg gttctactta tgtggcgcca agcgccacct    57000
agtggggtgg gaaatccctc ctggatgctg atgttctgct tctgagaccc ttagacgggc    57060
ttccaaaggg ggatgtggga agaaaatgta agaacagata tagtcatgtt tttaaaagta    57120
tgtctgtggc tattttttatc atatacccag tgtattaata cagaaatatg tagggctgtg    57180
tgttgaatgt ttactgatgg gagggcagtt tacaaagaag ttgaaggcca cagactattg    57240
aatatttgtt tctatcattt atttccattg tttttgcttt aagtctcaaa atggggccag    57300
tcatgaattt ccttttgccc atgcagatgt agatgtatag ccttgagtta actgggtgac    57360
cgatcctctt tttcctacat ttccatttttt tatagactgt ggcccccatt ttaaaactgt    57420
atttgagtat cagtaatctt tcttgcacat tctagctgaa cattctctct ctctcatatt    57480
tccgagcaat ccaaccacta accattccct tctgtcacca ccccccgccc tataaatagc    57540
attttgaagc atgcagtaac ttgccagttt gaggatttag gtcttttttca tcctgcttgc    57600 ctacttgact gtcagttcat gaagacagtt ggtgaacagg catgatgctt gggtgtttca    57660
cgcccgttaa ttaagtcaaa gatgatgggg cgcttacttg ctaagatata tatacatgta    57720
cacacctacc tatgtattct gtatgcacat atatatagct gtccatatat gtttgtgtat    57780
atgcacacat atacatgcaa gcatgtatat atttgtgtgt attagaatta ctgataatta    57840
gaattactga attactgatg gccatgtttt gcatagatta attgtaaacc taagtaagat    57900
aaaccataaa aagtactcag cacagggtct gacatctatc aaacactcca taaataactt    57960
tttaaattct ttttattact tttttaaattc ttttttattac ttttttaaatt ctttttattg    58020 ctttggatat ctaatcaagt atataatctt tttttttttt ttttttttga cagagtct    58080 cactctgtca cccaggctgg agtgcaatgg tgcgatctca gctcactgca acctccacct    58140
ccgagttcaa gcgattctcc tgcctcagcc tctccagtag ctgggactac aggcacacac    58200
caccacacct ggctagtttt tgtatttttta gtagagacgg ggttttgcca tgttggccag    58260
gctgttctcg aactcctgac ctcaggtgat ccacctgcct cagcccccca aaatgctggg    58320
attataggca tgagtcaccg cgcctggcta atcaattaca taatctcaag aggctaattc    58380
tatattcttc atacagtgaa aattttttaac atttttctttt tagtatacag tatctgggaa    58440
attttttcta ctcatcactt actctgtaca taaagtttat gttcaacatt tcatgtacta    58500
tattcataca ttatttaaca atttttttaa tttaagggt gacactcaac gtattgcttt    58560
tccatttgtt acatattctc aatcaaaatt cgttttctct agatttaaat ccatcaaaat    58620
ttccagaaat gtcccagata cccagacgtc ctgtaggctt taaatataat ttttcatctt    58680
```

```
caataatctt ctatttacca taagaatgct gaccacttcc tgcttgtagc ttatctgagg    58740
aaagtccctt ttagttgatc caagttccca gatttcccca attctgcttt ttcctgtgat    58800
cccacaagaa gttccaaaag tatgaagtag cgccaaatgt taacttgcat aaaaccctgt    58860
gatgatactt gtaagcatca gcattgagtt cttcctgttc ctacccaccc ctactcctga    58920
tttcctcctg actctgggta taattggtgt tctccatggt cacatgtgag tttaaattct    58980
tccagatgtt ttgataaaac ttcattttaa aagccatgtt gaaggagacc atagcagagt    59040
ttgtatgcaa aggtatggag tggtttcttc tgagaatggg cccagcaggg cttacctgcc    59100
tataagaggc actggtctcc aaagttgtgc caagtctagc cttcgtgaaa ttcacctggg    59160
aatttagaat cccagttgga atgcttgatg tttaggtgtt tcatgcctgc taattaagtc    59220
aaagacgttg gggtgcttac ttgctgagat atatatatat atatatatat atatatatat    59280
atatatatat atatatatgt acacatccac atatatattc tgtatacccca catatatacc    59340 tgtccatgta agtttgtgtg tatatgcata catatacatg caagtgtgta tatattttgt    59400
gtgtgtgtgt gtgtgagaat taccgataag ctcatagcca tgctttgtat agattagtta    59460
taaaactaag tgttcagaat tgttgggggct tgagggagct ggttactcac accctctcca    59520
gctgagcaat tcacactgca gacagtgcag ctgagagtga gcaggtgcat gaattccata    59580
ggccatagct tggacttgca ctcttgcaac tctccagtgc ctcccggtag caaagaagaa    59640
acgcaagcca tcaatccaga acaaaggatc cctgtcacag agagctcacc ttagggcagc    59700
agaaacaaac agagggtgca ctccacctat aggaaggctg tcccaagaga acaagagcca    59760
ggagacttga ggcagcagca gcagggacag tttcccccact gtcaccaatc ccacaagtca    59820
ctctgtctct tgtgagaagc ataggaagga ggaaagggga agagggacaa gtccccaccc    59880 ttccgtatttt caggggttga tttcgaaatg tagggagaag agaaaagttc ctctaaagta    59940
ccatcctgaa gctaataaat gaataaattc tcaaccagat tgtctacact gaggagacgg    60000
gtctgtaaaa catggtgccg tgcttggact catgacatga aaaagactct tccctgcaga    60060
gcagagacca aagcttgcag gtttcccctc attatgaatc tactgtacag aagatagaca    60120
gagtccctac cttcatgggg ctaaagatat aatttccaag acttggccgg gtgtggtggc    60180
tcacacctgc aatcccagca ctttgggagg ccaaggcaga tggatcatct aaggtcagga    60240
gttcgagacc agcctggcct cggtgaaatc cctaaacata caaaaaatta gccgacgtg    60300 gtggctcatg cctgtagtcc cagctactca gaaggctgag gcacaagaat tgcttgaacc    60360
caggagatgg aggttgcagt gagccgaggt tgtgccactg cactccagcc tgggtgacag    60420
agcaagactt catctcaaaa aaaaaaaaaa agaaagaatt tccaagactc attattattg    60480
attgggttct acaatttccc ctaggcatt ctgaaatggt atagaatata gctatgaaat    60540
ttgtattctg cattacatag atgtaatatt cagaaactgt tgattgcatt catccatcca    60600
tctatccatc catccatcca tccatccatc catccatcca ttcagtcagt cagtcaataa    60660
atatttatgg tgtggccacc atgggcctgg catgatgctt agggtgagga gacactggcg    60720
agccaaaata gaaatagtcc ctgttctcct ggagcttatt cagaaatcca ttaatcagat    60780
tattgcactg aaggagattc aagtgtgatg aaggaaagga agaggtttct ataagagtga    60840
tgacttggaa aagggagcga aaccagggag caggagaggc gggctgccct gaggaaggcc    60900
acccaaggtg agatgtgaaa aatgagttaa ttgaaccagg caacactgaa agatgaccat    60960
atttgggggc gggagacaaa gagtgtgtct tagtcatatg gcatttggga gccttcgaat    61020
caccaagtgg atggagatgc tgagtcagta ggtgcccata gtctacagag ctcaaagaat    61080
```

```
agagctgagc tggaaagatg cagttgaaca ctcctgtggc aatgggagta atggacacct    61140
tgggcggggt cttgctactc aaaccatggt ccctggacca gcaacatggg catccctgg     61200
gagttcatta gacatgctga ctctcaggct ccacctcaga cctgctaaat cagacacaca    61260
ggcagaagat gaccctgtcc catcaatgac aaggtttaca accagagatt tcagggtga     61320
ggataatacc acaatatccc agcagtgagt atatatttat tgtgagacag tctcagtgat    61380
ttttatttta ttttttttaag acagcgtctc actctgtcgc ctaggttgaa ctgcagttgt    61440
gaggtctcag ctcactgcag cctttgcctc ctgagcacaa gcaaacctcc acctcagcct    61500
ctcgcgtgtg cccccacact tggcgagttt ttttagtttt ttttgtagag acaaggtcca    61560
ggctggcctc gaactcctgg gctcaagcaa tccttttttca ccttggcttc tcaaagtgct    61620
aggattacag gtgtgagcca ctacacctgg ccagtcctag tgatttaggt atcaactccc    61680
caacctgtta cagtggctct taactttgcc tgcaccttgc aattacctgg gcagctttaa    61740
aaaaagacta tgtctgggtt ctaccataaa gattgtgatt taattggttt gggctacaga    61800
ctgagctttg ggattttaaa gctggagggc gattccaaca tgcaggcaaa gttgagaacc    61860
actgcttcag agtcattgct tgattgcaac agattctcaa gcatgagcag gcatcaaaat    61920
cacctgaggg gctagttaaa acagattgct gggccctact tctcagcttc tgattcagta    61980
ggtctggagt tggaacccga gaatttgcat ctcttacaag ataggtccaa gtgatgctgg    62040
tcttgctcta ttgagcggtt gtcaaacttg actggctaat agagtcacct atgggtgcct    62100
aggccttgtg ctagagcccc tggattaata gatatgaagg caaagtcctg acatctatgt    62160
tttaaataaa aacccaccca gatgatcctg atgtagatga cctaaagatg aacttttgca    62220
aaaccctgct ctagacacaa tttatattta taaccttaag cactgagatg acactgggag    62280
gtggagtaat cttcgagaat gccatctctt ctttctcttt tccttcatcc ccattcaagc    62340
tgatcctaaa ctgtatgcat tgcctcaggg ggcacgtgca ggggaagcaa cctagtcggc    62400
ttttgtcttc tacaggaagg cccaaaggcc ttaggggatc atagaagagc ccgtggaaca    62460
aagcgactct agggcatcaa ccaggtgtcc aggaagagaa gggataggc tgcttttctg      62520
cccttctgg agaaagacgt gaagagggaa ggggaggaag gtaatattaa cagatcaggg      62580
aggtctgtca gacctgagaa aagtgggacc ctgccaactc cacgtgagaa atgatcaatc    62640
ttccacagag ttgagatgaa ggagttgaat taaaaaatca attgtgtacc ccgcttccac    62700
acaccccact ctggtttgcc actgcatcag actcagaagc tgtacccaat ccctggcagg    62760
caaggactcc tgtgaaagga aaataccttg ggccccaac atcgctaagc taaaaggaaa     62820
agtcaagctg gaaactgctt agggcaaacc tgcctcccat tctattcaaa gtcatccctc    62880
tgctcactga gatagatgca tattctgatt gcctcctttg gaaacgctaa tcagaaactc    62940
aaagaatgca accgtttgtt tctcacctac ctgtgacctg gaagccccct ccctgcttcg    63000
agttgtcccc cctttctgga agaatcaatg tacttcttac agagattgac tgatgtctca    63060
tgtctcccaa aaatgtgtaa aaccaagctg tgccccaacc accttgggca catgtcgtca    63120
ggacatcctg aggctgtgtc acaagcacgc gtccttaact ttgtcaaatt aaactttcta    63180
aattaactga gacctctttc aaattttcgg ggttcacact ccccactcct ccgagggtct    63240
gagttgatct tctggagagt gaggtaggat gaaagctcag agacaaacac agaatggagt    63300
cataaaaaac aaacgtctct gcacatttca gttggtggac taagtcacag cagatacatt    63360
agacatatgt ttaactattt gaacattttt cacctgggta tatttcttgc ataattgtat    63420
```

| | |
|---|---|
| ttgttttgtt ttcaaaattt aactcagtaa gtagatttag aatatacatt gggaattctg | 63480 |
| agctcgattt tgtatcattc atcaattata aaagtgaccc ctccctagca tagaacgtag | 63540 |
| ttaaaatcct ctgtctgttc caaaatggga cgagcaaaag atcgtttcat gtttccttt | 63600 |
| cttacatctt aagcactttg gtgcctatag ggcaaactat gaatcaaagt tgttttttat | 63660 |
| ttagaaactt ggatttcctt aactgaagat gctcaaaagc ctgccgggcg cggtggctca | 63720 |
| cgcctgtaat cccagcactt tgggaggctg aggcgggcgg atcacgaggt caggagatcg | 63780 |
| agaccacggt gaaaccccgt ctctactaaa aatacaaaaa attagctggg cgtggtggcg | 63840 |
| ggcgcctgta gtctcagcta ctcgggaggc tggggcaggc gaatggcgtg aacccgggag | 63900 |
| gcggagcttg cggtgagccg agatcgcgcc acagcactcc agcctgggcg acagagagag | 63960 |
| attctgtcta aaaaaaaaaa aaaaaaaaaa agcctgaagc aaaacttttta gacatgtgta | 64020 |
| catttcataa acttaatccc agcactttgg gaggctgagg caggagaatc gcttgagccc | 64080 |
| aggagtttga gaccagcctg ggcaacatag caagaccccg tctctacaaa aaataaaaaa | 64140 |
| ttagctgggc atggtgtgtg cctgtagtct cagctatttg ggaagctgag gcaggaaggt | 64200 |
| cacttgagct gagaatttga ggctgcagtg agccgcgatt gcaccactgc actccagcct | 64260 |
| gggtgaaaga gcgacacact gtttaaaata taaaataaaa taaaatgaaa aaataaaatt | 64320 |
| ttatactgta cgttgccaca caaaaattat tacctacgag tctgatcagg aagcccgaga | 64380 |
| tattgggtgg tgggcgccat cttgtggcag catggttatt aacatcttgg ccattggctg | 64440 |
| gatcttcaag ccaatgctga cacgtgaagg cgtttctgca gtccctgaaa aaaggtgcag | 64500 |
| gtgcaggaag gaagaaacaa aaatgccttt ctcgaatgct aaaagcactg attctggaga | 64560 |
| taggaagact tgcaaaagag aactagaaaa aagaggaaa taaaacatat tgggggaag | 64620 |
| ggcagaggag tcctgagact gtgaggaatc aaatgaagat tccatggaga agtagcctgt | 64680 |
| ataacaggaa tggcccttct caaatcttct ccatgccaag ccccgggcct caaatctagc | 64740 |
| aggttgttct tgtgctttc caacagcccct catatatttg aatcaattat ccccaacatc | 64800 |
| ttcccacata ttttcagcat ttggtactga tccctctacc agatgccctg tccccaacaa | 64860 |
| gcagcctcgc ctcctatatc tgcccaccaa tggatgcgtc ctcaaattct gtcctctcta | 64920 |
| catcaaacat gttttatgtc accgacttca tcatcatcat ctcacaaaac ccagattctt | 64980 |
| tcctcacaga gcctatctgc attcgttctc attccaagga gaggtggccc ttcccttcct | 65040 |
| aaattgcaag cccacccacc actgcccctg gttcattcac tttccctact tgggaaagcg | 65100 |
| gctccatgag gttgactctg tccgttgcac atgtgaccac tcttctccat cctgccggct | 65160 |
| tttcctcctc acttgaacac acttctttta aaattatctt ccctccaaag atgtttgtcg | 65220 |
| cagcattgtt tgtaatttca aaaaattagg acaagcacaa atgccaatca atagaggatt | 65280 |
| cattaagcaa aataccacat gcataaccgg ctacagaaca cagccactga aaaaaagaa | 65340 |
| caagacagat ctgcatatcc aaaccagaat gctagctgga aaaaaaaaat gatgcagaat | 65400 |
| agcacgtatc atgtgaactc agttttcaaa aagaattctg tacgtaatta tatgtcagta | 65460 |
| tatacatagg aaaaatcttg aagaacatat accaaaccat taacaatggt caactctgag | 65520 |
| gagtggaatt tggagagctt tcatctgatg tgttctacat tcctttattg ggatatttag | 65580 |
| gaccatgtaa taacattata ctcagaaaaa ttttatatac aaaagaaact tcccttaatt | 65640 |
| ctatcaatat catcctctgt ttcccttaa ttttcaccaa catccatcca tccatccatc | 65700 |
| cattcgtccc catccatttt caccaacatc catgtgtaag accaggctgg atggataaa | 65760 |
| cagcccttgg gctcaaaact tgtacagtct ggtgaatgta acacggagcc accaaaatgt | 65820 |

```
catccagcag agaaagtggc aagtacgaca gagctttccg ttcagatcca agctttgctg   65880
ctgaatttgg gtaaatgact gagcctttat gagcctgttt cctcctctga aaatggggat   65940
tatagtaaca agcagagaga acaggagtgg tgggtgggta gcgccttaag taggtgttgg   66000
tgcagaggac tccatcccat ctgggccaca gaccatcagg aggcacgtgg ggacttgggg   66060
acaaagaaaa caagcagccc atatctgccg gcaggacctg gcaaagtggg cgtgacacca   66120
acaagttgca tcccagaggt gaccacaaag cgcccaggat ttgcaaagct aaggtcaagt   66180
ggaggcagga ggagacagtt tcaggaaaca cctgtggcct atctcacccg tgtcttccct   66240
ggccagggaa gggcagccgc ttaaaggggc caagggaagc tgcagcgtgg ctcctaaaca   66300
tggacgcaca gtagctgtcc tctcaggagc tctgcacccc cacttaaaac caggatcaca   66360
agagatttgt gtaaaggaag cctcttgtgc atttcttcat ctgaatcgtt gacttaaaag   66420
tttcttccac gtaagtcctt tcactttagc tttgtatata tttagcattg atttcacaac   66480
aaacaactga ttccaggcac ttggtgtttt cccagacctt gagcttttc cagggttgca   66540 cgttatttcc atatgtggta cttcgcggca gccccagtat ggggaagcca tttgctgcct   66600
tatgaattgt ctggtcatcc actcgagagg aaagggctgt gtccagggct ggggaaggcc   66660
ccaagagtgg ttcttcaggc ctactgttgg caacagccca ggaatgtgtg aagtctgtaa   66720
caacaagcgt agtaataata attccagctc tgctagttga acgctcactt tgtgccagct   66780
acttttctaa gagttccacg atatgaacaa tttaatcctc aaagccaaca tctgagaaag   66840
atactactat tcttatccca atttgacaga tgagaaaact aaggctcaga gaggcttgtc   66900
tgctggtgat ttgtgtgtct gggaagtgca cgttgtctgg caggcttgcc tggcagaagc   66960
ggttcatgac aggtcttctc cattttggaa tcaagatctg tgtcagcatg gatggcaagg   67020
ggaagagtaa ggaaagattg gtctaggaga tgcccaggag cttttggcct cacagtgcag   67080
ggtggggaga gcagacctgg ccaccaagga ccagtttctg ggcttgggca gaagccaatc   67140
atctggctac tttacaagca gatggagctt cttcctctca gtaaccttcc tgccctggtg   67200
tcaattccat tttcattttc atcttttatg gtactggttg tgtggagaaa actgaaggct   67260
catttggtat aagtaagtaa ctcatttta tgagtttgct tgacatagat actagactgt   67320
atgtgtgtat atatacatat aaacatgcat atgtacataa aaatatata tatatcatat   67380 atacatgatg atacacacac acacacacac acacacacac acatatat atatatcgt   67440 atacaagcat gctttacaag gccaattgac tggtctacaa ttggctgaca cttggtggcc   67500
tagaagccag ggtatgtgag tctcgctttt ctagaaagct gacaaactct ccagttccaa   67560
ggatccttgc tcagtcaacg gctggaagtc atttttactt cgctgttttt tgtttgtttg   67620
tttgtttgtt tttttagaca aagtctcatt ctgtcaccca ggctagagtg cagtggcact   67680
atcatggctc actgcaatct ccacctcctg ggctcaagcg atcctcccac ctcagccacc   67740
cgagtaactg ggactacagg tgcacaccac catgcctggc taattttgt atttttttag   67800 agacaaggtt ttgccatgtt gcccgggttg gtctcaaacc cctgagcaca agtgatcctc   67860
ctgcctcggc ctctacaaag tgctggaatt acaggtgtga gccactgcac tcgatccatt   67920 cttactact ttctttactt tatttccaag caaatgtttg gagggaaacc aagagacttg   67980
gatgcggcca gccgaggcct ttgggtttac aatcacaaat gttttggtt tgcccatgaa   68040 ggcccaggct gcactctctg atgtcacagg aatcacctct caaaccatgc accaggtctt   68100
gaattccctt agggtgtgat ctttagaggt ccatctaggt atacccaccc aagccattct   68160
```

```
ttgactgctg acaggccttc cttcataaca aggtgttcca cagtccattt atatatggat    68220
gtcatctctg cccaccctgc tgccaatttg gtttctccc actcctgggg tgtaaggcaa     68280
gatgaaacat atcacatccc gttctaaact ttattcttgt ggccagggt cagcaaactt     68340 tttctgtaaa gggccagatg gcaaatatct taggttttac aggccaagaa gcaaatttgg   68400
catattatgt agctacttat atagtaaaat aaaaatttcc acaattatgt aattgatgaa   68460
actcaaaatg taataataat aatcgaaggc agttttttg tagtataggt ttaataatga    68520
gaagaatgga atcattttg gaggtgctaa cattctgctt ggttggaatt taaagttagt    68580
gttctgtatc agcaaatcca ttgccaatgt tcatctaaaa atgttttcac ttctgggccg   68640
gatttcgttc aaaggctgca gtttgctgac ctctgctctt ggttacacct tttgaggccc   68700
ttgctctccg agcataaaat ggaatccatt tatcagacta aatcgggaag attaaatttt   68760
ccagcctcac gaatgctcag ccattgactc actcgttcat acaatgaaca ctcattgagc   68820
ttatactaca tgccaggtgc tggaggaggc atgggcgcc caggagaaag atgctcgctt    68880
tgcggccaca gcccagtggg agggagaccc ataccaccg gtgctgtctc agaaacttgt    68940
ggaacaaaga tgaagcaatg ttcatgttat tcgcctacat ctgtgaatta cacaaggaag   69000
acgagtttga gaaatccgaa gttcagtaca aattatggt aacttttta aaaagaata    69060 cactgaagtt ttcttagtga atggaataat gttccctttt tctcccctgt acacacaaat   69120
acacaaaaac taacaaaaat acgtcgtgtg tgtctgattt gggttgtatt taaatcattt   69180
cataaatgac ttttttcccat aacttcagtt tcaaagtttt aaagcacagt caattaatga  69240
tttggcaaca gctaagaaat cacaagttcc cttcttttca tgtaaacttc tgtaaaacac   69300
acgctacgtt ctgctgatgg taaatagagc catttcagga agttagccag tttctcttct   69360
cggccacctc ctgcatagag ggtaccattc tgcgctgctg caagttacgg aatgaaaat    69420 tagaacaaca gaaacatggt aagccacttc tatttcttta gcaaagcttt ccaacagaat   69480
atggggtttc tgacccagaa atctgggttg gtggcaaatg gtgtgagcct agaaagtaat   69540
aaatgggcaa ataaggataa aaattaaaga tcgaaacaac tgtaaatgca ggtaaagcgg   69600
cttgctatga tctttaattt gtgcacacgt tagtataaag gaattagaga gtaaattttg   69660
aaaatcaaat gcagtgatga tcttactaat ttggacagga aaataagaaa atttcaagtt   69720
agaaattgaa ctggaaatat tacttactgg ccctaccaga gacaatatcc tcttccagaa   69780
caacagggtt ggaagagaag gtgagggaaa tattcttcct ttgctatttc tgtagaaaag   69840
gacaaactct cttccttcac atacataggt caattgctag atcctagtga agcctgagct   69900
taacctactg ttggaggctt aaagttcgac attaattgct acttttcttg gtcagagttt   69960
taaataatta ggttggtaca aaaaactgtg attactttc caccaaccta ataacatgct    70020
acaatttctg taattattat tttacactgt caagacatag caggtggtcc gtttttgtta   70080
ttgtcaagaa ctgtcagact aaaaatgaac tttacacttc tttttaaatg atacattttc   70140
tagaaaattc aatgaggttt aagagcaatt gaaaagtctg atttcaagag agtctcatcc   70200
aaaatgtact atatatttt ccccaaagtc cttggagtta attttgacaa caatttaaag    70260
tacacttaag tcttttgaag ttaatgggtc tgccacccag gttggagtgc agtgcgtga    70320 tctcagctca ctgcaacctc cgcctccgg gttcaagcga ttctcctgcc tcaacctccc    70380
aagtagctgg gactacaggt gtgtgccacc acgcctggct aattttgta ttttagtag    70440 agacggggtt tctccatgtt ggccaggctg gtctcgaact cctgacctca ggtgatccgc   70500
ctgtctcagc ctcccaaagt gctgggatta caggcatgag ccaccgcgcc cggcctgaag   70560
```

```
ttaattttta taccaccta atgttcatta tggatcttga aggtaaatta attctgcact    70620
aaaattttac aatgctttac aaaatgactg taggtggccc atatggaatt cggtcaactg   70680
ggccaatgac acatatggga ttgcagttga aattatccaa ttcctacttg atatttgtaa   70740
gctgctgtga tagccagtat aattgtactg taagaatgtg gtaaatagcc ggggcccggt   70800
ggctcacgcc tataatccca gcactttggg aagccgacgt gggcggatca cttgaggtca   70860
gtaggtagag accagcccgg tcaacacggc aaaacctcgt ctctactaaa aatacaaaaa   70920
ttagccaggt gtggtggtac gcacctgtag tcccagctac tcaggaggct gaggcaggag   70980
aatcgcttga gcccatgagg tggatgttgc agtgagcaaa gatcgcacca ttgtactcca   71040
gcctgggcaa cggagtaaga ctctgtttca aaacaacaac aacaacaaca acaacagatt   71100
ggtaaataga gtaataataa aatcaaatta aacttgcaaa aaatggccac tttgctccca   71160
ctggtggcca atggaggtca aggacctggc tgacctcctg cctaaaggca gaggttgtta   71220
gccttcgcaa tggactcaaa tcagaggggg agctttcaaa actcctgctg cccagactga   71280
accccagatc aatgaaacca aaatctctgg atacagggct tggcatttgt agcttttaga   71340
gttcctaagt atctctactg tgcagccaaa gttaagaatc agtgccttag aacatcaaca   71400
gttttttggt ccttttgtta aaaagcacag tccgtttttt taggtggcta gaaatgctcc   71460
aggaagagct gaaatgtatt taccagccac cttggtttga ttttagaaag caaaatagaa   71520
gttctaagta tgctttctct gaaaagctga gactgcagat aagagtgagg gcagttgatg   71580
gagttcattc tcctctttca atcactgctt ctcatccttt cattataata atctaagaat   71640
ctcagagatt atgaaagaga aagcagtctt atggaagacc ccagactcac agaatattag   71700
ggtgtgtttc acagggaagg atgtcattac ccacagttag tctttgaaac gcagttggac   71760
attatttgta agtgcatcat agtgtcgcct ccaggttcca ttgaggggaa cgtcattcca   71820
atgcaacatc tctgagttca tctgggttat taaatgggt tgagggattt gttattttta   71880
aattagtagc cccaatttag gactactcaa gaccatagga caagcctgtc caaccctcgg   71940
cctgcgggct gcatatggcc gaggacagct ttgaatgcag cccaagacaa attcataaac   72000
tttctgaaaa tattatgcat ttgttttta gcccatcagc tactgttagt gttagtgtat   72060
tttatgtgtg gcccaagaca attcttcttc ttccagtgtg gcccagagaa gctgaaagat   72120
tggacacccc tgctataaga cacagtaata taaatacata acctgtggtt ctggattggc   72180
attagcagat acaggctgtg ttgattttgc agaaagttac aaagagctgc tagttggtgt   72240
gtatgtctaa aatcagtaga tttcctgtgg ttctaaggaa tgacaaagaa tctggaagtt   72300
ctctgtggta gcctgctcag tgcagaaagg gaacgtggaa aatccgccac cagcatttga   72360
gtcttggagg ttccacatag ggctatcagg tctctgctga tcactgaaac cagatcatgg   72420
ccaactagcc ccttggcttc agccctccca attcattaac tactcaggta aatctagggt   72480
cactttcaac tctaccacct accatctgag tgaccttgaa acattcatc tctctgagcc    72540 tcaggtccca tgtctgtaaa gcagggcct catggacttc tttgggtttt tttgttttg    72600 tttttgtttc tgaggattaa acaaatgctc cctaccctat ttcccagcat ccagtaacac   72660 agttttcat atttttgtgt atgttaagtc aggacccatc tctttaatga taagtgcact   72720
taatgtggtc atgttttctt ttgtcttcca aagctgttag tgaatccatt gaatttggga   72780
tgggtaaaat aaagtatcta ttattaattg taaatttcat ctaaagtgac aaatcctacc   72840
tgcataacca tttcttaatt tcctttcatc atgtatcagt ggtcaacatt gttaactgcg   72900
```

```
aatgaatcag aatccatcaa aaattagaac tatttccagt ctggcaaaaa ttcagctctg   72960
gttgaatcca acattgtgc tgaagcagct aagtaattca actgaggaga ttaattacat    73020
gttataatca ataggttctc ttgacacttc agtgttaggg aacatcagca agacccatcc   73080
caggagacct tgaaggaagc ctttgaaagg gagaatgaag gagtcatctt tgcaaaatag   73140
ctcctgcagc ctgggaaagg agactaaaaa ggtaaaaagc tgttaattcc aggaagacag   73200 cttacgccc ctcccagacc acctgcactg cacactacgt ggaatttatt ttagtctcac    73260
atggcagcgt ccctaccttt gtgcccacac atctggtctc cgccctggct gcagccctcc   73320
ccttcaggcg aattctgggt gtgtcctatc tgctcattgc aactcccagc gaatgagttt   73380
tcagcgaagg cagactttct gacctgttct tcaaactgca ctggtctttt aaaacgtgt    73440 ttggtggcca tcagcatcca atttcagaag aaagatttgg gtgaggactg agagaggctg   73500
ttgttgttgt gctgtctgtt tccttcagaa tctgcagaag aaaattggca ggtcatgtac   73560
tgtggaccta accaaaggac aaatgatgta tggaaaatag aaaaactgtt gtgaaattgc   73620
ttcctcatta gcaataactg tatttggcag ggagaggaga agttgggcac attttttttt   73680
cttttttttt tcatgattca tacgtttct ttaaagaagt gggttttgct tttcactggg    73740
tgctctaaga caacccagt gaaagatctg gaccacgaag acccagtcat cctcataagg    73800
gtgttcattg cagcaagctc aagggcatgc caggcaaagg cctttttct ggcagcttga    73860 acttgtctca gcagagggtt tcacagaaca actgtcattt acctgttctc tgctcttact   73920
tgattcgttt cccaggactg ctgaaacaaa gtaccacaaa cttggtggat caaaacagca   73980
gaaatatatc ctctcacagt tctggaaacc acaagtcaga aaccaatgtg ttgttggcag   74040
ggttggttcc ttcttaaggg gctagaggga aaatctgttt catgctcctc tcccagcttc   74100
tggtggtagc tagcaattct tgatgctctc tggcttgccg ctgcatctct ctagccttca   74160
cctctcctca tgtgggtggc cttctttcct gtgtgtctat ttccaaattc ccttttctt    74220 ataaggggac cagttattgg atcagggccc accttaattc agtagatccc attttaactt   74280
gatgacatca gcaaagtcca aataaggttg tattcacagg taccagggt tagaacttca    74340 agttatctat taggggacac aattcaacct aaaaactccc cttttttgat tctctattct   74400
gccacttcta ctcaatccag gttcttcact tcatcagctc ccaatctaat acttatctta   74460
tttctagtaa gcatctcttc cttatcttaa ctggtcctg gggcctggcc cgagcccat     74520 tataccatca gctgttgaca tcaagggtgg acttctcttt cggcacagaa ggcacagggc   74580
tgtaggcttc agccttctct gctttgctct gccccatcta ctgttcatcc acctgctttc   74640
cattttgcta aactttgtag aaaattcttg tcagctgttg tctcctccta cactttcttt   74700
gatcttagag gattctattc ttttactatg gctttaatcg gagcacccga ctgttaggtt   74760
caaccaacag aagttggttg tgctctctca ctctttcttt ctctctctct ctctttctct   74820
ctatttgcat agtggtattt ttttttttcct ctatttatt ggcagaattg ccatttctct   74880
aagttattgt agagttgctg tttctctatt ttatttgcat atttctcttc tgccaggctg   74940
gattgtttct attgattggt tctgctgtaa tgagggtgac ttctcattag tatccttctc   75000
acttcatctg ggaccagatg cccttttgata tccttttgga gccacaactt ttggtagtca   75060
gaggcatggg tgtggctcaa aggaagaact tggctcagaa ggtgcagctc ttgctgggcc   75120
tttggtctct gctctgtctt ctgagatcag tggctgctgg gacctggggt tcccccatgc   75180
cgggcatggt cacacagcac tcctatggac ttgagcagag caccctgcaa agtgagcatt   75240
agcaatccat tccaactctg tgcagtcctg cacggaatat agaaggtgga gcaatgacag   75300
```

```
tctccccaac ttctctgcaa gcaacctgct caccatttct tgcccttccc atttatgtac    75360
ttttcaaaat caggttattt ggaatttgtc gactcatgtt tcttacttca gtactttttt    75420
gggagggcag cattagaaac ctcaaactct taactaaaaa atgtctttgg gaatgttctg    75480
gccattttca tggcccacaa tttgctttaa gctgctttag actctcccag aggctatttt    75540
catcccgaaa gaacagagca gagctcaaaa gactccagtt ttggtctcta gcagccccta    75600
gaggatttcc ccctcaattc ctctctgcct tgtatgaaat agaattggat ttgaaatcgg    75660
atgttgaggc cttacctcca ggctagtgag gccacacaag atggatcctc tggacccgcc    75720
caagtgtcca cctaaacatg agttaccaac taacaatgtt ttgtttagca tgcaaaggga    75780
gtggtctgga atctggcctt gccctgacat attctccttg ggcctttta aaaaaataat    75840 ttgtgttaat ctgtagttaa aaattataat aaggacctga caaacactac ctcagtcaga    75900
tgatcaaggt acacataaat agtgaaagtc atgttgatag catgcaccct tcatatgata    75960
tggctagaat ggccctgcac ttctgtgatc ttcctcccct agactcatca gctcgatcta    76020
atcataacaa aagcatcaga taagtccccg cccagggaca ttctacataa ccatttccct    76080
tcccagttat attttctcc acaatacttt ccaccatcta acattctatc tttcaaaatg    76140
ggcaagtatt ttagcctggt ttgttcattg ttttatctgc aactcaaata cagttcctga    76200
aataaaatat ctgcctaata aatatttaat gaatgaatga atatagcatt gccttatccg    76260
tttaattgcc acatggtatt tcattgtgtg aacataatat cgtttattta cccagactac    76320
tactcatagg catttagatt atttccggtc ttttgctatt gctaacagcc tttgcaatga    76380
acatccttgt atacagacat ttgcatatat gagggtgtgt ctttaggatc tacttctaga    76440
attgaaattg ccaactccaa gtatatgttt ccaattgtga tagatattac acattaccct    76500
ccatcttaga ggtggtgtta atttagattc ctgccagcaa aatttaagag tgtttgtttc    76560
cccatatcct caactgccta acagaatcag tgaaaatgg tatgacagtg taattttga    76620 gtgaggttga gtatcttttc ctatgcttta agagcaattt atgtttcctt tttatgtgaa    76680
ctgtctgtta atatatttt tcaattttc tattgggtta tttgtctttt cattaatgca    76740
tatacctgtt acatatttat accaagtatg tattaaatac taacatattg atgaaacaga    76800
gcaaaaagcc tagaaataga tccaaataac agaagagtta gtatgtgata caggaagcct    76860
ataaaatcag tgagcaaaag accatccaat taataacgtt agggtaaatg ggtctccatt    76920
tagaaaaaaa taatgtgggt ctacacctca cattttatac ctaaacaatt ccagtgggat    76980
aagaaaatga aatcataaaa aattactagg aaaaagatga gaaaattgtt cataaaactg    77040
aagtgtggaa gatcctttat gccttacact gccctgagtg atctcattca tacccatggc    77100
ttcaattgtc atgaatccca aattcattcc tctgtcagaa ctctcttctg agcttcagac    77160
ccacatactc agctgcctac tggacacctc tacttgaata tcacaaactc aactcaaaag    77220
caaacctgtc aaatttaatt actagtagcc ctaccccaaa caatcttcct gctcagtgaa    77280
tgacacccat ccctccaggt gcacagacca ggaacctaga agtcactctg attgcatccc    77340
tctccctcac aacctctacc tcccttatt catccattgc tatgtctctc aaatgtacct    77400
cccaaatatc tcttgaacgc gttctttttct atctctattg ccaccaccct agttcaaact    77460
cccatcatct catgactgaa gttctgtgcc ctcttgccag tgaacactgt agaatcaatc    77520
taaacatggt gccacccctgc ttaaaaacct tcaaaggctc acatcacttc tcagatgaag    77580
agattgggga gacgttggta ataggacaca aaatttcagt taggcaggag gaaaaagttc    77640
```

```
tattgaagaa ctctattgta caatatggtg actatagtta ataacaacat attatacact  77700
tgaaaatcac taagagagtc catttttaagt gttctcatga ccaaaaaatg ataagtatat  77760
gaggtaatgc atatgtgaat tagcttgact gaggcattct acatgtatac atatttcgaa  77820
acatcatgtt gtacatcata aatgcataca ctttttagtt gtcaatttaa ttaatatttt  77880
ttaaacctac tctggccttt ttttcctttt ttgagacggg tggtctctgt ccccatgct   77940 agagtgcagt gcgcaatcat ggctcactgc agcctccacc tcccagtctc aggcgattct  78000
ccagtctcag cctcccaagt agctgggacc acaagcatga gccaccatgc ccgctattt   78060 gttttttgtat tttttgtaga gatgggatct cgccacatgg cccagtctgg tgtccaactc  78120
ctgagctcca gtgatccacc tgcctcagct tcccaaactg ctgggattac aggcgtgagc  78180
cactgtgcct ggtccactct ggtctttact caagtccctg gctttctctc agtctcttaa  78240
acttatgtgc ttagtaagat gaggactgaa aaatgtccac agaacatagt gacatggaga  78300
tactgagaac ctcaacgaca tctccattag ccacttcctc tgtgccattc cagtcctctg  78360
ggccccactg tggcaagcag tcctaccatg gcaaacatga aagctgatgt gccttgtctt  78420
agacccacac catatctctc tgaattcctg tcccagggct tctctggagg tacagcctgg  78480
gaaactcacg ggaatagaca cagggccttt gcacatgctg ctcccttttc ctgaaaaatt  78540
cctttgacat cttggttgtg ccttacacat gcctactcaa ccttaggatt gcagttcagg  78600
tttcactcct ttttttttttt tctttttgag acggagtttc actcttgttg cccaggctgg  78660
agtgcaatgg tgtgatcctg gctcaccaca acctctgcct cctgggttca agtgattctc  78720
ctgcctcaac ctcctgagta gctgggatta tagtcatgca ccaccacgcc cagctaattt  78780 tgtatttttta gtagagacag tgtttctcta tgttggccag gctggtctcg aactcccgac  78840
ctcaggtgat cggcccgcct cggcctaggt tccacttctt tatggaaatc ttccccagtt  78900
gccttgacta ggccaaagtc ccctcttctt aggctcttac agtgtcatgc acttctttttt 78960 tatcacagtg taaaccttgt aatgttgtgt ttaagtcata tctgttgtac ccatgagact  79020
gggagccaat tcatatattg tgagtgtaat cgaacagact tcccaggcca cccactagct  79080
aatcaaggca gggatgagtc cggaaagtga ctttgaaatc tagcaatgtt ggaacttgga  79140
aatcacacag gctgagatct gctcaggtgc ctgaacaaat atagcattgc ctgtggcgtc  79200
tccctcaaag tgccttgcat gtctgagccc cgttgcccct tcctttggtg tgcctgtgtc  79260
tcccggtaca gatgtgaagc ctggagacct gtggctgcct ctgcaggagc tccatgtttt  79320
caagccataa atcatcttag aattcatagc atctagatat attagttttc tattactgca  79380
gaacaaatcg ctcccaaatg tagaggcttc aaagaatgcc cattgattgg ccttaatttc  79440
tgtaagttag aatctgggca ggtttgcctg agttctccac tccaagtctc ataaagccaa  79500
gctgggctgt catctggagg ctctgagtaa aaatttgttt ccaggttcat ccagattgtc  79560
aggtgatttc agttccttgc agttgttgtt cgactcacta ccccaccacc accccgaaaa  79620
cctcatttcc ttgctagctg cctgcagaga gccactctca gcttccacag gctgcttgca  79680
ttccttgttg tggggccgct acctcctcaa gccagaaata gggcatccag ttcttctcat  79740
gcatcctacc cctctgactt ttccttctgc cgataaccaa aaaaaacgtt ccgccttcaa  79800 acgtcgtat gattagacta agcccatcca gataaattcc catatgccat atactataat   79860
gtcatcacag cagtaatacc cgggacaaaa ttcatggggg tcatcttaaa attctgccta  79920
tcacaccagg tatagtagag gcttgttttta gtgcaagtta aacattaagc agcaacatca  79980
cgatagtgct gcatttgaaa ataactacta gcaactgaac atgtctggga gttctgctcc  80040
```

```
actttaattt ccatctcaaa aggagctggg ttttccttgg ctgttacaaa tgggcaataa   80100
tgattgagct taagaataat caatgtccac ataaaaatct tttataacat agtgagagtg   80160
tgacatataa aggtgttagt tcaccggccc taaattttag gagaattttt aaaaaggcac   80220
ttatctggtt taatccataa taaagacatg agttgggctt tagtgaaaaa tctaggctgg   80280
tttctgtgtt cagtgaaaga agatttgaga gttctcttaa ttacaaccct tgatcaaacc   80340
taccacatta atctgtttat tgcattgtat ggttaccaaa agtgatatat tcagccctct   80400
atttattaag aaacagttac agaaagtgag gcactctcct gtgttactga gggtgcataa   80460
aaatataaag caccatgtgt cttccctaga gaagtttcaa aactagcaag caaatagcta   80520
ttaatgctaa tgtttgtgtg atagggaaca tatgagtagt aattattcca caaacaattt   80580
tttgagtgct gtttacattt gaggcacagt tcaggcacga ggatttcaaa aggagattgt   80640
gtagcatgat ggcttgttaa aaatatgatt ttggaatcag atttgctcaa gtcccagtgc   80700
tacagcatac catccttcaa aaaggtactt aagtctctga gtttgttttc tcatctgcaa   80760
aatataaata ataagaggac ctactgcgtc atgttcttgt gagcattaat gtgggtgatg   80820
aaatgtttat gaagcactta gcacaatacc tgacattttg tttgttatta ttatcaacat   80880
aaagtgccca ctttccagtc atgcaagaag aaaacataat atatgtcacc atagaagtat   80940
agaacaattg tgggaaatac cagtaagaga gatatagctg tataaataag gtaaagatga   81000
ctgcctagaa gatctaggat gataccatat tagaagttgc atctgaactc tccttgggga   81060
ctggccaaag tttcatcaag tgtcatgtca gtaggttggt gctataaata tatagcttgc   81120
aaagctatag acttactata aaccatagct gtggtccagc ttagactcat tatggtggtg   81180
gagtatcttg attaatggcc tctgcagaag cttcccaggt cttctcatca tcataatctc   81240
agatagcttc atcttcaact tcctttttt tgttgttttt gagacagggt ctcactctgt   81300
catccaggat ggagtgcagt ggcacaatca tggctcactg cagcctcgac ctcaggagct   81360
caagccatcc tcccacttca gcctcccgag tagttgggac tacaggcatg caccactacg   81420
cccggctaat ttttcattt ttttgtagag tcagggtctc cctatgctgc ccagtctggt   81480
ctcaaactcc tgggctcaaa ccatctttcc acctcggcct cccaaaatgt tgggattaca   81540
ggtgtgagcc accacacaca gcccatcttc aacttctttt agcaccatga agctgaacat   81600
agtaaaaaag taaaatcatt ctggacctaa tctgatgcaa tttatttaat tgttaagtga   81660
atgcacacat caaaattcat acaagtatgg ggcagcgctg ctaatttatt tacaaaacac   81720
ctggcaaata ctgctactct aatactgtgc ttccacttt gattttcctt aggaaaacat   81780
gttccttcag tcgtcaatgc tgacctgcat tttcctgcta atatctggtt cctgtgagtt   81840
atgcgccgaa gaaattttt ctagaagcta tccttgtgat gagaaaaagc aaaatgactc   81900
agttattgca gagtgcagca atcgtcgact acaggaagtt ccccaaacgg tgggcaaata   81960
tgtgacagaa ctagacctgt ctgataattt catcacacac ataacgaatg aatcatttca   82020
agggctgcaa aatctcacta aaataaatct aaaccacaac cccaatgtac agcaccagaa   82080
cggaaatccc ggtatacaat caaatggctt gaatatcaca gacggggcat tcctcaacct   82140
aaaaaaccta agggagttac tgcttgaaga caaccagtta ccccaaatac cctctggttt   82200
gccagagtct ttgacagaac ttagtctaat tcaaacaat atatacaaca taactaaaga   82260
gggcatttca agacttataa acttgaaaaa tctctatttg gcctggaact gctattttaa   82320
caaagtttgc gagaaaacta acatagaaga tggagtattt gaaacgctga caaatttgga   82380
```

```
gttgctatca ctatctttca attctctttc acacgtgcca cccaaactgc caagctccct   82440
acgcaaactt tttctgagca acacccagat caaatacatt agtgaagaag atttcaaggg   82500
attgataaat ttaacattac tagatttaag cgggaactgt ccgaggtgct tcaatgcccc   82560
atttccatgc gtgccttgtg atggtggtgc ttcaattaat atagatcgtt ttgcttttca   82620
aaacttgacc caacttcgat acctaaacct ctctagcact tccctcagga agattaatgc   82680
tgcctggttt aaaaatatgc ctcatctgaa ggtgctggat cttgaattca actatttagt   82740
gggagaaata gcctctgggg cattttaac gatgctgccc cgcttagaaa tacttgactt    82800 gtctttaac tatataaagg ggagttatcc acagcatatt aatatttcca gaaacttctc    82860 taaactttg tctctacggg cattgcattt aagaggttat gtgttccagg aactcagaga    82920
agatgatttc cagcccctga tgcagcttcc aaacttatcg actatcaact tgggtattaa   82980
ttttattaag caaatcgatt tcaaactttt ccaaaattc tccaatctgg aaattattta    83040
cttgtcagaa acagaatat caccgttggt aaaagatacc cggcagagtt atgcaaatag    83100
ttcctctttt caacgtcata tccggaaacg acgctcaaca gattttgagt ttgacccaca   83160
ttcgaacttt tatcatttca cccgtccttt aataaagcca caatgtgctg cttatggaaa   83220
agccttagat ttaagcctca acagtatttt cttcattggg ccaaaccaat ttgaaaatct   83280
tcctgacatt gcctgtttaa atctgtctgc aaatagcaat gctcaagtgt aagtggaac    83340 tgaattttca gccattcctc atgtcaaata tttggatttg acaaacaata gactagactt   83400
tgataatgct agtgctctta ctgaattgtc cgacttggaa gttctagatc tcagctataa   83460
ttcacactat ttcagaatag caggcgtaac acatcatcta gaattattc aaaatttcac    83520 aaatctaaaa gttttaaact tgagccacaa caacatttat actttaacag ataagtataa   83580
cctggaaagc aagtccctgg tagaattagt tttcagtggc aatcgccttg acattttgtg   83640
gaatgatgat gacaacaggt atatctccat tttcaaaggt ctcaagaatc tgacacgtct   83700
ggatttatcc cttaataggc tgaagcacat cccaaatgaa gcattcctta atttgccagc   83760
gagtctcact gaactacata taaatgataa tatgttaaag tttttttaact ggacattact  83820 ccagcagttt cctcgtctcg agttgcttga cttacgtgaa aacaaactac tcttttaac    83880 tgatagccta tctgacttta catcttccct tcggacactg ctgctgagtc ataacaggat   83940
ttcccaccta ccctctggct ttcttttctga agtcagtagt ctgaagcacc tcgatttaag   84000
ttccaatctg ctaaaaacaa tcaacaaatc cgcacttgaa actaagacca ccaccaaatt   84060
atctatgttg gaactacacg gaaacccctt tgaatgcacc tgtgacattg gagatttccg   84120
aagatggatg gatgaacatc tgaatgtcaa aattcccaga ctggtagatg tcatttgtgc   84180
cagtcctggg gatcaaagag ggaagagtat tgtgagtctg gagctaacaa cttgtgtttc   84240
agatgtcact gcagtgatat tatttttctt cacgttcttt atcaccacca tggttatgtt   84300
ggctgccctg gctcaccatt tgttttactg ggatgtttgg tttatatata atgtgtgttt   84360
agctaaggta aaaggctaca ggtctctttc cacatcccaa actttctatg atgcttacat   84420
ttcttatgac accaaagatg cctctgttac tgactgggtg ataaatgagc tgcgctacca   84480
ccttgaagag agccgagaca aaacgttct cctttgtcta gaggagaggg attgggaccc    84540
gggattggcc atcatcgaca acctcatgca gagcatcaac caaagcaaga aaacagtatt   84600
tgttttaacc aaaaaatatg caaaaagctg aactttaaa acagctttt acttggctt      84660 gcagaggcta atggatgaga acatggatgt gattatattt atcctgctgg agccagtgtt   84720
acagcattct cagtatttga ggctacggca gcggatctgt aagagctcca tcctccagtg   84780
```

```
gcctgacaac ccgaaggcag aaggcttgtt ttggcaaact ctgagaaatg tggtcttgac   84840
tgaaaatgat tcacggtata acaatatgta tgtcgattcc attaagcaat actaactgac   84900
gttaagtcat gatttcgcgc cataataaag atgcaaagga atgacatttc tgtattagtt   84960
atctattgct atgtaacaaa ttatcccaaa acttagtggt ttaaaacaac acatttgctg   85020
gcccacagtt tttgagggtc aggagtccag gcccagcata actgggtcct ctgctcaggg   85080
tgtctcagag gctgcaatgt aggtgttcac cagagacata ggcatcactg gggtcacact   85140
catgtggttg ttttctggat tcaattcctc ctgggctatt ggccaaaggc tatactcatg   85200
taagccatgc gagcctctcc cacaaggcag cttgcttcat cagagctagc aaaaaagaga   85260
ggttgctagc aagatgaagt cacaatcttt tgtaatcgaa tcaaaaaagt gatatctcat   85320
cactttggcc atattctatt tgttagaagt aaaccacagg tcccaccagc tccatggag    85380 tgaccacctc agtccaggga aaacagctga agaccaagat ggtgagctct gattgcttca   85440
gttggtcatc aactattttc ccttgactgc tgtcctggga tggcctgcta tcttgatgat   85500
agattgtgaa tatcaggagg cagggatcac tgtggaccat cttagcagtt gacctaacac   85560
atcttctttt caatatctaa gaacttttgc cactgtgact aatggtccta atattaagct   85620
gttgtttata tttatcatat atctatggct acatggttat attatgctgt ggttgcgttc   85680
ggttttattt acagttgctt ttacaaatat ttgctgtaac atttgacttc taaggtttag   85740
atgccattta agaactgaga tggatagctt ttaaagcatc ttttacttct taccattttt   85800
taaaagtatg cagctaaatt cgaagctttt ggtctatatt gttaattgcc attgctgtaa   85860
atcttaaaat gaatgaataa aaatgtttca ttttacaaga ggagtgtatg ataaatatat   85920
catagagaaa ttggtctttta atataaaaga aattgccata tacactgaat tttttcagaa   85980 ctcttttta aaaactattt ggtagaaatc aaaggggaag cagttttcat gacactttta    86040
ctttaagata cttattaata gataaattct atcttgattc cctactcaga agacataaag   86100
tcagaatgcc tggctgttgg tagcctttgt gcaattcccc caaatgaaac aactttggca   86160
accctttcca cttctactgt cccccttggtt cctctgcatc agtccatagc atcctctatc   86220
cagtatgaat cttgagatat ctaatgaaat ttacctgaga ataactagaa attatccaag   86280
cataagaaaa ggaagttgct tcagaatgaa aagaagataa acctccaata taccatcttt   86340 ccttttagt taaatcttac agcatgagtt acctttttaat atgtgcttct aagaaactga   86400
ccaaaataat gtgtcatagt gttatttaat acgcacaaag tggaaagcag tgcaagtttg   86460
ccaaggacaa tttaattttg tcacattgca tgctgttttg tgaccatgaa gagtttatac   86520
aaagatgttt atgcttgtgc ttgttgaggt atagggacaa atatctaaaa gcaagatcag   86580
atgggtgtgg tatctcacac ctataatcct tggattaaaa tctacctcaa ttgtaggact   86640
accagttgaa ccacatgctt cccactgccc tcagcaaagg gcaccttagt tagaggaaag   86700
gtagagcctt tctatggagg aggaatttgt gaggtttgag ttttatcagc tacctgggag   86760
tcagaccctg atagattctc cttcacactc cctggacctt ttcctgccaa gtggaggctc   86820
tcactcagag gaaatctcca ttctttgat gcaggtcatt catactcaga tattctgcac    86880
tgttcaagca ataaaaattg aatgagcacc tattatgtac accagttggc actgtgtcaa   86940
aatgtacttg tgcagagacc ttggatcatt ggtgacaggt cttcttctcc tctgcatttt   87000
tctcaagacc aggcctcagt gtagcatgtt tccatggagt gaaagagggg aaggaagagt   87060
gggctttgga aagtggcagc tgtgtcatag cagtcagcct ctgtgtatgt gaaggacttt   87120
```

```
ccagagcccc cccactaaag cctccatgct cctcctggga ctgccacagt tcttgaaact   87180
atccatacag tcttcatgag ttatttttaa tttttttttc ttcttttctc tttcctcctt   87240 ttccccttt ccccactccc tagttagatc tttaaaaatg caattgtaac ctttatcttc    87300
ccttcaccag acactcccta cagggcaagc ttatgtatac gcttacctaa aagctccaga   87360
gccagaaatc tctcccactc ggggactgcc tcaagagaca gcagtcaatt tacaacctaa   87420
agcatgccca caacaaaact ctctcccacc tggaggatat cttgaggcaa tggtcacttt   87480
acaacctagt tctgcctgca atggcaccag ctcaaccacc tggtacataa gacacaaaag   87540
caagttgcat agacctcacc ttctcactcc cttccctgca tgccattaat gccaactccc   87600
cctttaaaag cccctgcttt ctgccccaaa agcaaagtga tacccttaaa gtcaggagcc   87660
tatacttctt cccctaagc taattttgg aataaaagtc atttattga gaacctccat      87720 aaactgttgg tgggaatata aattagtaaa ccatgatgga gaacagtttg gagtttcctc   87780
aaagaactaa aaatcgaatt accatatgac ccagcaatcc cactgctggg tatacaccca   87840
aaagaaagga agtaattata ttgaagagat atctgcactc ccatgtttgc tgcagcactg   87900
tttacaatag ctgagatttg cagcaaccta agtgtctatc aacagatgaa tggataaaga   87960
aaatgtggta cacatacaaa atggagtact agtcagccat aaaaagaatg agatcctgtc   88020
atttgcaaca acatggatgg aactggaggt cattatgtta agtgaaataa gccagacaca   88080
gaaagacaaa tatcaaatgt tctcacttat ttgtgggatc taaaaattaa aacaattcaa   88140
ctcatggaca tagagagtag aaggatggtt accagaggct gggagggga gtggaagcta    88200 ggggaggtgg ggatggttaa tgggtacaaa aaaatagaaa gaatgaatta gatctactat   88260
ttgatagcac aacagagtga ctatagtcaa taataattta actgtacttt ttaaaaataa   88320
caaaaatcgt gtaattggac tgtttataac tcaaagaata aatgcttgag gggatggata   88380
tcccattctc catgatgtga ttacccattg catgtatcaa acatctcgt gtacccccta    88440 aatatataca cctactatgt atccacaaaa actaaaaata aaattttgtt taaaagtca    88500 cttctcttat accacatctc acccttgtta attggactct gcgagggtg aacaactgga    88560 cctgtgattc agttaaaatt agatcctcag gcaccttctg ttgagaaaga ataggtctca   88620
aatgttgcaa atctcttta cctttctcaa ggttctagcc tctcctatca ccaatttagg    88680
taagaatata aaatcatcag gcctgtgtta cctcaactat cttcctcttt gatccaaaac   88740
gtatacttag tggacaaagg cttttggac aactaatatg tgctaagtct taaggtgggt    88800
tcagaaatgg ccaggatcca tcaactaatc aatggataaa taaatgtga tctatccata    88860 caatggaata ttattcagcc ataaaatgta atgaagcact aatactatga tgcaacatgg   88920
atgaactttg aaaacatcat gctaatagac caataacagg ctctgaaatt gtggcaataa   88980
tcaatagctt gctaaccaaa aagagtccag gaccagatgg attcacagcc gaattctacc   89040
agaggtacaa ggaggaactg gtaccattcc ttctgaaact attccaatca atagaaaaag   89100 agggatcct ccctaactca ttttatgagg ccagagtcat cctgatacca aagccgggca    89160
gagacacaac caagaaagag aattttagac caatatcctt gatgaacatt gatgcaaaaa   89220
tcctcaataa aatactggca aaccgaatcc agcagcacat caaaaagctt atgcaccatg   89280
atcaagtggg cttcatccct gggatgcaag gctggttcaa tatatgcaaa tcaataaacg   89340
taatccagca tataaacaga accaaagaca aaaccacat gattatctca atagatgcag    89400
aaaaggcctt tgacaaaatt caacagcctt tcatgctaaa aactctcaat aaattaggta   89460
ttgatgggat gtatctcaaa ataataagag ctatctatga ccaacccaca gccagtatca   89520
```

```
tactgaatgg gcaaaaactg gaagcattcc ctttgaaaac tggcacaaga cagggatgcc   89580
ctctctcacc actcctattc aacatagtgt tggaagttct ggccaaggca attaggcagg   89640
agaaggaaat aaagggtatt caattaggaa aagaggaagt caaattgtcc ctgtttgcag   89700
atgacatgat tgtatatcta gaaaacccca tcgtctcagc cccaaatctc cttaagctga   89760
taagcaacat cagcaaagtc tcaggataca aaatcaatgt acaaaaatca caagcattcc   89820
tatacaccaa taacagacaa acagagagcc aaatcatgag tgaactccca ttcacaattg   89880
cttcaaagag aataaaatac ctaggaatcc aacttacaag ggatgtgaag gacctcttca   89940
aggagaacta caaaccactg ctcaaggaaa taaagagga cacaaacaaa tggaagaaca    90000
ttccatgctc atgggtagga agaatcaata tcgtgaaaat ggccatactg cccaaggtaa   90060
tttatagatt caatgccatc cccatcaagc taccaatgac tttcttcaaa gaattggaaa   90120
aaactacttt aaagttcata tggcaccaaa gaagagcccg catcgccaag tcaatcctaa   90180
gccaaaagaa caaagctgga ggcatcacgc tacctgactt caaactatac tacaaggcta   90240
cagtaaacaa aacagcatgg tactggtacc aaaacagaga tatagatcaa tggaacagaa   90300
cagagccctc agaaataacg ccgcacatct acaactatct gatctttgac aaacctgaga   90360 aaacaagca atggggaaaa gattccctat ttaataaatg gtgctgggaa aactggctag   90420
ccatatgtag aaagctgaaa ctggatccct tccttacacc ttatacaaaa attaattcga   90480
gatggattaa agacttaaac gttagaccta aaaccataaa accctagaa gaaacctag    90540 gcattaccat tcaggacata ggcatggaca aggacttcat gtctaaaaca tcaaaagcaa   90600
tggcaacaaa agccaaaatt gacaaatggg atctaattaa actaagagc ttctgcacag    90660 caaaagaaac taccatcaga gtgaacaggc aacctacaga atgggagaaa attttcgcaa   90720
cctactcatc tgacaagggg ctaatattca gaatctacaa ggaactcaaa caaatttaca   90780
agaaaaaaaa aaaacaaccc catcaaaaag tgggcaaagg acatgaacag acacttctca   90840
aaagaagaca tttatgcagc caaaaaacac atgaaaaaat gctcaccatc actggctatc   90900
agagaaatgc aaatcaaaac cacaatgaga taccatctca caccagttag aatggcaatc   90960
attaaaaagt caggaaacaa caggtgctgg agaggatgtg gagaaatagg aacactttta   91020
cactgttggt gggactgtaa actagttcaa ccgttgtgga agtcagtgtg gcaattcctc   91080
agggatctag aactagaaat accatttgac ccagccatcc cattactggg tatatacca    91140 aaggactata atcatgctg ctataaagac acatgcacac gtatgttat tgcggcacta     91200 ttcacaatag caaagacttg gaaccaaccc aaatgtccaa caatgataga ctggattaag   91260
aaaatgtggc acatatacac catggaagac tatgcagcca taaaaaatga tgagttcatg   91320
tcctttgtag ggacatggat gaaattgaa atcatcattc tcagtaaact atcgcaagaa    91380
caaaaaacca acaccgcat attctcactc ataggtggga attgaacaat gagaacacat    91440
ggacacagga aggggaacat cacattctgg ggactgttgt ggggtggggg gaagtgggag   91500
ggatagcttt aggagatata cctaatgcta aatgacgagt taatgggtgc agcacaccag   91560
catggcacat gtatacatat gtaactaacc ggcacattgt gcacatgtac cctaaaactt   91620
gaagtataat aataaaataa aataacgaaa acaaagcaga catagacagt atgcaaatta   91680
aaaaaaaaaa agaaaacatc atgctaagtg aaagaagcca gacacaaaag accctatatt   91740
gtatgattcc actgatatga aatgttcaga ataggcaaat gcacagagac agagagtagg   91800
taagtagttg cctgaggcag tagagggttg agggattggg agaagatggg catggctatt   91860
```

```
caggggtctg ggggtttcttg ttgaagttat gcaaatgttc taaaattgat tggagtgatg   91920
attacacaac tctgtgaata ttctgacagc aatatttctc ttcctggccc attttttggg   91980
tggtttttct ggcattgctg caccatgtct gaagctcctg gcacttacac tcttgaagtc   92040
ttctctatca gctttccgg accctctgct ttttcttgg aattgatcaa gatttgccag    92100
atcatagttt ggcactgacc tctgattgtt ggcttctgta agaaccccca aactacagga   92160
attggaatgc ctggtctggt caaaggagag gatctggttg attctggaca aatcactcca   92220
cctcgctgag tatgattctt catctataga gtggactgaa tgatctccaa gtactttcaa   92280
atatgaaaac tactctagtt tcctcaagct gccacaaact gcacggctta aaaaacagaa   92340
gtttattgtc tcatagttct ggaagttaaa agtctgaaat caaggtgtct gcagggccac   92400
gctccctctg aaacctatag agaaagatcc ttcttgcctc ttttggcgtc tggtgtttgc   92460
cagcaatcca cagtattcct taccttgaag acgcaggact ccagtctctg cctctgttgt   92520
cacatggcca tcttccctct atgtctctct cctcttctta agaacagaag tcatagtgga   92580
ttaaggaccc accctactcc tactatgacc tcatcttgac taatcacatc tgcaacaacc   92640
tcatttccaa atgaggtcag cttctgaggt cctgggggtt aagacttcaa catgtaattt   92700 tgtgggatg cagttcaacc cataaccaca accgtggctt ttcttcctta gaagttactg    92760
agaactccat gaaagttgaa aatgcccttg tgaatgggag agtcattcac gactattgga   92820
agaaaaaggc aattttcctg tcggctatta ataaagctat tatagcaata tggcaaggtt   92880
tctactctga ttatccttga acttaaagtc ataatagtat ccattatttc cagtgagtac   92940
aagggaaggt cacattactg tgttctcttc attgctgccc ttaaatgctt tcagggaaag   93000
ggggaataga taaagcccca ggccttactc agcaatcggg gcaagacgta gcagtgtttt   93060
gaacctgaag gagacaaccc agggcttcct gtgccaatga ctcagaatgg aaaatggtct   93120
ttataaatgt ccctccagtg tgcaaagggt agagactaga atttaaaatt catcagatat   93180
taataagaaa aaccaaagca aacaaaaaat ctacttatga tcatagaaca ttgccattgg   93240
ggagctgttt attatttgag ccttttaaa atttctttt ttgtgtgtga gaaacatatt     93300
tctaggagta gagagaaaag gctcccctgt tttatgtact cagtctttcc ctcctttgag   93360 attacccta aactatttta gggatagctc cctggttatc tcagtaatga tgaccccaga    93420
agttcagaga taattaagag ccatgtctgg gtttgtgaga gaagcccaaa tgcagttatt   93480
caaaccagaa accagagcct cgttgttgac tcttccctct caccgtgaga tccaaccact   93540
catcaaggac tctccatttg acctcctaaa ttcttctccc atccatcccc catctttgtg   93600
tccatcatca acaccccttg tccaagatac ctgcattgct cactagcttc ctggtatcca   93660
ctgtgttccc tccaattcag ttccagaagc tagagtgatt cttatcaaaa gtgtggcttc   93720
ttctgaatta ggctgacaat ctcaactcct ggagaagacc cacaatccct ttgtgacctt   93780
ccatttgtgc acccctccag cctccactct aagcacccc accagttgtc ttcggtttgt    93840
gctaagaaca caccaaactc ccatctcagc acctacacac atacgactgc cccaaggcac   93900
gtctgactcc agacttcact tagctaattc ctgcttaccc tacagggaga ggttaaatgc   93960
cactgagagc agcttattc taacctccaa atcccactca gacgtccccc ttatactatc    94020
ttctcagcat ttaccacaag ttttgttgga taaatgatag agaaatgaat agtgtggcta   94080
caacacgtgt cttccattag actgtaggcc ccaaagatca gggaaggtga ctttagtcc    94140 atcactctgt cccagtatt catcaccacg cctgatacac aacaaagact ttcaataaat    94200 actttttcaag tgaatgaatg aatgagcaaa ggttcaggtt ggcttctcta gctacaccct   94260
```

```
aggacagata cagtaaggtc aggccacatt gtcaaatgtc ccactgtagc agtcatgcat    94320
aagggtaggc cttctgcacc ttccatgttc ccattgccca ctcatggtgg caagcatgct    94380
gattgtctct tgagtactac acagcaccaa caatctcagg taccatgatg ctgattccat    94440
gaggctctga gcctgggcaa gaatcattta cattcttatt gagtgttggg ctatggttca    94500
gagcaagcac agcataagcc aagaagaagg caaaggatgt tatcatgaaa tggaagaagt    94560
gtgtaaattg agtgcaacta tgtagaaatc atgcgatggt ccataaacaa atatgggcat    94620
aagagcaagt ctgaattcag gctcatggaa ggctggtgtg gctctgccag catgtgctag    94680
ttcactagtt ctatgccacc attcaaagca gaatttcccc aagtcaattc catacgtaag    94740
tactccatta aaaacgctcc tgagttcaaa caggtttgga aacatcttag ttactatagt    94800
atttctcata tgccttgtga tctccaaaag agaactatac tacactgtgt cccaaactta    94860
cttgatcacg attcctttt ttctttttt gcagggcatc tcctagagct aatgttctct    94920
ctctctcttt ggaaatgcag atttgaaggc ctgagattta cccagcctaa tgaaccctg    94980 aaaatgttcc caggtatatg atgatagtca ccatattgac atgaattgtt ctgttttaaa    95040
aacagaaaaa aaaccacaa taatctaggc catgtcccct gaggcccttta tcaagatg    95100 attagctcct tgaactggtc ctattaggtc tctagaggag agattattgc ttctgaagag    95160
agatgtgaca acaaggcaga atatgattca gaagcggtaa ataataaaac taaaaatgat    95220
agcttctcct ttggtacagg gtggagaggt taatattcat ttctaaagca tcattagcca    95280
tataaagtat aatttcagca cttgacataa actgaaaaca cacataatcc tcccattgag    95340
tgggctaacc ttggctgtgg ctggatgagc tctctaggga cttattaggg aatatggtac    95400
tttcaaagat gttaaatcca gtggaagtga ctgaagcaat tagtctctga tcttgagaga    95460
atttccacct ttgaatcagc aaaccctatc caaccgaagt tgagtactct agagatgata    95520
ttgtttatac tggaaaccaa tatgaaatat gtgaatgtat gtataatgta catatataga    95580
cacatgtaga ggagtatta tatatagata gagatgttca ttattgactg cttagtagat    95640 ataagaaga gaataaaatt taaaaataag gaaataagga aaatgagagc atgatgtagt    95700
aatttttcta tttctatta aatgttcttt cctaacatcc agtttgttgt ggagtcacca    95760
aaaagcatca cctcatcaaa acacacacac acacacacac acacaccaac aaaagacata    95820
acctaccagc caaaaaaag cccaggacca gacggattta cagctgattt ctatcagagg    95880
tgcaaagaag aaaagagctg ggactctttc tactgaaact attccaaaaa attgaaaagg    95940
agggactcct ccctaactca ttctatgagg ccagcatcat cctgataccc aaacctggca    96000
gagacacaac aaaaaagaa aacttcaggc caatatcctt gatgaacatt gatgcaaaaa    96060
tcctcaacag gctgggtgtg gtggctcatg cctgtgatcc cagcactttg ggaggccaag    96120
gtgggcagat cacttgagag cagcagtttg gaccagcat ggcaaaaccc cctctctact    96180
aaaaatacag aaattagccg ggtgtggtgg cttgtaatct cagctacttg ggtggctgag    96240
gcatgagaat cacttgaacc caggagacgg agcctgcagt gagccatgat tataccactg    96300
cgctccagcc caggggacag agcaagactt tgtctcaata aaaaagtcc tcaacaaat    96360 actggcaaac tgaatccagc agtacatcaa aaagctaatc aaccacaatc aagtaggcct    96420
catccatggg atgcaaggtt ggttcaacat actcaaatca atagatgtaa ttaatcacat    96480
aaacagatct aaagacaaaa accacatgat tgtctcaata cgtgcagaaa aagcctttga    96540
taaaattcaa cattccttca tgttaaaaac tctcaataaa ctaggtattg aaggaacata    96600
```

```
cctcaaaata taagagcca tgtatgacaa acccatagcc aataccatat tgaatgggaa   96660
aaatctggaa gtattcccct tgaaaacaag aaagacaaaa tctgcatcat tccctgaggg   96720
gcatttcttt tcctggctca gcacataggc taaaagagg ccaagagtga gcagatctgt    96780
gagctgtggt tcaacgtctg gtggtgggga agagaaaaga agaaagaatt gggaaggaga   96840
gagaagaaac aaggccttgt gagtggggaa agatgcaggt aggagtcagt caagtattta   96900
tcttgaggtg tctatctcac atcagtttct ctttgaggca gtggttttca aattcggcct   96960
atatcaccta aagggcttgt taaaacacag tctggggcat gcctgacaag tgtgcagctc   97020
cagtgagtta ccaggtgctg ctgatgctgc tgattgggga acacactttg agaaccactg   97080
gtctaagcat cccccaagtg cacaactcaa aatcaacaat ttctacctcc accttagaca   97140
gcactttgct cctgtatcat ggcacttctt tgttttatct tggtcagagt tagtagcttg    97200
atctccctcc tctgtaaatt ctgtagggga ctgaagattg taaattcctg gaaggcagag   97260
gccacagttt actcatgcct gtatcctcca gagcacaaag tacggtacgt attagttagc   97320
agttgtttaa tcaatgtttg tggaataaaa ttctagaaag tgatctgata aatatgtgta   97380
ttatgtaact gatgcataca ttaacctttc cagagattta catggtttgt ttactgatgg   97440
caatatctta aaaccaaaca aatgcatttc taatgatgtt catttaagca atgcaccaga   97500
tctgttgagg ggatatagtt ttggcaaaga cgtgctgact ggttcttaaa ccacaacggc   97560 tggattttc tggctttcct gctcctctga cttatcagga gagctttgcg tacctcccga    97620
gcctccaaca gccagaagtt tcaagttagc cactaatctg aacacacgat tatcatgttc   97680
tgatcacaaa atatgaaaca ttacaaaagg aaggctcatt taattttcac atgtacacag   97740
tccaaagata aggtgtggct ccttattcgc attactctgc gaacccaaat gcacataggg    97800
agccacacca gatgggagtg gctccctatc tgcattactc tgtgaaccca aaatatctga   97860
gacaagcctc agtcaattta gaaagtttat tttgccaagg ttaaggatac acctatgaca   97920
cagcctcaag agggcctgac aacatgtgcc caaggtggtt tgggtgcagc ttagttctat   97980
acattttagg gagatatgag acatcagtat gtgtaagatg tacattggtt cggtccagaa   98040
aggctggaca actcgaagca ggggagggga cttcaggtc ataggtagat aagatacaaa     98100
aggttgcatt attttgggtc tctgatcagc cttcactga atatacaatt cacatggaag     98160
aggagttcga gatcagcctg gcgaacatgg caaaactcca tctctactga aataccaaaa    98220
attagctggg tgtagtggca ggtgcctgta atcccagcta ctctggaggc tgaggcagga   98280
gaattgcttc aacctgggag gcagagggtg cagtgagctg ggatcgtgcc actacactcc   98340
agcctaggcg acagagcaag actccatctc aaaaaaaaaa aaaaaattgt aatcattttg    98400
actgtaaaat ataatttcca taaacccttt tataaccttt tattaaggag tgggttaaca   98460
ttccaagaaa acttgttaat ctgacacagg ggcccatatg ctggtcttgc atcagtgtac   98520
cttcaatatt aatggttaat ttatagagaa actgaactaa ttttatctct caaaattggc   98580
ctttacaatc tcttacacca tcctcttcca tggtagtccc tgggccttga ggagttgaat   98640
agttttaatt tctggattgg tgcctcacaa acacagctta ttttgattgg catcttctac   98700
caggtctgaa gatgaggctt taactggtgt cagtgtttaa gatttagcag gcttggtgt    98760 cttttttaga cccaggagtc aaagccttga aacttaatgg cacaaagact ttaagagcaa   98820
aatacagaaa gttacatgga tgtgataatc ttaatttaaa acaattttta aagtctcagt   98880 tttttttctaa gcaaatcaaa agttagtaac aatgacatag gaattatttt gataaaatgt   98940
aaaatttgtt tgttagacca gtcaccaaaa ggcaaaagaa aagaccttct gcagtgcaat   99000
```

```
tgctgttcct atgggtgtcc atttagataa cctgcaagtc aaactaatga aaagggtaca    99060
tcaattaatc agacatagga agagtgtttc ttgggtaata agtgaaaatt tttggattca    99120
tagaacaatt taaagccaag agcacagaat gttatgttgg aataaaatat ttcctttaga    99180
catttataaa acatttttag catcagactt caacaaacag ttagaaccta agggaaaaaa    99240
aatcttacag gaactgaaaa tgagttgaag gatagagtta ttatttcagg ccttttaaaa    99300
agggagagaa agctgaaaat agcaagacac aaaaaagttg aactttgggt tcaaaaaaat    99360
taaaatctct ggtaatttta ttaagaataa accatacct taagaaaatt ccaggccagg     99420
cgtggtggct cacacctgta atcctagcac tttgggaggc tgaggtgggt ggatcacctg    99480
aggtcaggat ttcgagacta gcctggccaa tatggtgaaa ccctgtctct actaaaaatg    99540
caaaattaac caggcatggt ggcatatgcc tctaatccca actactgggg agactgaggc    99600
aggagaatca tttgaacctg ggaggcggag gttgcagtaa gccactgcac tccagcctgg    99660
gcaacaagag caaaactccg tctcaaaaaa aaaaaaaaag aaaattccat tgttctaccc    99720
aattctttag tgtataagtg ctctttaaat attaaagccc aatctctaga aagaccatca    99780
taaataattt ccctttaatt ttaggcaact tgatcataaa gaccctttt ttccataaat      99840 tctcttttta caaaccttat tacagcttac acaggccatt catgatattc atgacatgct    99900
tggactttgt ggattgtcct gaacatatct ctttcttaaa caaccagtca ttttattcta    99960
ggacaaaaat ttaccataca atattttttc tcatataaaa ttattttgtt tttaaccttt   100020
cttgccaaaa atacctcttt acatttataa cttttttac attgctttta tttactggtt    100080
accattactt tgttttataa ataactttta aataaacttt gaattagaca aaaattattt   100140
tcttttaaat aagaacacat ttctttttt tagaaaaaat gttttcttat cacttaaaaa    100200
aattggaaat gacccagaca ttcaatgaat atctattatt taactttaga ttttaaattt   100260
tataagttta tttataagca tttatctcat tacatttacc taattaattt ttaacatagt   100320
ttaaccagat tacttataaa aactgtgata gttatcattt aaagttattt ccctgttaac   100380
catttatata cctgtgaatt tcaggttttc ctaagtgaga acctaaggt tagataaata     100440 gttttttgg tgtgttttt ttttttgcc aataactcag gatttagctg ttttcattaa       100500
ttgaacaata ttaaatgatt tatcaaagtt tacataaaga taattttcct ttgggctgca   100560
ttcatagctt tacaaccctc atgccaaatt ttaacatgta gcagcgataa aatataaaac   100620
cactttacca ataaatctaa acaataatgt atgttgacaa ttctgaagcc atttctaatt   100680
ctgtttcatg aatactttca aaaccagctt atttactaaa aatttacttg agtcatatga   100740
acttgaaaaa gcatttggct taaagtattt ttttctgata atttgatttt ggctgggtgc   100800
agtggctcac atctgtaatc ccagcacttt gggaggccaa ggtaggcaga tcacttgagg   100860
tcaggagttc gagaccagcc tggccaacat ggtgaaaccc cgtctctacc aagaatacaa   100920
aaattagccg tggtggcaca cgcctgtact gccagctact tgggaggctg aggcacaaga   100980
atcacttgaa cctaggaggt agaggttgta gtcagctgag attatgccac tgcactccag   101040
cctgggcaac agagcaagac tctgtctcaa agaaaagaaa atttgattta agcgcttttt   101100
tttcctttaa gccaattaat tagagcttgt tggtgtattt ttagtagtga aacattatat   101160
acatgacaca taaatacata gatatattag acatgcagat agaccttata gattcataag   101220
acctcttctt ttttcctccta tttttagactt ccaattttctt gatgacccat tttattcccc  101280
taggtagctg tcagctagat agccccaaat ttgcatatca aaggaatagc tctcaggtga   101340
```

```
aaaatcagat attgaaattt atatctcaag gtagagagag agagtctggt ggtgctagga   101400
gattaaaaac aaatgccaaa tcaaacataa atttatagaa atctatcagg attgtataag   101460
gaaataaatt ttatttagat aggtagttct attaaataca tttagtctct atcttttaac   101520
tggatctctg agctctgagc agagcaccca ttgaatcctg ggtctccaaa aagcgagaat   101580
tattatggga ctagaacaca tgatgctttt acagtatact ttttttttaaa aaaaaagata   101640 tttcttttaag tgtctaaact atactcttcc ttacttttaaa cacccaagag aaacctctgt   101700
tataataact attttagtta aagaaaaaaa gaaagaaaga aatcaggtaa cacaataaaa   101760
aaacaagcag tttaagatct gagatgaact tgtctcttta cgctctttgt gttccataag   101820
gaaaaacaga ggtttctccc caaaagggag tctggcactg tctgttttct ttaaggaatc   101880
ccatgctatt agaaactgta ttggttccct catgcagcag agggtggcaa aagaaagtag   101940
agacagcaga agtaaatggc gaaaacagaa ttcagtctac tgagaagaga aaaaaaactt   102000
tttctcaaaa aaaaaacaag gtcctaggag agaaaaaaaa accataacaa cctttttaaa   102060
tacacacaca cacacacaca cacacacaca cacacacaca catcatcatc atcatcatca   102120
tcttggatat tagcttttaa ttaaactgac ttttaaccat tgagctccat ttaaaaaaaa   102180 accttttttaa tctcattacc atatttaac taggataaat tgctgatatt tcaaaagtaa   102240
cacaaatatc aaaccagaaa gggctttaga aaccaaaccc agactgtctt gatgaaaaaa   102300 aagtggggggc agaagcttag ctatggaact gctgcatggg gcgacagcca ttactctttc   102360
agtttggctt ggctaacaaa aactggcctt attatgtaaa taaagccctc agggtagtca   102420
aaatcaagaa cctttctctt ttatccccctt ttgctggact gttttttcctt ctccctgctt   102480 tttttttttt ttttttccagc tgtggaattt agccaattca gaggtcttgt tccccgtaat   102540
gtggaacttt ccttcagatt tgatcaagtt ggatagagtt ggtcaaaccc aattgtcagg   102600
cctctgagct caagctaagc catcatatcc cctgtgatct gcacgtacac atccagatgg   102660
ctggttcctg ccttaactga tgacattcca ccacaaaaga agtgaaaatg gcctgttcgt   102720
gccttaactg atgacattgt cttgtgaaat tccttctcct ggctcatcct ggctcaaaag   102780
ctcccccact gagtaccttg tgaccccccca ctcctgcccg ccagagaaca attccctttg   102840 actgtaatt tccctttatct acccaaatcc tataaaacgg ccccacccctt atctcccttc   102900 gctgactctc ttttttggact cagcccacct gcacccaggt gaaataaaca gccttgttgc   102960
tcacacaaag cctgtttggt ggtctcttca cagggacacg catgaaattt ggtgccgtga   103020
cttggatcgg gggacctccc ttgggagatc aatcccctgt cctcctgctc tctgctctgt   103080
gagaaagatg cacctacgac ctcaggtcct cagaccgacc agcccaagaa acatctcact   103140
aatttcaaat ctggtaagcg gcctcttttt actctcttct ccaacctccc tcactatccc   103200
tcaacctctt tctcctttca atcttggcgc cacacttcaa tctctccctt ctcttaattt   103260
caattccttt cattttctgg tagagacaaa ggagacatgc tttatccatg acccaaaaac   103320
tctggtgccg gtcacggact gggaaggcag ccttccttgg tgtttaatc attgcaggga   103380 tgcctctctg attattcacc cacgtttcag cggtgtcaga ccacccaggg atgcctgcct   103440
tggtcattca tgcttagcgg caagttccgc ttttctgtgg gaggggcaag tacccccaacc   103500 ccttctctcc gtgtctctac cccttctcca ctttctgggg ggaggggcca gaacccctca   103560
accccttctc cttcaccctt agtggcaagt cccgcttttc tagggggcaa gaatcccccaa   103620 tcccttattt ccgtgcccccg acctctcatc tctgcacctc aaccccttat ttccgtgccc   103680
cgaccccttt cccgcttttc tggaggttaa gaaccctcga acccctttccc tccatgtctc   103740
```

```
tactctctct tttctctggg cttgcctcct tcactatagg caaccttcca ccctccattc   103800
ctccgtctcc cttagcctgt gctctcaaga acttaaaacc tcttcaactc acacctgacc   103860
taaaacctaa atgccttatt ttcttctgca atgccgcttg accccaatac aaacttgaca   103920
gtggttccaa atagccagaa aatggcactt tcaattttc cattctacaa gatctaaata   103980
attcttgtca taaaatgggc aaatggtctg aggtgcctga cttccaagca ttgttttaca   104040
cattggtctc tccctagtct ctgtgcccag tgcaacttgt cccaaatctt ccttctttcc   104100
ctcccgcctg tccctcagt cccaaccca agtgttgctg agtctttcta atcttccttt   104160
tctacagacc catctgacct ctcccctcct ccccaggctg ctccttgcca ggccgagcta   104220
ggtcccaatt cttcctcagc ctccgctcct ccaccctata atctttttat cacctcccct   104280
cctcacaccc ggtctggttt acagtttcat tccgtgagtg gccctcccg acctgccag   104340
caatttcctc ttaaaaaggt ggctgaagct aaaggcatag tcaaggttaa tgctccttt   104400
tctttatcag atgtctccca aatcagtgag catttaggct ctttcatcaa atatgaaaaa   104460
cccagcccag ttcatggctc gttcggcaac aaccctgaga cgctttacag ccctagaccc   104520
taaaaggtca aaaggccgtc ttattctcaa tatacatgtt attacccaat ccgctcctga   104580
cattaaataa aactccaaaa attaaattcc ggccctcaaa ccccacaaca ggacttaatt   104640
aacctcgcct tcaaggtgta caataataga dacagccaag tagcaacata tttctgagtt   104700
gcaattcctt gcctccactg tgagacaaac cccagccaca tctccagcac acaagaactt   104760
ccaaacgact aaaccgcagt agccaggcat tcctccagaa ccgcctcccc caggagcttg   104820
ctacaagtgc cagaaatctg gccaccaggc caaggaatgc ccgcaaccca ggattcctcc   104880
taagccgtgt cccatctgtg cgggaccca ctggaaattg gatggaaatc ggactgttca   104940
actcacctgg cagccactcc cagagaccct ggaactctgg cccaaggctc tctgactgac   105000
tccttcccag atcttctcgg cttagcggct gaagactgac gctgcctgat tgcctcagaa   105060
gccctgtaga ccatcacaga tgccaagctt taggtaactc tcacagtgga gggtaagtcc   105120
gtccccttct taatcaatac ggaggctacc cactccacat taccttattt tcaagggcct   105180
gtttccttg cctccataac tgttgtgggt attgacggcc aggcttctaa acctcttaaa   105240
actcccaac tctggtgcca acttagacaa tactctttta agcactcctt tttagttatc   105300
cccacctgcc cagttccctt attaggccga gacactttaa ctaaattatc tgcttccctg   105360
actattcctg ggctacagcc acacctcatt gccaccttt cccctagctc aaagcctcct   105420
tcacatcctc cccttgtatc tccccacctt aacccacaag tataagacac ctctactccc   105480
tccttagcga ccgatcatgc accccttacc atcccattaa aacctcatca ctcttacccc   105540
gctcaatgcc aatatcccat cccacagcat gcttgaaag gactaaagcc tgttatcact   105600
cgcctgctac agcatggcct tttaaagcct ataaacgctc cttaccattc ccccatttta   105660
cctgtcctaa aaccagacaa ggcttacagg ttagttcaga atctgcgcct tatcaaccaa   105720
attgttttgc ctatccaccc cgtggtgcca aacctatata ctctcctcaa tgcctccctc   105780
tacaacccat tattctgttc tggatctcaa acgtgctttc tttactattc ctttgtaccc   105840
ttcatcccag cctctcttcg ctttcgctta gactgaccct gacacccatt aggctcagga   105900
aattacctgg gctgtactgc cgcaaggctt cacaggcagc cccattact tcagtcaagc   105960
ccaaatttca tcctcgtctg ttacctatct tggcataatt ttcataaaaa cacacgtgct   106020
ctccctgctg atcgtgtccg attaatctcc caaacctcaa tcccttacaa aacaacaact   106080
```

```
cctttccttc ctaggcatgg ttagtgtggt cagaattctt acacaagagc caggaccgca    106140
ccctgtagcc tttctgtcca gacaacttga ccttactgtt ttagcctagc cctcatgtct    106200
gtgggcagcg gctgccgctg ctttaatact tttagaggtc ctaaaaatca aactatgctc    106260
aactcactct ctacatttct cataacttcc aaaatctatt ttcttcctca tacctgatgc    106320
atatactttc tgctccccgg ctccttcagc tgtactcact ctttgttaag tcccacaatt    106380
accattgttc ctggcccaga cttcaatccg gcctcccaca ttattcctga taccacacct    106440 gaccccatg actgtatctc tctgatccac ctgacattca ccccatttcc ccatatttcc     106500
ttctttcctg ttcctccccc gatcacgctt gatttattga tggcagttcc accaggccta    106560
atcgccacac accagcaaag gcaggctatg ctatagtaca agccactagc ctgcctctta    106620
gaatctctcc tcattttctt tccattgtgg aaatctatca tcaaggaaat aacttctcag    106680
tgttccgtct gctattctac tactcctcag ggattattca ggcccctcc cttccctaca     106740 cattaagctc gaggatttgc ccccacccag gactggcaaa ttagctttac tcaacatgcc    106800
ccgagtcaga taactaaaat acctcttagt ctaggtagac actttcactg gataggtaca    106860
ggcctttcct acagggtctg agaaggccac cgcagtcatt tcttcccttc tgtcagacat    106920
aattcctcag tttagccttc ccacctctat acagtctgat aacagaccag cctttattag    106980
tcaaatcagc caagcagttt ttcaggctct tagtattcaa ggaaaccttt atgtccctta    107040
cggtcctccg tcttcaggaa aagtagaacg gactaaaggt cttttaaaaa cacacctcac    107100
caagctcagc caccagctta aaaaggactg gacaatactt ttaccacttt tccttctcag    107160
aagtcagacc tgtgctcaga atgctacagg gtacagccca tttgagctcc tgtatagacg    107220
ctccttttta ttaggcccca gtctcattcc agacaccaga ccaacttaga ctgtgcccca    107280
aaaaacttgt catccctact atcttctgtc tagtcatact cctattcacc gttctcaact    107340
actcatacat gccctgctct tgtttacact gccggtttac actgtttctc caagacatca    107400
cagctgatat ctcctggtgc tatccccaaa ctgccactct aaactcttga agtaaataaa    107460
taatctttac tggcaaggct atgctgaacc tccttaggca ctctctaatt agatgtccta    107520
ggtcctccca attcttagtc ctttaatacc tgttttctcc ttctcttatt ccgtttagtt    107580
tttcaattca tacaaaactg tatccaggcc atcaccaata attctaaatg acaaatgttt    107640
cttctaacaa ccccacaata tcaccccttg ccacaaaaac ttccttcagc ttaatctctc    107700
ccactctagg ttcccacgcc gcccctaatc ccgctcgaag cagccctgag aaacatcgtc    107760
cattatctct ccacaccacc cccaaaatt ttcaccgtcc caacacttta ccactatttc     107820
gttttatttt tcttattaat ataagaagac aggaatgtca ggcctctgag ctcaagctaa    107880
gccatcatat cccctgtgac ctgcacgtac acatccagat ggccggttcc tgccttaact    107940
gatgacattc caccacgaaa gaagtgaaaa tgacctgttc gtgccttaac tgatgacatt    108000
gtcttgtgaa attccttctc ctggctcatc ctggctcaaa agctccccca ctgagtacat    108060
tgtgaccccc actcctgccc gccagagaac agccccttt gactgtaatt ttcctttatc     108120
tacccaaatc ctataaaaca gccccacctt tatctccctt ggctgactct cttttcggac    108180
tcagcccgcc tgcacccagg tgaaataaac agccttgttg ctaacacaaa gcctgtttgg    108240
tggtctcttc acacggatgt gcatgaaacc aatgaaaaaa agaccaaaac aacaaccaaa    108300
acagaaacaa agaacaacaa aaaacagcta agcaaagcaa acaatgccac aatttatagg    108360
ttggtgcaaa agtaattgtg cttttttgcca ttaaaaagaa tgcaaaaccg caattacttt    108420
tgcaccaacc taatatatga ttaccaagcg ctctaatggt aaggataaat taaaaccagc    108480
```

```
tgattgttaa ttttaacttt agccaagaca aaagcccaat tcagctactt acctaggaat   108540
ggggctcagg ctgaacactg ctctctacca tctttgaagc aggaaaaaac tcaaactcgc   108600
cttccctgtt ggaagtgagc tgaaattcca gaaaggagtt acctgcactc ttcatcatgg   108660
aagcaggaaa acttgccttc ctttttggga gcaagtgaaa ctccagaaaa ggagttatac   108720
agcaaaataa actttagatc tcaaccaaat ttggagagat cagggattct cttggtcggg   108780
ggtgggggtg tctcccaggc ctcagccaat tgtcctactg gcttgagcca taaagatagc   108840
tcaagctggt accaagcacc aacagtagat ttgtcaaagg tcaggggtac ctccactcag   108900
aatcccttca tggttaccaa tttgtgaatc caaaatatct gagacaggcc tcagtcaatt   108960
tagaaagttt attttgccaa ggttaaggat gcacccatga cacagcctca agaggtcctg   109020
gctacatggg cccaaggtgg tcggagcaca gcttggttct acacatttta gggagacgtg   109080
agacatcaat caacatgtgt aagatgtaca ttggttccgt ccagacaggc aggacaactc   109140
gaatcagggg aggggcttc cagatcacag gtagataaga gacatttgtt gcattctatt    109200
gggtctctga ttagccttc actgaatata caattcacat gggagaggag ggtggaggaa    109260
tagtcactta tgcctggtct gccttggtga aacgacaggg cagaggaagc aatcagatat   109320
gcatttgtct cacatgagcc tcagagggat gactttgagc tctgtctgtc ctttgtccac   109380 gaggaattc cttgtgggca aattgtgagg gaggtatgtc ttttttttt ttttatcttt     109440 gtagctgtct tatttaggaa taaaatggga ggcaggtttg cttgacgcag ttcccagctt   109500
gacttccctt tagcttagtg attttggggt cccaagattt attttccttt cacaactccc   109560
atctgatata tttaagggg aattcttttg tgcctacagc attgttagtg gaatgtggag    109620
cgacagcaag ggatgggcct agctggaatt taccaccagg gggcttggac tctttctcat   109680
gcgtcaacac caatcactgc caataggggg cagcaacaat ttgcctacag cctttaggct   109740
ttggttttag actcaaggag ctcagggtgt ggaatctcca ttgttttcc tctgaaactt    109800 ggcttcttat ctgcctgcgg actcaaatcc tcctcctgcc aatactacaa cagccacaga   109860
acaaatgcat tgaaactgag agaactggta agaggctaga tctagtgtaa atcagagaat   109920
gggcctcata aaaggagcag tttggaggaa cctaatcctt cacagtttgt ctagcaattt   109980
ctaggttcaa tcaattgagg gcttaactgg taaactcaag tggaaatttt ttattggctc   110040
ctggtgatgt cactcctggt gagtgtggga gaactggttt tctaggtgtg gggattcttt   110100
attctctgaa acacccacta ggaaacgccc tgaggccttt tcaccttctg tggtgtcagg   110160
acctctcatg taactggata cagtgctttt cccaaacaga ctatacacaa cagaaactca   110220
aaaaatagaa acgctaagtg ggaataaggg aaataaacta caagagtagt ggttctcgac   110280
cttggctgca catgggaatc acctgggagc ttcaatccgc aaggaccaat gccagggacc   110340
cccctacccc ctgcccccga gatttggatt aactggtctg catgcaacca gggcagctgg   110400
cgttttgaaa ggtccccagg tggttcccat gtacagccaa actgagaacc attgtcagat   110460
gtgcagtctt tgctcctggg tcaattaatt cctcacgccc actaactact ttagatgtct   110520
tatgctttga gcacatttaa aataaaaccc aaaacttaat aaaacaaagt tagtacacag   110580
agaaatagga acctgattaa aatagaacat gaagtcaagt cagtttggtt ttgttttaaa   110640
tctccaattg ccaccattaa ttctgctccc aaaggtcaat aatgctagcc tgctatttgc   110700
tttgttcact tctgaatgaa gcacttgtgt ttgctgacct tcaaacactt ccaggttgtc   110760
taagaggaag ccatgtggca ctttgacttt tgtgtgacct ggcaatttgt ttacatcaaa   110820
```

```
tccctttttaa ccctctgcag ttgacagtgg agaattcagt attttcatat gctgcctaac 110880
ctctagggtg gaaggcttta aacttgattt aggtcaagtt ggcagtgacc caggtgagcc 110940
cccaggaaac tgcacttcca cagccaaaac gtggccatcc accaacttag gcatgacagt 111000
tacagttttg aacctgctat taagtcccac aattctcttg gttagttaga gtaatcaaac 111060
ctgtcaaggg taggcagaac tggaggagtg aagaatggtt ttgagggtac agtggaaaaa 111120
tcaactttgg agtatgacaa gccagcctca acactcagtc actcttacca gctgtgagat 111180
cttaggtggg tttatcactg gctgtgagct tgacttgcct atctatacta taaaggaata 111240
aaagcccctt caggtggttt ttcttaaata aatggaatag acctgtcatg tgctggtaaa 111300
tgtttaacaa ctggttctca aggtggtggg ggcagccctg atttggagta tttccatggt 111360
gtaaatactg tcaccatggc agatctcaag acaccagtgt gacagctctg aatgtggaat 111420
tgggaagagg tatgcgccat ctgggataaa ccatctccta gtacctacct agaatgcagc 111480
agacactcag gatgttatcc cctgcccttc cccctcatag gaacatctat gctgacagag 111540
acctttgcca ttattaaagc atttttacaa acactatctc attacattct caggtgagat 111600
gggcagggcg ggtcttattt ctacttttta cagacaagaa gcctcaggct cagagagact 111660
ggacaaaatt gctcaggggc acacagcaag taatctacaa aatgagcata gcaggcagag 111720
tagcagcccc aaaacatgtc tgcatcctaa tccctggaac ctatgaatat ttggttacat 111780
ggcaaaaggg aattttgact gcagacggat ttaatattgc tagtcaggtg acctccaagt 111840
agggagatca tcctagatta tccgggtggg cctagtgtag tgacaagggc ccttaaaagt 111900
gaaggagggc agctcaagag gagagtcagg gggaaatgtg actatgcagg actggtcaga 111960
gagatgtgac attgccagct ttgaagatgg aggaagcaag gaatctagaa ggcctctaga 112020
agctggaaag gcagggaagc agcttctccc ccagaacctc catgaaaaga tgtagcctac 112080
caggtacgtt gattttggcc cagtgagact tctgacctcc agaactttaa gatgatcaat 112140
ttgtgttgtt taagctgctg gatctgtggt cctttgctac tacagggata ggaaatgaat 112200
tcaacgggac tggcaatcag atctccttat ccctcaaatc tcagctcaaa tttcacctct 112260
tgagggagcc atgttttttcc tgccttttct aggcctctgg ttttacccga gttctgataa 112320
tatctggctt taggcactca ccagatggtt gtgaatcttt gcatacttgc tggttttctc 112380
cctaatcccc aagtggcaag aatattcttt tcactttgca tcactttcca ctagcacagc 112440
tccttcccca agaccacagc ataataactg cattcagaat gtgtgagtgt gaaaatagag 112500
gaatgaatga atgggagctg acattaacaa tagtactgca ccccagcacc accaggaatc 112560
acgatgctga gctgtcactg ttgcagaaca attaaaagca tctcctgcta gtatcctgag 112620
ctacctaccc ccttcctgca ggaaagactt cccgtcttcc cactggctca cagaagtggc 112680
cttttcctcc ggaaaccagc gtgcatctgt tagcatcttt tgtcttttgt gggaaaggga 112740
ggattctggc tccagactga agagggacag gcatggtgtg tgggttcaca gagccccaga 112800
ctccagactc tgatgccagc atctttgtct cagcaaaggt cataattgga tttgatgtt 112860 taaggcagtc actgatttac tgttctcatt tttcaagtgt gagaaatact aactctgtgc 112920
tttgcttact tctaaaggaa caaaggcagt atgagcagcc tttaaatact gccacataat 112980
acactgagag cagacatgac cacgtgctac aaagagtcag ggctacgtag gaaagttcac 113040
atcggcgtgg gaagtgaaag taagccacgt caccgtttct gtcacgtgac agctgtgggg 113100
tgtggagcaa ctcactgagc ctcttttcctg gtgtgtaaga tggggataat gatagctccc 113160
attcactgac cgcttccaaa gtgcctgacc ctgttctaag ccttcactgt catcctgatt 113220
```

```
ttatagttag acagtttgtc agtgtcagaa gcagaattgg ctacatagtt tgcaagtcca   113280
gtgccctggt tcaaaaatga ttaagaattt caagatggtg gtagcagagc aaaaaaccaa   113340
gcccggagcc ctccttagtg tggctcttat gtgactgcac aggctgcaca ccctgggcag   113400
aattagtata caaatcctgc agcctgactc cagaaccttc catcttaaca tctatgccac   113460
aagagctgtc tcctaaggtg gccgtgaggt tggaaatgag actaaggcat tcctggcaga   113520
gggcacagtg tgaatgatct ggaaatacag gcgtggacag gaagatgagg aaggaatgat   113580
aaactctcat ggctaaagct ttggtgagct gaaggaaaca gaagtgtgct ggtaggcagt   113640
actggctgca aactgtgccc tccctgaagg ccaactataa agtgcaaggc ccttgtactt   113700
tataggcgac tggtgttgag gatcgctgga aggtttagaa gcaggggta gcatggacgc    113760 aggcagagaa ctgcccctag ggggaagtgt ggagcagagc agactggggc ctgggcaccc   113820
gctagaggag gccgttacaa ccacactcta gggatctcat agtgagaggc tcagggagta   113880
gaggaaggaa acagggaaaa ctgaaggtct tcaaggtaag tagaaattat gctttggaa    113940 tacgatctgg aaacaggaaa ctgggggaaa ggaaaagctt ctgatgcctg ctggcctggc   114000
cttctgtttg agcgccatca ggcccgtatg gagtatcatg atgtacacag actgcctttg   114060
cacccataga aaacagggta catctcttca ggaagtagaa actctttgag caaaagaaat   114120
cgatttaact tcctaaaaac aacagctgtt actggctata aactcagtca tttctcaatt   114180 tgggttttc ccccaaaata ttcccttcca attttcagag gcataatcag ttctgtgatt    114240
atgttgcttg cacataatta gatcacacag taataataat aactgtaaac tctggaggaa   114300
acagagtgca attaaaacca gaaagaaaaa aatctcccaa acctctccca gattcttctc   114360
tcaaacttgg gagtggggca cctcaagccc agtgaaggaa tcaacatatt ttaccccaaa   114420
atatatttct ttgacatatt ttgagatggc tgttcacagg gcccgcaaac agaagcagcc   114480
ctacaaaact gtctcatgtg gcgaagattt gcatctgcag agaaaaacta cgttgataca   114540
gccaggcttt ctctgaggct ctctcttgtc catatctagg aaaaactgag agtctgatac   114600 cttaaaggt ctgaaagaaa catttactat ctattctgtc tgagagcggc tacctctgag    114660
atttctccta tgtaacaaga acgcctttgc cagccaggcc tcctcttctc cccatgccat   114720
aatctctttg ccaagatcca agcctccagt cttcctgtaa cctcaaggct tctgtacccc    114780
actgcgggga ttggtaatca ctctatggtt ctcctccatg tgcacaataa atttgtatgc   114840
tttttctcca attaatctgc cttttaattt attattatta taaatttttt ttgagacgga   114900
gtcttgctct gttgcccagg ctggagtgca gtggtgtgat ctcagctcac tgcaacctcc   114960
gcctcccagg ttcaagcaat tctcctgcct cagcctcccg agtagctggg attacaggtg   115020
cacgccacca gcctggcta atttttgtat ttttagtaga gacagggttt caccatgttg    115080
gccaggctgg tctcaaactc ctgaccttgt gatccgcctg ccttggcctc ccaaagtgct   115140
gggattacag gcgtgagcca ccatgcccgg cctattatat atattttaat gctctctctc   115200
agcagagtca agaggattag ttatcggtgt gttggacata ctgagtatag ggggtctgtg   115260
ggatatgtaa gaagaaatga ctactgggct gttgcatatg tggttcttca tctcattttg   115320
ttttagagcc agagtctcac tctgtcactt agactggagt tcagtggcga ggcttttttt   115380 ttttagaca gggtcttaac tctgttgttt aggctggagt gcagtggcac aatcatagct    115440
cactgtaacc ttgaactcct gggctcaagc aaccctccca cttcagcctc ctgagtagct   115500
gagatgacag gcacgtacca ccactcctga attttttaaa aaatgtttta ggcatgtacc   115560
```

```
accacaacta aaaattaggc gtgtgccacc acacctagta tttaaaaaaa tgttttcgta   115620
gagacggtga tctcgttatg ttgcccaggc tagtctcaaa ctcctggacc catgtgatcc   115680
tctggcctca agcgatcctc cagcctcagc ctcagcctcc caaagtgctc agattatacc   115740
cagtgtgccc agtctattaa tctgccttt ttgagttgat ttttcagtaa accttcagag   115800
ggcgaagggg aggttttccc ttggcccta ccctggattc aaatcctagc tcccacttcc   115860
caacaatgtg actttgggca agtcaggtaa cctggttctc ttctataatg tgagggaacc   115920
attctagcac ttaacctcaa tcatactgca ttaccttgtt ctgaagttta aatgagaaat   115980
tcttagacta gccttcagca tgtagtaaag caggccataa atgtcagata ttatcataat   116040
ctccagattt tctacagtga ttcttgaatg acatttaaga tcagaaacat ccatgtaatt   116100
ctcatattac tatcattgtt atgtattctt tctctccgaa tgaagaatga aggtaccatc   116160
cactgacacc acagtcacga ggtttgggtca agccttatga ccaccctaga agcctagaca   116220
gaagggttca aaggctcttc ctctcatatg ggctagtaat aaacagggtc tctaacagaa   116280
tagcggaaac ctgagttgag catgttcatg agggaggga agctgacgcc cacatcagca   116340
cttgttttcg aagaggagct gtcttggccc agagccgtgg ctcacgcctg taatcccagt   116400
attttgggag gccaaagtgg gagaattgct tgagcccaag agttcaagtc tagcctgggc   116460
aacatagtga gaccgtgtct ctagaaaaaa tttaaaaaat tagacaggca tggtggtgtg   116520
tgcctgtgat cccagctact cgggaggctg aggtgggaag attgcttgag cctaggaggt   116580
cgaggctaca gtgagctatg atcacaccac tgcactccag cctgagcaac agagcaagac   116640
cccgtcttaa aaaaaaaaaa aaaaaaaaa agaggagctc tccagattaa taacaatctc   116700
cccagttttc atgattcagg cgtcaaatcc tgctgcccca tatggttctc accactcaac   116760
gagtattatt tacagagggc cgtcgttgct atgtcctgga gatacagaga caaataggac   116820
ccaggccgac cactgaggag atccaacctg atggggaaag aagacagaga acacacaagt   116880
ggggctagac acggtggctc acacctgtaa tcccagcact ttgggaggct gaggcgagtg   116940
gatcaccaga gatcaggagt tcaagactgg catggccaac atggtgaaac cctgtcgcta   117000
ctacaaaatac aaaaattagc cgagtatggt cctgtagtcc cagctactgg ggaggctgag   117060
gcaagagaat cgcttgaacc caggagggag gggttgtagt gagccgggat gcgccactg   117120
tactccagcc tgggcgacag agagagactc catctctaaa taaataaaaa taaaagaga   117180
acacacaggt ggcagcaatt gggacaaatg tcactgcaga agaccttcca aggggtatt   117240
gggggtgag gaccacattt tgccttaggg tgacaaagaa ggttcacaca gtgggccact   117300
ttccggggtg ttggtgatct gaatcttgat ggggagggtg gttacatgcg cgtacatggt   117360
tgtctagcac tcatcgaggt acattcaaga tgaattttat gtcaattaaa cctcagtcag   117420
gttgatagta aagagtctga aacatcgtgt tagcacttag tgggctcttg ggaattcttg   117480
cagaatgaga acgtgagggg tatggagggt gggagtactg gcactttctg catcccagg   117540
agctggctcc acattgctcc tggctctgca tcctgctttt gggtggccac ggggagaaga   117600
cagggctgaa gccagcctcc acagcggagg gtcctctagc aaggcccagc agggcctcag   117660
ggagttcaga gggaggcttg cttttgcttg cttgtctcaa cacaggccca ccttgactaa   117720
acacaggctt cttgctgggc gggccagctc tgagccttgc aggccacttt atcacgttgg   117780
tggctcccat ctgttcttag agtccacatt tccactgggt tgagctctca gccacctctg   117840
cctaggctgc tctcttctga aactttcttc ttcctctgcc tccctactt cccctcaccc   117900
cttcctcacc cctcccattc tctctcccct agggcagagg acccagctgg agcagggctg   117960
```

```
acaggagccc ctgagaggag aacttagagg cctgagaccc gttgagggtg tgtgtgtgtg   118020
tgtgtgtgtg tgtgtgtgtc tatgtttggg agaatttgga taaagagaca ggctggtagc   118080
ggtggctccc acctgtaatc ccagcacttt gggaagccga ggtgggctga tcacttgagg   118140
tcaggagttc aaaatcaacc atgccaaatg gtgaaacccc gtctctacta aaaatacaaa   118200
aattagctgg gcgtggtggc acgcacctgt aatcccagct acttgggagg ctgaggcacg   118260
agaatcactt gaacccggga ggcagtagct gcagcgagcc gagatcatgc cactgtactc   118320
cagcctgggc aacagagcga gactccgtct caaaaataaa aataaaaaaa taaaaaaaaa   118380
acagagacag ccaaagtagc aatgtgcctg tgagagggcc taagttttcc ccctcagggt   118440
agtcttgtca gatgaaatac aggatgccca gttaaattgg aatttcacag aaataaaata   118500
atttctatgg tctcaaatat tgcatgggac atattcatac taaaaagcta tttgttattt   118560
acctgaaatt cccatttaaa tttgagggcg tcttccattt ttattggcta aatctggcca   118620
ccctccctca gggtgtgacg gcaggaagcg ggagagaaca cagatgtccc ctgttatctc   118680
cctgggccct gcgtggccct ctcagggaac cacaagccag ggccaagccc atccaatcct   118740
cctgcaccag gagcagcaga agccatgccg ctaatggcag tcacctcggt ggaagtagag   118800
cgggcctgtg gcggcgtgag gcttttctgc tctgcttctg tggaagtgat tatccaataa   118860
ctagtaggaa tcgggcagtt ggcagacgcc tcccatgcta taaagccaca caaggcaggc   118920
aagtgtgggc acagatgaga ggctgagagc ggaggtagga tgtcacccct gccctcgcca   118980
gcctcatctg ttttcccagg cgtcccccaa ccactaccca cgtggattct ccctcgaaga   119040
gccccctttc agggccccat tggcacttca ctcttgaggg aggcctagga gaagctagtg   119100
gaaagttact tccacataaa cggtcagaca gacggatgat gaaaccacag gaaaccacag   119160
ctcctcccct gccggggcac caggccagaa gccgacctgc taggcttggg gaccccttct   119220
ggtcttgcta ggggctcaga gaccctgggg aagtcccttta ctgtgtgtct catgtcttca   119280
cttatggatg ggatgccagc tgccctctca tgccctcaca gggctgttgg gaggcaaggg   119340
tgagctagca gatgcaaaat aatggcaaaa ttaagaaacc aagtacctgt acaaatgtac   119400
acctttatag tggttcaatt tggccacacg tgcttctact tagagaaaca ccatacatga   119460
atattcaggc acatatacat atcactatat gatcctacga gcaacttccc tacctcactg   119520
aaaatatgat tcacttcacc aaaatgtaat gctatggtca cattctacaa ggaaaacatc   119580
caaagcacag ccactgtaag tgaggatagt tctcaactgg gcctatggtg ggctggctga   119640
ctacacttgc agtctagaac ggggcctact gcagactggc ctgcagttag tttgatctag   119700
ggttatgaca gcagttgact tgaaaataac tttcctcctg ccccttttaag aacacgggtt   119760 ccttcccttg cagataagca ggaagtcccc ctccctctgt cttggtgctt ggtggtgtgt   119820
ttcacttcct ttcaaaggtg ttttcttact aaagaaaccc taagcccagg gtcacattct   119880
gtttctttca caggcatact caactgcgtg ttgttgattc tgtgacaagt ttcttgagca   119940
agaaaataca cagaaaaaat gttaaatgta taaaatatga agtaaaaaca tcaataatgt   120000
tttaaatatt taaatataaa agtaatgca tgcttctggt aaaaatgtaa atggtagagg   120060
tttctctatt tccttttcccc agaggtaagc tcttaaaatt cccttccgga aatggtctct   120120
ctacacctca cttttttatt gcacagaagg gatcagacac tatttatgag gctctttatt   120180
ttccacttaa gagtattctg gctgggcgcg gtggctcaca cctgtaatcc tagcactttg   120240
ggaggccgag gtgggtggat cacgaagtca ggagttggag accagcctgg ccaacatggt   120300
```

```
gaaacccat  ttctactaaa  aatacaaaaa  gtagctggtg  tggtggtggg  tgcctctaat  120360
cccagctact  cgggaggctg  aggcaggaga  attgtttgaa  cccaggaggc  agaggttgca  120420
gtgagccaag  atcgcgccac  tgcactccag  cctgggtgac  agagcgagac  tctgtctcgg  120480
gggaaaaaaa  aaaagagtat  tctttggaca  tccttccaca  gcatatcatg  aataaatctg  120540
cctcaatctt  tttttaacag  ctgcatagtt  ttccattgtt  tgggtactct  atcatgtatt  120600
taattaatct  cccaattaat  atacacttag  gttgattgta  gcttttactc  ttatctacaa  120660
tgctatgggg  gaaagatcta  gatgtttgtg  catgtgtatg  tatatgtata  tgtaagtgtg  120720
ttagtatggc  tatagaatga  gagtcctgtc  actggactta  aactgaaat  gctgggttca  120780
actgaaatg  ctgttttaat  tgtgacagcc  accggtgcct  ctgaaaagtc  cctacgaatt  120840
gacccttcca  acaacagcat  ataagagctt  tcacttttct  ttccctgcat  tctggccaac  120900
tggagccact  actcaacctt  ttcattttg  tcagtctgaa  atgagcagag  aggtcctcat  120960
tgtttgattt  gcatttgaaa  gcctaccata  cacgggcatc  ttctcatgtt  gttcttagct  121020
cagtgaggag  ggccttagag  accagacttt  ggaaccagat  agagctggat  accgtcccag  121080
ctcagccact  tgccaactgt  gatctctgga  gcctcggttt  atccatctgt  aaaatgagca  121140
tccttagact  aaattcatgg  gatttactga  gaaggtgcaa  caaagcaaca  aaaaatgttt  121200
atcactacaa  atgttagtgt  gttttctcatc  caaacaaaca  aaaaaacata  tatatatata  121260
tatatatata  tatacatatt  tacatatagt  catgcatcgc  ttaacaatgg  ggatacgttc  121320
taggcgattt  cctcattgtg  cgaagatcac  agagtgtact  tacacaaacc  tagatggtac  121380
agcctactac  atacctaggt  tatatggtac  agcccattgt  tcctagcttg  caaacctgta  121440
cagcatgtca  ctgcactaaa  tactgtaggc  aactgtaaca  caatgctaag  tatttgtgta  121500
tctaaaatta  gaaaaggtac  agtaaaaaat  acagtattat  tttatgggat  cactgaaatg  121560
tcatcacaca  gtacatgact  gtgtgtgtgt  gtatatatat  atatatatat  acacatacat  121620
atatgcacat  acacacagtc  ttatactgta  tatgtataca  gatgtgtgta  tatatatagt  121680
cttataccat  atatgtatat  agcgtatgtg  tgtgtgtgtg  tgtgtgtata  tatatatata  121740
tatatacagt  gtgtgtatat  atatatatat  atatacacac  acacacacac  acacacacac  121800
acacacatac  acagggatat  atatatactt  ttttgaccta  gtcaatggcc  aatttaaccg  121860
tctctacagc  atctgagatc  tcaccttctc  ctcactgctg  cccctgcttg  agggtagaaa  121920
atgtaaataa  aatgctgaaa  ataaaaactt  aaaactgtca  cattcaatgg  ttggtcttac  121980
tagctgagca  accttggcca  tggtacttct  cggagctcca  gtttctttct  ctgtaaaatg  122040
gggtgttcac  tctacctacc  ccacaatgtc  actgggagaa  tgaagaggcg  cttaaggcag  122100
tgcctggctc  tggcaagcac  tcgataaatg  atccttgtgg  ttgttcttct  tggccaggga  122160
tccccttaag  tgctcaggcc  actttcccca  gtgggatagg  aggaaaatag  tcacctcaac  122220
taacagaggg  taatctatca  aacacctact  gggctagttg  aagacccttt  gggcctataa  122280
acactgcagt  agggtgtggt  ggaagggcat  ctccaactct  ctggtccagt  ctttgagaca  122340
caattagatc  ctgccatgct  cagcaagcag  gttgagccat  cagaccctgt  ttttttttgtt  122400
tgttgttttg  ttttgttttg  ttttttcttt  cttctctct  ctcttctct  ctttccttcc  122460
tttctttctt  tcgacggggt  cttgctctgt  gacccaggct  ggagtgcagt  ggtgccaagg  122520
ctacagctca  ctgcagcctt  gacctcacgt  gctcaagcca  ccttccatc  tcagcctgcc  122580
aagtagctgg  gactacaggc  atgtactaca  atgcctagct  aatttttcta  ttttttgtag  122640
agacagggtt  ttgccgtgtt  gcccaggctg  gtctcgaact  cctgggctca  agcgatcctc  122700
```

```
ccacctcagc ctcccaaagt gctgggatta caggcatgaa ccacctcgcc cggcctcact 122760
cctccattgt cttttaatct cctttgtaga ggtcatcaac aaccccattc gttagcgttt 122820
aacaagaaaa gaacttcttg gggtggggcg gggagtggga agttattgtg aatctccttt 122880
gtgagaaaca aatgccattt tctgaatgat ttttgccacg ttttattttt taaaaatttt 122940
ctcctttgga agcagggtgc actgtgtata ctgtcatgtt gctcagatga caggtaagtt 123000
acccgtgagt aggcataagt gctgatgtcg tttctgggtc cttcaatacc acacagaatc 123060
tccttgggtt tatgcatggt gaggagagta attcgccctc atcaaggcta tgatttatcc 123120
cgccataact gagctaaggt ttttgtgaag acagctgaaa tatccacacc atgcagggaa 123180
cagagacaca ttaaacaaca acacatctca aaaatacta cttttgcagt ggagaaacct 123240
gagtggtaac acattaatca attgatccaa gttaacatcc caataacgga acataccaac 123300
ttcatgggcc cccggctgtg agacaccgag aaggtcacag tgtccctcgc tcgagtagca 123360
ttcctgccaa aaaggcaagc ccaaatctaa tcccgaggaa acatcagtca aacttaaatc 123420
aagggaaatt ccacaaaata agcggccagt cttcttcaaa aatagtgtca tggaatacag 123480
acaggctgag aaagttctaa attaaaagat actagtgggg catatcaatt acatgccatg 123540
catgatcctg gattggaaca tggaccggaa aaagctgtta taagaatgtt attgggctaa 123600
tagacaaaat ttgaataagg tctgcacatc agataatagt cttgtagcaa tgtgacattt 123660
cctggtactg acaattgtac tgtggctatg ttggagaatg accttattag aaaatgcata 123720
cctagtattt gtgggtaaaa aggtgtcata ttcacaactt attctcacat ggtctagaaa 123780
aaataagtaa gtaggtagac agaaagaacg ataggtagat agaaaaatag atatagatag 123840
atagatagat agtaaaatat tgataaagca agtatggcca attattaaca actggtgaat 123900
ctgggttaag ggtataccac agttctttac tgtcttttg cagcttttct gtaagtttga 123960
aattattcta aagtgaaaaa ttttaaacat tctagtaact gcaaccatgg tgcatgttac 124020
aaactaaata ataaataagt cctaattaat aaaggaagcg aaacattaac gttgcagaaa 124080
tgtaaaacca aaaacaaatg acaaagcact ctccctctgc tggcagtttt agcattcttg 124140
tacacagaat gatcattgat tttgttttgt tttgttttc aagttcctct tagtacaaaa 124200
tttaaatctc tttcatttaa catgcctgca caaagtactc agtaggtgcc aagcaatgac 124260
tcacaacaaa gccagttccc aatggctctt gttctcattg gaagtgaagg ccatattcta 124320
tatgtatgta tcctctctgc cttcagtaga gaaggcagga acactgggag gaaggaagaa 124380
ggtaaaaaaa tctttattaa aatgcctcct gacatgtcca cttggactct actaggcaaa 124440
tcaaatgtcc tacattccat ccgagctcct gatcatctat cctaaaacct gagcacactg 124500
cgcctcccca tcccctgccc agttaagttt ctccacttca gtggatggcc actccatcct 124560
tccagttgct cagaccaaaa tctttgcatc agcctggact cctcactttc tctccccctc 124620 catccctgt agatcagcaa atcctattgg ctctaccttc aaaatacatc cagcatctgt 124680
ccactcatca ccactccact ttcccatcct ggtctgtcct ccacctgaat tgttgcaatg 124740
gcctgtaaag cagcctccct gctcctagtc tagtctcaac ccaggagcca gagtggctgt 124800 ggtcccttc aaacctgaat caggtcatgg gacttctctg atggcaaact gccagtggct 124860
tcctaactca tgcaaaaaaa ggaaggccaa agttcttaaa atggcctggg aagctcctca 124920
tgtttggcac catccatccc acactcccat aagggtgatt tgacctattt ggcttcacgt 124980
tgtacgactc cagggaacac tgctgctctc ctgcttcagc catgctggct ttcgtgtgtg 125040
```

-continued

```
gtcatggtcc ctgctcaggg ccttggagtt ggctgtgacc tctccctgga gcacctcccc   125100
caggcatctg cgtggctcac ttcctctttc ccttgaagtc ttgcctctga tggcttacct   125160
ggaccatccc tcctacacac tccctgttca tttcccttac cctactctca ctttccatgg   125220
tcatcttcta gtatactatg cacactactt attttttaaaa atatgtattc tcgattccac   125280
acaaaagtcc ctctccctct ccctctccct ttccctctcc cctctttcca cggtctccct   125340
ctccctctct ttccacggtc tccctctccc tctctttgtc tccctctccc tctctttcca   125400
cggtctccct ctgatgccaa gccgaagctg gactctactg ctgccatctc ggctcactgc   125460
aacctccctg cctgattctc ctgcctcagc ctgccgagtg cctgcgatta caggcgcgcg   125520
cccccacgcc tgactggttt tcctactttt ttggtggaga cggggtttcg ctgtgttggc   125580
caggctggtc tccagctcct aaccgcgagt gatccgccag cctcggcctc ccgaggtgcc   125640
gggtttgcag acggagtctg gttcactcag tgctcaatgg tgcccaggct ggagtgcagt   125700
ggcgtgatcg cggctcgcta caacctccac ctcccagccg cctgccttgg cctcccaaag   125760
tgccgagatt gcagcctctg cccggccgcc accccatctg ggaagtgaag tgaggagcgt   125820
ctctgcccgg ccgcccatcg tctgggacgt gaggagcccc tctgcctggc tgcccagtct   125880
ggaaagtgag gagcgtctct gcccggccgc catcccatct aggaagtgag gagcgcctct   125940
tcccggccgc catcccatct aggaagtgag gagcgtctct gccgggccgc ccatcgtctg   126000
agatgtgggg agcacctctg ccccgccgcc cgtctgggat gtgaggagc gcctctgccc   126060 ggccgcgacc ccgtctggga gatgaggagc gtctctgccc ggctgcccca tctgggaagc   126120
gaggagaccc tccgcctggc aaccgccccg tctgggaagt gaggagcatc tccgcccggc   126180
agccacccca tccgggaggg aggtgggggt cagcccccac caggccagcc gccccgtccg   126240
ggagggaggt gggggggtc agcccccgc ccggccagcc gccccgtccg ggagggaggt   126300
gggggggtca gcccccgcc cggccagccg ccccgtccgg gaggtgaggg gtgcctcttc   126360
ccagccgccc ctactgggaa gggaggagcc cctctgcctg gccagccgcc ccatccggga   126420
gggaggtggg ggggtcagcc ccctgcccgg ccagccgccc cgtccgggag ggaggtgggg   126480
gggtcagccc cccaccccggc cagccttccc gtccggagg gaggtgggg ttcagccccc   126540 cgcccggcca gccgccccgt ccgggaggtg aggggcgcct ctgcccggcc gccctactg   126600 ggatgtgagg agcccctctg cccggccacc acccgtctg ggaggtgtac ccaacagctc   126660
attgagaacg ggccgggatg acaatggcgg ttttgtggaa tagaaacggg gcaaaggtgg   126720
ggaaaagatt gagaaatcgg atggttgccg tgtctgtgta gaaagaagta gacatgggag   126780
acttttcatt ttgttctgta ctaagaaaaa ttcttctgcc ttgggatcct gctaatcggt   126840
gaccttaccc ccaaccctgt actctctgaa acatgtgctg tgtccactca gagttgaatg   126900
gattaagggc ggtgcaagat gtgctttgtt aaacagatgc ttgaaggcag catgctcgtt   126960
aagaatcatc accactccct aatctcaagt acccagggac acaaacactg cggaaggccg   127020
cagggtcctc tgcctaggaa aaccagagac ctttgttcac ttgtttatct gctgaccttc   127080
cctccactat tgtcctatga ccctgccaaa tccccctctg cgagaaacac ccaagaatga   127140
tcaataaaaa aaataataa aaaataaaaa ataaaaaaaa aaaatatgta ttctctcttt   127200
ctggcccgct agaaagtaaa ctccttaaag gcagaagttt tgtttattga gatatccttg   127260
gctcctacaa caatgcttgc cacacagtag taactcaata aaaattggtt gaacaaataa   127320
agactatttc aaaaattaag catgggagat caatgtagtt gcatattaaa atgatttcta   127380
taaaaataaa catgatcagt cgagatcttt tttttttttt ttttttgag acggagtttc   127440
```

```
gctcctgtgt cccaggctag agtgcaatgg tacaatctcg gctcactgca acctccgcct   127500
cccgggttca agcgattctc tcctccctca gcctcccagt agctgggatt gcaggcgcct   127560
gctaccacac ccggctaatt tttgtatttt tagtagagat gcgggtttcg ccatgttggc   127620
caggctggtc tcgaactcct gacctgaggt gatccaccgc ctcggcctcc caaagtgctg   127680
ggattacagg catgagccac cgcgcccggc ccagtcaaga ttttttaaca aaattttaa    127740 attatgtctt tcaacaaagg tgtttattct gggttttgga gtttgcattc aaaatttgc    127800 attcaaatct gaatttagct ttgtgattcc tgagtttcag tttccttcca gcaaaaccaa   127860
aaatagaagg acttggcttg aagggtttta actgaggatt aaattagatg atacacctgg   127920
cactggttta ataaatgaga gtacaagctt tttctcattt tgtcattctg taaatctacc   127980
cagagttaag ccaaacttca caagttaaat tctctacaag acagccctca cttcagacac   128040
cagtccccag ggtcactcac tcttccaacc aactggctaa aattgaggga ttcccgtgac   128100
caccctctgg ctcaataatt tgctagaacg attcacagaa ctcagggaag tgctatactt   128160
acagttttat tacagtaaaa ggatacagcc caaagaagaa atgcgcaggg caacatctgt   128220
cagggttcca agtgcaatgc ttctgtcatc cttaaggacg tgttatcctc ccagcctgaa   128280
agtgtgacaa tactcaagga gtaatgtcag tcaaggaggc tcacttgagc tttggtgtac   128340
taaaatgttt actgaggcct actgaggcct catacaggca tgattgatag aaccactggt   128400
cacatggttc attctccagc tcccctttc ccctccagag gttgggctta tatctcatgg   128460
cttaaagccc caaccctcta atcacatatt tgatctttcc ggcctggcca gccctattc    128520 tgaatcgttt cattagcata aactgtccag tgtgagccac ctcattatca taaacaatca   128580
agcctggtcc aaggggccca ccatgaataa caaagacact ccaatcactc aggaaattct   128640
aagggtttag aagctacatc tcaggaacta gagataatgg ccagccaaat tcttcattac   128700
acaaaaccaa acacagtgtt ctagctaaaa agtaaggcat ttatgcaaac ataaccacag   128760
agtacaaaat ataaaattca gacattaaaa tacctcctcc tggcccaaac taaaattgtg   128820
ttcctgtctg tgtatacata gaaaaataga aaaatttaag tgcaaatgta tgctcactct   128880
ttgtgccaag gaccttaagt agtaaaaaaa aaaaaaaaa aaaaaagact aggaagccat   128940
tttcatgaat gagtaaattt aggtctttag aagccacgtg tgtaatttca aatctgagaa   129000
atggatgctt gtatgacaaa aactaacaat atacaccacc atcaccacca ctgccactac   129060
caaaacaaaa tcaggtctat tattgtttgg ttagcactgg gaacaattcc agtattggtg   129120
aaccatccta tgtttaggta aaatacacat tctgagttga ctgagtttca tatatgactg   129180
aatctgaatt tggctccttc tcatcttaga tatacaatct tcctcctaaa gtatggattc   129240
tatgagatct agcacctaaa attatgccta aaggactatg ggcccacagt tgaatacaag   129300
gagttttggt ttatggtctt ggctctgcaa accaactgaa taccttgaa tgggtggctt    129360 aacctctctg tgctgaattc catcctctgc aaaatattga tacgaatatc tagtccctt    129420 atctgcctac aagtactta aggataaaat gacacaaaag gtgagagaat attttgatga   129480
agttcactaa aactagataa atatgagttg cattacataa ggaattacta aacaccaaaa   129540
tgtaaggtga cacctataag ctggtcttcc ccccgccccc accagctgtt gtccaatttg   129600
ttgctttctc tgagctggtg cccaaaccct ttcaggtaag ctgctggtat agatggtgaa   129660
atttagatca agcagagaat attcagaggt aaatggtaaa ttaaatttca aaagcagggt   129720
tattggttta tcacattcat cggtagccac gccatcactt ccatttttt ctcaaaaac    129780
```

```
gctgttggtg gccgggcgca gtggctcaca cctgtaatcc cagcactttg ggaggccaag   129840
gcaggcagat cacgaggtca ggagattgag aacatcctgg ctaacacagg tgaaaccccg   129900
tctctactaa aaatacaaaa aaaattagc cgggcgtggt ggcgggcgcc tgtggtccca    129960
gctactccgg aggctgaggc aggaggatgg tgtgaacccg ggaggcggag cttgcagtga   130020
gccgagatcg cgccactgca ctccagcctg gcgacagag caagactctg tctcaaaaaa    130080
caaaacgaaa caaaaaaaac aaaaacgctg ttggtgactt tctctagttt aagaaaccgt   130140
tcctttagtt tggggtccac ggacacccaa gagattttg aagagaatct agggaactta    130200
gaaggaaaaa aacccatctt tattttcatt aacctctgaa tgttagcggt ttcttcaaat   130260
acgcatgtag tcaagaaacc tctgaaatct tagcagttcc tgtgcttgta tcaacaaaag   130320
aaattacaga tattttata tctgttaacg ttgtgtagat atcaaacact gatcactatt    130380
ttgaatttat agtggatatg agactgactg ctagactgtg ttctttaata tataaagaag   130440
cacatatatt acatcacaat tattaaaaac ttttggtaac tgtatgtaaa tataattttc   130500
atttgtgatc ccaggttttt gttttaagca ttgacataat tctgagaaag gatccatgag   130560
ggggtggggt ggtccccaac cccctgctgt gcagttagga accgggccac acagcaggaa   130620
gtgagacgcc agtgatcgag cattaccaca tgaccgcctg agctatgcct cctgtgagat   130680
cagggcggca ttagattttc ataggatcgc caaccctatt tcaaactgca catcgaggg    130740
atccaggttg tgcactcctt atgagaagct aatgcctaat gatctcaggt ggaacagttt   130800
catcctgaaa ccagcaccct cccgaccctg tccatggaaa gattgtcttc cacgaaaccg   130860
gtctctggtg ccaaaaaggt taggaaccgc tgatctatgg gactattggg tcagtttcaa   130920
ttctccttca ttggccttgg tacatgcaag tcaattctga ggcacaagta agctgaaagt   130980
tgcagccatc cctcagacag gaaaaaataa cccggcagaa aggaagagaa cagaactggt   131040
gtgtgcacct cacagaggcc tagaaaacgg tggcggctgc tccaaaacac cagctccaag   131100
ggcacctagg ctcagatcga agcattgcag gtggcaaaga ggctggagca tcctgtgtac   131160
acactcagac tgatccacca gtgaaaggaa ggggttaaag aggaggagca tggaaaactt   131220
ccaggagagc tgacaaactt agctgcaaag tcaggataaa acagtccaag aaccccaaca   131280
aggaactact ggaggtgatg tcggagagtt cctctctctc ataaagatca aagatttctt   131340
gggattgtct gctgtgcaca agcgtggccc ggcctgggt caacaagaat gtccctcaac    131400
tggaaagaaa atagagggat gaagaattcc aattctggca ctggtgccac cagctctact   131460
ggtgccagca gtctgagaac cttggtctgg tatccgcacc tcctcccagg tgctctggga   131520
atgggtaagg gaactaagat gctgtggccc ttaagctctg ccggtcaaat caacctatga   131580
tgaagctcta tagcattgtt aagaagccca ttgttttgta ctttaaaatt tgttttcctc   131640
tagtttccta ataaaaagtt ttttttttt tcctaaattg gcaccacttt ctcagctcaa    131700
gaagaacagg gagtttccac acctgagaag tgttaatggg catgacctga gagggcatta   131760
taggcagagg aagaggcacg tgtgtaaggg cccattcctg ggtccaggaa aagacagtag   131820
cactggaggc actcaaagaa tgagaatcta aaaagggcag gactggcttc agaatttggg   131880
ggacacagta caaaatagaa atgtggggta agaatttcaa aatggcggca gcagtacatt   131940
aagccaagca ccagggactt ctgagcgtaa ggcccagtgc agctgcacag ctgtgcacct   132000
gtgaagccag tcctggagag gccaaatcgt cagggtcagc caaggaagtt gatcttggcc   132060
tatgtgggtt ttcccctcag atttgagcca gtgctccatt acctacactc cattttcctc   132120
accataaagc tattaaccat cttctgctga tgatctggga actatatttt atataaagct   132180
```

```
ttggcaccca cagaaaaaac acattaaaaa atacaaacac ttgttacttg ctaagcataa    132240
ttctgcttca caatggaatc aaaggtttgt cattttttaac acagaaagcc attgggagtg   132300
tgtaatgcct cccctttcaa tatgctattg aacctactaa ttttttttagc cattgtaata   132360 tgaatgactt cttagaaaaa tattgtagta aggccaggct cacgcctgta atcccagcac    132420
tttgggaggc cgaggcgggt agatcacgag gtcaggagat caagaccatt ctggccaaca    132480
cggtgaaacc ctgtctctac taaaatacaa aaaattagct gggagtggtg gtgtgcacct    132540
gtaaccccag ctactcagga ggctgaggca ggggaatcgc ttgaacctgg gaggcggggg    132600
ttgcagtaag ccgagattgc accactgcac tccagcctgg tgacagagca agactccgac    132660
tcaaaaaaaa aaaaaagaa aagaaaaaga aaagaaaaa tatttaagta gtgaaaagct      132720
gaggaaaact actaacgttc aggatacaaa ttctctttat tgccagtgcc ttggccatgc    132780
aggaggagga aaaagagcag attgaatttc tgtaatgaaa taatttgaaa attggggcag    132840
ggaaaatttt aatgtatatg acattattac gatatctatg tttaaatgtc ttcatgatgt    132900
aggctgggtg cggtggctca cgcctgtaat cccagcactt tgggaggccg aggtggaagg    132960
attgcttgag cccaggaact tgagaccagc ctgggcaaca tagagagaac ctgtttctta    133020 aaaaaaaaa agaaaaaaag agaaaaaaca tctacatgat gaaaaagcta gacagctgat    133080
tgagacagaa tataaccttta cccttatctg gcgtatggaa caaagccttt aaaaggcctt   133140
aggattctag agaagagtag tgtttaaatg aggcggcttc tgagccagcc agtctgagtt    133200
caaatcctgc ctttggcttt cgttgtgttt tcttggggaa gttattttaat ccctctagaa   133260 ttctctcatc tgcaaaatga ggagaataat ggtgccactg tcataggatt gtgtgaggat    133320
tcgggaaata ctacatggaa agcttcccag tatatggaaa gcactcagaa agcacttgct    133380
gttattactg ctatgggtac agccatgatt gttactatca ttattctaca acctggcccc    133440
tgcctggttc ccagcgttat ttcctgtcac tttctctcat tttacgcaag tgcctgccaa    133500
gctaagctac tcattgcccc ctgcgttaac tcgaagattc tctgcttccg tattgttccc    133560
tggctgtgtg gaggctgagt aaccacttgg aggggatgtt gtagaggaaa attcaagcca    133620
cagaagggaa actgggttga atgagatccc cttttacatt tcttttggct ctaaagtttc    133680
catcggatca ataaagcaaa caggacaatt agcagcacgg cactcagcac tgagcacagg    133740
cgagggtgtt ctttcactcc tctttgcttt cctgccaccc cctgctcgcc ttcctctttg    133800
caccatgtgg gtccgctctg ggtgggagtc ctggagaaag atacttcaac taaagataag    133860
gcagagatag gcctcggtgg aaagacttgg tagacagacc tgggcatttg attaagcaga    133920
aattgcttaa attctcggag cctcaatttc tttagtagta aaatggggat attagtactc    133980
actccatagg gtaagaatgg aatcagatat tgttaaaag ggcttatagc tgaggttaca     134040
agatatagct agtctactaa atatcctttc tcttttcatt ttcctgttat tcacaggggg    134100
gacttaggct gtgtctttaa ggggttttag attccaatca gtggaaggag ggctctgctg    134160
tgagggagac cagatggaga ctgcagggggc cacagggaa cgtgggtgc aggcaggtgg     134220 ggcagatggt aggaggccct gaaactcaga caaagggatc tgggcttgag aaagcaagag    134280
ctgggagctc agctttgttc ctgttcttcc gttcctccct cctcttcctt cttctcttct    134340
tctggtaagt ttttggcaca aaattaaata ggttcaaact aatagaactc attttcatga    134400
attcagactt ctagccaact tctccatggt tagaaatagc cacgactcta tcccaggccc    134460
gccctggaaa gcaaaataaa actgcgtccc ctgccaccctt ttccgggttc caccagacac   134520
```

```
agggttggag gggaaccgcc cttcaacgca ggcaatgttg gcacattttt cattgggcgc    134580
tgtggcccgt gagatgagga aggcaggaca ggcgcaaagt ggactctact tatctttcac    134640
cagagagccc caaggccaga gtgcaccata caacccggag tcacccaagg ccttttttt    134700 tggggggggg tctcactggg aacaatgtct gcacccattg taagcagttc ctttgccct    134760 gtgtgcctct gtcttttaa ttgggatcga aaactgctac ctcaatggta gttgtgcccg    134820
gcacatacta acagacttat aaatgtagct gcctggggca gggatgatcc tggaacattc    134880
tgacatctag aacattaaga ctaaatggat ttaattatct ggggagaaga aagcaagaca    134940
attagagtca caggttcaac acctgagttc aagtacctcc ctcatttaag aaaatcaatt    135000
catggaaggc tgaggcagag aatggcttga atccgggagg tggaggttgc agtgagccga    135060
gatcacatca ctgcactcca gcctgggtga cagagcgaga ctgtctcaaa aaagaaaaag    135120 aaagaaaat caattcaatg cagtgggaga actgttattg agcaattact atccaccaga    135180
cgctgtggaa agcacaactg cctagctcct cacactcttc ctggtgattc tcgggtacag    135240
actaagagga tgtggggagg acttttacat gctcttggca tatataacag agtggctacc    135300
agctgaggta acccaatgat ggctctctaa gcctcagttt ccccatctgg aaatttctta    135360
tggaaaggcg gtgggaaaga aaggaaaaaa caaatgtaaa acttacgtta caatgcctga    135420
ctcttagaaa atatcaaccg acaggagttg tcatgtttta tttgctgtaa aactaccaaa    135480
agatcttcta tcaacatttt gtaagtgaaa ataataatat atattcatat gtattaatta    135540
tatagaaata atatataata atatataaat gtctctatag gagaaataat atcaagacac    135600
ctaaaatttt taattaattc taaacactaa gacaattatt ttattatttt tcctcaacct    135660
tccatcctaa atcatacgaa taataacaat agaaagagct tactaattgt catgcactgt    135720
ccgaagcatt tactcctccc aacaaccctg tgaggtcggt gttgcaatga acccatttta    135780
cagatgagaa aactccagca cagaaagatt cattcacatg gccagagtca tgcaacttt    135840 aagaatattc ctttggtttg catttccttg tatctgcacc acccttccct ttcctgtctc    135900
tctaggtctc ctgaccggtt ggcaggtcag tcccaatcat gggaactctt ttcctttaag    135960
cagtcgtctc tcttctctt cctctctgtt tccacctgcc ctccatcagt gtctcagcac    136020
agtggaaggc tgcttgctac cgcactggaa aacttctcca gacatttcca agtttgcatt    136080
cgtccatctc ctttggagaa ttgcttcagt gaggcctaac cctttctgag gaaaggccct    136140
tgggagaaga agccaggaga aggtagtggc actcctttgt catcaggaga cattgggagg    136200
aaagaaatga ttttcgacag cagctgggtg aggggaaaca gaatcacaga acctgcggaa    136260
acggtgtcgg tacaacggca gctgccagct aaacggggcga aaaggcaccc tgcaagatct    136320
tttctgtgtt tcaacgatga agtagactcc caacatggaa caggggcggg gggctgtta    136380 ccagacaggt gacatttggt gcatgcacga acaggtccag tgccccattc ggaggccagg    136440
aaggcagcca cccagcagag cattaactag gggaccagac ggtcacctgc ccctgctcac    136500
ccccacctcc ttcctcccca ggaaaaagga agtcaagtag atggagaaac ggggaagtcc    136560
aagctgctgg cagtggcatt caagggtcta tatataaggt tgactctaat ccccagcgag    136620
acaaaagcct gtgccataaa aatgattagc aaggggtttc taaaaacatt tccccaggcc    136680
acggaaaagg agaaggaata ttttgcacac tgccttgtct cttagaaata atcacagcta    136740
ggcctcttta taaccggcga gtcttttcc tttcacacgc catttgcagg cgcgtggcat    136800
ggtatttgta actaatttc agtagcaagt gggtcactgg tattcacaga gtcaggtgcc    136860
attttgaaaa ctgcttccct ctacccgaat ctcttatatt tccagatgca gatgcacttc    136920
```

```
agcgatgtcc tagtgctgga aacgctccct tgaaaatata atttgatttt tgaatttcat 136980
cttaagacat tagagataat gtaactgtag tctttggaat tccgcggatc cttctatagt 137040
gtcacctaaa tgtcgacggc caggcggccg ccaggcctac ccactagtca attcgggagg 137100
atcgaaacgg cagatcgcaa aaacagtac atacagaagg agacatgaac atgaacatca 137160
aaaaaattgt aaaacaagcc acagttctga cttttacgac tgcacttctg gcaggaggag 137220
cgactcaagc cttcgcgaaa gaaaataacc aaaaagcata caagaaacg tacggcgtct 137280 ctcatattac acgccatgat atgctgcaga tccctaaaca gcagcaaaac gaaaaatacc 137340
aagtgcctca attcgatcaa tcaacgatta aaaatattga gtctgcaaaa ggacttgatg 137400
tgtgggacag ctggccgctg caaaacgctg acggaacagt agctgaatac aacggctatc 137460
acgttgtgtt tgctcttgcg ggaagcccga agacgctga tgacacatca atctacatgt 137520
tttatcaaaa ggtcggcgac aactcaatcg acagctggaa aaacgcgggc cgtgtcttta 137580
aagacagcga taagttcgac gccaacgatc cgatcctgaa agatcagacg caagaatggt 137640
ccggttctgc aacctttaca tctgacggaa aaatccgttt attctacact gactattccg 137700
gtaaacatta cggcaaacaa agcctgacaa cagcgcaggt aaatgtgtca aaatctgatg 137760
acacactcaa aatcaacgga gtggaagatc acaaaacgat ttttgacgga gacggaaaaa 137820
catatcagaa cgttcagcag tttatcgatg aaggcaatta tacatccggc gacaaccata 137880
cgctgagaga ccctcactac gttgaagaca aaggccataa ataccttgta ttcgaagcca 137940
acacgggaac agaaaacgga taccaaggcg aagaatcttt atttaacaaa gcgtactacg 138000
gcggcggcac gaacttcttc cgtaaagaaa gccagaagct tcagcagagc gctaaaaaac 138060
gcgatgctga gttagcgaac ggcgccctcg gtatcataga gttaaataat gattacacat 138120
tgaaaaaagt aatgaagccg ctgatcactt caaacacggt aactgatgaa atcgagcgcg 138180
cgaatgtttt caaatgaac ggcaaatggt acttgttcac tgattcacgc ggttcaaaaa 138240
tgacgatcga tggtattaac tcaaacgata tttacatgct tggttatgta tcaaactctt 138300
taaccggccc ttacaagccg ctgaacaaaa cagggcttgt gctgcaaatg ggtcttgatc 138360
caaacgatgt gacattcact tactctcact tcgcagtgcc gcaagccaaa ggcaacaatg 138420
tggttatcac aagctacatg acaaacagag gcttcttcga ggataaaaag gcaacatttg 138480
cgccaagctt cttaatgaac atcaaaggca ataaaacatc cgttgtcaaa aacagcatcc 138540
tggagcaagg acagctgaca gtcaactaat aacagcaaaa agaaaatgcc gatacttcat 138600
tggcattttc ttttatttct caacaagatg gtgaattgac tagtgggtag atccacagga 138660
cgggtgtggt cgccatgatc gcgtagtcga tagtggctcc aagtagcgaa gcgagcagga 138720
ctgggcggcg gccaaagcgg tcggacagtg ctccgagaac gggtgcgcat agaaattgca 138780
tcaacgcata tagcgctagc agcacgccat agtgactggc gatgctgtcg gaatggacga 138840
tatcccgcaa gaggcccggc agtaccggca taaccaagcc tatgcctaca gcatccaggg 138900
tgacggtgcc gaggatgacg atgagcgcat tgttagattt catacacggt gcctgactgc 138960
gttagcaatt taactgtgat aaactaccgc attaaagctt atcgatgata agctgtcaaa 139020
catgagaatt gatccggaac ccttaatata acttcgtata atgtatgcta tacgaagtta 139080
ttaggtccct cgactatagg gtcaccgtcg acagcgacac acttgcatcg gatgcagccc 139140
ggttaacgtg ccggcacggc ctgggtaacc aggtattttg tccacataac cgtgcgcaaa 139200
atgttgtgga taagcaggac acagcagcaa tccacagcag gcatacaacc gcacaccgag 139260
```

```
gttactccgt tctacaggtt acgacgacat gtcaatactt gcccttgaca ggcattgatg   139320
gaatcgtagt ctcacgctga tagtctgatc gacaatacaa gtgggaccgt ggtcccagac   139380
cgataatcag accgacaaca cgagtgggat cgtggtccca gactaataat cagaccgacg   139440
atacgagtgg gaccgtggtc ccagactaat aatcagaccg acgatacgag tgggaccgtg   139500
gttccagact aataatcaga ccgacgatac gagtgggacc gtggtcccag actaataatc   139560
agaccgacga tacgagtggg accatggtcc cagactaata atcagaccga cgatacgagt   139620
gggaccgtgg tcccagtctg attatcagac cgacgatacg agtgggaccg tggtcccaga   139680
ctaataatca gaccgacgat acgagtggga ccgtggtccc agactaataa tcagaccgac   139740
gatacgagtg gaccgtggt cccagtctga ttatcagacc gacgatacaa gtggaacagt   139800
gggcccagag agaatattca ggccagttat gctttctggc ctgtaacaaa ggacattaag   139860
taaagacaga taaacgtaga ctaaaacgtg gtcgcatcag ggtgctggct tttcaagttc   139920
cttaagaatg gcctcaattt tctctataca ctcagttgga acacgagacc tgtccaggtt   139980
aagcaccatt ttatcgccct tatacaatac tgtcgctcca ggagcaaact gatgtcgtga   140040
gcttaaacta gttcttgatg cagatgacgt tttaagcaca gaagttaaaa gagtgataac   140100
ttcttcagct tcaaatatca ccccagcttt tttctgctca tgaaggttag atgcctgctg   140160
cttaagtaat tcctctttat ctgtaaaggc ttttttgaagt gcatcacctg accgggcaga   140220
tagttcaccg gggtgagaaa aaagagcaac aactgattta ggcaatttgg cggtgttgat   140280
acagcgggta ataatcttac gtgaaatatt ttccgcatca gccagcgcag aaatatttcc   140340
agcaaattca ttctgcaatc ggcttgcata acgctgacca cgttcataag cacttgttgg   140400
gcgataatcg ttacccaatc tggataatgc agccatctgc tcatcatcca gctcgccaac   140460
cagaacacga taatcacttt cggtaagtgc agcagcttta cgacggcgac tcccatcggc   140520
aatttctatg acaccagata ctcttcgacc gaacgccggt gtctgttgac cagtcagtag   140580
aaaagaaggg atgagatcat ccagtgcgtc ctcagtaagc agctcctggt cacgttcatt   140640
acctgaccat acccgagagg tcttctcaac actatcaccc cggagcactt caagagtaaa   140700
cttcacatcc cgaccacata caggcaaagt aatggcatta ccgcgagcca ttactcctac   140760
gcgcgcaatt aacgaatcca ccatcggggc agctggtgtc gataacgaag tatcttcaac   140820
cggttgagta ttgagcgtat gttttggaat aacaggcgca cgcttcatta tctaatctcc   140880
cagcgtggtt taatcagacg atcgaaaatt tcattgcaga caggttccca aatagaaaga   140940
gcatttctcc aggcaccagt tgaagagcgt tgatcaatgg cctgttcaaa acagttctc   141000 atccggatct gacctttacc aacttcatcc gtttcacgta caacattttt tagaaccatg   141060
cttccccagg catcccgaat ttgctcctcc atccacgggg actgagagcc attactattg   141120
ctgtatttgg taagcaaaat acgtacatca ggctcgaacc ctttaagatc aacgttcttg   141180
agcagatcac gaagcatatc gaaaaactgc agtgcgagg tgtagtcaaa caactcagca   141240
ggcgtgggaa caatcagcac atcagcagca catacgacat taatcgtgcc gatacccagg   141300
ttaggcgcgc tgtcaataac tatgacatca tagtcatgag caacagtttc aatggccagt   141360
cggagcatca ggtgtggatc ggtgggcagt ttaccttcat caaatttgcc cattaactca   141420
gtttcaatac ggtgcagagc cagacaggaa ggaataatgt caagccccgg ccagcaagtg   141480
ggctttattg cataagtgac atcgtccttt tccccaagat agaaaggcag gagagtgtct   141540
tctgcatgaa tatgaagatc tggtacccat ccgtgataca ttgaggctgt tccctggggg   141600
tcgttacctt ccacgagcaa aacacgtagc cccttcagag ccagatcctg agcaagatga   141660
```

```
acagaaactg aggttttgta aacgccacct ttatgggcag caaccccgat caccggtgga 141720
aatacgtctt cagcacgtcg caatcgcgta ccaaacacat cacgcatatg attaatttgt 141780
tcaattgtat aaccaacacg ttgctcaacc cgtcctcgaa tttccatatc cgggtgcggt 141840
agtcgccctg ctttctcggc atctctgata gcctgagaag aaaccccaac taaatccgct 141900
gcttcaccta ttctccagcg ccgggttatt ttcctcgctt ccgggctgtc atcattaaac 141960
tgtgcaatgg cgatagcctt cgtcatttca tgaccagcgt ttatgcactg gttaagtgtt 142020
tccatgagtt tcattctgaa catcctttaa tcattgcttt gcgttttttt attaaatctt 142080
gcaatttact gcaaagcaac aacaaaatcg caaagtcatc aaaaaaccgc aaagttgttt 142140
aaaataagag caacactaca aaggagata agaagagcac atacctcagt cacttattat 142200
cactagcgct cgccgcagcc gtgtaaccga gcatagcgag cgaactggcg aggaagcaaa 142260
gaagaactgt tctgtcagat agctcttacg ctcagcgcaa gaagaaatat ccaccgtggg 142320
aaaaactcca ggtagaggta cacacgcgga tagccaattc agagtaataa actgtgataa 142380
tcaaccctca tcaatgatga cgaactaacc cccgatatca ggtcacatga cgaagggaaa 142440
gagaaggaaa tcaactgtga caaactgccc tcaaatttgg cttccttaaa aattacagtt 142500
caaaaagtat gagaaaatcc atgcaggctg aaggaaacag caaaactgtg acaaattacc 142560
ctcagtaggt cagaacaaat gtgacgaacc accctcaaat ctgtgacaga taaccctcag 142620
actatcctgt cgtcatggaa gtgatatcgc ggaaggaaaa tacgatatga gtcgtctggc 142680
ggcctttctt tttctcaatg tatgagaggc gcattggagt tctgctgttg atctcattaa 142740
cacagacctg caggaagcgg cggcggaagt caggcatacg ctggtaactt tgaggcagct 142800
ggtaacgctc tatgatccag tcgatttca gagagacgat gcctgagcca tccggcttac 142860
gatactgaca cagggattcg tataaacgca tggcatacgg attggtgatt tctttgtttt 142920
cactaagccg aaactgcgta aaccggttct gtaacccgat aaagaaggga atgagatatg 142980
ggttgatatg tacactgtaa agccctctgg atggactgtg cgcacgtttg ataaaccaag 143040
gaaaagattc atagccttt tcatcgccgg catcctcttc agggcgataa aaaaccactt 143100
ccttccccgc gaaactcttc aatgcctgcc gtatatcctt actggcttcc gcagaggtca 143160
atccgaatat ttcagcatat ttagcaacat ggatctcgca gataccgtca tgttcctgta 143220
gggtgccatc agatttctg atctggtcaa cgaacagata cagcatacgt ttttgatccc 143280
gggagagact atatgccgcc tcagtgaggt cgtttgactg gacgattcgc gggctatttt 143340
tacgtttctt gtgattgata accgctgttt ccgccatgac agatccatgt gaagtgtgac 143400
aagtttttag attgtcacac taaataaaaa agagtcaata agcagggata actttgtgaa 143460
aaaacagctt cttctgaggg caatttgtca cagggttaag ggcaatttgt cacagacagg 143520
actgtcattt gagggtgatt tgtcacactg aaagggcaat tgtcacaac accttctcta 143580
gaaccagcat ggataaaggc ctacaaggcg ctctaaaaaa gaagatctaa aaactataaa 143640
aaaaataatt ataaaaatat ccccgtggat aagtggataa ccccaaggga agttttttca 143700
ggcatcgtgt gtaagcagaa tatataagtg ctgttccctg gtgcttcctc gctcactcga 143760
gggcttcgcc ctgtcgctca actgcggcga gcactactgg ctgtaaaagg acagaccaca 143820
tcatggttct gtgttcatta ggttgttctg tccattgctg acataatccg ctccacttca 143880
acgtaacacc gcacgaagat ttctattgtt cctgaaggca tattcaaatc gttttcgtta 143940
ccgcttgcag gcatcatgac agaacactac ttcctataaa cgctacacag gctcctgaga 144000
```

```
ttaataatgc ggatctctac gataatggga gattttcccg actgtttcgt tcgcttctca  144060
gtggataaca gccagcttct ctgtttaaca gacaaaaaca gcatatccac tcagttccac  144120
atttccatat aaaggccaag gcatttattc tcaggataat tgtttcagca tcgcaaccgc  144180
atcagactcc ggcatcgcaa actgcacccg gtgccgggca gccacatcca gcgcaaaaac  144240
cttcgtgtag acttccgttg aactgatgga cttatgtccc atcaggcttt gcagaacttt  144300
cagcggtata ccggcataca gcatgtgcat cgcataggaa tggcggaacg tatgtggtgt  144360
gaccggaaca gagaacgtca caccgtcagc agcagcggcg gcaaccgcct ccccaatcca  144420
ggtcctgacc gttctgtccg tcacttccca gatccgcgct ttctctgtcc ttcctgtgcg  144480
acggttacgc cgctccatga gcttatcgcg aataaatacc tgtgacggaa gatcacttcg  144540
cagaataaat aaatcctggt gtccctgttg ataccgggaa gccctgggcc aacttttggc  144600
gaaaatgaga cgttgatcgg cacgtaagag gttccaactt tcaccataat gaaataagat  144660
cactaccggg cgtattttt gagttatcga gattttcagg agctaaggaa gctaaaatgg  144720 agaaaaaat cactggatat accaccgttg atatatccca atggcatcgt aaagaacatt  144780
ttgaggcatt tcagtcagtt gctcaatgta cctataacca gaccgttcag ctggatatta  144840
cggccttttt aaagaccgta aagaaaaata agcacaagtt ttatccggcc tttattcaca  144900
ttcttgcccg cctgatgaat gctcatccgg agttccgtat ggcaatgaaa gacggtgagc  144960
tggtgatatg ggatagtgtt cacccttgtt acaccgtttt ccatgagcaa actgaaacgt  145020
tttcatcgct ctggagtgaa taccacgacg atttccggca gtttctacac atatattcgc  145080
aagatgtggc gtgttacggt gaaaacctgg cctatttccc taaagggttt attgagaata  145140
tgtttttcgt ctcagccaat ccctgggtga gtttcaccag ttttgattta aacgtggcca  145200
atatggacaa cttcttcgcc cccgttttca ccatgggcaa atattatacg caaggcgaca  145260
aggtgctgat gccgctggcg attcaggttc atcatgccgt ttgtgatggc ttccatgtcg  145320
gcagaatgct taatgaatta caacagtact gcgatgagtg cagggcggg gcgtaatttt  145380 tttaaggcag ttattggtgc ccttaaacgc ctggttgcta cgcctgaata agtgataata  145440
agcggatgaa tggcagaaat tcgatgataa gctgtcaaac atgagaattg gtcgacggcg  145500
cgccaaagct tgcatgcctg cagccgcgta acctggcaaa atcggttacg gttgagtaat  145560
aaatggatgc cctgcgtaag cggggcacat ttcattacct ctttctccgc acccgacata  145620
gataataact tcgtatagta tacattatac gaagttatct agtagactta attaaggatc  145680
gatccggcgc gccaatagtc atgccccgcg cccaccggaa ggagctgact gggttgaagg  145740
ctctcaaggg catcggtcga gcttgacatt gtaggactat attgctctaa taaatttgcg  145800
gccgctaata cgactcacta tagggagagg atccgcg                           145837
```

<210> SEQ ID NO 2  
<211> LENGTH: 23  
<212> TYPE: RNA  
<213> ORGANISM: Artificial Sequence  
<220> FEATURE:  
<223> OTHER INFORMATION: PN-based TLR7 ligand stabilized immunomodulatory RNAt  
<220> FEATURE:  
<221> NAME/KEY: misc_feature  
<222> LOCATION: 2,5,11,13,19,22  
<223> OTHER INFORMATION: n = 7-deazaguanosine  
<220> FEATURE:  
<221> NAME/KEY: misc_feature  
<222> LOCATION: 12  
<223> OTHER INFORMATION: n = Glycerol

<400> SEQUENCE: 2
uncuncuucu nnnucuucnu cnu                                           23

<210> SEQ ID NO 3
<211> LENGTH: 25
<212> TYPE: RNA
<213> ORGANISM: Artificial Sequence
<220> FEATURE:
<223> OTHER INFORMATION: PN-based TLR8 ligand stabilized
      immunomodulatory RNA
<220> FEATURE:
<221> NAME/KEY: misc_feature
<222> LOCATION: 1,25
<223> OTHER INFORMATION: n = C6-linker
<220> FEATURE:
<221> NAME/KEY: misc_feature
<222> LOCATION: 13
<223> OTHER INFORMATION: n = Glycerol

<400> SEQUENCE: 3
nugcugcuug ugnguguucg ucgun                                         25

<210> SEQ ID NO 4
<211> LENGTH: 1041
<212> TYPE: PRT
<213> ORGANISM: Homo sapiens
<220> FEATURE:
<223> OTHER INFORMATION: TLR8 Sequence of GENBANK Accession No.
      NP_619542.1

<400> SEQUENCE: 4

Met Glu Asn Met Phe Leu Gln Ser Ser Met Leu Thr Cys Ile Phe Leu
1               5                   10                  15

Leu Ile Ser Gly Ser Cys Glu Leu Cys Ala Glu Glu Asn Phe Ser Arg
            20                  25                  30

Ser Tyr Pro Cys Asp Glu Lys Lys Gln Asn Asp Ser Val Ile Ala Glu
        35                  40                  45

Cys Ser Asn Arg Arg Leu Gln Glu Val Pro Gln Thr Val Gly Lys Tyr
    50                  55                  60

Val Thr Glu Leu Asp Leu Ser Asp Asn Phe Ile Thr His Ile Thr Asn
65                  70                  75                  80

Glu Ser Phe Gln Gly Leu Gln Asn Leu Thr Lys Ile Asn Leu Asn His
                85                  90                  95

Asn Pro Asn Val Gln His Gln Asn Gly Asn Pro Gly Ile Gln Ser Asn
            100                 105                 110

Gly Leu Asn Ile Thr Asp Gly Ala Phe Leu Asn Leu Lys Asn Leu Arg
        115                 120                 125

Glu Leu Leu Leu Glu Asp Asn Gln Leu Pro Gln Ile Pro Ser Gly Leu
    130                 135                 140

Pro Glu Ser Leu Thr Glu Leu Ser Leu Ile Gln Asn Asn Ile Tyr Asn
145                 150                 155                 160

Ile Thr Lys Glu Gly Ile Ser Arg Leu Ile Asn Leu Lys Asn Leu Tyr
                165                 170                 175

Leu Ala Trp Asn Cys Tyr Phe Asn Lys Val Cys Glu Lys Thr Asn Ile
            180                 185                 190

Glu Asp Gly Val Phe Glu Thr Leu Thr Asn Leu Glu Leu Leu Ser Leu
        195                 200                 205

Ser Phe Asn Ser Leu Ser His Val Pro Pro Lys Leu Pro Ser Ser Leu
    210                 215                 220

Arg Lys Leu Phe Leu Ser Asn Thr Gln Ile Lys Tyr Ile Ser Glu Glu

```
            225                 230                 235                 240
        Asp Phe Lys Gly Leu Ile Asn Leu Thr Leu Leu Asp Leu Ser Gly Asn
                        245                 250                 255
        Cys Pro Arg Cys Phe Asn Ala Pro Phe Pro Cys Val Pro Cys Asp Gly
                        260                 265                 270
        Gly Ala Ser Ile Asn Ile Asp Arg Phe Ala Phe Gln Asn Leu Thr Gln
                        275                 280                 285
        Leu Arg Tyr Leu Asn Leu Ser Ser Thr Ser Leu Arg Lys Ile Asn Ala
                        290                 295                 300
        Ala Trp Phe Lys Asn Met Pro His Leu Lys Val Leu Asp Leu Glu Phe
        305                 310                 315                 320
        Asn Tyr Leu Val Gly Glu Ile Ala Ser Gly Ala Phe Leu Thr Met Leu
                        325                 330                 335
        Pro Arg Leu Glu Ile Leu Asp Leu Ser Phe Asn Tyr Ile Lys Gly Ser
                        340                 345                 350
        Tyr Pro Gln His Ile Asn Ile Ser Arg Asn Phe Ser Lys Leu Leu Ser
                        355                 360                 365
        Leu Arg Ala Leu His Leu Arg Gly Tyr Val Phe Gln Glu Leu Arg Glu
                        370                 375                 380
        Asp Asp Phe Gln Pro Leu Met Gln Leu Pro Asn Leu Ser Thr Ile Asn
        385                 390                 395                 400
        Leu Gly Ile Asn Phe Ile Lys Gln Ile Asp Phe Lys Leu Phe Gln Asn
                        405                 410                 415
        Phe Ser Asn Leu Glu Ile Ile Tyr Leu Ser Glu Asn Arg Ile Ser Pro
                        420                 425                 430
        Leu Val Lys Asp Thr Arg Gln Ser Tyr Ala Asn Ser Ser Ser Phe Gln
                        435                 440                 445
        Arg His Ile Arg Lys Arg Ser Thr Asp Phe Glu Phe Asp Pro His
                        450                 455                 460
        Ser Asn Phe Tyr His Phe Thr Arg Pro Leu Ile Lys Pro Gln Cys Ala
        465                 470                 475                 480
        Ala Tyr Gly Lys Ala Leu Asp Leu Ser Leu Asn Ser Ile Phe Phe Ile
                        485                 490                 495
        Gly Pro Asn Gln Phe Glu Asn Leu Pro Asp Ile Ala Cys Leu Asn Leu
                        500                 505                 510
        Ser Ala Asn Ser Asn Ala Gln Val Leu Ser Gly Thr Glu Phe Ser Ala
                        515                 520                 525
        Ile Pro His Val Lys Tyr Leu Asp Leu Thr Asn Asn Arg Leu Asp Phe
                        530                 535                 540
        Asp Asn Ala Ser Ala Leu Thr Glu Leu Ser Asp Leu Glu Val Leu Asp
        545                 550                 555                 560
        Leu Ser Tyr Asn Ser His Tyr Phe Arg Ile Ala Gly Val Thr His His
                        565                 570                 575
        Leu Glu Phe Ile Gln Asn Phe Thr Asn Leu Lys Val Leu Asn Leu Ser
                        580                 585                 590
        His Asn Asn Ile Tyr Thr Leu Thr Asp Lys Tyr Asn Leu Glu Ser Lys
                        595                 600                 605
        Ser Leu Val Glu Leu Val Phe Ser Gly Asn Arg Leu Asp Ile Leu Trp
                        610                 615                 620
        Asn Asp Asp Asp Asn Arg Tyr Ile Ser Ile Phe Lys Gly Leu Lys Asn
        625                 630                 635                 640
        Leu Thr Arg Leu Asp Leu Ser Leu Asn Arg Leu Lys His Ile Pro Asn
                        645                 650                 655
```

Glu Ala Phe Leu Asn Leu Pro Ala Ser Leu Thr Glu Leu His Ile Asn
            660                 665                 670

Asp Asn Met Leu Lys Phe Phe Asn Trp Thr Leu Leu Gln Gln Phe Pro
        675                 680                 685

Arg Leu Glu Leu Leu Asp Leu Arg Gly Asn Lys Leu Leu Phe Leu Thr
    690                 695                 700

Asp Ser Leu Ser Asp Phe Thr Ser Ser Leu Arg Thr Leu Leu Leu Ser
705                 710                 715                 720

His Asn Arg Ile Ser His Leu Pro Ser Gly Phe Leu Ser Glu Val Ser
                725                 730                 735

Ser Leu Lys His Leu Asp Leu Ser Ser Asn Leu Leu Lys Thr Ile Asn
            740                 745                 750

Lys Ser Ala Leu Glu Thr Lys Thr Thr Thr Lys Leu Ser Met Leu Glu
        755                 760                 765

Leu His Gly Asn Pro Phe Glu Cys Thr Cys Asp Ile Gly Asp Phe Arg
    770                 775                 780

Arg Trp Met Asp Glu His Leu Asn Val Lys Ile Pro Arg Leu Val Asp
785                 790                 795                 800

Val Ile Cys Ala Ser Pro Gly Asp Gln Arg Gly Lys Ser Ile Val Ser
                805                 810                 815

Leu Glu Leu Thr Thr Cys Val Ser Asp Val Thr Ala Val Ile Leu Phe
            820                 825                 830

Phe Phe Thr Phe Phe Ile Thr Thr Met Val Met Leu Ala Ala Leu Ala
        835                 840                 845

His His Leu Phe Tyr Trp Asp Val Trp Phe Ile Tyr Asn Val Cys Leu
    850                 855                 860

Ala Lys Val Lys Gly Tyr Arg Ser Leu Ser Thr Ser Gln Thr Phe Tyr
865                 870                 875                 880

Asp Ala Tyr Ile Ser Tyr Asp Thr Lys Asp Ala Ser Val Thr Asp Trp
                885                 890                 895

Val Ile Asn Glu Leu Arg Tyr His Leu Glu Glu Ser Arg Asp Lys Asn
            900                 905                 910

Val Leu Leu Cys Leu Glu Glu Arg Asp Trp Asp Pro Gly Leu Ala Ile
        915                 920                 925

Ile Asp Asn Leu Met Gln Ser Ile Asn Gln Ser Lys Lys Thr Val Phe
    930                 935                 940

Val Leu Thr Lys Lys Tyr Ala Lys Ser Trp Asn Phe Lys Thr Ala Phe
945                 950                 955                 960

Tyr Leu Ala Leu Gln Arg Leu Met Asp Glu Asn Met Asp Val Ile Ile
                965                 970                 975

Phe Ile Leu Leu Glu Pro Val Leu Gln His Ser Gln Tyr Leu Arg Leu
            980                 985                 990

Arg Gln Arg Ile Cys Lys Ser Ser Ile Leu Gln Trp Pro Asp Asn Pro
        995                 1000                1005

Lys Ala Glu Gly Leu Phe Trp Gln Thr Leu Arg Asn Val Val Leu Thr
    1010                1015                1020

Glu Asn Asp Ser Arg Tyr Asn Asn Met Tyr Val Asp Ser Ile Lys Gln
1025                1030                1035                1040

Tyr

<210> SEQ ID NO 5
<211> LENGTH: 5
<212> TYPE: PRT

```
<213> ORGANISM: Homo sapiens

<400> SEQUENCE: 5

Arg Gln Ser Tyr Ala
1               5
```

TRANSGENIC MICE EXPRESSING HUMAN TOLL-LIKE RECEPTOR 8

CROSS-REFERENCE TO RELATED APPLICATIONS

This application claims the benefit of U.S. Provisional Patent Application No. 61/469,055, filed Mar. 29, 2011, which is hereby incorporated by reference herein in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 377882005000SeqList.txt, date recorded: Mar. 29, 2012, size: 184 KB).

FIELD OF THE INVENTION

This application relates to human Toll-like receptor 8 (TLR8)-expressing transgenic animals and methods of use thereof.

BACKGROUND OF THE INVENTION

Immunity can generally be classified as innate immunity or as adaptive immunity. Innate immune responses typically occur immediately upon infection to provide an early barrier to infectious disease, whereas adaptive immune responses occur later with the generation of antigen-specific effector cells and immunological memory. Innate immune responses do not generate lasting protective immunity, but appear to play a role in the generation of later arising adaptive immune responses.

Toll-like receptors (TLRs) are essential for innate immune responses as they recognize several different antigens and initiate immune responses (e.g., activation of dendritic cells and macrophages, and cytokine production). TLRs are type-I transmembrane proteins that recognize a variety of pathogen-associated molecular patterns (PAMPs) from bacteria, viruses and fungi. In this way PAMPs serve as a first-line of defense against invading pathogens. Human TLRs can elicit overlapping yet distinct biological responses due to differences in cellular expression and activation of downstream signal transduction pathways (Akira et al., *Adv. Immunol.* 78: 1-56, 2001).

TLRs are characterized by an ectodomain composed of leucine-rich repeats and a cytoplasmic domain, known as a Toll/interleukin-1 receptor domain. The ectodomain is responsible for recognition of PAMPs, while the cytoplasmic domain is required for downstream signaling. TLRs usually undergo dimer formation and/or a conformation change to activate downstream signal transduction pathways. Studies have shown that LRR8 is involved in DNA and RNA recognition, whereas LRR17 is involved in nucleic acid binding (Smits et al., *Oncologist*, 13: 859-875, 2008).

The family of TLRs consists of ten members in human (TLR1-TLR10) and twelve members in mice (TLR1-TLR9 and TLR11-TLR13). The TLRs that are located in the plasma membrane recognize bacterial membrane components, whereas the TLRs that detect nucleic acid-based ligands are predominately located within endosomal compartments. The nucleic acid-sensing TLRs include TLR3, TLR7, TLR8, and TLR9. Upon ligand-binding, TLRs initiate a signal transduction cascade leading to activation of NFκB through the adapter protein myeloid differentiation primary response gene 88 (MyD88) and recruitment of the IL-1 receptor associated kinase (IRAK). Phosphorylation of IRAK in turn leads to the recruitment of TNF-receptor associated factor 6 (TRAF6), which results in the phosphorylation and degradation of the NF-κB inhibitor, I-κB, thereby releasing NF-κB. NF-κB enters the cell nucleus and initiates gene transcription, leading to production of proflammatory cytokines, chemokines, and type I interferons (IFNs), as well as the upregulation of costimulatory molecules.

TLR8 belongs to the same subfamily as the TLR7 and TLR9 endosomal receptors and is highly homologous to TLR7 (Liu et al., *Mol. Immunol.* 47:1083-90, 2010). The role of TLR8, and of its close homologue TLR7, is to detect the presence of "foreign" single-stranded RNA within a cell, as a means to respond to viral invasion (Heil et al., *Science* 303: 1526, 2004; and Diebold et al., *Science* 303:1529, 2004). While the TLR8 gene in humans is closely related to TLR7, TLR8 has distinct, but overlapping specificity for RNA and synthetic small molecules with a structure related to nucleic acids (Medzhitov et al., *Immunol. Rev.* 173:89-97, 2000). Some ssRNA synthetic sequences containing repetitive A/U motifs are able to specifically activate TLR8 but not TLR7 (Gorden et al. *J. Immunol.* 174:1259-68, 2005). Further, in humans, TLR8 is highly expressed in monocytes, macrophages, myeloid dendritic cells (mDC) and neutrophils, whereas TLR7 in blood cells is principally expressed in pDCs, B-cells, and neutrophils. Because of this difference in cellular expression, triggering by RNA through TLR7 in blood leads to a response dominated by Type I IFN production, whereas activation through TLR8 induces multiple proinflammatory cytokines: TNF, IL-12, IL-6, IL-8 and IL-1 (Barrat et al., *J Exp Med.* 2202:1131-9, 2005; and Gorden et al., *J. Immunol.* 174:1259-68, 2005).

Although TLR8 polymorphisms have been associated with some autoimmune diseases, the role of TLR8 and its specific ligands has not been clearly defined. One key limitation in elucidating TLR8 biology is the lack of an animal model. For example, mouse TLR8 has a very different specificity than human TLR8. Mouse TLR8 lacks the ability to respond to ssRNA ligands, RNA viruses or small molecules; all of which have been shown to activate human TLR8 (Heil et al. Science 303:1526-9, 2004; Jurk et al. *Nat Immunol* 3:499, 2002; Hemmi et al. *Nat. Immunol* 3:196-200, 2002; and Lund et al. *PNAS* 101:5598-603, 2004). Further, by comparing the amino acid sequence, TLR8 of mice and rats lack a five amino-acid sequence required for ligand recognition in man (Liu et al. *Mol. Immunol.* 47:1083-90, 2010). The lack of useful animal models and the very different ligand specificities of human TLR8 and its rodent orthologs have proven to be major limitations to the study of TLR8 biology.

SUMMARY OF THE INVENTION

Provided herein are transgenic animals comprising a nucleotide sequence encoding human Toll-like receptor 8 (TLR8), wherein the human TLR8 is expressed in the transgenic animal. In some embodiments, the transgenic animal is a nonhuman mammal. In some embodiments, the transgenic animal is a small mammal selected from the group consisting of a mouse, hamster, rat, guineas pig, and rabbit. In some embodiments, the transgenic animal is a mouse. In some embodiments, the transgenic animal is a chimeric transgenic animal. In some embodiments, both germ cells and somatic cells of the transgenic animal comprise the nucleotide sequence encoding human TLR8. In some embodiments, the nucleotide sequence encoding human TLR8 is stably integrated into the genome of the transgenic animal. In some embodiments, the nucleotide sequence encoding human TLR8 is present at a copy number of from 1 to 15 (e.g., from 1 to 5, from 6 to 10, from 11 to 15, or 1, 2, 3, 4, 5, 6, 7, 8, 9, 10, 11, 12, 13, 14 or 15). In some embodiments, the nucleotide sequence encoding human TLR8 is operatively linked to a promoter and/or other regulatory regions. In some embodiments, the promoter and/or other regulatory regions are those of human TLR8. In some embodiments, the human TLR8 is expressed in a similar expression pattern in the transgenic animal as human TLR8 is expressed in humans. In some embodiments, the levels of expression of human TLR8 in the transgenic animal is similar to the level of expression of human TLR8 in humans. In some embodiments, the transgenic animal is predisposed to development of inflammation in one or more organs (e.g., pancreas, kidney, liver, joints, reproductive tissue, etc.). In some embodiments, the inflammation comprises an autoimmune disease (e.g., pancreatitis, nephritis, hepatitis, rheumatoid arthritis, diabetes, diabetes-related disorder, reproductive disease, etc.). In some embodiments, the present disclosure provides a cell obtained from the transgenic animal described herein, wherein the human TLR8 is expressed in the cell. In some embodiments, the cell is a hematopoietic cell. In some embodiments, the hematopoietic cell is a monocyte. Provided herein are also methods of screening candidate agents, the methods comprising: administering a candidate agent to the transgenic animal; and determining the effect of the candidate agent on the animal (e.g., as compared to a control such as untreated animal or an animal receiving a placebo). Some methods comprise administering a candidate agent to the transgenic animal; and determining the effect of the candidate agent on a TLR8-mediated response of the animal (e.g., as compared to a control such as an untreated animal or an animal receiving a placebo). Additionally, provided herein are methods of screening candidate agents, the method comprising: contacting the cell obtained from the transgenic animal with a candidate agent; and determining the effect of the candidate agent on the cell (e.g., as compared to a control such as an untreated or mock-treated cell). Some methods comprise contacting the cell obtained from the transgenic animal with a candidate agent; and determining the effect of the candidate agent on the cell (e.g., as compared to a control such as untreated or mock-treated cell). In some embodiments, the effect comprises inhibition of the TLR8-mediated response (e.g., reduction of the response to less than 50, 60, 70, 75, 80, 85, 90 or 95% of that observed in the absence of the candidate agent). In alternative embodiments, the effect comprises stimulation of the TLR8-mediated response (e.g., elevation of the response to at least 150, 160, 170, 180, 190 or 200% of that observed in the absence of the candidate agent). In some, the TLR8-mediated response is evidenced by a change in TLR8-mediated cytokine production, cell proliferation, and/or cell surface marker expression. A TLR8-mediated response is one that is stimulable by a TLR7/8 agonist such as R848 and CL075 or a TLR8 agonist such as a TLR8 ligand stabilized immunomodulatory RNA (e.g., SEQ ID NO:3). TLR8-mediated responses are assessed by measuring expression of a cytokine or a cell surface marker. Suitable cytokines are selected from but not limited to TNF-α, IFN-α, IFN-β, IFN-γ, IL-1α, IL-1β, IL-6, IL-8, IL-10, IL-12, IL-23, IP-10, MIP-1, and MCP-1. Suitable cell surface molecules are selected from but not limited CD40, CD80, CD86, ICAM-1, ICAM-2, ICAM-3, and CCR7. In some embodiments, the cytokine comprises one or more of the group consisting of TNF, IL-12, IL-6, MIP-1α, IFNγ, IP-10, IL-1α, and IL-1β. In some embodiments, the candidate agent is an antibody. In some embodiments, the candidate agent is a small molecule. In some preferred embodiments, the candidate agent is a polynucleotide. In some preferred embodiments, the TLR8-mediated cytokine production comprises production of one or more of the group consisting of TNF, IL-12, IL-6, MIP-1α, IFNγ, IP-10, IL-1α, and IL-1β.

Moreover, the present disclosure provides methods for screening, and/or identifying, TLR8 modulators, the method comprising: providing a candidate agent to a cell culture, wherein cells of the cell culture comprises cells derived from a TLR8 transgenic animal which comprises a nucleotide sequence encoding human TLR8; and determining the effect of the candidate agent on the cell culture (as compared to a control such as untreated or mock-treated cell culture). Further, provided are methods of screening for, and/or identifying, TLR8 modulators, the method comprising: providing a candidate agent to a cell culture, wherein cells of the cell culture are obtained or prepared from a transgenic animal described herein which comprise a nucleotide sequence encoding human TLR8; and determining the effect of the candidate agent on the cell culture (as compared to a control such as untreated or mock-treated cell culture). In some embodiments, the cells are hematopoietic cells. In some embodiments, the cells are monocytes. In some embodiments, the effect is inhibition of cytokine production, cell proliferation and/or cell surface molecule expression. In some embodiments, the effect is stimulation of cytokine production, cell proliferation and/or cell surface molecule expression. Suitable cytokines are selected from but not limited to TNF-α, IFN-α, IFN-β, IFN-γ, IL-1α, IL-1β, IL-6, IL-8, IL-10, IL-12, IL-23, IP-10, MIP-1, and MCP-1. Suitable cell surface molecules are selected from but not limited CD40, CD80, CD86, ICAM-1, ICAM-2, ICAM-3, and CCR7. In some embodiments, the cytokine comprises one or more of the group consisting of TNF, IL-12, IL-6, MIP-1α, IFNγ, IP-10, IL-1α, and IL-1β. In some embodiments, the candidate agent is an antibody (e.g., antibody fragment). In some embodiments, the candidate agent is a small molecule. In some embodiments, the candidate agent is a polynucleotide. In some embodiments, the polynucleotide comprises a TLR8 immunoregulatory sequence (IRS). In some embodiments, the polynucleotide comprises a TLR8 immunostimulatory sequence (ISS). In some embodiments, the candidate agent is an antagonist. In some embodiments, the candidate agent is an agonist.

BRIEF DESCRIPTION OF THE DRAWINGS

FIG. 6A shows the survival curve of human TLR8 chimeric mice from clone 6 (number of mice=14), clone 23 (number of mice=8), clone 12 (number of mice=18), and clone 8 (number of mice=18). FIG. 6B shows the TLR8 expression levels as relative CT in these mice. FIG. 6C shows the elevated level of inflammatory cytokines in serum of TLR8Tg mice from clone 12 (n=15) as compared to control, wild-type C57BL/6 mice (n=18).

FIG. 7A-F shows upregulation of expression of inflammatory cytokines IFN-γ, IL12-p40, TNF-α, IP-10, IL-1α, IL-1β by relative CT in the pancreas from chimeric mice from clone 6, 12 and 23 (total number of mice=6) compared to wild-type mice C57BL/6 (total number of mice=6). FIG. 7G-7I shows the titers of anti-nuclear antibody (ANA), anti-double stranded DNA (dsDNA) antibody and anti-ribonucleoprotein (RNP) antibody in the serum of TLR8TgCL12 (n=27) and age-matched controls (n=37).

FIG. 8A-D shows the levels of CD80, GITRL, CD40, and OX40L as determined by FACS analyses of myeloid dendritic cells (MDC) from chimeric TLR8TGCL23 mice as compared to wild-type C57BL/6 mice.

FIG. 15A provides a representative section of a joint from WT (C57BL/6 CTLR) mice. FIG. 15B provides a representative section of a joint from a TLR8Tg mouse. The histological changes, degree of inflammation and cartilage damage were evaluated by a pathologist in a blinded fashion and scored 1 to 5 as follows: 1=minimal, 2=mild, 3=moderate, 4=marked, 5=severe. Two paws and two ankles were evaluated for each mouse, and the scores were summed to obtain the histological disease score shown in FIG. 15C.

DETAILED DESCRIPTION OF THE INVENTION

Figure 1:
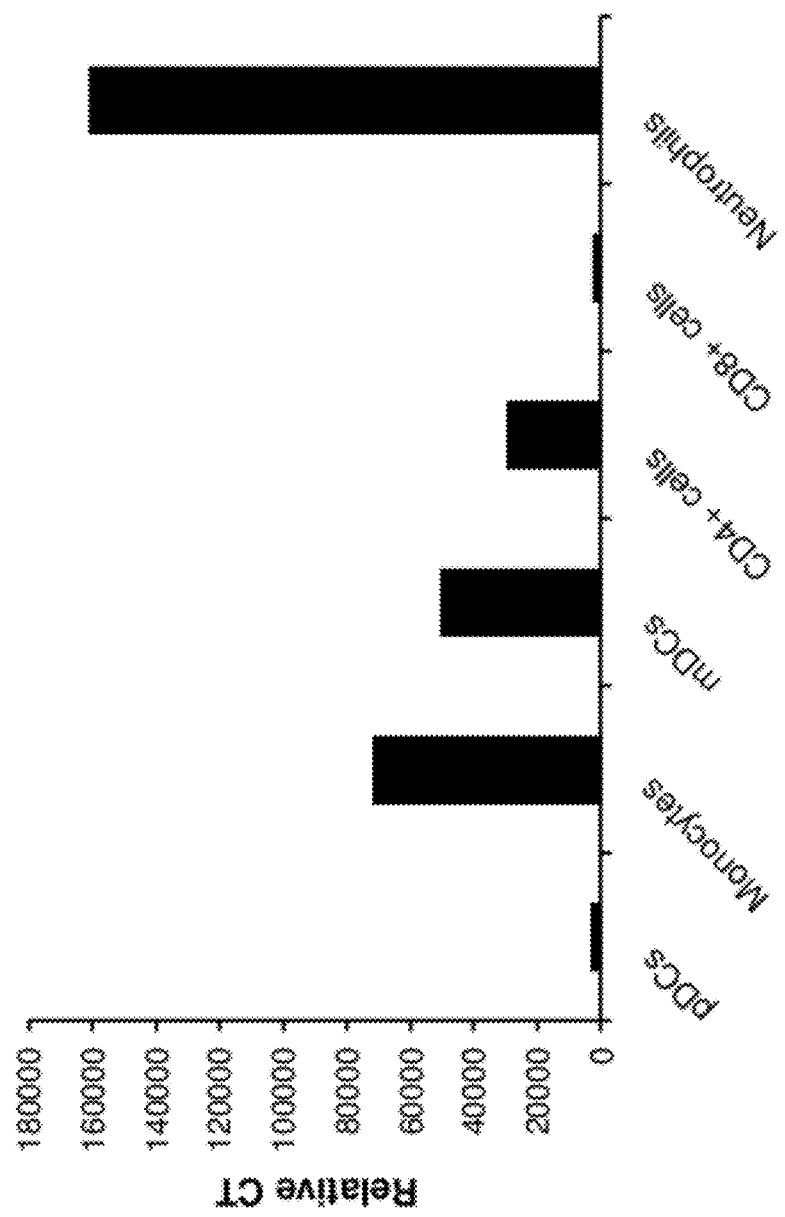
FIG. 1 shows the level of expression of human TLR8 in purified human subsets: plasmacytoid dendritic cells (PDC), monocytes, myeloid dendritic cells (MDC), CD4+ T-cells, CD8+ T-cells, and neutrophils.

Provided herein are hTLR8 transgenic animals, and cells therefrom that express human TLR8. Also provided are methods of screening for and/or identifying TLR8 modulators using the hTLR8 transgenic animals or cells expressing human TLR8.

Unless otherwise indicated, reference to an agent can include the compound in any pharmaceutically acceptable form, including any isomer (e.g., diastereomer or enantiomer), salt, solvate, polymorph, and the like. In particular, if a compound is optically active, reference to the compound can include each of the compounds enantiomers as well as racemic mixtures of the enantiomers.

definitions

The terms "nucleic acid," "polynucleotide," and "oligonucleotide" include single-stranded DNA (ssDNA), double-stranded DNA (dsDNA), single-stranded RNA (ssRNA) and double-stranded RNA (dsRNA), modified polynucleotides and polynucleosides or combinations thereof. The polynucleotide can be linearly, branched, or circularly configured, or the polynucleotide can contain one or more linear, branched, and/or circular segments. Polynucleotides are polymers of nucleosides joined, generally, through phosphodiester linkages, although alternate linkages, such as phosphorothioate esters may also be used in polynucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, thymidine, and deoxycytidine. A nucleotide is a phosphate ester of a nucleoside.

The term "peptide" includes polypeptides that are of any length and composition to affect a biological response, e.g., antibody production or cytokine activity whether or not the peptide is a hapten. The term "peptide" further includes modified amino acids (whether or not naturally or non-naturally occurring), such modifications including, but not limited to, phosphorylation, glycosylation, pegylation, lipidization and methylation.

The terms "promoter element" or "promoter" refer to a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease Si), as well as protein binding domains (consensus sequences) responsible for the binding of RNA polymerase. The promoter may be operably associated with other expression control sequences, including enhancer and repressor sequences.

The term "vector" refers to a nucleic acid assembly capable of transferring gene sequences to target cells (e.g., viral vectors, non-viral vectors, particulate carriers, and liposomes). The term "expression vector" refers to a nucleic acid assembly containing a promoter that is capable of directing the expression of a sequence or gene of interest in a cell. Vectors typically contain nucleic acid sequences encoding selectable markers for selection of cells that have been transfected by the vector. Generally, "vector construct," "expression vector," and "gene transfer vector," refer to any nucleic acid construct capable of directing the expression of a gene of interest and which can transfer gene sequences to target cells. Thus, the term includes cloning and expression vehicles, as well as viral vectors.

The term "wild-type" refers to a nucleic acid, protein, and/or animal (e.g., mouse) that has the characteristics of that nucleic acid, protein, and/or animal (e.g., mouse) when isolated from a naturally occurring source. A wild-type nucleic acid, protein, and/or animal (e.g., mouse) is that which is most frequently observed in a population and is thus arbitrarily designed the "normal" or "wild-type" form of that molecule. In contrast, the term "modified" or "mutant" refers to a nucleic acid, protein, and/or animal (e.g., mouse) that displays modifications in sequence and/or functional properties (i.e., altered characteristics) when compared to the wild-type nucleic acid, protein, and/or animal (e.g., mouse).

The term "agonist" is used in the broadest sense and refers to a molecule that can elevate or stimulate an induced cellular activity The term "antagonist" or "inhibitor" is used in the broadest sense, and refers to a composition that can reduce or inhibit an induced cellular activity.

The term "antibody" is used in the broadest sense and specifically covers, for example, monoclonal antibodies (including agonist, antagonist, and neutralizing antibodies), antibody compositions with polyepitopic specificity, polyclonal antibodies, single chain antibodies, and fragments of antibodies as long as they exhibit the desired biological or immunological activity. The term "immunoglobulin" (Ig) is used interchangeably with antibody herein.

The term "small molecule" as used herein refers to a low molecular weight organic compound (e.g., not a polymer). In some embodiments, the small molecule has a molecular weight of less than 2000, 1600, 800, or 400 daltons.

The term "immunostimulatory" or "stimulating an immune response" as used herein includes stimulation of cell types that participate in immune reactions and enhancement of an immune response to a specific antigenic substance. An immune response that is stimulated by an immunostimulatory nucleic acid is generally a "Th1-type" immune response, as opposed to a "Th2-type" immune response. Th1-type immune responses are normally characterized by "delayed-type hypersensitivity" reactions to an antigen and activated macrophage function and can be detected at the biochemical level by increased levels of Th1-associated cytokines such as IFN-γ, IL-2, IL-12, and TNF-α. Th2-type immune responses are generally associated with high levels of antibody production, especially IgE antibody production and enhanced eosinophils numbers and activation, as well as expression of Th2-associated cytokines such as IL-4, IL-5 and IL-13.

The term "immunoregulatory compound" or "IRC", as used herein, refers to a molecule which has immunoregulatory activity and which comprises a nucleic acid moiety comprising an IRS. The IRC may consist of a nucleic acid moiety that comprises more than one IRS or consists of an IRS. The IRC may comprise a modified and/or unmodified IRS. The IRC may consist of a polynucleotide (a "polynucleotide IRC") or it may comprise additional moieties. Accordingly, the term IRC includes compounds which incorporate one or more nucleic acid moieties, at least one of which comprises an IRS, covalently linked to a non-nucleotide spacer moiety.

The term "immunoregulatory sequence" or "IRS", as used herein, refers to a nucleic acid sequence that inhibits and/or suppresses a measurable immune response as measured in vitro, in vivo, and/or ex vivo. The term "immunoregulatory sequence" or "IRS", as used herein, refers to both nucleic acid sequences that comprise a modification (i.e., modified IRS) as well as nucleic acids which do not comprise a modification (i.e., unmodified IRS).

The term "TLR8 modulator" is used in the broadest sense, and includes TLR8 agonists and antagonists.

The term "cells," as used herein, is understood to refer not only to the particular subject cell, but to the progeny or potential progeny of such a cell. Because certain modifications may occur in succeeding generations due to either mutation or environmental influences, such progeny may not in fact be identical to the parent cell, but are still included within the scope of the term as used herein.

The term "transfection" refers to the uptake of DNA by a cell. A cell has been "transfected" when exogenous (i.e., foreign) DNA has been introduced inside the cell membrane. Transfection can be either transient (i.e., the introduced DNA remains extrachromosomal and is diluted out during cell division) or stable (i.e., the introduced DNA integrates into the cell genome or is maintained as a stable episomal element).

"Stimulation" of a response or parameter includes eliciting and/or enhancing that response or parameter when compared to otherwise same conditions except for a condition or parameter of interest, or alternatively, as compared to another condition. For example, "stimulation" of an immune response means an increase in the response, which can arise from eliciting and/or enhancement of a response. Similarly, "stimulation" of production of a cytokine (such as IL-1α, IL-1β, IL-6, and/or TNF-α) or "stimulation" of cell type (such as CTLs) means an increase in the amount or level of cytokine or cell type.

"Suppression" or "inhibition" of a response or parameter includes decreasing that response or parameter when compared to otherwise same conditions except for a condition or parameter of interest, or alternatively, as compared to another condition.

"Correlate" or "correlating" as used herein refer to comparing, in any way, the performance and/or results of a first analysis or protocol with the performance and/or results of a second analysis or protocol. For example, one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The term "innate immune response" or "innate immunity" as used herein includes a variety of innate resistance mechanisms by which a cell or individual recognizes and responds to the presence of a pathogen. As used herein, an "innate immune response" includes the intracellular and intercellular events and reactions that occur when the cell recognizes pathogen associated molecular patterns or signals. Cellular receptors active in an innate immune response include a family of Toll-like receptors (TLRs) and microbial ligands have been identified for several TLRs, as described herein.

The term "individual" refers to a mammal, including humans. An individual includes, but is not limited to, human, bovine, horse, feline, canine, rodent, or primate.

The term "animal" is used herein to include all vertebrate and invertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extra-chromosomally replicating DNA.

The term "germ cell-line transgenic animal" refers to a transgenic animal in which the genetic information was introduced into a germ line cell, thereby conferring the ability to transfer the information to offspring. If such offspring in fact possess some or all of that information, then they, too, are transgenic animals.

"Adjuvant" refers to a substance which, when added to an immunogenic agent such as antigen, nonspecifically enhances or potentiates an immune response to the agent in the recipient host upon exposure to the mixture.

Administration "in combination with" one or more further therapeutic agents includes simultaneous (concurrent) and consecutive administration in any order.

"Chronic" administration refers to administration of the agent(s) in a continuous mode as opposed to an acute mode, so as to maintain the initial therapeutic effect (activity) for an extended period of time. "Intermittent" administration refers to treatment that is not consecutively and/or continuously done without interruption, but rather is cyclic in nature.

An "effective amount" of an agent disclosed herein is an amount sufficient to carry out a specifically stated purpose. An "effective amount" may be determined empirically and in a routine manner, in relation to the stated purpose.

A "growth inhibitory amount" as used herein is an amount capable of inhibiting the growth of a cell, especially tumor, e.g., cancer cell, either in vitro or in vivo. A "growth inhibitory amount" for purposes of inhibiting neoplastic cell growth may be determined empirically and in a routine manner.

The term "therapeutically effective amount" refers to an agent effective to "treat" a disease or disorder in a subject or mammal. In the case of cancer, the therapeutically effective amount of the agent may reduce the number of cancer cells: reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

As used herein, "sample" refers to a composition which contains a molecule which is to be characterized and/or identified, for example, based on physical, biochemical, chemical, physiological, and/or genetic characteristics.

As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. Thus, "treating" or "treatment" does not require complete alleviation of signs or symptoms, and does not require a cure.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

It is understood that aspects and embodiments described herein include "consisting" and/or "consisting essentially of" aspects and embodiments.

Human TLR8 Transgenic Animals and Cells

Provided herein are TLR8 transgenic animals and transgenic cells, which comprise a nucleotide sequence encoding human TLR8. For example, provided herein are transgenic animals comprising a nucleotide sequence encoding human TLR8, wherein the human TLR8 is expressed in the transgenic animal.

In some embodiments, the TLR8 transgenic animal is a chimeric TLR8 transgenic animal. In some embodiments, the TLR8 transgenic animal is a TLR8 transgenic animal with germ cells and somatic cells containing a nucleotide sequence encoding human TLR8. In some embodiments, the nucleotide sequence encoding human TLR8 is stably integrated into the genome of the TLR8 transgenic animal. In some embodiments, the nucleotide sequence encoding human TLR8 is extrachromosomal. In some embodiments, the extrachromosomal nucleotide sequence encoding human TLR8 is provided as a minichromosome, yeast artificial chromosome, or bacterial artificial chromosome. In some embodiments, the TLR8 transgenic animal comprises one or more copies of the nucleotide sequence encoding human TLR8. In some embodiments, the TLR8 transgenic animal comprises more than about any of 1, 2, 3, 4, 5, 6, 7, 8, 9, 10, 11, 12, 13, 14, or 15 copies of the nucleotide sequence encoding human TLR8. In some embodiments, the TLR8 transgenic animal comprises about any of 1, 2, 3, 4, 5, 6, 7, 8, 9, 10, 11, 12, 13, 14, or 15 copies of the nucleotide sequence encoding human TLR8. For example, provided herein are transgenic animals comprising a nucleotide sequence encoding human TLR8, wherein the human TLR8 is expressed in the transgenic animal, wherein the TLR8 transgenic animal comprises about any of 1 to 2 copies of the nucleotide sequence encoding human TLR8.

The terms "human Toll-like receptor 8," "human TLR8," "hTLR8," and "CD288" as used herein refer to a protein and functional variants thereof that bind to viral and synthetic single-stranded RNAs (e.g., ssRNA derived from viruses, synthetic guanosine-rich ssRNA, and uridine-rich ssRNA), as well as small molecules resembling nucleic acids. The amino acid sequence of a common isoform of hTLR8 is set forth as SEQ ID NO:4. Accordingly, hTLR8 comprises the amino acid sequence of SEQ ID NO:4 or variants having at least 90, 91, 92, 93, 94, 95, 96, 97, 98 or 99% identity to SEQ ID NO:4. In particularly preferred embodiments, the "RQSYA" motif (SEQ ID NO:5) in the ectodomain of hTLR8 is retained.

e.g., Altschul et al. [1990] *J. Mol. Biol.* 215:403-410; Henikoff et al. [1989] *Proc. Natl. Acad. Sci. USA* 89:10915; Karin et al. [1993]*Proc. Natl. Acad. Sci. USA* 90:5873; and Higgins et al. [1988] *Gene* 73:237-244). Software for performing BLAST analyses is publicly available through the National Center for Biotechnology Information. Databases may also be searched using FASTA (Pearson et al. [1988] *Proc. Natl. Acad. Sci. USA* 85:2444-2448).

In some embodiments, the TLR8 transgenic animal expresses differential levels of human TLR8. In some embodiments, the TLR8 transgenic animal expresses high levels of human TLR8. In some embodiments, the high levels of human TLR8 expression is the result of multiple copy number, the site of integration of the nucleotide sequence encoding human TLR8, and/or the promoter and/or regulatory region operably linked to the nucleotide sequence encoding human TLR8. In some embodiments, the expression level is between a relative CT value of 10 and 10,000, for example about any of between 100-500, 200-400, or 1500-1700. In some embodiments, the expression level is at least about a relative CT value of any one of 10, 100, 200, 300, 400, 500, 1000, 1500, 2000, 3000, 4000, 5000, 6000, 7000, 8000, 9000, or 10,000. Relative CT values can be evaluated, for example, by obtaining threshold cycle (CT) values for each gene of interest and normalizing to a housekeeping gene using the formula: relative $CT=1.8^{(Avg\ CT\ Housekeeping\ Gene-CT\ Gene\ of\ Interest)}*100,000$. In some embodiments, the gene expression is evaluated by the average relative CT. In some embodiments, the Avg CT housekeeping gene is the mean CT of

```
Human TLR8 Sequence of GENBANK Accession No. NP_619542.1 (SEQ ID NO: 4):
   1 menmflqssm ltcifllisg scelcaeenf srsypcdekk qndsviaecs nrrlqevpqt 61 vgkyvteldl sdnfithitn esfqglqnlt kinlnhnpnv qhqngnpgiq snglnitdga 121 flnlknlrel llednqlpqi psglpeslte lsliqnniyn itkegisrli nlknlylawn 181 cyfnkvcekt niedgvfetl tnlellslsf nslshvppkl psslrklfls ntqikyisee 241 dfkglinltl ldlsgncprc fnapfpcvpc dggasinidr fafqnltqlr ylnlsstslr 301 kinaawfknm phlkvldlef nylvgeiasg afltmlprle ildlsfnyik gsypqhinis 361 rnfskllslr alhlrgyvfq elreddfqpl mqlpnlstin lginfikqid fklfqnfsnl 421 eiiylsenri splvkdtrqs yansssfqrh irkrrstdfe fdphsnfyhf trplikpqca 481 aygkaldlsl nsiffigpnq fenlpdiacl nlsansnaqv lsgtefsaip hvkyldltnn 541 rldfdnasal telsdlevld lsynshyfri agvthhlefi qnftnlkvln lshnniytlt 601 dkynlesksl velvfsgnrl dilwndddnr yisifkglkn ltrldlslnr lkhipneafl 661 nlpasltelh indnmlkffn wtllqqfprl elldlrgnkl lfltdslsdf tsslrtllls 721 hnrishlpsg flsevsslkh ldlssnllkt inksaletkt ttklsmlelh gnpfectcdi 781 gdfrrwmdeh lnvkiprlvd vicaspgdqr gksivslelt tcvsdvtavi lffftffitt 841 mvmlaalahh lfywdvwfiy nvclakvkgy rslstsqtfy dayisydtkd asvtdwvine 901 lryhleesrd knvllcleer dwdpglaiid nlmqsingsk ktvfvltkky akswnfktaf 961 ylalqrlmde nmdviifill epvlqhsgyl rlrqrickss ilqwpdnpka eglfwqtlrn 1021 vvltendsry nnmyvdsikq y.
```

Thus the variants comprise homologous TLR8 amino acid sequences having one or more deletions, additions or substitutions as long as the requisite level of sequence identity across the full length of TLR8 is achieved. Sequence identity may be determined using known programs such as BLAST, ALIGN, and CLUSTAL using standard parameters. (See, triplicate housekeeping gene runs and/or Avg CT Gene of Interest is the mean CT of duplicate runs of the gene of interest. In some embodiments, the house keeping gene is ubiquitin, myosin, hsp90, and/or actin.

In some embodiments, the expression level is about the same or greater than the expression level of human TLR8 in TLR8TGCL12. In some embodiments, the expression level is about the same or greater than the expression level of human TLR8 in TLR8TGCL6. In some embodiments, the expression level is about the same or greater than the expression level of human TLR8 in TLR8TGCL23. In some embodiments, the expression level is about the same or greater than the expression of human TLR8 in TLR8TGCL8. In some embodiments, the human TLR8 is expressed in a similar expression pattern in the transgenic animal as human TLR8 is expressed in humans. In some embodiments, the levels of expression of human TLR8 in the transgenic animal is similar to the level of expression of human TLR8 in humans. In some embodiments, the levels of expression of human TLR8 in the transgenic animal is about any of 1, 2, 3, 4, 5-fold the level of expression of human TLR8 in humans. In some embodiments, the levels of expression of human TLR8 in the transgenic animal is similar to the level of expression of mouse TLR8 in mice.

In some embodiments, the TLR8 transgenic animal has reduced survival (e.g., life span), for example, compared to a wild-type animal. For example, in some embodiments, the transgenic animal survives less than about any of 150, 140, 130, 120, 110, 100, 90, 80, 70, 60 or 50 days. For example, provided herein are transgenic animals comprising a nucleotide sequence encoding human TLR8, wherein the human TLR8 is expressed in the transgenic animal, wherein the TLR8 transgenic animal survives less than about 150 days. In some embodiments, the TLR8 transgenic animal has survival (e.g., life span) similar or substantially the same as compared to a wild-type animal.

The human TLR8 gene may be of natural or artificial origin. It may be genomic DNA (gDNA), complementary DNA (cDNA), hybrid sequences or synthetic or semi-synthetic sequences. To be expressed, the human TLR8 gene should be operably linked to one or more regulatory regions. Selection of the appropriate regulatory region or regions is a routine matter, within the level of ordinary skill in the art. Regulatory regions may be used to increase, decrease, or regulate the expression of a gene or to designate the expression of a gene to certain tissues or to certain stages of development. In some embodiments, the regulatory region increases expression of the gene or increases expression of the gene in neutrophils. The regulatory regions may comprise a promoter region for functional transcription, as well as a region situated 3' of the gene of interest, and which specifies a signal for termination of transcription and a polyadenylation site. All these elements constitute an expression cassette.

Promoters that may be used include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell which it is desired to infect Likewise, it may be promoter sequences derived from the genome of a virus, including the adenovirus used. The promoters of the EIA, MLP, HCMV and RSV genes and the like may be used. In addition, the promoter may be modified by addition of activating or regulatory sequences, or sequences allowing a tissue-specific or predominant expression. The promoter need not be a naturally occurring promoter. The promoter may be an inducible promoter. In some embodiments, the human TLR8 gene is operably linked to the human TLR8 promoter. In some embodiments, the human TLR8 gene is operably linked to the human TLR8 promoter and human TLR8 regulatory region.

Tetracycline-inducible systems can be used, as described in Hickman-Davis et al. (*Pediatric Respiratory Reviews* 2006 7: 49). Two independent transgenic mouse lines are generated: (1) transactivator mice, in which a tetracycline-controlled transactivator is expressed under the control of a tissue-specific promoter and (2) responder mice, in which expression of the DNA of interest is under the control of a tetracycline-dependent promoter (a minimal RNA polymerase II promoter fused to tet operator sequences). The breeding of these two strains of mice generates a double-transgenic mouse that responds to tetracycline or its derivatives (doxycycline) to control expression of the transgene. There are two possible mirror image tetracycline-inducible systems. In the first system, the absence of doxycycline allows for transcription of the transgene and addition of tetracycline or its derivatives causes transcriptional downregulation (tet-OFF). In the second system transcription of the transgene occurs in the presence of doxycycline and therefore removal of the activator results in transcriptional downregulation (tet-ON).

Additional useful promoters are the ubiquitous promoters HPRT, vimentin, actin, and tubulin; the intermediate filament promoters desmin, neurofilaments, keratin, and GFAP; the therapeutic gene promoters MDR, CFTR, and factor VIII; promoters which are preferentially activated in dividing cells; cytomegalovirus immediate-early; retroviral LTR, metallothionein; SV-40; E1a and MLP promoters. Tetracycline-regulated transcriptional modulators and CMV promoters are described in WO 96/01313, U.S. Pat. Nos. 5,168,062 and 5,385,839, the contents of which are incorporated herein by reference.

In some embodiments, a cre/loxP recombinase system is utilized for generation of the transgenic animals. For example, the Cre/loxP recombinase systems described in Hickman-Davis et al. (*Pediatric Respiratory Reviews* 2006 7: 49) can be used. For this system, the generation of two independent mouse lines requires: (1) mice that contain the target gene or gene segment flanked by two 34 bp, asymmetric nucleotide sequences (loxP) sites in the same orientation ('floxed' sequence) and (2) mice that contain a fusion transgene expressing the Cre recombinase of the P1 bacteriophage. The Cre recombinase promotes recombination by recognition of the loxP sites, and when these two mouse strains are crossed, the floxed gene is deleted and a null mutation is created. Cre/loxP recombinase system is also useful in the targeted mutagenesis of embryonic stem cells in vitro to create [clean] mutations that lack a selection cassette that might interfere with gene regulation, in which pluripotent stem cells containing the gene of interest and only one loxP site with foreign sequence are generated for use in the creation of a transgenic mouse. Several methods have been demonstrated for controlling Cre expression including the creation of fusion proteins containing Cre and having specific ligand-binding domains (i.e., Cre is expressed only in the presence of a specific ligand), as well as a tetracycline-inducible Cre system.

In some embodiments, the transgenic animal is a mouse or a rat. In some embodiments, the transgenic animal is a mouse. Mouse strains useful for generating transgenic mice include, but are not limited to CD-1® Nude mice, CD-1 mice, NU/NU mice, BALB/C Nude mice, BALB/C mice, NIH-III mice, SCID™ mice, outbred SCID™ mice, SCID™ Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice.

The transgenic animals are produced by introducing one or more trangenes into the germline of the transgenic animal. The methods enabling the introduction of DNA into cells are generally available and well-known in the art and different methods of introducing transgenes could be used. See, for example, Hogan et al. *Manipulating the Mouse Embryo: A Laboratory Manual Cold Spring Harbor Laboratory*, 2$^{nd}$ edition, Cold Spring Harbor Laboratory (1994) and U.S. Pat. Nos. 5,602,299; 5,175,384; 6,066,778 and 6,037,521, which are incorporated herein in their entirety. Technology used in developing transgenic animals include pronuclear microinjection (Gordon, J. W., *PNAS* 77, 7380-7384 (1980) and U.S. Pat. No. 4,873,191), homologous recombination (targeted transgenesis by transferring embryonic stem cells into blastocysts; Thompson et al., *Cell* 56:313-321 (1989)), RNA interference (RNAi) for silencing of specific gene function; retrovirus gene transfer into germ lines (Van der Putten et al., *Proc. Nat. Acad. Sci.* 82:6148-6152 (1985)); electroporation of embryos (Lo, *Mol. Cell. Biol.* 3:1803-1814 (1983)); and sperm-mediated gene transfer (Lavitrano et al., *Cell* 57:717-723 (1989)).

Generally, the zygote is the best target for microinjection. In mice, for example, the male pronucleus reaches the size of approximately 20 µm in diameter, which allows reproducible injection of 1-2 pL of DNA solution. The use of zygotes as a target for gene transfer has a major advantage. In most cases, the injected DNA will be incorporated into the host gene before the first cleavage. Consequently, nearly all cells of the transgenic non-human animal will carry the incorporated transgene. Generally, this will also result in the efficient transmission of the transgene to offspring of the founder since 50% of the germ cells will harbor the transgene. Microinjection of zygotes is one method for incorporating transgenes in practicing the invention. The pronuclear microinjection method of producing a transgenic animal results in the introduction of linear DNA sequences into the chromosomes of the fertilized eggs. Bacterial Artificial Chromosome (BAC) containing the gene of interest or an alternative plasmid construct containing the gene of interest is injected into pronuclei (i.e., fertilized eggs at a pronuclear state). The manipulated pronuclei are subsequently injected into the uterus of a pseudopregnant female. Mice generated can have one or multiple copies of the transgene, which can be assayed by southern blot technology.

The transgenic animals can also be generated by introduction of the targeting vectors into embryonal stem (ES) cells. ES cells are obtained by culturing pre-implantation embryos in vitro under appropriate conditions (Evans et al., *Nature* 292:154-156 (1981); Bradley et al., *Nature* 309:255-258 (1984); Gossler et al., *PNAS* 83:9065-9069 (1986); and Robertson et al., *Nature* 322:445-448 (1986)). Transgenes can be efficiently introduced into the ES cells by DNA transfection using a variety of methods known to the art including electroporation, calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (reviewed in Jaenisch, *Science* 240: 1468-1474 (1988)). Prior to the introduction of transfected ES cells into the blastocoel, the transfected ES cells can be subjected to various selection protocols to enrich for ES cells that have integrated the transgene if the transgene provides a means for such selection. Alternatively, PCR can be used to screen for ES cells that have integrated the transgene. This technique obviates the need for growth of the transfected ES cells under appropriate selective conditions prior to transfer into the blastocoel.

Retroviral infection can also be used to introduce a transgene into a non-human animal. The developing non-human embryo can be cultured in vitro to the blastocyst stage. During this time, blastomeres may be targets for retroviral infection. Efficient infection of the blastomeres is obtained by enzymatic treatment to remove the zona pellucida. The viral vector system used to introduce the transgene is typically a replication-defective retrovirus carrying the transgene. Transfection is easily and efficiently obtained by culturing the blastomeres on a monolayer of virus-producing cells. Alternatively, infection can be performed at a later stage. Virus or virus-producing cells can be injected into the blastocoel. Most of the founder animals will be mosaic for the transgene since incorporation occurs only in a subset of the cells which formed the transgenic non-human animal. Furthermore, the founder animal may contain retroviral insertions of the transgene at a variety of positions in the genome; these generally segregate in the offspring. In addition, it is also possible to introduce transgenes into the germ line, albeit with low efficiency, by intrauterine retroviral infection of the midgestation embryo.

Viral vectors may be used to produce a transgenic animal. Preferably, the viral vectors are replication defective, that is, they are unable to replicate autonomously in the target cell. In general, the genome of the replication defective viral vectors which are used lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

The retroviruses are integrating viruses which infect dividing cells. The retrovirus genome includes two LTRs, an encapsidation sequence and three coding regions (gag, pol and env). The construction of recombinant retroviral vectors has been described: see, in particular, EP 453242, EP178220, Bernstein et al. Genet. Eng. 7 (1985) 235; McCormick, Bio-Technology 3 (1985) 689, etc. In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus"), MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line 17 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene. Recombinant retroviral vectors are purified by standard techniques known to those having ordinary skill in the art. Additional means of using retroviruses or retroviral vectors to create transgenic animals known to the art involve the micro-injection of retroviral particles or mitomycin C-treated cells producing retrovirus into the perivitelline space of fertilized eggs or early embryos (WO 90/08832 (1990); Haskell and Bowen, *Mol. Reprod. Dev.* 40:386 (1995)).

Once the founder animals are produced, they can be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the physiological effects of expression.

Methods of Screening for and/or Identifying TLR8Modulators

Provided herein is a method of screening for and/or identifying TLR8 modulators using the transgenic animals described herein or cells therefrom. In some embodiments, the cells are primary cells, for example in cell culture, obtained or prepared from the transgenic animals described herein, which comprise a nucleotide sequence encoding human TLR8. In some embodiments, the cells are of a stable cell line derived from primary cells of the transgenic animals. In some embodiments, the cells are an early passage of the primary cells. Provided herein are also methods of screening for, and/or identifying, TLR8 modulators, the methods comprising: administering a candidate agent to the transgenic animal or providing a candidate agent to cell(s) and/or cell culture obtained and/or derived from the transgenic animal described herein; and determining the effect of the candidate agent on the transgenic animal or cell culture (e.g., as compared to an untreated or mock treated control). Further, provided are methods of screening for, or identifying, TLR8 modulators, the method comprising: providing a candidate agent to a cell culture, wherein cells of the cell culture are obtained and/or derived from the transgenic animals described herein which comprise a nucleotide sequence encoding human TLR8; and determining the effect of the candidate agent on the cell culture (e.g., as compared to an untreated or mock treated control). In some embodiments, the cells are from a transgenic animal. In some embodiments, the cells are from a transgenic mouse. In some embodiments, the nucleotide sequence encoding human TLR8 results in inflammation or autoimmune diseases in one or more organs as compared with a control non-transgenic animal and/or elevated levels of cytokine production as compared with a control non-transgenic animal. In some embodiments the effect is a TLR8-mediated response, evidenced by a change in TLR8-mediated cytokine production, cell proliferation, and/or cell surface marker expression. A TLR8-mediated response is one that is stimulable by a TLR7/8 agonist such as R848 and CL075 or a TLR8 agonist such as a TLR8 ligand stabilized immunomodulatory RNA (e.g., SEQ ID NO:3). TLR8-mediated responses are assessed by measuring expression of a cytokine or a cell surface marker. Suitable cytokines are selected from but not limited to TNF-α, IFN-α, IFN-β, IFN-γ, IL-1α, IL-1β, IL-6, IL-8, IL-10, IL-12, IL-23, IP-10, MIP-1, and MCP-1. Suitable cell surface molecules are selected from but not limited CD40, CD80, CD86, ICAM-1, ICAM-2, ICAM-3, and CCR7. In some embodiments, the cytokine comprises one or more of the group consisting of TNF, IL-12, IL-6, MIP-1α, IFNγ, IP-10, IL-1α, and IL-1β.

In some embodiments, the candidate agent is selected and/or identified if the candidate agent modulates a TLR8-mediated immune response. In some embodiments, the immune response is evidenced by level or extent of TLR8-mediated inflammation. In some embodiments, the immune response is evidenced by level or extent of TLR8-mediated cytokine production, proliferation, marker gene production, and/or cell surface markers. In some embodiments, the modulation of TLR8-mediated immune response is inhibition of a TLR8-mediated immune response as compared to a control. In some embodiments, the level or extent of TLR8-mediated inflammation in the transgenic animal is reduced upon administration or providing the candidate agent compared to the control. In some embodiments, levels or extent of TLR8-mediated cytokine production, proliferation, marker gene production, and/or cell surface markers in the transgenic animal and/or cell(s) and/or cell culture obtained and/or derived from the transgenic animal described herein is reduced upon administration or providing the candidate agent compared to the control. In some embodiments, the modulation of a TLR8-mediated immune response is stimulation of a TLR8-mediated immune response as compared to a control. In some embodiments, the level or extent of TLR8-mediated cytokine production, proliferation, marker gene production, and/or cell surface markers in the transgenic animal and/or cell(s) and/or cell culture obtained and/or derived from the transgenic animal described herein is increased upon administration or providing the candidate agent compared to the control.

The control may be cells and/or animals, which do not express human TLR8. In some embodiments, the control may be untreated or mock-treated transgenic cells and/or animals, that express human TLR8. In some embodiments, the effect of the TLR8 modulator on modulating immune responses is compared to its effect in a non-transgenic animal and/or cell(s) and/or a cell culture obtained and/or derived from a non-transgenic animal. In some embodiments, the effect of the TLR8 modulator on modulating immune responses is compared to the effect of the TLR8 modulator in an animal and/or cell(s) and/or a cell culture obtained and/or derived from the transgenic animal described herein that do not express human TLR8 or express a different level of human TLR8. In some embodiments, the effect of the TLR8 modulator on modulating immune responses is compared to the effect of a known TLR8 modulator in a TLR8 transgenic animal and/or cell(s) and/or a cell culture obtained and/or derived from the transgenic animal described herein. In some embodiments, the effect of the TLR8 modulator on modulating immune responses is compared to the effect of an agent which does not affect human TLR8 in a TLR8 transgenic animal and/or cell(s) and/or a cell culture obtained and/or derived from the transgenic animal described herein.

In some embodiments, the TLR8 transgenic animal is a chimeric TLR8 transgenic animal. In some embodiments, the TLR8 transgenic animal is a TLR8 transgenic animal with germ cells and somatic cells containing a nucleotide sequence encoding human TLR8. In some embodiments, the nucleotide sequence encoding human TLR8 is stably integrated into the genome of the TLR8 transgenic animal. In some embodiments, the nucleotide sequence encoding human TLR8 is extrachromosomal. In some embodiments, the extrachromosomal nucleotide sequence encoding human TLR8 is provided as a minichromosome, yeast artificial chromosome, or bacterial artificial chromosome.

For example, provided herein are methods of screening for and/or identifying TLR8 modulators, the method comprising administering a candidate agent to a transgenic animal having a genome comprising a stably integrated transgene encoding human TLR8; wherein the transgene results in inflammation in one or more organs (e.g., pancreas, kidney, liver, joints, reproductive tissue, etc.) or an autoimmune disease (e.g., pancreatitis, nephritis, hepatitis, rheumatoid arthritis, diabetes, diabetes-related disorder, reproductive disease, etc.) as compared with a control non-transgenic animal (or elevated levels of cytokine production as compared with a control non-transgenic animal); and determining the effect of the candidate agent on the inflammation or the autoimmune disease of the transgenic animal. Also, for example, provided herein are methods of screening for and/or identifying TLR8 modulators, the method comprising administering a candidate agent to a transgenic animal having an extrachromosomal nucleotide sequence comprising a transgene encoding human TLR8; wherein the transgene results in inflammation in one or more organs (e.g., pancreas, kidney, liver, joints, reproductive tissue, etc.) or an autoimmune disease (e.g., pancreatitis, nephritis, hepatitis, rheumatoid arthritis, diabetes, diabetes-related disorder, reproductive disease, etc.) as compared with a control non-transgenic animal (or elevated levels of cytokine production as compared with a control non-transgenic animal); and determining the effect of the candidate agent on the inflammation or the autoimmune disease of the transgenic animal.

Further, for example, provided herein are methods of screening for and/or identifying TLR8 modulators, the methods comprising incubating a transgenic animal cell culture with a candidate agent, the transgenic animal cell culture being derived from a parent transgenic animal, cells of the culture comprising a stably integrated transgene encoding human TLR8; and determining the effect of the candidate agent on the cell culture.

Provided herein are also methods of screening for and/or identifying TLR8 modulators, the methods comprising: incubating a transgenic animal cell culture with a candidate agent, the transgenic animal cell culture being derived from a parent transgenic animal, cells of the culture comprising an extrachromosomal nucleotide sequence comprising a transgene encoding human TLR8; and determining the effect of the candidate agent on the cell culture.

Further provided herein are methods of screening for and/or identifying TLR8 modulators, the methods comprising incubating a transgenic animal cell culture with a candidate agent, the transgenic animal cell culture being derived from a parent transgenic animal, cells of the culture comprising a stably integrated transgene encoding human TLR8; wherein the transgene results in inflammation in one or more organs (e.g., pancreas, kidney, liver, joints, reproductive tissue, etc.) or an autoimmune disease (e.g., pancreatitis, nephritis, hepatitis, rheumatoid arthritis, diabetes, diabetes-related disorder, reproductive disease, etc.) as compared with a control non-transgenic animal (or elevated levels of cytokine production as compared with a control non-transgenic animal cell culture); and determining the effect of the candidate agent on the cell culture.

Provided herein is a method of screening for and/or identifying TLR8 modulator, the method comprising incubating a transgenic animal cell culture with a candidate agent, the transgenic animal cell culture being derived from a parent transgenic animal, cells of the culture comprising an extrachromosomal nucleotide sequence comprising a transgene encoding human TLR8; wherein the transgene results in inflammation in one or more organs (e.g., pancreas, kidney, liver, joints, reproductive tissue, etc.) or an autoimmune disease (e.g., pancreatitis, nephritis, hepatitis, rheumatoid arthritis, diabetes, diabetes-related disorder, reproductive disease, etc.) in one or more organs (e.g., pancreas, kidney, liver, joints, reproductive tissue, etc.) as compared with a control non-transgenic animal (or elevated levels of cytokine production as compared with a control non-transgenic animal cell culture); and determining the effect of the candidate agent on the cell culture.

In some embodiments, the TLR8 modulator is a TLR8 agonist or antagonist. In some embodiments, the TLR8 modulator is an anti-TLR8 antibody. In some embodiments, the TLR8 modulator is a TLR8 agonist or antagonist antibody. In some embodiments, the TLR8 modulator comprises a polynucleotide. In some embodiments, the polynucleotide comprises a TLR8 immunoregulatory sequence (IRS). In some embodiments, the polynucleotide comprising a TLR8 IRS further is not capable of modulating TLR7 and/or TLR9 and/or does not comprise (i.e., lacks) a TLR7 and/or TLR9 IRS sequence. In some embodiments, the polynucleotide comprising a TLR8 IRS further is capable of modulating TLR7 and/or TLR9 and/or comprises a TLR7 and/or TLR9 IRS sequence. In some embodiments, the TLR8 modulator does not comprise (i.e., lacks) an immunostimulatory sequence. For example, in some embodiments, the TLR8 modulator does not comprise (i.e., lacks) a CG sequence or TCG sequence wherein the C is unmethylated. In some embodiments, the TLR8 modulator is not (i.e., excludes) an antisense oligonucleotide and/or does not operate by a RNAi pathway. In some embodiments, the TLR8 modulator is not (i.e., excludes) a microRNA and/or siRNA. In some embodiments, the TLR8 modulator is an antisense oligonucleotide. In some embodiments, the TLR8 modulator is a small molecule.

In some embodiments, the effect of the TLR8 modulator on modulating immune responses is determined by measuring TLR8-mediated cytokine production, proliferation, marker gene production, and/or cell surface markers. In some embodiments, the effect on modulating immune responses is inhibition of TLR8. Inhibition of a TLR response, e.g., a TLR8 response, includes, but is not limited to, inhibition at the receptor site, e.g., by preventing or blocking effective ligand-receptor binding, and inhibition of the downstream signal pathway, e.g., after effective ligand-receptor binding.

The concentration of the candidate agent being assayed by the above methods may range, for example, from about 0.001 µM to about 100 µM, although in some embodiments the assay may be performed with a test compound present in concentrations outside this range. In some embodiments, the concentration of the candidate agent is 0.001 µM, 0.01 µM, 0.1 µM or 1.0 µM or greater. In some embodiments, the concentration of the candidate agent is 100 µM, 10 µM, 1.0 µM or 0.1 µM or less. The cell culture may be incubated with the test compound, for example, from about 10 minutes to about 24 hours, although in some cases the incubation period may be outside this range. The density of cells incubated with the compound to be tested may be, for example, from about $1 \times 10^4$ to about $1 \times 10^7$ cells/ml, although in some embodiments the assay may be performed using a cell culture having a cell density outside this range.

In some embodiments, cytokine levels are determined using a commercially available ELISA assay. In other embodiments, cytokine levels are determined using such techniques as, for example, antibody detection and quantitation (e.g., flow cytometry, western blotting, immunohisto/cytochemistry, proteome array assays), and bioassays (e.g., L929 cytotoxicity assay where the amount of cell death is directly proportional to the amount of TNF-α in the sample). See, e.g., Current Protocols in Immunology, John Wiley and Sons, Inc. (2001).

Many different cytokines and/or markers can be assayed in the methods described above. Suitable measurable cytokines include, but are not limited to one or more of TNF-α, IFN-α, IFN-β, IFN-γ, IL-1α, IL-1β, IL-6, IL-8, IL-10, IL-12, IL-23, IP-10, MIP-1, and MCP-1. In some preferred embodiments, the cytokine is selected from the group consisting of TNFα, IL-12, IL-6, IFNγ, IP-10, IL-1α, and IL-1β. Suitable measurable cell surface markers include co-stimulatory markers (e.g., CD40, CD80, CD86), intercellular adhesion molecules (e.g., ICAM-1, ICAM-2, or ICAM-3), and maturation markers such as, for example, CCR7.

Also provided by the present disclosure are kits comprising the transgenic mice or cells derived therefrom, and instructions for use of the mice to screen for and/or to identify a TLR8 modulators. In some embodiments, the kits further comprise a TLR8 agonist. In some embodiments, the kits further comprise a TLR8 antagonist.

Candidate Agents

Suitable candidate agents to screen for TLR8 modulatory activity include, but are not limited to, polynucleotides (e.g., singe or double stranded nucleic acids), polypeptides (e.g., antibodies or antibody fragments), antisense oligonucleotides, and small molecules (e.g., organic compounds having a molecular weight of less than 2000, 1600, 800, or 400 daltons).

In some embodiments, the TLR8 modulatory activity is TLR8 agonism (e.g., stimulation). In other embodiments, the TLR8 modulatory activity is TLR8 antagonism (e.g., inhibition). Suitable agonist molecules include polynucleotides comprising a TLR8 immunostimulatory sequence (ISS), agonist antibodies or antibody fragments, fragments or amino acid sequence variants of native polypeptides, peptides, and small molecules. Suitable antagonist molecules include polynucleotides comprising a TLR8 immunoregulatory sequence (IRS), antagonist antibodies or antibody fragments, fragments or amino acid sequence variants of native polypeptides, peptides, antisense oligonucleotides, and small molecules.

Antibodies

In some embodiments, the TLR8 modulator is an anti-TLR8 antibody. In some embodiments, the TLR8 modulator is an antibody, which can reduce and/or inhibit a TLR8-induced cellular activity disclosed herein. In some embodiments, the TLR8 modulator comprises an antibody, which can cause and/or enhance a TLR is an agonist antibody. In some embodiments, the anti-TLR8 antibody is an antagonist antibody.

In some embodiments, the TLR8 antibody directly binds to TLR8. Alternatively, an antibody may combine with TLR8 indirectly by, for example, (a) forming a complex with another molecule that directly binds to TLR8, or (b) otherwise causing the modification of another compound so that the other compound directly binds to TLR8. In some embodiments, the anti-TLR8 antibody specifically binds TLR8, for example, specifically binds TLR8, but not TLR7 and/or TLR9. In some embodiments, the binding of the receptor is measured in a cell-free assay.

An antibody "which binds" TLR8 is one that binds TLR8 with sufficient affinity such that the antibody is useful as a diagnostic and/or therapeutic agent, e.g., in targeting a cell expressing TLR8, and does not significantly cross-react with other proteins. In such embodiments, the extent of binding of the antibody to a "non-target" protein will be less than about 10% of the binding of the antibody to its particular TLR8 protein as determined by fluorescence activated cell sorting (FACS) analysis or radioimmunoprecipitation (RIA). An antibody that "specifically binds to" or is "specific for" TLR8 polypeptide or an epitope on TLR8 is one that binds to that TLR8 polypeptide or epitope on TLR8 without substantially binding to any other polypeptide or polypeptide epitope.

In some embodiments the anti-TLR8 antibody is a monoclonal antibody, a polyclonal antibody, a chimeric antibody, a humanized antibody, a human antibody, an intact antibody, a single chain antibody, or an antibody fragment. In some embodiments, the antibody fragment is Fab, Fab', F(ab')2, Fv fragments; diabodies; or linear antibody. In some embodiments, the anti-TLR8 antibody or fragment thereof is isolated (e.g., identified and separated and/or recovered from a component of its natural environment).

The anti-TLR8 antibody may be from any of the five classes of immunoglobulins: IgA, IgD, IgE, IgG, and IgM, having heavy chains designated α, δ, ε, γ, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

In some embodiments, the anti-TLR8 antibody suppresses and/or reduces TLR8-mediated cytokine production. In some embodiments, the anti-TLR8 antibody suppresses and/or reduces extent and/or levels of TLR8-mediated cytokine production as compared to, for example, extent and/or levels of cytokine produced during untreated conditions (e.g., media alone or buffer alone). In some embodiments, the anti-TLR8 antibody causes and/or enhances TLR8-mediated cytokine production. In some embodiments, the anti-TLR8 antibody causes and/or enhances extent and/or levels of TLR8-mediated cytokine production as compared to, for example, extent and/or levels of cytokine produced during untreated conditions (e.g., media alone or buffer alone).

Small Molecules

In some embodiments, the TLR8 modulator is a TLR8 modulating chemical compound (e.g., small molecule). In some embodiments, the TLR8 modulator is a TLR8 modulating chemical compound (e.g., small molecule), which can reduce and/or inhibit a TLR8-induced cellular activity disclosed herein. In some embodiments, the TLR8 modulator is a TLR8 modulating chemical compound (e.g., small molecule), which can cause and/or enhance a TLR8-induced cellular activity disclosed herein. A TLR8 modulating (e.g., small molecule) may be a ligand that directly binds to TLR8. Alternatively, a compound may combine with TLR8 indirectly by, for example, (a) forming a complex with another molecule that directly binds to TLR8, or (b) otherwise causing the modification of another compound so that the other compound directly binds to TLR8.

In some embodiments, the compound suppresses and/or reduces TLR8 induced-cytokine production. In some embodiments, the compound suppresses and/or reduces extent and/or levels of cytokine production as compared to, for example, extent and/or levels of cytokine produced during untreated conditions (e.g., media alone or buffer alone). In some embodiments, the compound causes and/or enhances TLR8 induced-cytokine production. In some embodiments, the compound causes and/or enhances extent and/or levels of cytokine production as compared to, for example, extent and/or levels of cytokine produced during untreated conditions (e.g., media alone or buffer alone).

Polynucleotides

In some embodiments, the TLR8 modulator is a TLR8 modulating polynucleotide (e.g., polynucleotide).

In some embodiments, the TLR8 modulating polynucleotide is a TLR8 polynucleotide agonist. In some embodiments, the TLR8 polynucleotide agonist causes and/or enhances a TLR8-induced cellular activity. In some embodiments, the TLR8 polynucleotide agonist further comprises a motif, which causes and/or enhances a TLR9-induced cellular activity such as an unmethylated CG or unmethylated TCG. In some embodiments, the TLR8 polynucleotide agonist further comprises a motif, which causes and/or enhances a TLR7-induced cellular activity. In some embodiments, the TLR8 polynucleotide agonist further causes and/or enhances a TLR7 and TLR9 induced cellular activity. In some embodiments, the TLR8 polynucleotide agonist does not cause and/or enhance a TLR7 and/or TLR9 induced cellular activity. In some embodiments, the TLR8 polynucleotide agonist causes and/or enhances TLR8 induced-cytokine production. In some embodiments, the TLR8 polynucleotide agonist causes and/or enhances extent and/or levels of cytokine production as compared to, for example, extent and/or levels of cytokine produced during untreated conditions (e.g., media alone or buffer alone). In some embodiments, the TLR8 polynucleotide agonist causes and/or enhances TLR8 induced-immune response. In some embodiments, the TLR8 polynucleotide agonist causes and/or enhances extent and/or levels of immune response as compared to, for example, extent and/or levels of immune response produced during untreated conditions (e.g., media alone or buffer alone).

In some embodiments, the TLR8 polynucleotide antagonist comprises a TLR8 IRS. In some embodiments, the TLR8 IRS reduces and/or inhibits a TLR8-induced cellular activity. In some embodiments, the TLR8 IRS further comprises a motif which reduces and/or inhibits a TLR7 and/or TLR9-induced cellular function. In some embodiments, the TLR8 IRS does not comprise (i.e., lacks) a motif which reduces and/or inhibits a TLR7 and/or TLR9-induced cellular function. In some embodiments, the TLR8 IRS does not comprise an immunostimulatory sequences such as unmethylated CG or unmethylated TCG. In some embodiments, the TLR8 modulator is not (i.e., excludes) an antisense oligonucleotide and/or does not operate by a RNAi pathway. In some embodiments, the TLR8 modulator is an antisense oligonucleotide. In some embodiments, the TLR8 modulator is not a microRNA or siRNA. In some embodiments, the TLR8 modulator is a microRNA or siRNA.

In some embodiments, the TLR8 IRS suppresses and/or reduces TLR8 induced-cytokine production. In some embodiments, the TLR8 IRS suppresses and/or reduces extent and/or levels of cytokine production as compared to, for example, extent and/or levels of cytokine produced during untreated conditions (e.g., media alone or buffer alone). In some embodiments, the TLR8 IRS suppresses and/or reduces TLR8 induced-immune response. In some embodiments, the TLR8 IRS suppresses and/or reduces extent and/or levels of TLR8 induced-immune response as compared to, for example, extent and/or levels of immune response produced during untreated conditions (e.g., media alone or buffer alone).

In some embodiments, a TLR8 modulating polynucleotide comprises an IRS, as described herein, which inhibits and/or suppresses a measurable immune response as measured in vitro, in vivo, and/or ex vivo. In some embodiments, the TLR8 immune response is an innate TLR8 immune response. In some embodiments, the immune response is an adaptive TLR8 immune response.

General Techniques

The practice of the present application employs, unless otherwise indicated, conventional techniques of molecular biology (including recombinant techniques), microbiology, cell biology, chemistry, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (Gait, ed., 1984); *Animal Cell Culture* (Freshney, ed., 1987); *Handbook of Experimental Immunology* (Weir & Blackwell, eds.); *Gene Transfer Vectors for Mammalian Cells* (Miller & Calos, eds., 1987); *Current Protocols in Molecular Biology* (Ausubel et al., eds., 1987); *PCR: The Polymerase Chain Reaction* (Mullis et al., eds., 1994); *Current Protocols in Immunology* (Coligan et al., eds., 1991); *The Immunoassay Handbook* (Wild, ed., Stockton Press NY, 1994); *Bioconjugate Techniques* (Hermanson, ed., Academic Press, 1996); and *Methods of Immunological Analysis* (Masseyeff, Albert, and Staines, eds., Weinheim: VCH Verlags gesellschaft mbH, 1993).

EXAMPLES

Abbreviations: BAC (bacterial artificial chromosome); BM (bone marrow); CT (threshold cycle); CTRL (control); FACS (fluorescence activated cell sorter); hTLR8Tg (human Toll-like receptor 8 transgenic); IRS (immunoregulatory sequence); KO (knock out); MDC (myeloid dendritic cells); PBMC (peripheral blood mononuclear cells); PDC (plasmacytoid dendritic cells); PN (polynucleotides); TLR (Toll-like receptor); and WT (wild type).

Example 1

TLR8Expression

TLR8 expression was analyzed in human cellular subsets (FIG. 1). Plasmacytoid dendritic cells (PDC), monocytes, myeloid dendritic cells (MDC), CD4+ T-cells, CD8+ T-cells, and neutrophils were purified by means of magnetic beads (Miltenyi Biotech) according to manufacturer's instructions. RNA was purified with a micro RNA KIT (Qiagen) according to manufacturer's instructions. cDNA from RNA was generated with SuperScript First-Strand Synthesis System (Invitrogen). Threshold cycle (CT) values for each gene were normalized to the housekeeping gene Ubiquitin using the formula: relative $CT=1.8^{(Avg\ CT\ Ubi-CT\ Gene)}*100,000$ where Avg CT Ubi is the mean CT of triplicate housekeeping gene runs, Avg CT Gene is the mean CT of duplicate runs of the gene of interest, and 100,000 is arbitrarily chosen as a factor to bring all values above one. Neutrophils showed the highest level of expression. TLR8 was also expressed in monocytes, mDCs and CD4+ T-cells (FIG. 1).

Example 2

Activity of TLR7 and TLR8RNA Polynucleotides (PN) in Human and Mouse Cells

Figure 2:
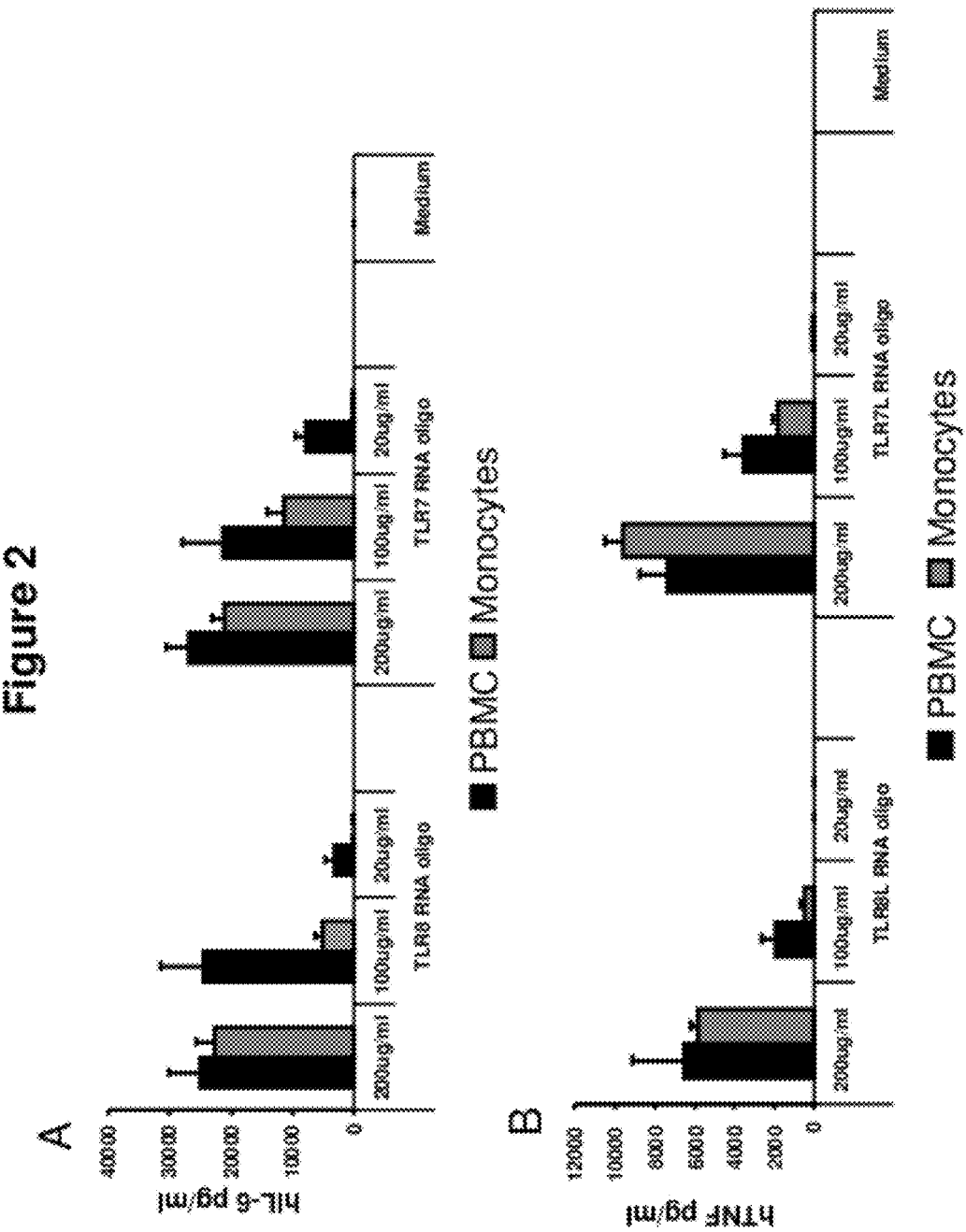
FIG. 2A-B shows the effect of 200, 100, and 20 μg/mL of TLR7 or TLR8-stimulating RNA polynucleotides (PN) (SEQ ID NO:2 and SEQ ID NO:3, respectively) or medium alone on hIL-6 and hTNF production (pg/mL) by human peripheral blood mononuclear cells (PBMC) and monocytes.

PN-based TLR8 ligand stabilized immunomodulatory RNA (5'-M2UGCUGCUUGUG-/glycerol/-GUG- UUCGUCGUM2-5' (M2=C6-linker); SEQ ID NO:3) and PN-based TLR7 ligand stabilized immunomodulatory RNA (5'-URCURCUUCUR-/glycerol/-RUCUUCRUCRU-5' (R=7-deazaguanosine); SEQ ID NO:2) were previously identified (Lan et al., *PNAS* 104:13750-13755, 2007). The effect of these TLR7— and TLR8-stimulating RNA PN was evaluated by measuring production of IL-6 and TNF-α in human peripheral blood mononuclear cells (PBMCs) and human monocytes (FIG. 2). $5 \times 10^5$ PBMCs or $2 \times 10^5$ monocytes from healthy human donors were stimulated with 20 μg/mL, 100 μg/mL, or 200 μg/mL of either TLR8 agonist or TLR7 agonist as indicated in FIG. 2. Twenty-four hours later supernatants were assessed for presence of inflammatory cytokines IL-6 and TNF-α by standard ELISA procedure. TLR7 and TLR8RNA PN stimulated production of IL-6 and TNF-α in PBMCs and, to a lesser extent, in monocytes (FIG. 2).

Figure 3:
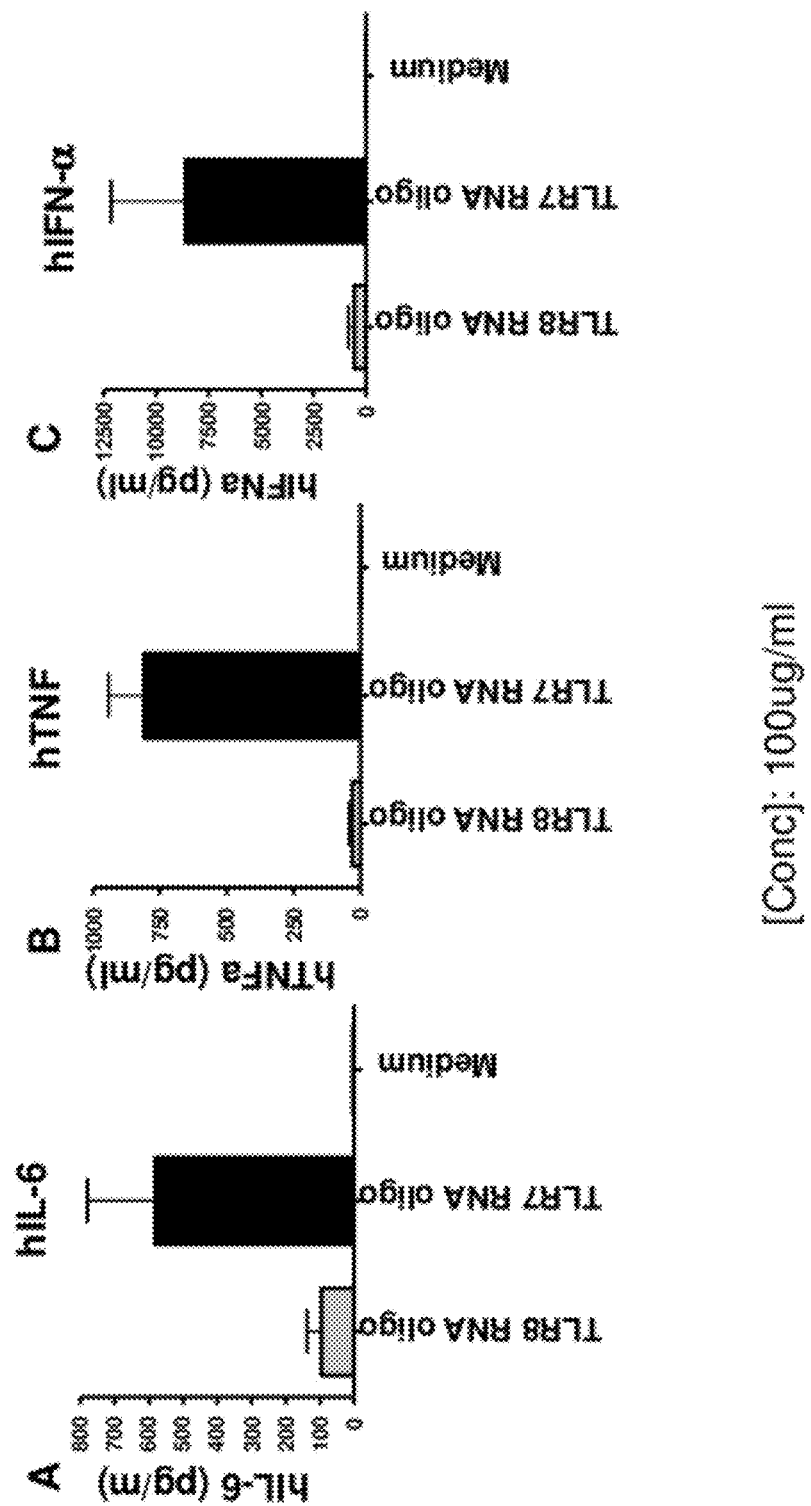
FIG. 3A-C shows the effect of 100 μg/mL of TLR7-stimulating RNA PN (SEQ ID NO:2), 100 μg/mL of TLR8-stimulating RNA PN (SEQ ID NO:3), or medium alone on hIL-6, hTNF and hIFN-α production (pg/mL) by human PDC.

The effect of TLR7 and TLR8-stimulating RNA PN were also evaluated in human pDCs by measuring production of IL-6, TNF-α, and IFN-α. As shown in FIG. 1, human pDCs were negative for the expression of TLR8. $1 \times 10^5$ pDCs from healthy human donors were stimulated with 100 μg/mL of either TLR8 agonist or TLR7 agonist (Lan et al., *PNAS* 104: 13750-13755, 2007) or medium alone as indicated in FIG. 3. Twenty-four hours later supernatants were assessed for presence of inflammatory cytokines IL-6, TNF-α and IFN-α by standard ELISA procedure. The TLR8 agonist did not stimulate the pDCs proving its specificity for TLR8 (FIG. 3)

Figure 4:
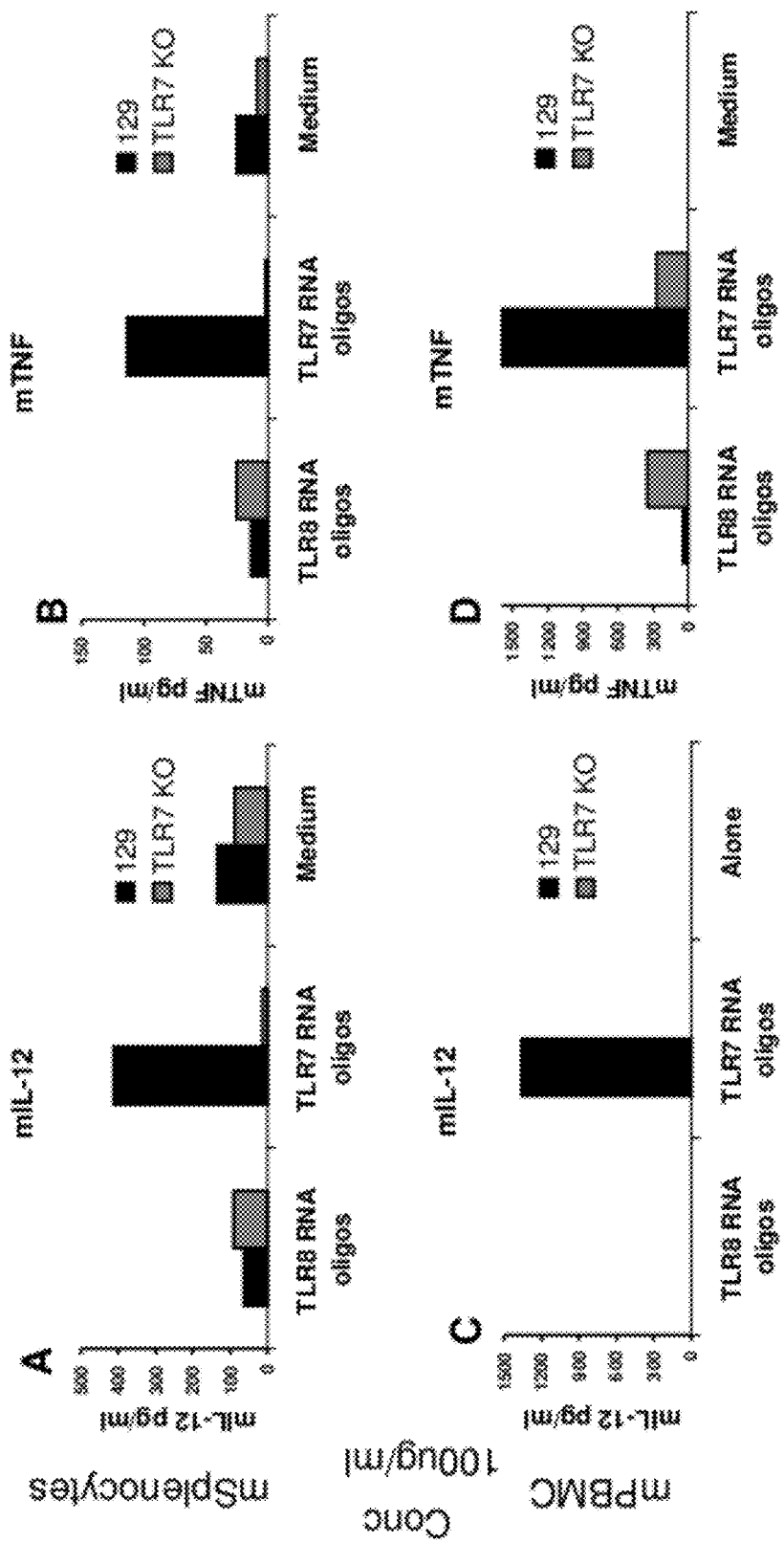
FIG. 4A-D shows the effect of 100 μg/mL of TLR7-stimulating RNA PN (SEQ ID NO:2), 100 μg/mL of TLR8-stimulating RNA PN (SEQ ID NO:3), or medium alone on mIL-12 production (pg/mL) and mTNF production (pg/mL) by mouse splenocytes and mouse PBMC, respectively.

The effect of TLR7 and TLR8-stimulating RNA PNs was further evaluated in mouse cells by measuring IL-12 and TNF-α production (FIG. 4). Mouse splenocytes and PBMCs were prepared from 129 wt mice and TLR7KO mice, and $5 \times 10^5$ cells were stimulated with 100 μg/ml of either TLR8 or TLR7 agonist as indicated in FIG. 4. IL-12 and TNF-α were measured by ELISA using standard techniques. The TLR8 agonist did not stimulate mouse splenocytes and PBMCs (FIG. 4).

Example 3

Generation of Human TLR8 (TLR8) Transgenic Mice

Transgenic TLR8 mice were generated using BAC/ES technologies (Sparwasser et al., *Immunology* 121:308-313, 2007). Briefly, the human BAC carrying TLR8 gene was obtained from the RPCIB-753 BAC library. The human BAC contains both human TLR7 and TLR8 genes in a cluster. The BAC was modified to knock out TLR7 gene to retain the chromosomal region at the 5'UTR of mouse TLR8 that likely contains the promoter. Human TLR7 gene was knocked out by inserting a neomycin cassette (FRT-PGK-gb2-neo-FRT). The FRT-PGK-gb2-neo-FRT template encoded the neomycin/kanamycin resistance gene, which combined a prokaryotic promoter (gb2) for expression of kanamycin resistance in *E. coli* with a eukaryotic promoter (murine phosphoglucokinase gene (PGK)) for expression of neomycin resistance in mammalian cells. A synthetic polyadenylation signal inhibited the kanamycin/neomycin expression. The cassette was flanked by FRT sites for later excision by Flp-recombinase. The appropriate modification was introduced into the BAC using bacterial recombination procedures. After purification of the modified BAC, its quality was checked using pulse-field gel electrophoresis and Southern blot analysis. Important regions of the gene of interest (such as exons or proximal promoter), as well as the introduced modification were confirmed by sequencing. The sequence of construct BAC_RP11-1137P1_TLR7-KO: is provided as SEQ ID NO:1.

Figure 5:
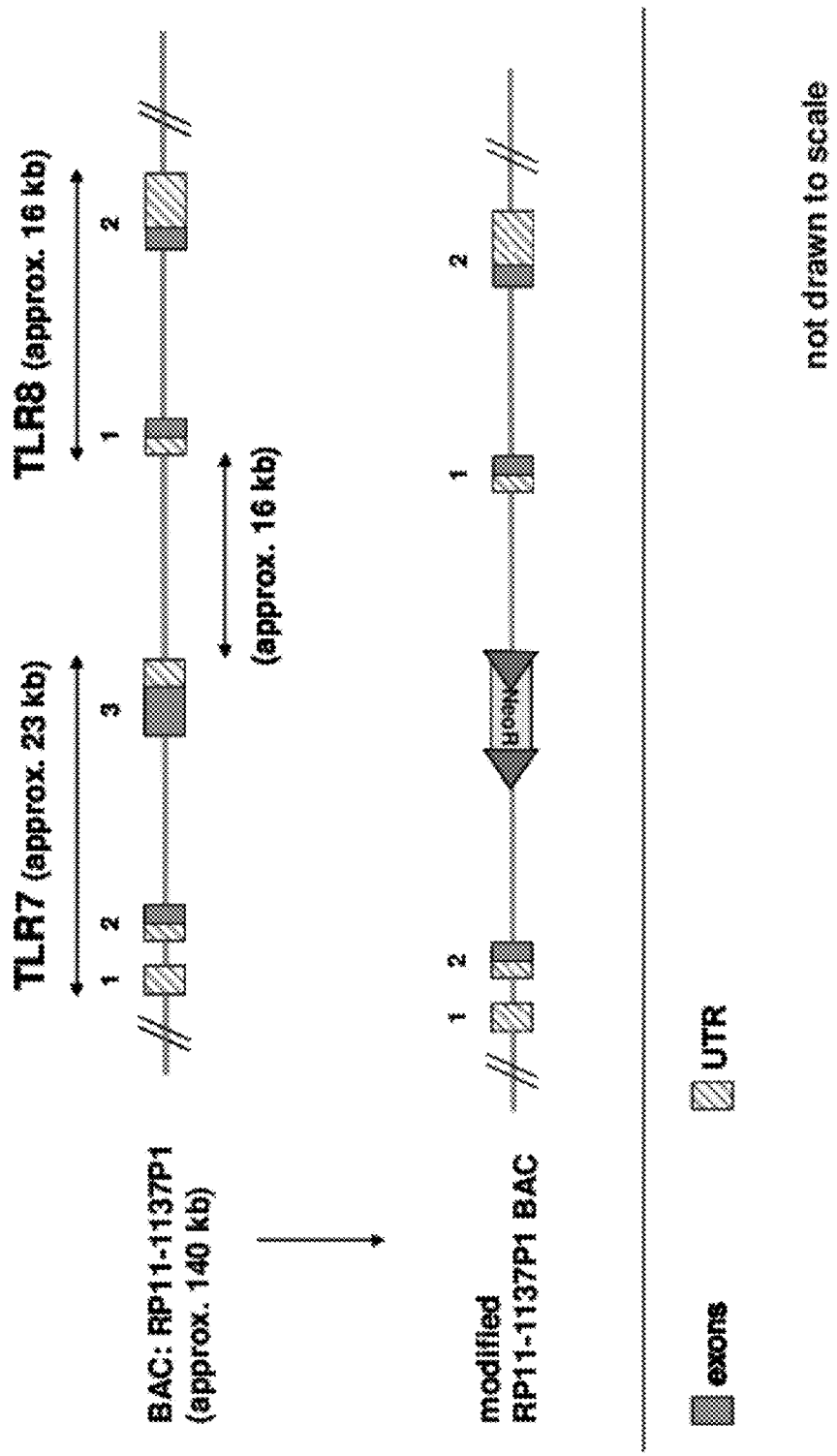
FIG. 5 shows the TLR8 BAC construct used to produce the TLR8 transgenic mice.

The modified BAC construct, BAC_RP11-1137P1_TLR7-KO (FIG. 5), was transfected into an ES cell line, C57BL/6NTac ES cell line. The C57BL/6NTac ES cell line was grown on a mitotically inactivated feeder layer comprised of mouse embryonic fibroblasts (MEF) in DMEM High Glucose medium containing 20% FBS (PAN) and 1200 U/mL Leukemia Inhibitory Factor (Millipore ESG 1107). For manipulation $1.5 \times 10^5$ ES cells were plated on 3.5 cm dishes and transfected one day later with purified BAC_RP11-1137P1_TLR7-KO DNA and Lipofectamine™ 2000 Reagent from Invitrogen (Catalog No. 11668-027) according to manufacturer's protocol. From day 2 onwards the medium was replaced daily with medium containing 200 μg/mL G418 (Geneticin; Invitrogen; Catalog No. 10131-019). Seven days later single clones were isolated, expanded and analyzed by Southern Blot.

The ES clones generated were validated for presence of the TLR8 gene integrated on the genome by using southern blot techniques. Five ES clones were chosen: Clone 8 and clone 6 with about 1-2 copies of TLR8 integrated in the genome, Clone 12 with 2-4 copies of TLR8 integrated in the genome, clone 16 with about 5 copies of TLR8 integrated in the genome and Clone 23 with about 15 copies of TLR8 integrated in the genome, respectively.

ES cells were injected into the blastocoel of 3.5 day old mouse blastocysts from BALB/c females. Subsequently, the injected embryos were transferred to the uterine horns of appropriately timed pseudopregnant recipient BALB/c females. Embryos gestated for about 18 days and the resulting pups were chimeras, whose tissues have developed from both the ES cells carrying TLR8 gene and the recipient blastocyst cells of BALB/c background. This mix of starter cells was visible in the mouse's coat, which exhibited patches of coat color from the host embryo and patches from the injected ES clone. Chimeras with 50-75% ES contribution (based on fur color) were then put to breed with C57BL/6 animals to pass germline transmission.

Example 4

Analysis of TLR8Chimeric Mice

The clones described above were evaluated in more detail. Chimeric ratio was about 30% TLR8 transgene and 70% wild-type. Chimeric mice of four out of five clones (clones 6, 12, 16 and 23) died before germline transmission. Only chimeric mice of clone 8 were able to breed and pass germline transmission. Clones 6, 12, 16, and 23 resulted in chimera lethality.

Figure 6:
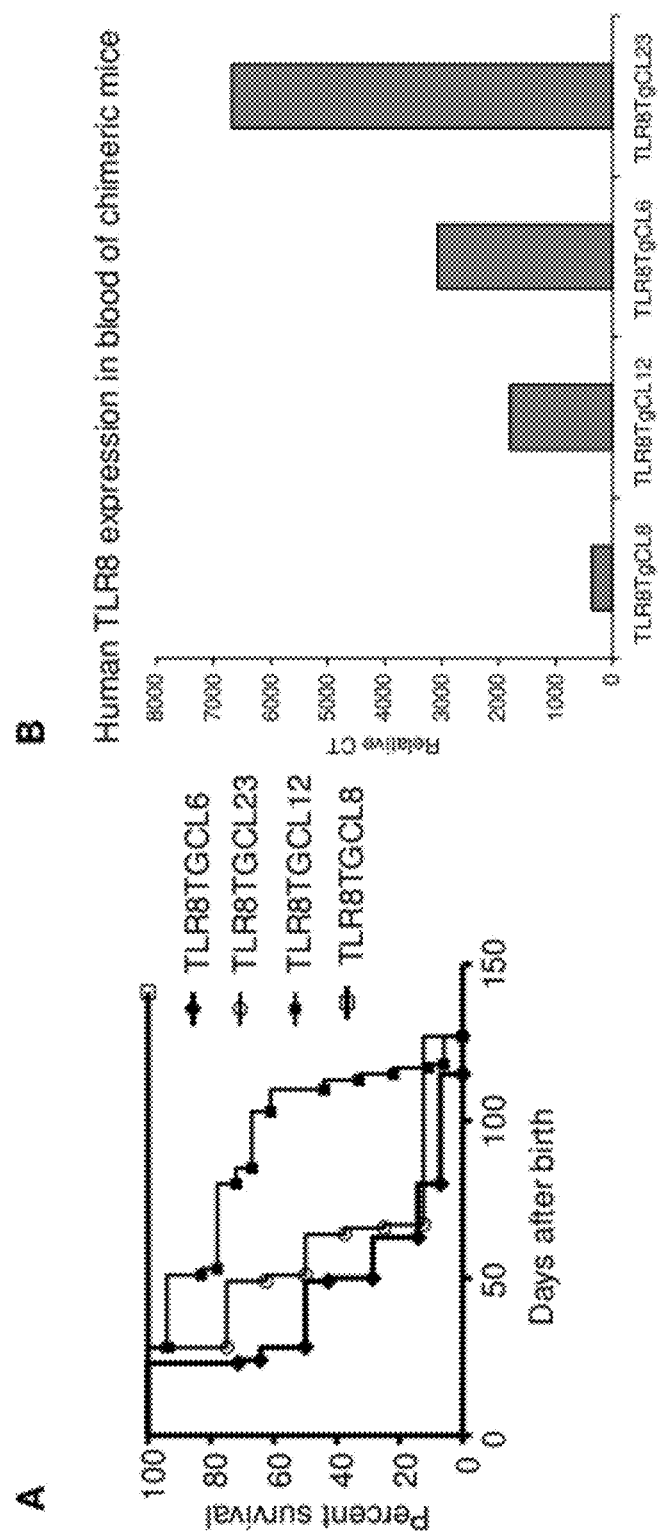
FIG. 6A-C shows the correlation between survival and the level of human TLR8 gene expression in chimeric mice, and the elevated level of expression of TNF, IL-6, IL-17, IL-12p40, CCL-2 and IP10 in sera of TLR8Tg mice.

To determine TLR8 expression 200 μl of blood was harvested from mice and RNA and cDNA were prepared according to standard procedures. TAQMAN assay was used to evaluate TLR8 gene expression. TLR8 expression correlated with survival time (FIG. 6A-B). The highest expressing clones (6, 12, and 23) caused lethality of the chimeric mice. Only Clone 8 with about 1-2 copies of TLR8 integrated in the genome survived (FIG. 6A-B) and passed germline transmission (TLR8TGCL8 mice). Additionally, increased inflammatory cytokine levels were detected in the serum of TLR8Tg mice (n=15) as compared to control WT C57BL/6 mice (FIG. 6C).

Example 5

Gross and Histopathological Analysis of TLR8Chimeras with High TLR8Expression To further evaluate the phenotype of the chimeras with high expression of TLR8, biopsy specimens from chimeric mice of clone 12, 23, and 6 were harvested from mice that showed evident sign of distress and needed to be euthanized. Organs were fixed in formalin and embedded in paraffin. Organs from wild type C57BL/6 (CTRL B6) mice were also harvested as controls. Sections were stained with hematoxylin-eosin. Blinded evaluation of the liver, kidney, intestine, lung, brain, heart and pancreas was conducted by a pathologist during the course of the study. Inflammation was scored 1 to 4 as follow: 1=Minimal; 2=Mild; 3=Moderate; 4=Marked. Statistical significance among groups was calculated with a Mann-Whitney U-test with P values comparing chimeric mice to CTRL B6 animals. P values were considered statistically significant at $p \leq 0.05$.

As shown in Table 5-1, histopathology of the TLR8 chimera's organs revealed multi-organ inflammation with massive autoimmune pancreatitis. Inflammation was found in liver, kidney, and pancreas of human TLR8 expressing mice. Pancreas histological data revealed abundant lymphocytes and macrophages/neutrophils infiltration, while acinar cells were intact. Kidney histological data revealed interstitial inflammation, glomerular changes with segmental hypercellularity, and pyelitis renal pelvis.

TABLE 5-1

Histopathology of the TLR8 Chimeric Mice Organs

| ID Name | Pancreas Pancreatitis | Kidney Glomerulo-nephritis | Kidney Pyelitis | Liver Cholangio-hepatitis |
|---|---|---|---|---|
| CL#12 1-1 | 3 | 2 | 0 | 1 |
| CL#12 2-2 | 3 | 3 | 0 | 3 |
| CL#23 138800 | 4 | 3 | 3 | 2 |
| CL#23 3-1 | 4 | — | — | 3 |
| CL#23 4-1 | 4 | 3 | 2 | 4 |
| CL#23 T4720 | 4 | 3 | 0 | 2 |
| CL#23 136833 | 4 | 3 | 3 | 0 |
| CL#23 138782 | 4 | 3 | 2 | 1 |
| CL#23 138785 | 4 | 3 | 3 | 2 |
| CL#23 3-2 | 4 | 3 | 3 | 4 |
| CL#23 5-4 | 4 | 3 | 3 | 3 |
| CL#23 T4715 | 4 | 3 | 3 | 1 |
| Average | 3.7 | 2.4 | 1.8 | 2.0 |
| SEM | 0.2 | 0.1 | 0.4 | 0.3 |
| P value | <0.001 | <0.001 | N.S. | <0.001 |
| CTRL B6 #1 | 0 | 0 | 0 | 0 |
| CTRL B6 #2 | 0 | 0 | 0 | 0 |
| CTRL B6 #3 | 0 | 2 | 3 | 0 |
| CTRL B6 #4 | 0 | 2 | 0 | 0 |
| Average | 0 | 1.0 | 0.6 | 0 |
| SEM | 0 | 0.3 | 0.4 | 0 |

Example 6

Pathological Characterization of Chimeric Mice with High TLR8Expression

To further analyze the phenotype observed in chimeric mice with high expression of TLR8, pancreatic cytokine production was determined (FIG. 7). Pancreases from TLR8 chimeric mice of Clone 12, 6, or 23 (total number of mice=6) or CTRL WT C57BL/6 mice (total number of mice=6) were harvested and RNA was extracted with fibrous tissue RNA extraction kit (Qiagen) according to manufacturer's instructions. cDNA from RNA was generated with SuperScript First-Strand Synthesis System (Invitrogen). Relative CT values for each gene were normalized to the housekeeping gene Ubiquitin using the formula: Gene expression=$1.8^{(Avg\ CT\ Ubi - CT\ Gene)}$*100,000 where Avg CT Ubi is the mean CT of triplicate housekeeping gene runs, Avg CT Gene is the mean CT of duplicate runs of the gene of interest, and 100,000 is arbitrarily chosen as a factor to bring all values above one. Results show a strong up-regulation of a number of inflammatory cytokines such as IFN-gamma, TNF-$\alpha$, IL12, IP-10, IL-1$\alpha$, and IL-1$\beta$ in the chimeric mice compared to the C57BL/6 control mice. (FIG. 7A-F).

Aberrant recognition of self RNA and DNA has been implicated in the development of pathogenic autoantibodies in human lupus patients and in mouse models of this disease. The presence of nucleic acid-specific autoantibodies in the serum of the TLR8 chimeric mice was assessed using commercially available kits from Alpha Diagnostic. Sera was collected from TLR8 chimeric mice of clone 12 when the mice became moribund. Significantly increased levels of anti-ANA Ig, anti-dsDNA Ig and anti-RNP Ig were detected in the serum from the TLR8 chimeric mice (FIG. 7G-I). Thus, over-expression of hTLR8 is associated with development of anti-self nucleic acid antibodies.

In addition, myeloid dendritic cells (MDCs) were analyzed in chimeric TLR8TGCL23 and wild type B57BL/WT mice (FIG. 8A-D). Chimeric and wild-type mice were sacrificed and spleens were harvested. Flow cytometric analyses were performed using fluorochrome-conjugated monoclonal antibodies to mouse CD11c, and costimulatory molecules CD80, GITRL, OX40L and CD40 (BD bioscience). These data show that MDCs were highly activated in TLR8TGCL23 chimeric mice (FIG. 8).

Example 7

Analysis of Mice Receiving Bone Marrow from TLR8Chimeras

To examine whether epithelial cells or leukocytes are responsible for the phenotype observed in chimeric mice with high levels of TLR8 expression, bone marrow (BM) from TLR8 chimeras of Clone 6, 12 and 23 was transferred to recipient C57/BL6 (SJL) mice and animals were monitored for BM uptake and pathology. Recipient mice (C57/BL6 (SJL)) were irradiated with 900 rad using a cobalt irradiator. Four hours later, $2 \times 10^6$ BM cells extracted from the femurs of TLR8 chimeras were transferred intravenously. Reconstitution of the BM of the recipient mice with the BM of TLR8 chimeras was verified using flow cytometry on blood samples. 25 mice were obtained of which the BM was reconstituted with 80% of TLR8 BM.

Figure 9:
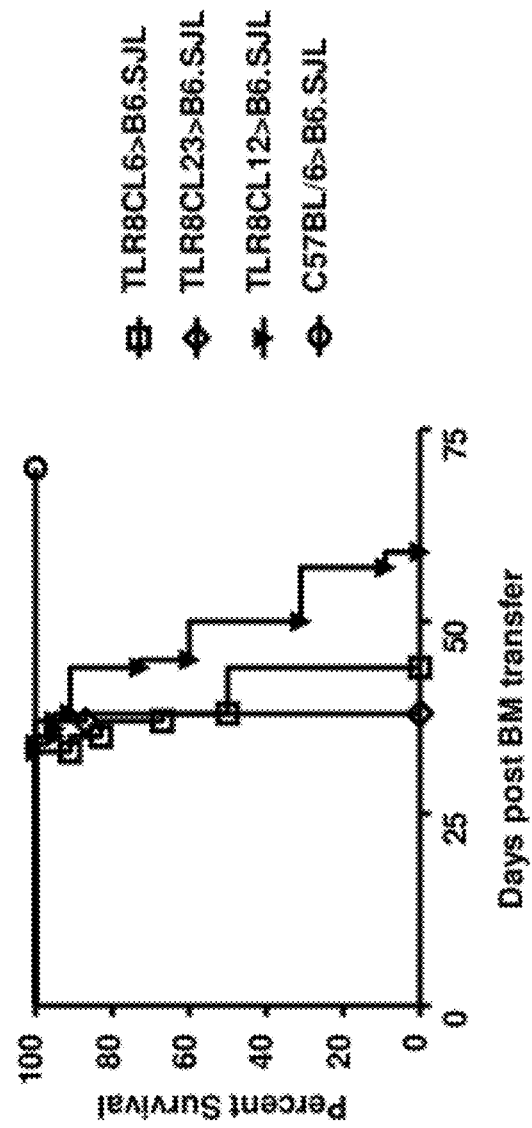
FIG. 9 shows the percentage survival per day post-bone marrow transplant of mice receiving bone marrow from TLR8 chimeric mice from clones 6, 12 and 23.

Mice that were transplanted with TLR8 transgenic mice bone marrow cells (TLR8TG>C57BL/6SJL mice) were monitored daily. Mice died very quickly within 30-60 days after introduction of the TLR8 BM or were euthanized when moribund (FIG. 9). Wild-type mice reconstituted with bone marrow from huTLR8 chimeras developed a spontaneous inflammatory disease remarkably similar to that in the original ES chimeras. In contrast, wild type mice reconstituted with WT BM (C57BL/6>C57BL/6SJL mice) did not show any signs of illness. These data suggest that high level TLR8 expression in the hematopoietic compartment is sufficient to cause the phenotype observe in chimeric TLR8 mice.

TABLE 7-1

Histopathology of the TLR8TG > C57BL/6SJL Bone Marrow Transplanted Mice*

| Clone BM | Pancreas | Kidney D1 | Kidney D2 | Liver | Salivary Gland | Small Intestine |
|---|---|---|---|---|---|---|
| CL 23 | 4 | 1 | 0 | 1.5 | 3 | NT |
| CL 23 | 3.5 | 0 | 2 | 3 | NT | NT |
| CL23 | 3.5 | 0 | 1 | 2.5 | 3.5 | NT |
| CL 6 | NT | 0 | 0 | 1.5 | 2 | NT |
| CL 6 | 4 | 0 | 0 | 2 | 2.5 | NT |
| CL 6 | 4 | 0 | 0 | 3.5 | 2 | NT |
| CL 12 | 4 | 0 | 0 | 1.5 | 3.5 | 0 |
| CL 12 | 4 | 0 | 0 | 2 | 2.5 | 2.5 |
| CL 12 | 4 | 0 | 0 | 1.5 | 3.5 | 2.5 |
| CL 12 | 4 | 0 | 1 | 2.5 | 4 | 1 |
| CL 12 | 4 | 0 | 0 | 2.5 | 3.5 | 0 |
| CL 12 | 4 | 0 | 1 | 1.5 | 3.5 | 1 |
| CL 12 | 4 | 0 | 0 | 2 | 1.5 | 1 |
| CL 12 | 4 | 0 | 0 | 2.5 | 3 | 0 |
| CL 12 | 4 | 0 | 0 | 1.5 | 3 | 1 |
| CL 12 | 4 | 0 | 0 | 1.5 | 2 | 1 |
| CL 12 | 4 | 1 | 1 | 2 | 4 | 2.5 |
| CL 12 | 4 | 0 | 0 | 2 | 1.5 | 3 |
| CL 12 | 4 | 0 | 0 | 3 | 1.5 | 0 |
| CL 12 | 4 | 0 | NT | 1.5 | 3.5 | 1 |
| CL 12 | 4 | 0 | 0 | 2.5 | 3.5 | 3.5 |
| CL 12 | 4 | 0 | IS | 1.5 | 2 | 2 |
| CL 12 | 4 | 0 | NT | 2 | 3.5 | 2 |
| CL 12 | 4 | 0 | 0 | 2.5 | 2.5 | 2.5 |
| CL 12 | 3.5 | 0 | 0 | 0 | 0.5 | 1 |
| Average | 3.9 | 0.1 | 0.3 | 2.1 | 2.7 | 1.4 |
| SEM | 0.03 | 0.06 | 0.11 | 0.14 | 0.19 | 0.25 |
| P value | <0.001 | <0.001 | 0.61 | <0.001 | <0.001 | 0.23 |
| B6 CTRL | 0 | 0 | 0 | 1 | 0 | 1 |
| B6 CTRL | 0 | 1 | 0 | 1 | 0 | 0 |
| B6 CTRL | 0 | 1 | 0 | 1 | 0 | 1 |
| B6 CTRL | 0 | 1 | 0.5 | 1 | 0 | 1 |
| Average | 0.0 | 0.8 | 0.1 | 1.0 | 0.0 | 0.8 |
| SEM | 0.00 | 0.25 | 0.13 | 0.00 | 0.00 | 0.25 |

*Gross Pathology: pancreas pancreatitis, kidney D1 glomerulonephritis, kidney D2 pyelitis, liver cholangiohepatitis, salivary gland inflammation, and small intestine inflammation.

To evaluate the histopathology of TLR8TG>C57BL/6SJL mice, biopsy specimens were harvested from mice that showed evident signs of distress and needed to be euthanized. Organs were fixed in formalin and embedded in paraffin. Organs from C57BL/6SJL (CTRL B6) mice were also harvested as controls. Sections were stained with hematoxylin-eosin. Blinded evaluation of the liver, kidney, intestine, lung, brain, heart and pancreas were conducted by a pathologist. Inflammation was scored 1 to 4 as follow: 1=Minimal; 2=Mild; 3=Moderate; 4=Marked. Statistical significance among groups was calculated with a Mann-Whitney U-test. P values compare chimeric mice to CTRL B6 animals. P values are considered statistically significant at p≤0.05. As shown in Table 7-1 histopathology of the TLR8TG>C57BL/6SJL bone marrow transplanted mice revealed multi-organ inflammation with massive autoimmune pancreatitis.

Figure 10:
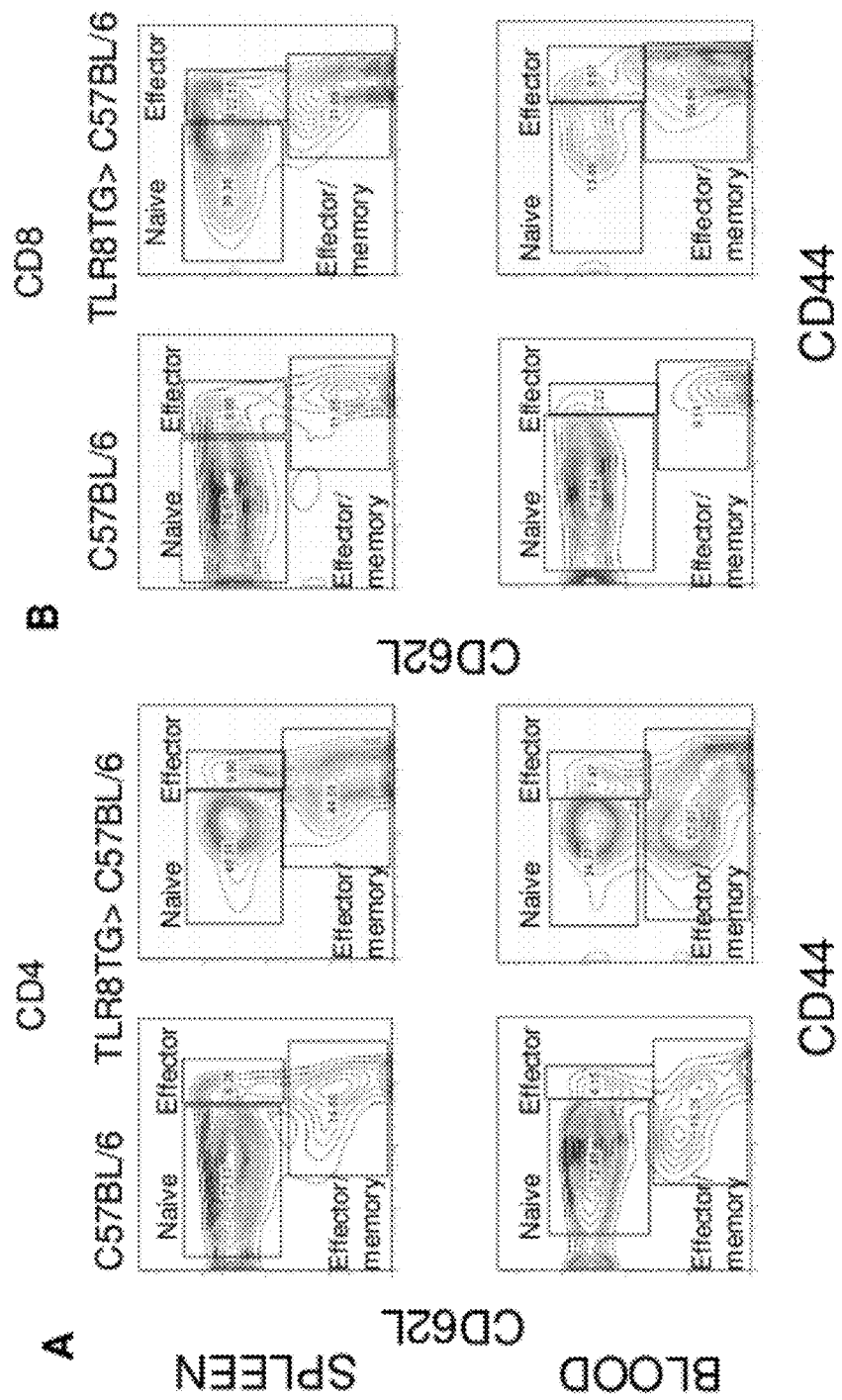
FIG. 10A-B shows example of dot blot results of FACS analyses of T-cells from the spleen and blood of mice transplanted with bone marrow from chimeric TLR8TGCL12 mice. Examples of dot blots for both CD4 T-cells (FIG. 10A) and for CD8 T-cells (FIG. 10B) are provided.
Figure 11:
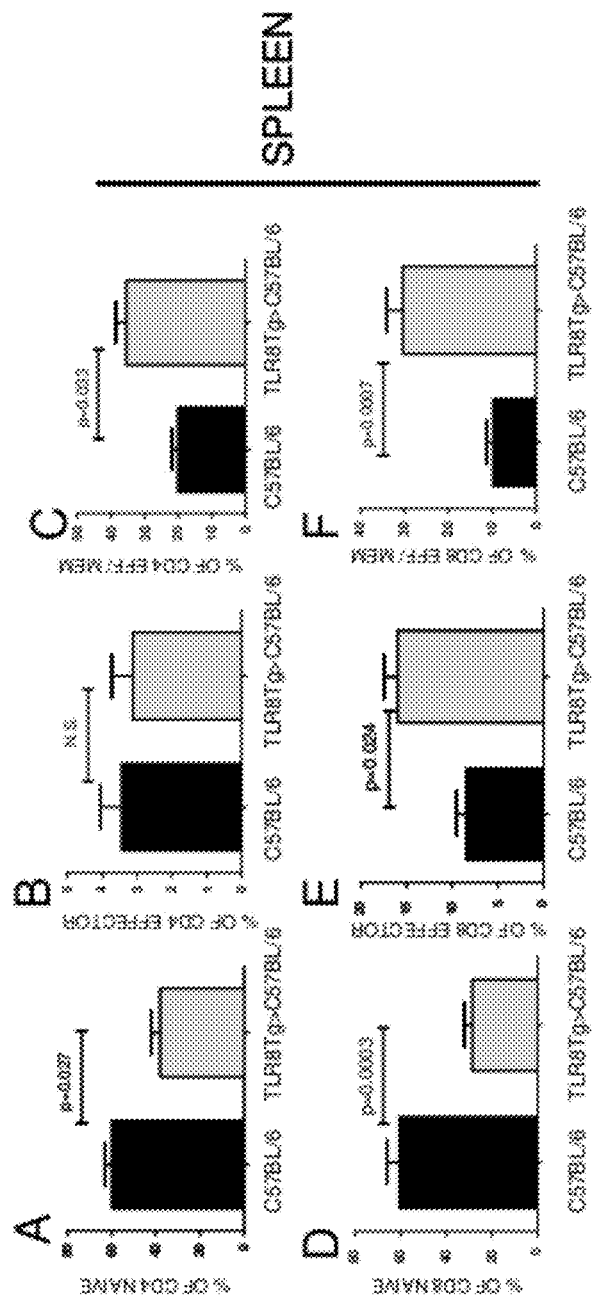
FIG. 11A-L shows cumulative data of FACS analyses of T-cells from the spleen and blood of mice transplanted with bone marrow from chimeric TLR8TGCL12 mice.
Figure 11:
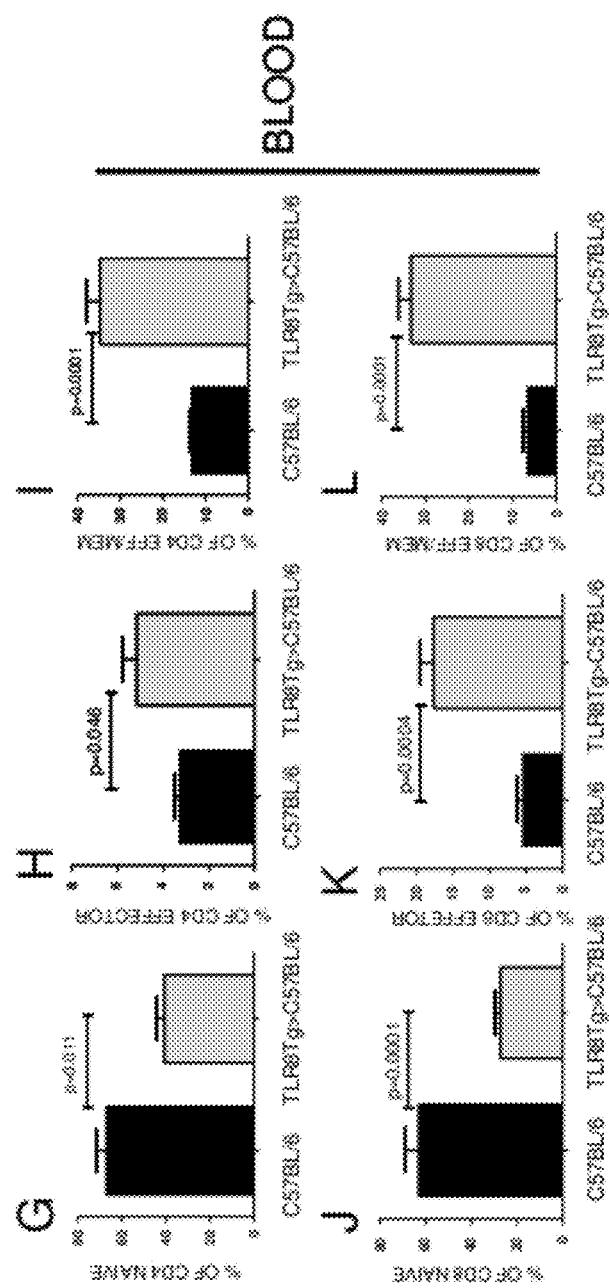

Flow cytometric analyses of T cells of TLR8TGCL12>C57BL/6SJL and wild-type C57BL/6SJL mice were performed using fluorochrome-conjugated monoclonal antibodies to mouse CD4, CD8, CD44, CD62L (BD bioscience) (FIG. 10A-B). 30-40 days after bone marrow transplantation, TLR8TG>C57BL/6SJL mice (n=19) were sacrificed and blood and spleens were harvested. C57BL/6SJL WT mice (n=9) were used as controls. Dot blot analysis (FIG. 10) and cumulative data (FIG. 11) show that naive cells were CD44 low and CD62L high, effector cells were CD44 high and CD62L high, and effector memory cells were CD44 high and CD62L negative. P values were calculated with a Mann-Whitney U-test and were considered statistically significant at p≤0.05. The presence of effector and effector memory cells shows that T cells were highly activated in TLR8TG>C57BL/6SJL mice.

Figure 12:
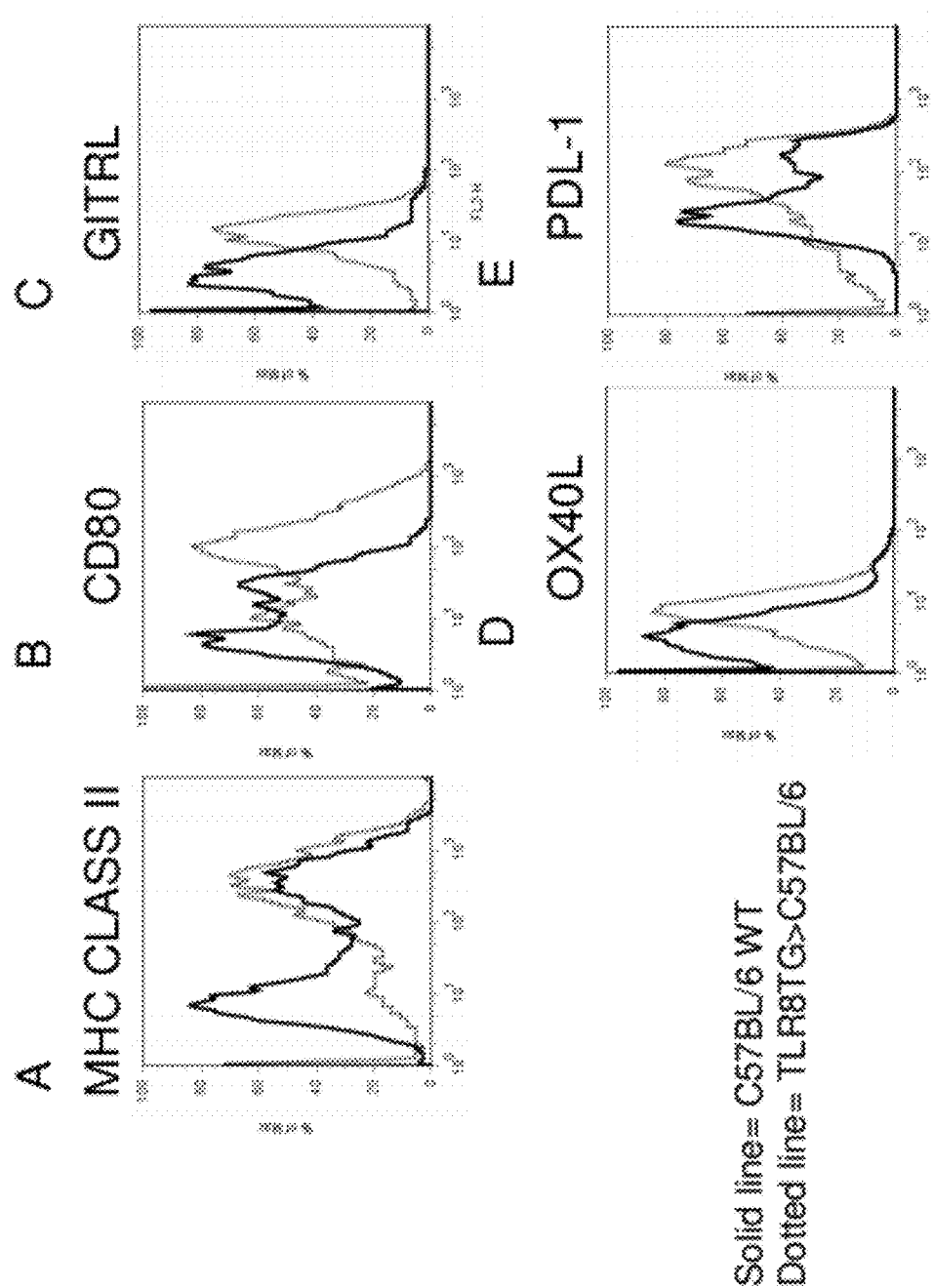
FIG. 12A-E shows expression of MHC Class II, CD80, GITRL, OX40L, and PDL-1, respectively, as determined by FACS analyses of dendritic cells of mice transplanted with human TLR8 transgenic mouse bone marrow.

In addition, flow cytometric analyses of MDC of TLR8TG>C57BL/6SJL and wild-type C57BL/6SJL mice were performed using fluorochrome-conjugated monoclonal antibodies to mouse CD11c, and costimulatory molecules CD80, GITRL, OX40L, PDL-1, and MHC CLASS II (BD bioscience) (FIG. 12). TLR8TG>C57BL/6SJL mice were sacrificed and spleens were harvested. C57BL/6SJL wild-type mice were used as controls.

These data suggest that high level TLR8 expression in leukocytes and not epithelial cells is responsible for the phenotype observed in chimeric TLR8 mice. In these mice, the bone-marrow originated from the TLR8-transgenic animal while the hosts are wild-type. Therefore, this means that the entire hematopoietic compartment carries the transgene but the tissues (and thus all epithelial cell) are wild-type.

Example 8

Transgenically Expressed TLR8 is Functional

Figure 13:
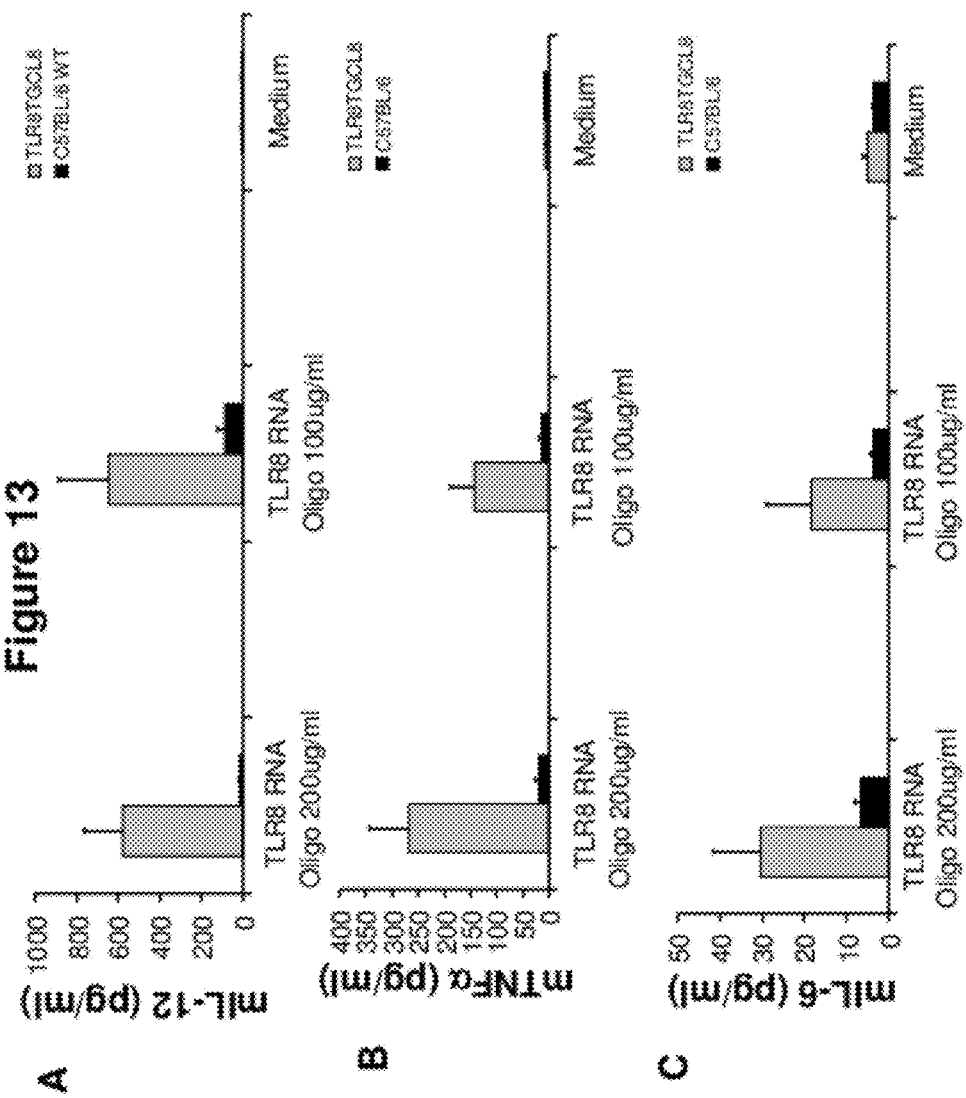
FIG. 13A-C shows activation of TLR8 expressed from the human TLR8 transgene in blood cells in TLR8TGCL8 mice as compared to C56BL/6 wild-type mice upon activation with 200 μg/mL or 100 μg/mL of TLR8-stimulating RNA PN (SEQ ID NO:3), or media alone as assayed by measuring levels of mIL-12 (pg/mL), mTNF-α (pg/mL), and mIL-6 (pg/mL), respectively.
Figure 14:
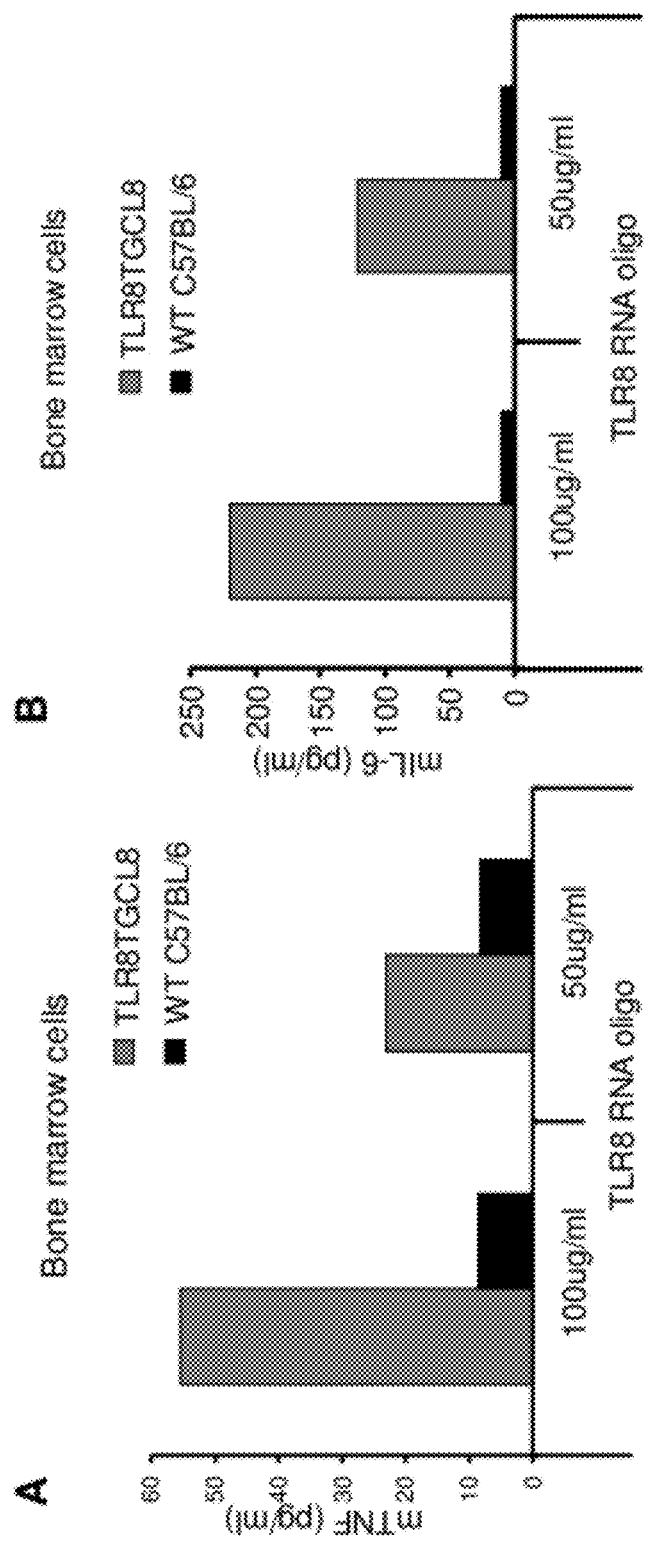
FIG. 14A-B shows activation of TLR8 expressed from the human TLR8 transgene in bone marrow (BM) cells from TLR8TGCL8 mice upon activation with 100 μg/mL or 50 μg/mL of a TLR8-specific ligand (SEQ ID NO:3) as assayed by measuring levels of mTNF-α (pg/mL) and mIL-6 (pg/mL), respectively.

PN-based TLR8 ligand stabilized immunomodulatory RNA (5'-M2UGCUGCUUGUG-/glycerol/-GUG-UUCGUCGUM2-5' (M2=C6-linker); SEQ ID NO:3) and PN-based TLR7 ligand stabilized immunomodulatory RNA (5'-URCURCUUCUR-/glycerol/-RUCUUCRUCRU-5' (R=7-deazaguanosine); SEQ ID NO:2) were previously identified (Lan et al., *PNAS* 104:13750-13755, 2007). To confirm that human TLR8 expressed from the transgene in TLR8TGCL8 mice is functional and sensitive to stimulation, the effect of TLR8-stimulating RNA PN (SEQ ID NO:3) on cytokine production was assessed. $5\times10^5$ blood cells from TLR8TGCL8 transgenic mice or C57BL/6 WT animals were stimulated with TLR8 agonist at different concentrations as shown in FIG. 13. 24 hours later supernatants were harvested and assayed for mouse IL-12, TNF-α and IL-6 using standard ELISA procedures. In addition, $5\times10^5$ bone marrow cells from TLR8TGCL8 transgenic mice or C57BL/6 WT animals were stimulated with TLR8 agonist (SEQ ID NO:3) at different concentrations as shown in FIG. 14. Mouse TNF-α and IL-6 production was assayed in supernatants harvested after 24 hours. Only cells from transgenic animals responded to the TLR8 agonist demonstrating that human TLR8 is functional in these mice (FIGS. 13 and 14).

Example 9

TLR8 Mediated Diseases

The role of TLR8 in disease and/or disease susceptibility was evaluated by using the TLR8 over-expressing mice and/or bone marrow from the TLR8 over-expressing mice as described below.

Figure 15:
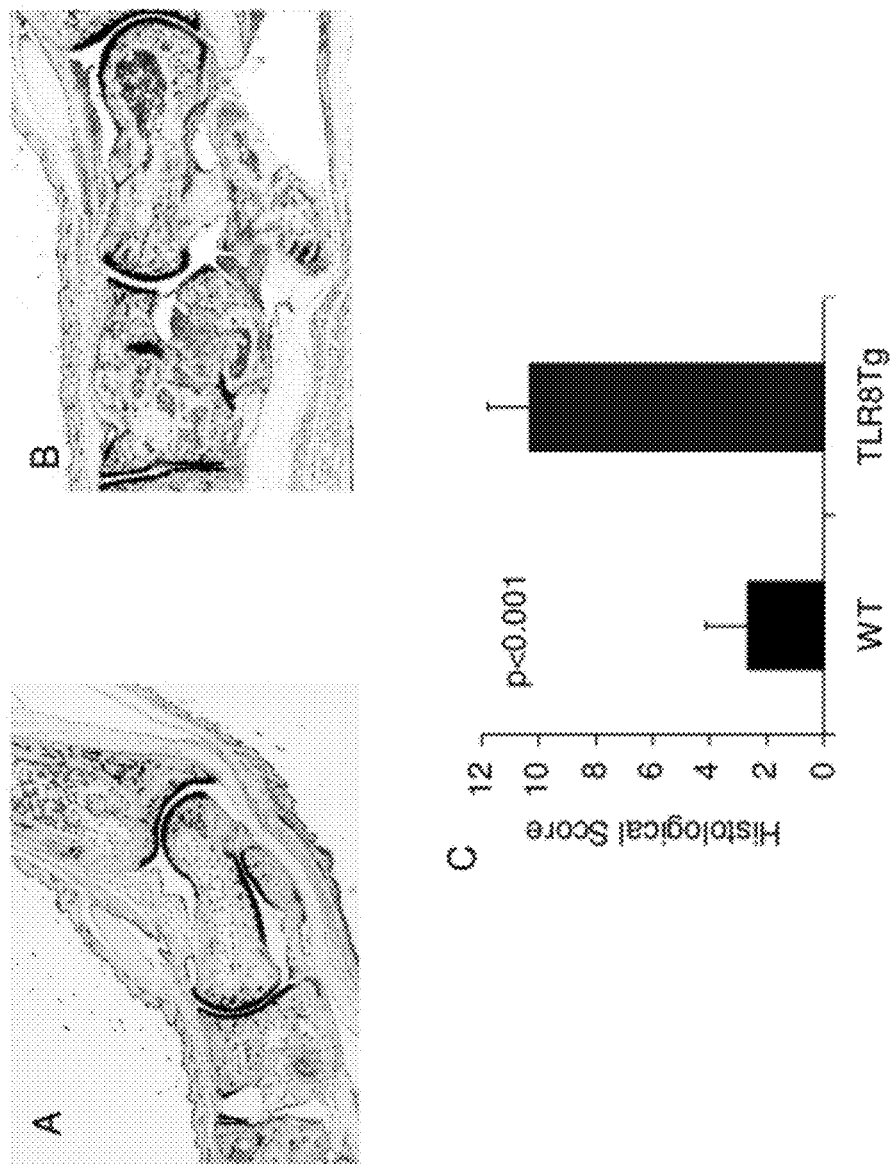
FIG. 15A-C shows that mice over expressing human TLR8 spontaneously develop arthritis. Chimeric mice from clone 12 (n=6) and C57BL/6 CTLR animals (n=6) were euthanized 90 days after birth. All the hTLR8 animals exhibited signs of swelling in forelimbs and hindlimbs. Paws and joints were fixed, sectioned and stained with toluene blue.

Spontaneous Arthriti.

hTLR8Tg chimeric mice from clone 12 (n=6) and C57BL/6 CTLR animals (n=6) were euthanized 90 days after the birth. Paws and joints were fixed, sectioned and stained with toluene blue. Representative sections of joints from WT mice (FIG. 15A) and hTLR8Tg mice (FIG. 15B) were examined. All of the hTLR8Tg mice showed signs of swelling in fore limbs and hind limbs. The histological changes, degree of inflammation and cartilage damage were evaluated by a pathologist in a blinded fashion and scored 1 to 5 as followed: 1=minimal, 2=mild, 3=moderate, 4=marked, 5=severe. Two paws and two ankles were evaluated for each animal and the scores were summed to obtain the histological disease score (FIG. 15C).

Rheumatoid Arthritis

To investigate whether TLR8 had a role in rheumatoid arthritis, wild-type (C57BL/6) and TLR8 transgenic mice (TLR8TGCL8) were immunized per a published immunization schedule and protocol (Campbell, *Eur J Immunol* 30:1568-1575, 2000). On day 0 of collagen immunization, collagen (Chicken Type II Collagen from Chondrex; 2 mg/mL) was emulsified with Complete Freund's Adjuvant (CFA from Chondrex; 5 mg/mL concentration of *Mycobacterium tuberculosis* H37Ra) as follows:

(i) one volume of CFA was mixed with an equal amount of the collagen solution;

(ii) mixing was continued until a stable, stiff emulsion resulted;

(iii) to ascertain the desired stability of the emulsion, 1 drop of emulsion was added into a water-filled beaker (the emulsion was considered stable if it remained in the water as a solid); and (iv) 100 μl was injected subcutaneously at the base of the tail.

A second injection was performed at day 21. Animals were assessed for redness and swelling of the 4 limbs and the cumulative score of each mouse was the sum of the score obtained for each limb. The Clinical Score Guidelines were as follows: 0—Normal; 1—Mild, but definite redness and swelling of the ankle or wrist, or apparent redness and swelling limited to individual digits, regardless of the number of affected digits; 2—Moderate redness and swelling of ankle of wrist; 3—Severe redness and swelling of the entire paw including digits; and 4—Maximally inflamed limb with involvement of multiple joints and a clinical score allocated.

Figure 16:
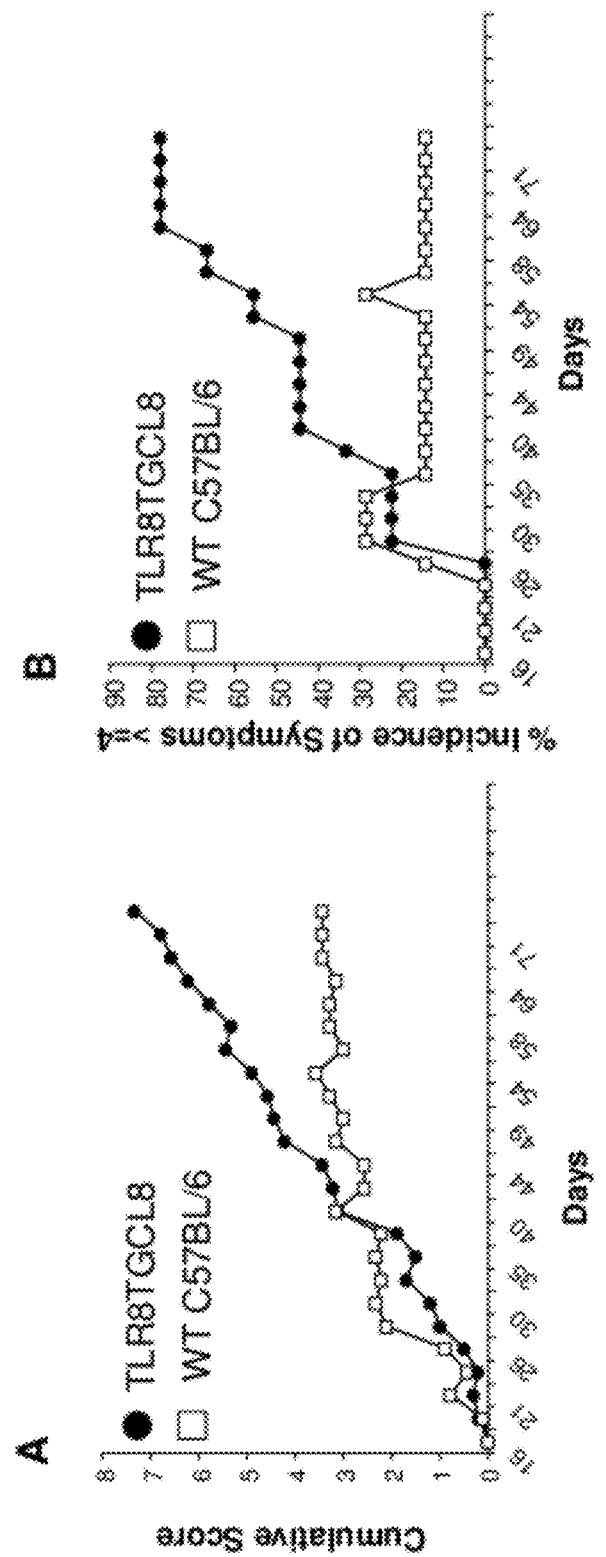
FIG. 16A-B shows the cumulative score and the percentage incidence of symptoms with a clinical score of greater than or equal to four, respectively, using a collagen-induced rheumatoid arthritis (CIA) model for wild-type mice (C57BL/6) and TLR8 transgenic mice (TLR8TGCL8) in days after first collagen injection.
FIG. 16C-E shows that hTLR8, F4/80 and TNF were significantly elevated in joints of hTLR8 transgenic mice (TLR8Tg clone 8) as compared to wild-type mice (C57BL/6).
FIG. 16F-H shows hTLR8, F4/80 and TNF expression relative to the disease score or level of hTLR8 expression respectively. Clearly, the levels of F4/80 and TNF were directly correlated with the level of hTLR8 in the transgenic mice. Likewise, the levels of proinflammatory cytokines (IL-1beta, IL-1alpha, IL-6, IL-18, IP-10, and MMP-9) were found to be directly correlated with hTLR8 expression.
Figure 16:
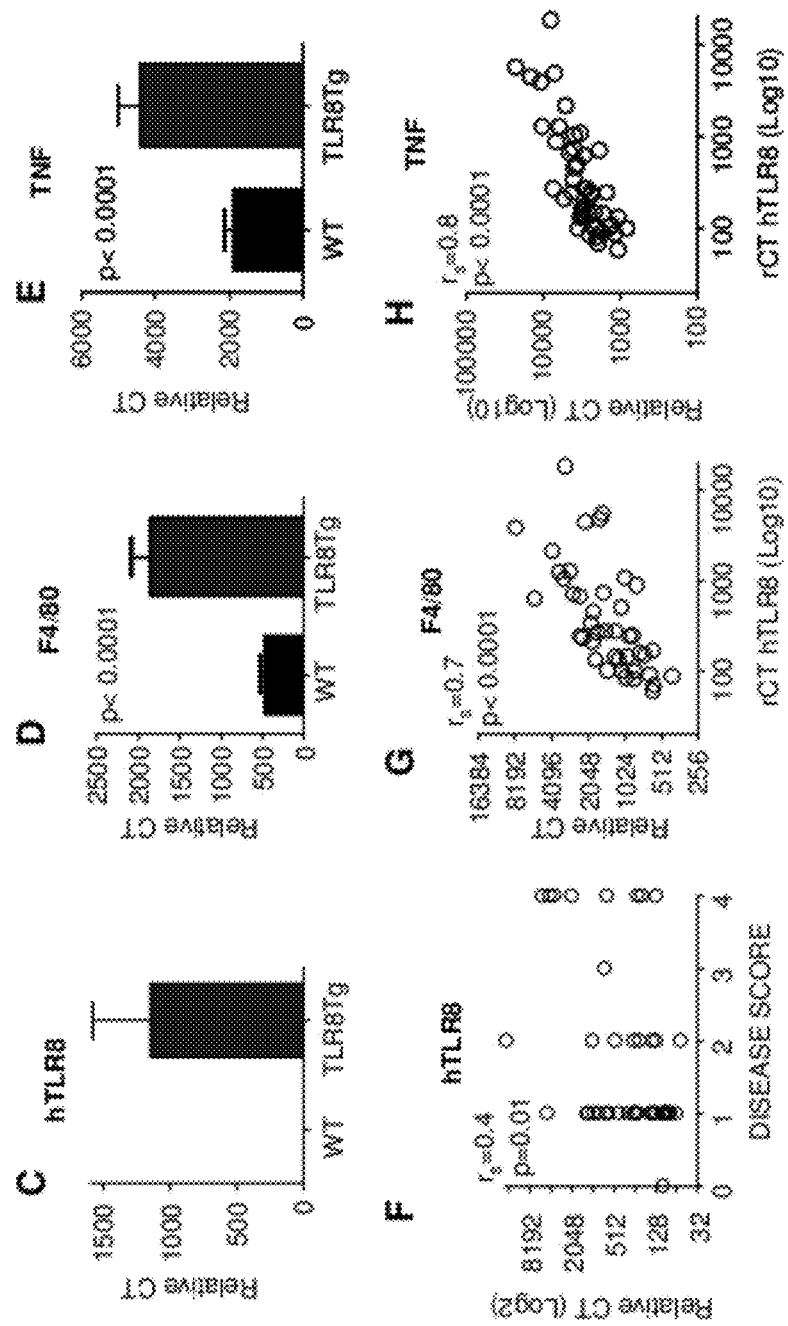

Animals were sacrificed 80 days after CIA induction. The two front joints of each animal were used to prepare RNA to measure expression of various genes using TAQMAN assays (46 joints per group). The data shown are cumulative of two independent experiments. The TLR8 transgenic mice had a higher cumulative clinical score and a significant increase in the incidence of symptoms with a clinical score 4 or greater over time than wild-type mice (FIG. 16A-B). Based on this data, expression of TLR8 was confirmed to play a role in the development of rheumatoid arthritis. FIG. 16C-E shows significantly elevated expression of hTLR8, F4/80 and TNF in the joints of TLR8 transgenic mice (TLR8TGCL8) as compared to wild-type mice (C57BL/6). In addition, the level of expression of hTLR8 was found to correlate with the clinical score (FIG. 16F). Moreover, expression of F4/80 and TNF correlated with levels of hTLR8 expression (FIG. 16G-H). Likewise, expression of various pro-inflammatory cytokines (e.g., IL-1B, 1L1A, IL-6, IL-18, IP-10, MMP-9) was found to correlate with hTLR8 levels (data not shown).

Diabetes

Figure 17:
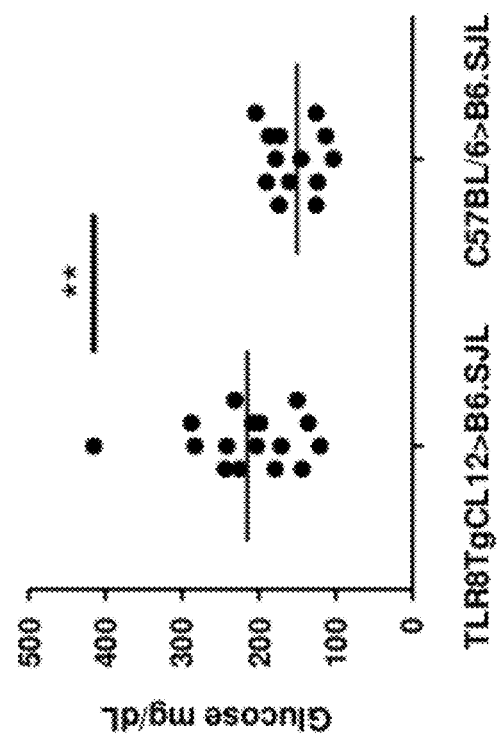
FIG. 17 shows a significant increase in blood glucose level (mg/dL) in mice over-expressing human TLR8 (C57BL/6-SJL WT mice transplanted with TLR8TGCL12 bone marrow cells) compared to C57BL/6-SJL WT mice transplanted with WT C57BL/6 bone marrow cells.

To investigate whether TLR8 had a role in diabetes, C57BL/6-SJL WT Mice were transplanted with WT C57BL/6 bone marrow cells or with TLR8TGCL12 bone marrow cells as described Example 7. Mice were monitored daily. Blood was collected from moribund mice, and glucose levels in the blood were assayed. Blood glucose levels in mice reconstituted with TLR8 BM were significantly elevated as shown in FIG. 17. 62% of the mice showed a level equal or exceeding 200 mg/dL and were therefore considered diabetic (See Lee et al., *Nutrition Research* 26:474-479, 2006; Serrano et al., *Proc. Intl. Soc. Mag. Reson. Med.* 15 2463, 2007; and Tanquilut et al., *J. of Med. Plants Research* 3: 1066-1071, 2009, which are incorporated by reference in their entirety).

Blood Disorders

Figure 18:
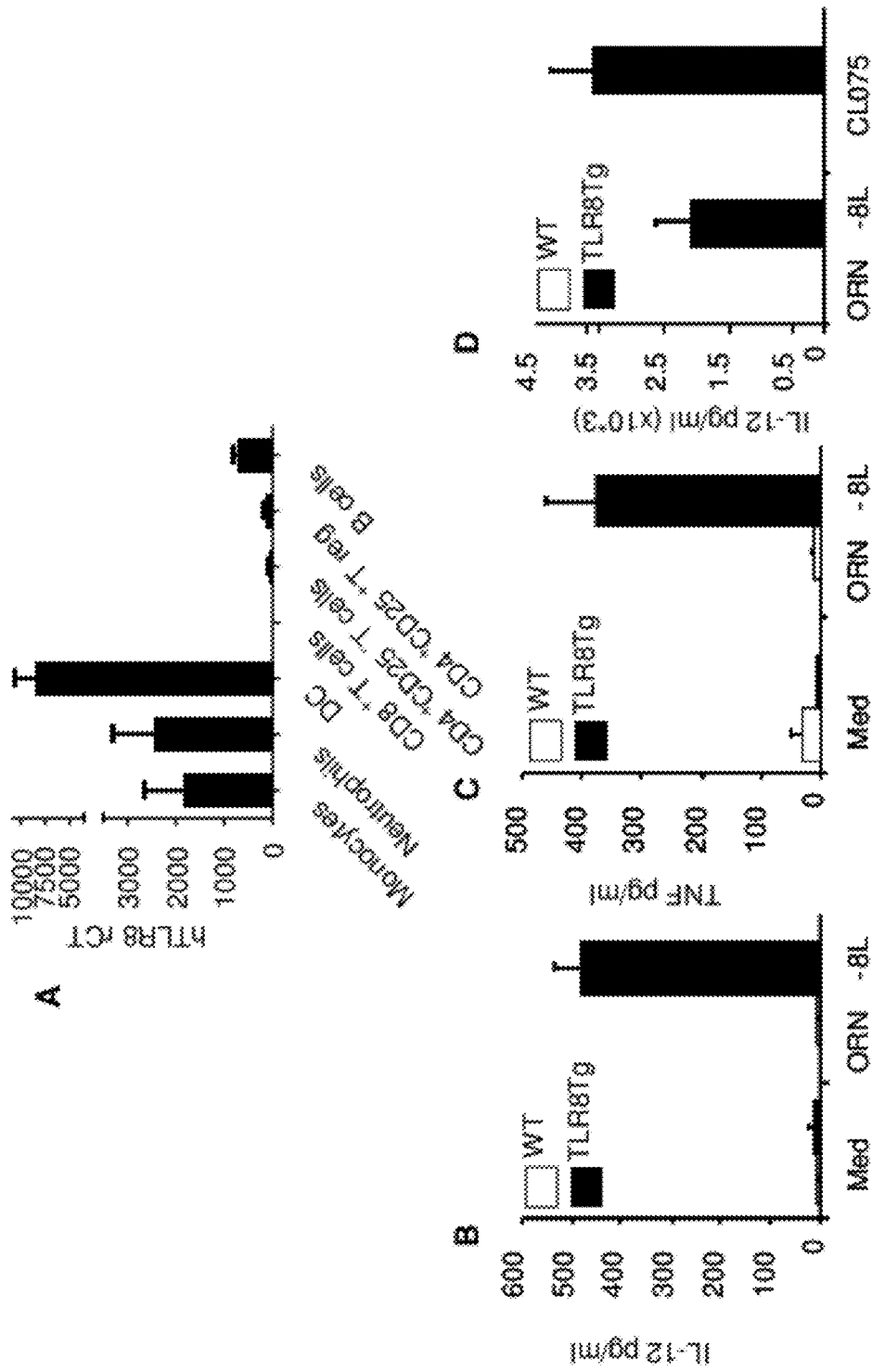
FIG. 18A shows that human TLR8 is expressed in monocytes, neutrophils and dendritic cells of hTLR8Tg mice. The expression pattern of huTLR8 in leukocyte subsets from these mice is very similar to its expression in human leukocytes.
FIG. 18B-D shows that hTLR8 is functional in hTLR8Tg mice. Briefly, PBMC from hTLR8Tg chimeras, but not from wild-type mice produced IL-12 and TNF when stimulated with an RNA-based TLR8 agonist, ORN-8L (FIG. 18B-C). Similarly, elevated levels of IL-12 were detected in the serum from hTLR8Tg mice, but not from wild-type mice, which were injected intravenously with an RNA-based TLR8 agonist (ORN-8L) or a small molecule-based TLR8 agonist (CL075).

Cellular subsets were isolated from spleens of B6.5JLmice transplanted with bone marrow from TLR8TgCL12 mice. Expression of hTLR8 was evaluated by TAQMAN. Cumulative data from at least three independent experiments is shown (n=5-10, mean±SEM). Human TLR8 is expressed in monocytes, neutrophils and dendritic cells of the hTLR8Tg mice (FIG. 18A). The expression pattern huTLR8 in leukocyte subsets from these mice is very similar to its expression in human leukocytes.

Approximately $5 \times 10^5$ PBMC from TLR8Tg chimeras or C57BL/6 WT animals were stimulated with a TLR8 agonist and 24 hr later supernatants were harvest and assayed for cytokine levels by ELISA (n=4 mice, mean±SEM). The RNA-based TLR8 agonist ORN-8L (300 μg) induced secretion of IL-12 and TNF by PBMC from hTLR8Tg mice (FIG. 18B-C).

Figure 19:
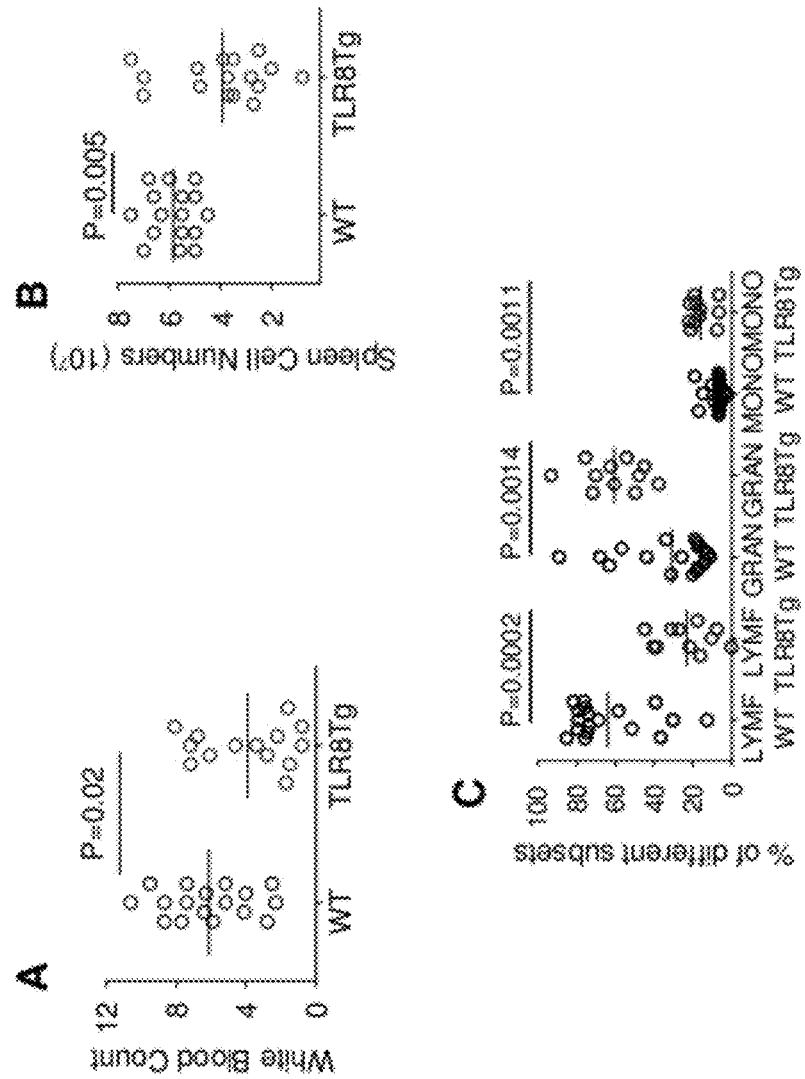
FIG. 19A-C shows that hTLR8Tg mice develop lymphopenia (decrease in number of circulating lymphocytes), granulocytosis (increase in number of granulocytes, which are primarily neutrophils) and monocytosis (increase in number of monocytes). Cell number was assessed in peripheral blood (FIG. 19A) and in spleens of hTLR8Tg chimeras or age-matched control C57BL/6 mice (FIG. 19B). There is a significant decrease in circulating lymphocytes paralleled by an increase in granulocytes and monocytes in the blood of the hTLR8-expressing mice as compared to WT mice CTRL (FIG. 19C).

Mice from TLR8Tg Clone 8 line were injected intravenously with a TLR8 agonist. Serum was collected 6 hr later and assayed for cytokine levels (n=3 mice, mean±SEM). The RNA-based TLR8 agonist ORN8-L (300 μg) or the small molecule-based TLR8 agonist CL075 (5 μg) induced secretion of IL-12 in vivo in hTLR8Tg mice. Thus human TLR8 is functional in these mice The number of various white blood cells was assessed in peripheral blood and in spleens of TLR8Tg chimeras or age-matched C57BL/6 controls (FIG. 19A-B). TLR8Tg mice develop lymphopenia (decrease in number of circulating lymphocytes), granulocytosis (increase in number of granulocytes, which are primarily neutrophils) and monocytosis (increase in number of monocytes). As shown in FIG. 19C there is a significant decrease in circulating lymphocytes paralleled by an increase in granulocytes and monocytes in the blood of the TLR8 expressing mice as compared to WT controls.

Figure 20:
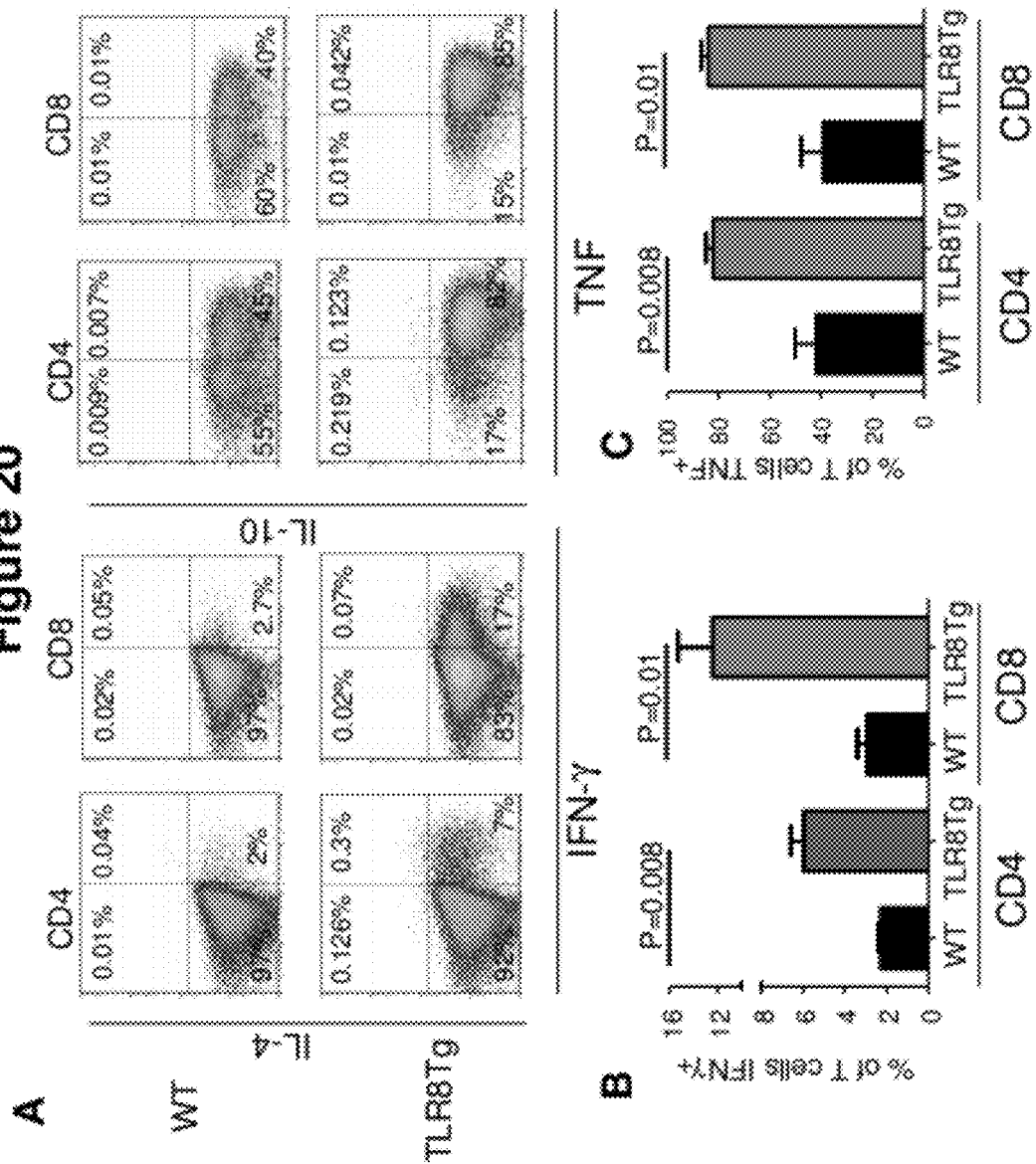
FIG. 20A-C shows that T lymphocytes from mice over-expressing human TLR8 produce more TNF and IFN-gamma as compared to T lymphocytes from wild type mice.

Cells from spleens from TLR8Tg clone 12 chimeric mice and from WT mice were stimulated in vitro for 2 hr with PMA (5 ng/ml) and ionomycin (500 ng/ml). The percentage of CD4 and CD8 T cells producing TNF and IFN-gamma was increased in TLR8Tg chimeric mice as compared to CD4 and CD8 T cells from wild type control mice (FIG. 20A-C).

Example 10

Screening for and/or Identifying TLR8Antagonists and Agonists

TLR8 antagonists and agonist can be screened for and/or identified using the transgenic mice expressing human TLR8 described above.

In Vitro Assays

Human primary monocytes and splenocytes from TLR8TGCL8 mice are used to screen for human TLR8 antagonists and agonists. Cells are stimulated with TLR8-specific ligands and the activation or inhibition of TLR8-related immune responses are measured by standard in vitro assays described herein (e.g., cytokine production, cell proliferation, marker gene expression, and/or cell surface markers).

In Vivo Assays

Clone 8 TLR8 transgenic mice either with germline transmission or TLR8 chimeras or without germline transmission are used to screen for TLR8 antagonists and agonists. Furthermore, new chimeras can be generated using TLR8 transgenic mice with high copy number TLR8ES expressing clones. Mice are injected with either TLR8 agonist or antagonist candidates. TLR8 agonists activate, while TLR8 antagonists inhibit the TLR8-dependent signal transduction pathway and TLR8-associated immune responses. Mice are injected with TLR8 agonist known in the art prior to injection of TLR8 antagonist candidate. Alternatively, TLR8 antagonist candidates can be assessed in spontaneous disease mouse models in the absence of administration of a TLR8 agonist Autoimmune mouse models employing the TLR8 transgenic mice of the present disclosure include, for example, models for rheumatoid arthritis, diabetes, pancreatitis, glomerulonephritis, pyelitis, cholangiohepatitis, and reproductive disorders.

We claim:

1. A transgenic mouse whose genome comprises a nucleotide sequence encoding human Toll-like receptor 8 (TLR8), wherein said human TLR8 is expressed in the transgenic mouse, and wherein at least one inflammatory cytokine selected from the group consisting of tumor necrosis factor-alpha (TNF-alpha), interleukin-6 (IL-6), interleukin-17 (IL-17), interleukin-12 p40 (IL-12B), chemokine cc motif ligand 2 (CCL-2) and interferon-gamma-inducible protein 10 (IP10) is present in sera from the transgenic mouse at an elevated level as compared to a control, non-transgenic mouse.

2. The transgenic mouse of claim 1, wherein said transgenic mouse is a chimeric transgenic mouse in which both human TLR8 and mouse TLR8 is expressed.

3. The transgenic mouse of claim 1, wherein said nucleotide sequence encoding human TLR8 is present at a copy number of from 1 to 5.

4. The transgenic mouse of claim 1, wherein said nucleotide sequence encoding human TLR8 is present at a copy number of 1 or 2.

5. The transgenic mouse of claim 1, wherein said transgenic mouse is predisposed to development of inflammation in one or more organs as compared to a control, non-transgenic mouse.

6. The transgenic mouse of claim 1, wherein said transgenic mouse is predisposed to development of arthritis as compared to a control, non-transgenic mouse.

7. A method of screening candidate agents, the method comprising:

administering a candidate agent to the transgenic mouse of claim 1; and determining the effect of said candidate agent on a TLR8-mediated response of said mouse.

8. The method of claim 7, wherein the effect comprises inhibition of said TLR8-mediated response.

9. The method of claim 7, wherein the effect comprises stimulation of said TLR8-mediated response.

10. The method of claim 7, wherein the effect is evidenced by a change in TLR8-mediated cytokine production, cell proliferation, and/or cell surface marker expression.

11. The method of claim 10, wherein said TLR8-mediated cytokine production comprises production of one or more of the group consisting of TNF, IL-12, IL-6, MIP-1α, IFNγ, IP-10, IL-1α, and IL-1β.

* * * * *